（12) United States Patent
Pfau et al.

(10) Patent No.: US 8,916,599 B2
(45) Date of Patent: Dec. 23, 2014

(54) 1H-BENZ IMIDAZOLE-5-CARBOXAMIDES AS ANTI-INFLAMMATORY AGENTS

(75) Inventors: Roland Pfau, Biberach (DE); Kirsten Arndt, Ravensburg (DE); Henri Doods, Warthausen (NL); Norbert Hauel, Schemmerhofen (DE); Klaus Klinder, Oggelshausen (DE); Raimund Kuelzer, Mittelbiberach (DE); Juergen Mack, Biberach (DE); Henning Priepke, Warthausen (DE); Dirk Stenkamp, Biberach (DE)

(73) Assignee: Orexo AB, Stockholm (SE)

( * ) Notice: Subject to any disclaimer, the term of this patent is extended or adjusted under 35 U.S.C. 154(b) by 368 days.

(21) Appl. No.: 13/119,834

(22) PCT Filed: Sep. 25, 2009

(86) PCT No.: PCT/EP2009/062421
§ 371 (c)(1),
(2), (4) Date: Jun. 7, 2011

(87) PCT Pub. No.: WO2010/034796
PCT Pub. Date: Apr. 1, 2010

(65) Prior Publication Data
US 2011/0312935 A1    Dec. 22, 2011

Related U.S. Application Data

(60) Provisional application No. 61/099,987, filed on Sep. 25, 2008.

(30) Foreign Application Priority Data

Sep. 25, 2008  (EP) .................... 08165120

(51) Int. Cl.
| | | |
|---|---|---|
| A61K 31/4184 | (2006.01) | |
| C07D 235/30 | (2006.01) | |
| C07D 417/12 | (2006.01) | |
| C07D 401/14 | (2006.01) | |
| C07D 263/58 | (2006.01) | |
| C07D 401/12 | (2006.01) | |
| C07D 405/12 | (2006.01) | |
| C07D 413/12 | (2006.01) | |
| C07D 403/12 | (2006.01) | |
| C07D 471/04 | (2006.01) | |
| C07D 277/82 | (2006.01) | |

(52) U.S. Cl.
CPC .......... *C07D 235/30* (2013.01); *C07D 417/12* (2013.01); *C07D 401/14* (2013.01); *C07D 263/58* (2013.01); *C07D 401/12* (2013.01); *C07D 405/12* (2013.01); *C07D 413/12* (2013.01); *C07D 403/12* (2013.01); *C07D 471/04* (2013.01); *C07D 277/82* (2013.01)
USPC ............ 514/390; 548/308.7; 548/309.1

(58) Field of Classification Search
USPC .................... 548/308.7, 309.1; 514/390
See application file for complete search history.

(56) References Cited

U.S. PATENT DOCUMENTS

| | | | |
|---|---|---|---|
| 4,929,623 A | 5/1990 | Abe et al. | |
| 6,608,084 B1 | 8/2003 | Bourzat et al. | |
| 7,355,052 B2 * | 4/2008 | Poitout et al. ............. | 548/307.4 |
| 8,466,186 B2 | 6/2013 | Priepke et al. | |
| 2004/0198768 A1 | 10/2004 | Choo et al. | |
| 2004/0209892 A1 | 10/2004 | Di Pietro et al. | |
| 2005/0267147 A1 | 12/2005 | Poitout et al. | |
| 2006/0173036 A1 | 8/2006 | Poitout et al. | |
| 2006/0287344 A1 | 12/2006 | Alberts et al. | |
| 2007/0060598 A1 | 3/2007 | Albers et al. | |
| 2007/0173488 A1 | 7/2007 | Bounaud et al. | |
| 2010/0004301 A1 | 1/2010 | Pelcman et al. | |
| 2010/0256188 A1 | 10/2010 | Pfau et al. | |
| 2011/0275656 A1 | 11/2011 | Pfau et al. | |
| 2011/0312935 A1 | 12/2011 | Pfau et al. | |

(Continued)

FOREIGN PATENT DOCUMENTS

| | | |
|---|---|---|
| EP | 0034743 A1 | 9/1981 |
| EP | 0295656 A1 | 12/1988 |
| EP | 0419210 A1 | 3/1991 |
| EP | 1069124 A1 | 1/2001 |
| FR | 2851563 A1 | 8/2004 |

(Continued)

OTHER PUBLICATIONS

Lala et al., Cancer and Metastasis reviews (1998), 17 (1), 91-106.

(Continued)

*Primary Examiner* — Patricia L Morris

(57) ABSTRACT

There are provided compounds of formula (I), wherein $R^1$, $R^6$, $R^8$, $Q^2$, $Q^3$, $Q^{3a}$, $Q^4$, L and A have meanings given in the description, and pharmaceutically-acceptable salts thereof, which compounds are useful in the treatment of diseases in which inhibition of the activity of a member of the MAPEG family is desired and/or required, and particularly in the treatment of inflammation and/or cancer.

4 Claims, No Drawings

(56) References Cited

U.S. PATENT DOCUMENTS

| | | |
|---|---|---|
| 2012/0115902 A1 | 5/2012 | Pfau et al. |
| 2012/0122930 A1 | 5/2012 | Pfau et al. |
| 2012/0149676 A1 | 6/2012 | Priepke et al. |
| 2012/0196897 A1 | 8/2012 | Pfau et al. |
| 2012/0208839 A1 | 8/2012 | Priepke et al. |
| 2012/0214786 A1 | 8/2012 | Priepke et al. |
| 2012/0309738 A1 | 12/2012 | Priepke et al. |
| 2012/0309755 A1 | 12/2012 | Priepke et al. |

FOREIGN PATENT DOCUMENTS

| | | |
|---|---|---|
| FR | 2852957 A1 | 10/2004 |
| WO | 00/15612 A1 | 3/2000 |
| WO | 00/49005 A1 | 8/2000 |
| WO | 00/61580 A1 | 10/2000 |
| WO | 00/68213 A1 | 11/2000 |
| WO | 01/25238 A1 | 4/2001 |
| WO | 03/053939 A1 | 7/2003 |
| WO | 03/074515 A1 | 9/2003 |
| WO | 03/082272 A1 | 10/2003 |
| WO | 2004/005323 A1 | 1/2004 |
| WO | 2004/035740 A1 | 4/2004 |
| WO | 2004/072068 A1 | 8/2004 |
| WO | 2004/085425 A1 | 10/2004 |
| WO | 2004/089951 A1 | 10/2004 |
| WO | 2005/044793 A1 | 5/2005 |
| WO | 2005070906 A1 | 8/2005 |
| WO | 2005070920 A1 | 8/2005 |
| WO | 2005/123674 A1 | 12/2005 |
| WO | 2006/077366 A1 | 7/2006 |
| WO | 2006/090167 A1 | 8/2006 |
| WO | 2007/095124 A1 | 8/2007 |
| WO | 2007/127382 A1 | 11/2007 |
| WO | 2008/009924 A1 | 1/2008 |
| WO | 2008/035956 A1 | 3/2008 |
| WO | 2008/071944 A1 | 6/2008 |
| WO | 2008/129276 A1 | 10/2008 |
| WO | 2010034796 A1 | 4/2010 |
| WO | 2010034797 A1 | 4/2010 |
| WO | 2010034798 A1 | 4/2010 |
| WO | 2010034799 A1 | 4/2010 |
| WO | 2010100249 A1 | 9/2010 |

OTHER PUBLICATIONS

Golub et al., Science (1999), vol. 286, 531-537.

Cancer [online], [retrieved on Jul. 6, 2007]. Retrieved from the internet, URL http://www.nlm.nih.gov/medlineplus/cancer html>.

Cancer [online], [retrieved on Jul. 6, 2007]. Retrieved from the internet, URL http://en.wikipedia.orglwikilCancer.

D.J. Gale et al., The Amidomethylation of Some N,N-Dialkylanilines; Aust.J. Chem.; pp. 2447-2458; vol. 28; 1975.

International Search Report Form PCT/ISA/210 and Written Opinion Form PCT/ISA/237 for corresponding PCT/EP2009/062421; date of mailing: Dec. 10, 2009.

European Search Report, for corresponding application No. EP 08 16 5120; date of mailing: May 6, 2009.

R.D. Carpenter et al., Carbodiimide-based benzinidazole library method, Journal of Combinatorial Chemistry, Oct. 27, 2006, pp. 907-914, vol. 8, No. 6.

Silverman et al., The Organic Chemistry of Drug Design and Drug Action, Chapter 2: Drug Discovery, Design, and Development, Academic Press, p. 5-51, 1992.

Samuelsson et al., Pharmacology Review, vol. 59, No. 3, pp. 207-224, 2007.

Friesen et al., Microsomal Prostaglandin E2 Synthase-1 (mPGES-1): A Novel Anti-Inflammatory Therapeutic Target, Journal of Med. Chem., May 2008, vol. 51, No. 14, pp. 4059-4067.

\* cited by examiner

1H-BENZIMIDAZOLE-5-CARBOXAMIDES AS ANTI-INFLAMMATORY AGENTS

FIELD OF THE INVENTION

This invention relates to novel pharmaceutically-useful compounds, which compounds are useful as inhibitors of enzymes belonging to the membrane-associated proteins in the eicosanoid and glutathione metabolism (MAPEG) family. Members of the MAPEG family include the microsomal prostaglandin E synthase-1 (mPGES-1), 5-lipoxygenase-activating protein (FLAP), leukotriene $C_4$ synthase and microsomal glutathione S-transferases (MGST1, MGST2 and MGST3). The compounds are of potential utility in the treatment of inflammatory diseases including respiratory diseases. The invention also relates to the use of such compounds as medicaments, to pharmaceutical compositions containing them, and to synthetic routes for their production.

BACKGROUND OF THE INVENTION

There are many diseases/disorders that are inflammatory in their nature. One of the major problems associated with existing treatments of inflammatory conditions is a lack of efficacy and/or the prevalence of side effects (real or perceived).

Inflammatory diseases that affect the population include asthma, inflammatory bowel disease, rheumatoid arthritis, osteoarthritis, rhinitis, conjunctivitis and dermatitis. Inflammation is also a common cause of pain. Inflammatory pain may arise for numerous reasons, such as infection, surgery or other trauma. Moreover, several diseases including malignancies and cardiovascular diseases are known to have inflammatory components adding to the symptomatology of the patients.

Asthma is a disease of the airways that contains elements of both inflammation and bronchoconstriction. Treatment regimens for asthma are based on the severity of the condition. Mild cases are either untreated or are only treated with inhaled β-agonists which affect the bronchoconstriction element, whereas patients with more severe asthma typically are treated regularly with inhaled corticosteroids which to a large extent are anti-inflammatory in their nature.

Another common disease of the airways with inflammatory and bronchoconstrictive components is chronic obstructive pulmonary disease (COPD). The disease is potentially lethal, and the morbidity and mortality from the condition is considerable. At present, there is no known pharmacological treatment capable of changing the course of the disease.

The cyclooxygenase (COX) enzyme exists in two forms, one that is constitutively expressed in many cells and tissues (COX-1), and one that in most cells and tissues is induced by pro-inflammatory stimuli, such as cytokines, during an inflammatory response (COX-2).

COXs metabolise arachidonic acid to the unstable intermediate prostaglandin $H_2$ ($PGH_2$). $PGH_2$ is further metabolized to other prostaglandins including $PGE_2$, $PGF_{2\alpha}$, $PGD_2$, prostacyclin and thromboxane $A_2$. These arachidonic acid metabolites are known to have pronounced physiological and pathophysiological activity including pro-inflammatory effects. $PGE_2$ in particular is known to be a strong pro-inflammatory mediator, and is also known to induce fever and pain. Consequently, numerous drugs have been developed with a view to inhibiting the formation of $PGE_2$, including "NSAIDs" (non-steroidal antiinflammatory drugs) and "coxibs" (selective COX-2 inhibitors). These drugs act predominantly by inhibition of COX-1 and/or COX-2, thereby reducing the formation of $PGE_2$.

However, the inhibition of COXs has the disadvantage that it results in the reduction of the formation of all metabolites downstream of $PGH_2$, some of which are known to have beneficial properties. In view of this, drugs which act by inhibition of COXs are therefore known/suspected to cause adverse biological effects. For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

An alternative treatment of inflammatory diseases that does not give rise to the above-mentioned side effects would thus be of real benefit in the clinic. In particular, a drug that inhibits (preferably selectively) the transformation of $PGH_2$ to the pro-inflammatory mediator $PGE_2$ might be expected to reduce the inflammatory response in the absence of a corresponding reduction of the formation of other, beneficial arachidonic acid metabolites. Such inhibition would accordingly be expected to alleviate the undesirable side-effects mentioned above.

$PGH_2$ may be transformed to $PGE_2$ by prostaglandin E synthases (PGES). Two microsomal prostaglandin E synthases (mPGES-1 and mPGES-2), and one cytosolic prostaglandin E synthase (cPGES) have been described.

The leukotrienes (LTs) are formed from arachidonic acid by a set of enzymes distinct from those in the COX/PGES pathway. Leukotriene $B_4$ is known to be a strong proinflammatory mediator, while the cysteinyl-containing leukotrienes $C_4$, $D_4$ and $E_4$ (CysLTs) are mainly very potent bronchoconstrictors and have thus been implicated in the pathobiology of asthma. The biological activities of the CysLTs are mediated through two receptors designated $CysLT_1$ and $CysLT_2$. As an alternative to steroids, leukotriene receptor antagonists (LTRas) have been developed in the treatment of asthma. These drugs may be given orally, but do not control inflammation satisfactorily. The presently used LTRas are highly selective for $CysLT_1$. It may be hypothesised that better control of asthma, and possibly also COPD, may be attained if the activity of both of the CysLT receptors could be reduced. This may be achieved by developing unselective LTRas, but also by inhibiting the activity of proteins, e.g. enzymes, involved in the synthesis of the CysLTs. Among these proteins, 5-lipoxygenase, 5-lipoxygenase-activating protein (FLAP), and leukotriene $C_4$ synthase may be mentioned. A FLAP inhibitor would also decrease the formation of the proinflammatory $LTB_4$.

mPGES-1, FLAP and leukotriene $C_4$ synthase belong to the membrane-associated proteins in the eicosanoid and glutathione metabolism (MAPEG) family. Other members of this family include the microsomal glutathione S-transferases (MGST1, MGST2 and MGST3). For a review, c.f. P.-J. Jacobsson et al in *Am. J. Respir. Crit. Care Med.* 161, S20 (2000). It is well known that compounds prepared as antagonists to one of the MAPEGs may also exhibit inhibitory activity towards other family members, c.f. J. H Hutchinson et al in *J. Med. Chem.* 38, 4538 (1995) and D. Claveau et al in *J. Immunol.* 170, 4738 (2003). The former paper also describes that such compounds may also display notable cross-reactivity with proteins in the arachidonic acid cascade that do not belong to the MAPEG family, e.g. 5-lipoxygenase.

Thus, agents that are capable of inhibiting the action of mPGES-1, and thus reducing the formation of the specific arachidonic acid metabolite $PGE_2$, are likely to be of benefit in the treatment of inflammation. Further, agents that are capable of inhibiting the action of the proteins involved in the synthesis of the leukotrienes are also likely to be of benefit in the treatment of asthma and COPD.

In addition to their anti-inflammatory effect, mPGES-1 inhibitors are also known to be of potential use in treating or preventing a neoplasia, for example as described in international patent application WO 2007/124589. The rationale behind this may stem from the fact that the production of PGE2 is believed to promote the formation, growth and/or metastasis of neoplasias. As mPGES-1 is often expressed with COX-2 in benign and cancerous neoplasias, the inhibition of mPGES-1 (rather than COX-2) may cause the reduction of PGE2 and therefore mPGES-1 inhibitors may be useful the treatment of benign or malignant neoplasias.

The listing or discussion of an apparently prior-published document in this specification should not necessarily be taken as an acknowledgement that the document is part of the state of the art or is common general knowledge.

The synthesis of various benzimidazoles has been disclosed by Carpenter et al in the *Journal of Combinatorial Chemistry* (2006), 8(6), 907-914. However, no apparent medical use has been ascribed to such compounds.

DISCLOSURE OF THE INVENTION

There is provided a compound of formula I,

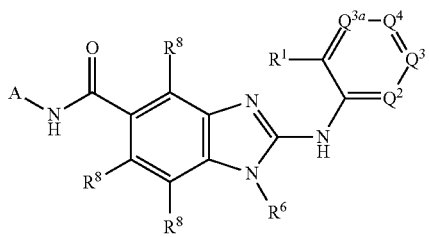

I wherein
$Q^2$, $Q^3$, $Q^{3a}$ and $Q^4$ respectively represent —$C(R^2)$=, —$C(R^3)$=, —$C(R^{3a})$= and —$C(R^4)$=;
$R^1$ represents halo, —CN, —$OR^{y10}$;
$C_{1-7}$ alkyl, $C_{2-7}$ alkenyl, $C_{2-7}$ alkynyl, cycloalkyl (which latter four groups are optionally substituted by one or more substituents selected from fluoro, —$N(R^{y1})R^{y2}$, —$N(R^{y3})$—$C(O)$—$R^{y4}$, —$N(R^{y5})$—$S(O)_2$—$R^{y6}$, —$C(O)OR^{y7}$, —$C(O)N(R^{y8})R^{y9}$, —$OR^{y10}$, —$S(O)_m$—$R^{y11}$, —$S(O)_2O$—$R^{y12}$, —$S(O)_2N(R^{y13})R^{y14}$ and —$C(O)R^{y15}$);
$R^2$, $R^3$, $R^{3a}$ and $R^4$:
independently represent hydrogen, halo, —CN, —$N(R^{y1})R^{y2}$, —$N(R^{y3})$—$C(O)$—$R^{y4}$, —$N(R^{y5})$—$S(O)_2$—$R^{y6}$, —$C(O)OR^{y7}$, —$C(O)N(R^{y8})R^{y9}$, —$OR^{y10}$, —$S(O)_m$—$R^{y11}$, —$S(O)_2O$—$R^{y12}$, —$S(O)_2N(R^{y13})R^{y14}$, —$C(O)R^{y15}$;
$C_{1-7}$ alkyl, $C_{2-7}$ alkenyl, $C_{2-7}$ alkynyl, cycloalkyl [which latter four groups are optionally substituted by one or more substituents selected from fluoro, —CN, —$N(R^{y1})R^{y2}$, —$N(R^{y5})$—$S(O)_2$—$R^{y6}$, —$C(O)OR^{y7}$, —$C(O)N(R^{y8})R^{y9}$, —$OR^{y10}$, —$S(O)_m$—$R^{y11}$, —$S(O)_2O$—$R^{y12}$, —$S(O)_2N(R^{y13})R^{y14}$ and —$C(O)R^{y15}$] provided that if $R^3$ or $R^{3a}$ is a substituted $C_1$ alkyl group, then the substituent cannot be —$N(R^{y5})$—$S(O)_2$—$R^{y6}$;
or any adjacent pair of $R^1$, $R^2$, $R^3$, $R^{3a}$ and $R^4$ (i.e. $R^1$ and $R^{3a}$, $R^2$ and $R^3$, $R^3$ and $R^4$ and $R^4$ and $R^{3a}$) may be linked together to form, along with the essential carbon atoms of the $Q^2$ to $Q^4$-containing ring to which they are necessarily attached, a further 5- to 7-membered ring, optionally containing one to three heteroatoms, which ring may contain one or two further unsaturations and which is optionally substituted by one or more $C_{1-3}$ alkyl and/or =O substituents;
$R^6$ represents hydrogen;
heterocycloalkyl, aryl, heteroaryl (which latter three groups are optionally substituted by one or more substituents selected from $R^9$); or
$C_{1-6}$ alkyl, $C_{2-6}$ alkenyl, $C_{2-6}$ alkynyl, cycloalkyl, which latter four groups are optionally substituted by one or more substituents selected from fluoro, —$N(R^{y1})R^{y2}$, —$N(R^{y3})$—$C(O)$—$R^{y4}$, —$N(R^{y5})$—$S(O)_2$—$R^{y6}$, —$C(O)OR^{y7}$, —$C(O)N(R^{y8})R^{y9}$, —$OR^{y10}$, —$S(O)_m$—$R^{y11}$, —$S(O)_2N(R^{y13})R^{y14}$, —$C(O)R^{y15}$, heterocycloalkyl, cycloalkyl, aryl and heteroaryl (which latter four groups are optionally substituted by one or more substituents selected from $R^9$);
each $R^8$ independently represents hydrogen, halo, —$N(R^{y1})R^{y2}$, —$OR^{y10}$, —$S(O)_2$—$R^{y11}$;
$C_{1-6}$ alkyl, $C_{2-6}$ alkenyl, $C_{2-6}$ alkynyl, cycloalkyl, —O—$C_{1-6}$ alkyl, —O—$C_{2-6}$ alkenyl, —O—$C_{2-6}$ alkynyl, —O-cycloalkyl, —O-heterocycloalkyl [which latter nine groups are optionally substituted by one or more substituents selected from fluoro, —CN, —$N(R^{y1})R^{y2}$, —$N(R^{y3})$—$C(O)$—$R^{y4}$, —$N(R^{y5})$—$S(O)_2$—$R^{y6}$, —$C(O)OR^{y7}$, —$C(O)N(R^{y8})R^{y9}$, —$OR^{y10}$, —$S(O)_m$—$R^{y11}$, —$S(O)_2O$—$R^{y12}$, —$S(O)_2N(R^{y13})R^{y14}$, —$C(O)R^{y15}$, cycloalkyl, heterocycloalkyl, aryl and heteroaryl (which latter four groups are optionally substituted by one or more substituents selected from $R^9$)];
heterocycloalkyl or heteroaryl (which latter two groups are optionally substituted by one or more substituents selected from $R^9$);
A represents aryl, heteroaryl, heterocycloalkyl, cycloalkyl, $C_{1-12}$ alkyl, $C_{2-12}$ alkenyl or $C_{2-12}$ alkynyl, all of which are optionally substituted by one or more substituents selected from $R^9$;
$R^9$ represents, on each occasion when used herein:
halo, —CN, —$N(R^{y1})R^{y2}$, —$N(R^{y3})$—$C(O)$—$R^{y4}$, —$N(R^{y5})$—$S(O)_2$—$R^{y6}$, —$C(O)OR^{y7}$, —$C(O)N(R^{y8})R^{y9}$, —$OR^{y10}$, —$S(O)_m$—$R^{y11}$, —$S(O)_2O$—$R^{y12}$, —$S(O)_2N(R^{y13})R^{y14}$ and —$C(O)R^{y15}$;
$C_{1-7}$ alkyl, $C_{2-7}$ alkenyl, $C_{2-7}$ alkynyl, cycloalkyl, heterocycloalkyl (which latter five groups are optionally substituted by one or more substituents selected from fluoro, —CN, —$N(R^{y1})R^{y2}$, —$N(R^{y3})$—$C(O)$—$R^{y4}$, —$N(R^{y5})$—$S(O)_2$—$R^{y6}$, —$C(O)OR^{y7}$, —$C(O)N(R^{y8})R^{y9}$, —$OR^{y10}$, —$S(O)_m$—$R^{y11}$, —$S(O)_2O$—$R^{y12}$, —$S(O)_2N(R^{y13})R^{y14}$ and —$C(O)R^{y15}$); or
aryl or heteroaryl [which latter two groups are optionally substituted by one or more substituents selected from halo, —CN, $C_{1-7}$ alkyl, $C_{2-7}$ alkenyl, $C_{2-7}$ alkynyl, cycloalkyl (which latter four groups are optionally substituted by one or more substituents selected from fluoro and —$OR^{x2}$), —O—$C_{1-7}$ alkyl, —O—$C_{2-7}$ alkenyl, —O—$C_{2-7}$ alkynyl and —O-cycloalkyl (which latter four groups are optionally substituted by one or more fluoro atoms)]; or
any two $R^9$ substituents:
when attached to the adjacent atoms of the A group; and, in the case where the $R^9$ substituents are attached to a non-aromatic A group, when attached to the same atoms, may be linked together to form, together with the essential atoms of the A group to which the relevant $R^9$ substituents are necessarily attached, a further 3- to 8-membered ring, optionally containing a further one or two heteroatoms, and which further ring optionally contains one or two unsaturations and which is optionally substituted by one or more $C_{1-3}$ alkyl and/or =O substituents;

m represents 0, 1 or 2;

each $R^{y4}$, $R^{y6}$, $R^{y11}$ and $R^{y15}$:
independently represent $C_{1-7}$ alkyl, $C_{2-7}$ alkenyl, $C_{2-7}$ alkynyl, cycloalkyl, which latter four groups are optionally substituted by one or more fluoro atoms;

each $R^{x2}$, $R^{y1}$, $R^{y2}$, $R^{y3}$, $R^{y5}$, $R^{y7}$, $R^{y8}$, $R^{y9}$, $R^{y10}$, $R^{y12}$, $R^{y13}$ and $R^{y14}$:
independently represent hydrogen or $C_{1-7}$ alkyl, $C_{2-7}$ alkenyl, $C_{2-7}$ alkynyl, cycloalkyl, heterocycloalkyl, which latter five groups are optionally substituted one or more substituents selected from fluoro and —$CC_{1-3}$ alkyl; or any two groups, when attached to the same nitrogen atom (i.e. $R^{y1}$ and $R^{y2}$, $R^{y8}$ and $R^{y9}$, and $R^{y13}$ and $R^{y14}$), may, together with that nitrogen atom to which they are necessarily attached, be linked together to form a 3- to 8-membered ring, optionally containing one or two further heteroatoms and which ring optionally contains one or two unsaturations and is optionally substituted by one or more $C_{1-3}$ alkyl and/or =O substituents, or a pharmaceutically acceptable salt thereof, provided that it is not:

(a) N-[(4-Methoxyphenyl)methyl]-2-[(2-o-tolyl)amino-1H-benzimidazole-5-carboxamide

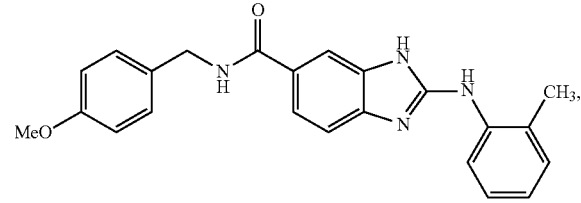 [SMILES: COc1ccc(CNC(=O)c2ccc3nc(Nc4ccccc4C)[nH]c3c2)cc1]

or (b) N-[2-(1H-indol-2-yl)ethyl]-2-[(2-o-tolyl)amino-1H-benzimidazole-5-carboxamide

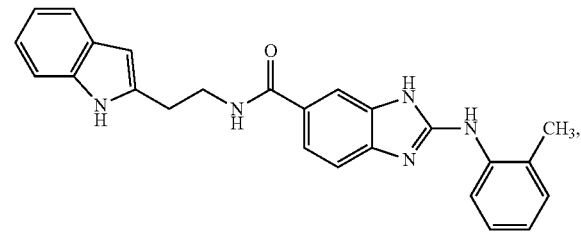 [SMILES: Cc1ccccc1Nc1nc2ccc(C(=O)NCCc3cc4ccccc4[nH]3)cc2[nH]1]

which compounds are hereinafter referred to as 'the compounds of the invention'.

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention. For instance, a compound containing the moiety "1H-benzimidazole" may be considered to be identical to a corresponding compound containing a "3H-benzimidazole" moiety.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise specified, $C_{1-q}$ alkyl, and $C_{1-q}$ alkylene, groups (where q is the upper limit of the range), defined herein may be straight-chain or, when there is a sufficient number (i.e. a minimum of two or three, as appropriate) of carbon atoms, be branched-chain. For the avoidance of doubt, such groups are fully saturated.

Unless otherwise specified, $C_{2-q}$ alkenyl, and $C_{2-q}$ alkenylene, groups (where q is the upper limit of the range) refer to a hydrocarbon chain (in the case of alkenylene, the chain links two moieties) containing one or more double bond. Such groups as defined herein may be straight-chain or, when there is a sufficient number (i.e. a minimum of two or three, as appropriate) of carbon atoms, be branched-chain.

Unless otherwise specified, $C_{2-q}$ alkynyl, and $C_{2-q}$ alkynylene, groups (where q is the upper limit of the range) refer to a hydrocarbon chain (in the case of alkynylene, the chain links two moieties) containing one or more triple bond. Such groups as defined herein may be straight-chain or, when there is a sufficient number (i.e. a minimum of three or four, as appropriate) of carbon atoms, be branched-chain.

In the instance where a 'cycloalkyl' group (e.g. $C_{3-q}$ cycloalkyl) is specifically mentioned, such groups may be monocyclic or bicyclic non-aromatic alkyl groups, which may further be bridged (so forming, for example, fused ring systems). Such cycloalkyl groups may be saturated or unsaturated, e.g. containing one or more double bond (forming for example a $C_{5-q}$ cycloalkenyl). Optional substituents may be attached at any point on the cycloalkyl group. Cycloalkyl groups that may be mentioned preferably include $C_{3-12}$ cycloalkyl, for instance a 3- to 7-membered monocyclic cycloalkyl group, a $C_{7-11}$ (e.g. $C_{8-11}$) bicyclic cycloalkyl group or a $C_{8-12}$ (e.g. $C_{9-11}$) tricyclic cycloalkyl group. As stated above, cycloalkyl groups may further be bridged, so forming, for example, an adamantyl group (for example when a bicyclic cycloalkyl group is bridged). The term 'acyclic' alkyl group when used herein refers to an alkyl group that is not cyclic, but may be branched-chain or, is preferably, straight-chain.

For the avoidance of doubt, the term "bicyclic", when employed in the context of cycloalkyl, refers to such groups in which the second ring is formed between two adjacent atoms of the first ring (i.e. systems of two rings share one bond formed with two adjacent carbon atoms).

The term "bridged", when employed in the context of cycloalkyl groups refers to monocyclic or bicyclic groups in which two non-adjacent atoms are linked by an alkylene chain.

The term "halo", when used herein, includes fluoro, chloro, bromo and iodo.

Aryl groups that may be mentioned include $C_{6-14}$ (e.g. $C_{6-10}$) aryl groups. Such groups may be monocyclic, bicyclic or tricyclic and have between 6 and 14 ring carbon atoms, in which at least one ring is aromatic. $C_{6-14}$ aryl groups include phenyl, naphthyl and the like, such as 1,2,3,4-tetrahydronaphthyl, indanyl, indenyl and fluorenyl. The point of attachment of aryl groups may be via any atom of the ring system, for instance when aryl groups are bicyclic or tricyclic, they are linked to the rest of the molecule via an atom of an aromatic or non-aromatic ring.

Heteroaryl groups that may be mentioned include those which have between 5 and 14 (e.g. 10) members. Such groups may be monocyclic, bicyclic or tricyclic, provided that at least one of the rings is aromatic and wherein at least one (e.g. one to four) of the atoms in the ring system is other than carbon (i.e. a heteroatom). Heteroaryl groups that may be mentioned include acridinyl, benzimidazolyl, benzodioxanyl, benzodioxepinyl, benzodioxolyl (including 1,3-benzodioxolyl), benzofuranyl, benzofurazanyl, benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothiadiazolyl (including 2,1,3-benzothiadiazolyl), benzothienyl, carbazolyl, chromanyl, cinnolinyl, furanyl, imidazolyl, imidazopyridyl (including imidazo[4,5-b]pyridyl, imidazo[5,4-b]pyridyl and imidazo[1,2-a]pyridyl), indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,3,4-oxadiazolyl), oxazolyl, phenazinyl, phenothiazinyl, phthalazinyl, pteridinyl, purinyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,3,4-thiadiazolyl), thiazolyl, oxazolopyridyl (including oxazolo[4,5-b]pyridyl, oxazolo[5,4-b]pyridyl and, in particular, oxazolo[4,5-c]pyridyl and oxazolo[5,4-c]pyridyl), thiazolopyridyl (including thiazolo[4,5-b]pyridyl, thiazolo[5,4-b]pyridyl and, in particular, thiazolo[4,5-c]pyridyl and thiazolo[5,4-c]pyridyl), thiochromanyl, thienyl, triazolyl (including 1,2,3-triazolyl and 1,2,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. When heteroaryl groups are bicyclic or tricyclic, they may be linked to the rest of the molecule via an atom of an aromatic or non-aromatic ring. Heteroaryl groups may also be in the N- or S-oxidised form (so forming, for example, a pyridine N-oxide).

Heterocycloalkyl groups that may be mentioned include non-aromatic monocyclic and bicyclic heterocycloalkyl groups (which groups may further be bridged) in which at least one (e.g. one to four) of the atoms in the ring system is other than carbon (i.e. a heteroatom), and in which the total number of atoms in the ring system is between three and twelve (e.g. between five and ten). Further, such heterocycloalkyl groups may be saturated or unsaturated containing one or more double and/or triple bonds, forming for example a $C_{2-q}$ heterocycloalkenyl (where q is the upper limit of the range) or a $C_{7-q}$ heterocycloalkynyl group. $C_{2-q}$ heterocycloalkyl groups that may be mentioned include 7-azabicyclo-[2.2.1]heptanyl, 6-azabicyclo[3.1.1]heptanyl, 6-azabicyclo [3.2.1]-octanyl, 8-azabicyclo[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo [3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. Further, in the case where the substituent is another cyclic compound, then the cyclic compound may be attached through a single atom on the heterocycloalkyl group, forming a so-called "spiro"-compound. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form.

Heteroatoms that may be mentioned include phosphorus, silicon, boron, tellurium, selenium and, preferably, oxygen, nitrogen and sulfur.

For the avoidance of doubt, in cases in which the identity of two or more substituents in a compound of formula I may be the same, the actual identities of the respective substituents are not in any way interdependent. For example, the —$R^8$ groups on the benzimidazole core may be the same or different. Similarly, when groups are substituted by more than one substituent as defined herein, the identities of those individual substituents are not to be regarded as being interdependent. For example, when an A group is substituted by two $R^9$ substituents, in which, in both cases, $R^9$ represents $C_{1-7}$ alkyl substituted by —$N(R^{y1})R^{y2}$, then the identities of the two —$N(R^{y1})R^{y2}$ groups are not to be regarded as being interdependent, i.e. the two —$N(R^{y1})R^{y2}$ moieties may be the same or different, i.e. at each occurrence, $R^{y1}$ and $R^{y2}$ may also be the same or different.

For the avoidance of doubt, when a term such as "$R^{y1}$ to $R^{y15}$" is employed herein, this will be understood by the skilled person to mean $R^{y1}$, $R^{y2}$, $R^{y3}$, $R^{y4}$, $R^{y5}$, $R^{y6}$, $R^{y7}$, $R^{y8}$, $R^{y9}$, $R^{y10}$, $R^{y11}$, $R^{y12}$, $R^{y13}$, $R^{14}$ and $R^{y15}$ inclusively. Further, when a term such as "$R^1$ to $R^5$" is employed herein, the skilled person will understand this to mean $R^1$, $R^2$, $R^3$, $R^{3a}$, $R^4$ and $R^5$ inclusively. Similarly, when the term "$Q^2$ to $Q^4$" is employed, this will be understood to mean $Q^2$, $Q^3$, $Q^{3a}$ and $Q^4$ inclusively.

For the avoidance of doubt, when the compound of formula I is substituted by a heterocycloalkyl or heteroaryl group, for example when $R^1$ or $R^8$ represent such substituents, then the point of attachment may be via a carbon atom or heteroatom (e.g. nitrogen heteroatom), assuming that the valency of the heteroatom permits. Similarly, when heterocycloalkyl or heteroaryl groups are substituted with further substituents, then those substituents may be attached at any position including on a carbon atom or heteroatom (e.g. a nitrogen heteroatom), again assuming that the valency permits.

For the avoidance of doubt, where it is mentioned herein that alkyl, alkenyl, alkynyl or cycloalkyl groups may be substituted with one or more halo atoms, then those halo atoms are preferably fluoro atoms.

The skilled person will appreciate that there may be free rotation around the nitrogen-carbon bond to which the requisite phenyl ring bearing the $R^1$ to $R^4$ substituents is pending. In view of this (when $Q^2$ to $Q^4$ respectively represent —$C(R^2)$=, —$C(R^3)$=, —$C(R^{3a})$= and —$C(R^4)$=), the $R^1$ and $R^2$ positions are 'identical' (as are the $R^3$ and $R^{3a}$ positions) relative to the point of attachment of that phenyl ring. Hence, the definitions of $R^1$ and $R^2$ may be interchanged (in which case the definitions of $R^3$ and $R^{3a}$ are also 'interchanged', relative to the definitions of $R^1$ and $R^2$), in view of the fact that both $R^1$ and $R^2$ represent ortho phenyl substituents. The important aspect in relation to the $R^1$ to $R^4$ substituents is therefore their positions relative to one another, rather than their positions relative to the point of attachment of that phenyl ring to the rest of the compound of formula I.

For the avoidance of doubt, when preferred features are mentioned herein, then such features may be taken independently of others preferred features or conjunctively with other preferred features.

The skilled person will appreciate that compounds of formula I that are the subject of this invention include those that are stable. That is, compounds of the invention include those that are sufficiently robust to survive isolation from e.g. a reaction mixture to a useful degree of purity.

Compounds of the invention that may be mentioned include those in which, for example when either one of $R^3$ and $R^4$ or $R^{3a}$ and $R^4$ (or both $R^3$ and $R^4$ or both $R^{3a}$ and $R^4$) represent a substituent other than hydrogen, then those substituents may represent:

halo, —CN, —$N(R^{y1})R^{y2}$; or $C_{1-7}$ alkyl, $C_{2-7}$ alkenyl or $C_{2-7}$ alkynyl (which latter three groups are optionally substituted by one or more substituents selected from fluoro and —$OR^{y10}$).

In one embodiment, the invention provides compounds of formula I as described above and in which $R^1$ represents $C_{1-3}$ alkyl (optionally substituted by one or more fluoro atoms), $C_{3-6}$ cycloalkyl, halo.

In another embodiment, the invention provides compounds of formula I according to any of the preceding embodiments and in which $R^2$ represents $C_{1-3}$ alkyl [optionally substituted by one or more atoms selected from fluoro, —CN, —$N(R^{y1})R^{y2}$, —$N(R^{y3})$—C(O)—$R^{y4}$, —$N(R^{y5})$—$S(O)_2$—$R^{y6}$, —C(O)$OR^{y7}$, —$C(O)N(R^{y8})R^{y9}$, —$OR^{y10}$, —$S(O)_m$—$R^{y11}$, —$S(O)_2O$—$R^{y12}$, —$S(O)_2N(R^{y13})R^{y14}$ and —$C(O)R^{y15}$], $C_{3-6}$ cycloalkyl, halo, —CN or —O—$C_{1-3}$ alkyl (optionally substituted by one or more fluoro atoms).

In another embodiment, the invention provides compounds of formula I according to any of the preceding embodiments and in which $R^3$, $R^{3a}$ and $R^4$ independently represent hydrogen, $C_{1-3}$ alkyl (optionally substituted by one or more fluoro atoms) or halo.

In another embodiment, the invention provides compounds of formula I according to any of the preceding embodiments and in which $R^9$ represents halo, —CN, —$N(R^{y1})R^{y2}$, —$N(R^{y3})$—C(O)—$R^{y4}$, —$N(R^{y5})$—$S(O)_2$—$R^{y6}$, —C(O)$OR^{y7}$, —$C(O)N(R^{y8})R^{y9}$, —$OR^{y10}$, —$S(O)_m$—$R^{y11}$, —$S(O)_2O$—$R^{y12}$, —$S(O)_2N(R^{y13})R^{y14}$ and/or —$C(O)R^{y15}$; or $C_{1-7}$ alkyl optionally substituted by one or more substituents selected from halo, —CN, —$N(R^{y1})R^{y2}$, —$N(R^{y3})$—C(O)—$R^{y4}$, —$N(R^{y5})$—$S(O)_2$—$R^{y6}$, —C(O)$OR^{y7}$, —$C(O)N(R^{y8})R^{y9}$, —$OR^{y10}$, —$S(O)_m$—$R^{y11}$, —$S(O)_2O$—$R^{y12}$, —$S(O)_2N(R^{y13})R^{y14}$ and/or —$C(O)R^{y15}$; or aryl, heteroaryl (which latter two groups are optionally substituted by one or more substituents selected from —O—$C_{1-3}$ alkyl, —CN, halo and $C_{1-2}$ alkyl optionally substituted by one or more fluoro atoms; or any two $R^9$ groups may be linked together as defined above.

In another embodiment, the invention provides compounds of formula I according to any of the preceding embodiments and in which $R^8$ represents hydrogen, halo, $C_{1-3}$ alkyl [optionally substituted by one or more substituents selected from fluoro, —$OR^{y10}$, —$N(R^{y1})R^{y2}$, —$N(R^{y3})$—C(O)—$R^{y4}$, and —$C(O)N(R^{y8})R^{y9}$] or —$OR^{y10}$.

In another embodiment, the invention provides compounds of formula I according to any of the preceding embodiments and in which $R^6$ represents hydrogen or $C_{1-6}$ alkyl optionally substituted by one or more substituents selected from fluoro, —$N(R^{y1})R^{y2}$, —$N(R^{y3})$—C(O)—$R^{y4}$, —$N(R^{y5})$—$S(O)_2$—$R^{y6}$, —C(O)$OR^{y7}$, —$C(O)N(R^{y8})R^{y9}$, —$OR^{y10}$, —$S(O)_2R^{y11}$ and a 4- to 6-membered heterocycloalkyl group (containing two or one heteroatom(s) selected from oxygen and nitrogen).

In another embodiment, the invention provides compounds of formula I according to any of the preceding embodiments and in which $R^{x2}$, $R^{y1}$, $R^{y2}$, $R^{y3}$, $R^{y5}$, $R^{y7}$, $R^{y8}$, $R^{y9}$, $R^{y10}$, $R^{y12}$, $R^{y13}$ and $R^{y14}$ independently represent hydrogen or $C_{1-4}$ alkyl optionally substituted by one or more halo atoms or —$OC_{1-2}$ alkyl groups; or any pair of $R^{y1}$ and $R^{y2}$, $R^{y8}$ and $R^{y9}$ and/or $R^{y13}$ and $R^{y14}$ are linked together to form a 3- to 7-membered ring, optionally containing one further nitrogen or oxygen heteroatom, one or two further double bonds, and which ring is optionally substituted by one or more $C_{1-2}$ alkyl or =O substituents.

In another embodiment, the invention provides compounds of formula I according to any of the preceding embodiments and in which $R^{y4}$, $R^{y6}$, $R^{y11}$ and $R^{y15}$ independently represent $C_{1-4}$ alkyl.

In another embodiment, the invention provides compounds of formula I according to any of the preceding embodiments and
in which
A represents $C_{1-12}$ linear or branched alkyl, aryl, heteroaryl, 5- or 6-membered heterocycloalkyl; or $C_{3-10}$ cycloalkyl, all of which groups are optionally substituted by one or more substituents selected from $R^9$.

In another embodiment, the invention provides compounds of formula I according to any of the preceding embodiments and
in which
A represents $C_{1-12}$ linear or branched alkyl, aryl, heteroaryl, 5- or 6-membered heterocycloalkyl; or $C_{3-10}$ cycloalkyl, all of which groups are optionally substituted by one or more substituents selected from:
—C(O)OR$^{10a}$; —N(R$^{10b}$)R$^{10c}$; halo; cyano; $C_{1-6}$ alkyl optionally substituted with one or more halo groups; aryl optionally substituted by one or more halo atoms; —OR$^{10d}$; —C(O)R$^{10e}$; and —S(O)$_2$R$^{10f}$, wherein R$^{10a}$, R$^{10b}$, R$^{10c}$, R$^{10d}$, R$^{10e}$ and R$^{10f}$ independently represent H or $C_{1-4}$ alkyl optionally substituted by one or more halo atoms and/or —OC$_{1-2}$ alkyl.

In another embodiment, the invention provides compounds according to any of the preceding embodiments, namely compounds of formula Ia:

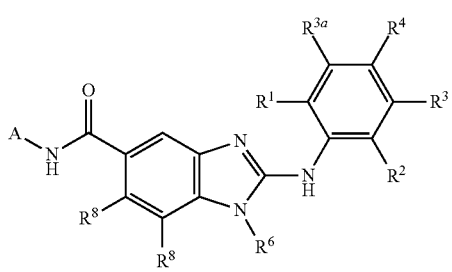

in which:
R$^1$ and R$^2$ independently represent $C_{1-3}$ alkyl (optionally substituted by one or more fluoro atoms), $C_{3-6}$ cycloalkyl, fluoro, chloro, bromo.
R$^3$, R$^{3a}$ and R$^4$ independently represent hydrogen, fluoro, chloro, bromo, $C_{1-3}$ alkyl (optionally substituted by one or more fluoro atoms);
R$^6$ represents hydrogen or $C_{1-6}$ alkyl optionally substituted by one or more substituents selected from fluoro, —N(R$^{y1}$)R$^{y2}$, —N(R$^{y3}$)—C(O)—R$^{y4}$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_2$R$^{y11}$ and a 4- to 6-membered heterocycloalkyl group (containing two or one heteroatom(s) selected from oxygen and nitrogen);
R$^8$ independently represents hydrogen, fluoro, chloro, bromo, —OR$^{y10}$ or $C_{1-3}$ alkyl (optionally substituted by one or more fluoro atoms);
A represents phenyl, pyridyl, 5- or 6-membered heterocycloalkyl, $C_{3-10}$ cycloalkyl, $C_{1-12}$ linear or branched alkyl, all of which are optionally substituted by one or more substituents selected from R$^9$;
R$^9$ represents on each occasion when used herein: halo, —CN, —N(R$^{y1}$)R$^{y2}$, —N(R$^{y3}$)—C(O)—R$^{y4}$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$,
—S(O)$_2$O—R$^{y12}$, —S(O)$_2$N(R$^{y13}$)R$^{y14}$ and/or —C(O)R$^{y15}$, $C_{1-6}$ alkyl optionally substituted by one or more substituents selected from halo, —CN, —N(R$^{y1}$)R$^{y2}$, —N(R$^{y3}$)—C(O)—R$^{y4}$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$, —S(O)$_2$O—R$^{y12}$, —S(O)$_2$N(R$^{y13}$)R$^{y14}$ and/or
—C(O)R$^{y15}$;
aryl or heteroaryl [which latter two groups are optionally substituted by one or more groups selected from $C_{1-7}$ alkyl (optionally substituted by one or more substituents selected from fluoro and —OR$^{x2}$), halo, —CN and/or —O—$C_{1-7}$ alkyl (optionally substituted by one or more fluoro atoms)]; or
any two R$^9$ substituents,
when attached to the adjacent atoms of the A group and, in the case where the R$^9$ substituents are attached to a non-aromatic A group, when attached to the same atoms, may be linked together to form, together with the essential atoms of the A group to which the relevant R$^9$ substituents are necessarily attached, a further 3- to 8-membered ring, optionally containing a further one or two heteroatoms, and which further ring optionally contains one or two unsaturations and which is optionally substituted by one or more $C_{1-3}$ alkyl and/or =O substituents;
and
the substituents R$^{x2}$, R$^{y1}$, R$^{y2}$, R$^{y3}$, R$^{y4}$, R$^{y5}$, R$^{y6}$, R$^{y7}$, R$^{y8}$, R$^{y9}$, R$^{y10}$, R$^{y11}$, R$^{y12}$, R$^{y13}$, R$^{y14}$ and R$^{y15}$ have the meaning as defined in the embodiments above.

In another embodiment, the invention provides compounds according to any of the preceding embodiments, namely compounds of formula Ib:

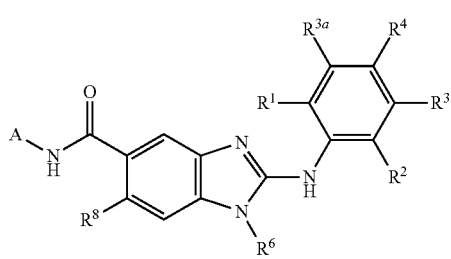

in which:
R$^1$ and R$^2$ independently represent chloro, bromo, fluoro, $C_{1-3}$ alkyl (which latter alkyl group is optionally substituted by one or more fluoro-atoms);
R$^3$, R$^{3a}$ and R$^4$:
independently represent hydrogen, chloro, bromo, fluoro, $C_{1-3}$-alkyl (which latter alkyl group is optionally substituted by one or more fluoro atoms);
R$^6$ represents hydrogen or $C_{1-4}$ alkyl optionally substituted by one or more fluoro atoms;
R$^8$ represent hydrogen, fluoro, chloro, —O—$C_{1-4}$ alkyl (optionally substituted by one or more fluoro atoms);
A represents phenyl, 2-pyridyl, 5- or 6-membered heterocycloalkyl, $C_{3-10}$ cycloalkyl, $C_{1-12}$ linear or branched alkyl, all of which are optionally substituted by one or more substituents selected from R$^9$;
R$^9$ represents, on each occasion when used herein: halo, —OR$^{y10}$;
$C_{1-7}$ alkyl, cycloalkyl, (which latter two groups are optionally substituted by one or more substituents selected from fluoro, —OR$^{y10}$); or aryl or heteroaryl (which latter two groups are optionally substituted by one or more substituents selected from halo, $C_{1-7}$ alkyl, cycloalkyl (which latter two groups are optionally substituted by one or more substituents selected from fluoro and —$OR^{x2}$), —O—$C_{1-3}$ alkyl (which latter group is optionally substituted by one or more fluoro atoms);
and
the substituents $R^{x2}$, $R^{y1}$, $R^{y2}$, $R^{y3}$, $R^{y4}$, $R^{y5}$, $R^{y6}$, $R^{y7}$, $R^{y8}$, $R^{y9}$, $R^{y10}$, $R^{y11}$, $R^{y12}$, $R^{y13}$, $R^{y14}$ and $R^{y15}$ have the meaning as defined in the embodiments above.

In a further embodiment, the invention provides compounds namely those of the examples described hereinafter.

Compounds of the invention may be made in accordance with techniques that are well known to those skilled in the art, for example as described hereinafter.

According to a further aspect of the invention there is provided a process for the preparation of a compound of formula I, which process comprises:
(i) for compounds of formula I, reaction of a compound of formula II,

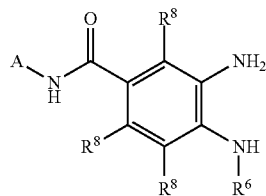

wherein: in each case, $R^6$, $R^8$ and A are as hereinbefore defined, with a compound of formula III,

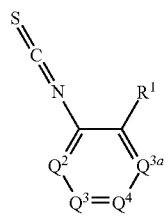

III wherein $R^1$, $Q^2$, $Q^3$, $Q^{3a}$ and $Q^4$ are as hereinbefore defined, under standard conditions known to those skilled in the art, for example in the presence of a suitable solvent (such as diethyl ether, or, preferably, dimethylformamide, dichloromethane, acetononitrile and/or tetrahydrofuran) and preferably in the presence of a suitable 'coupling' reagent (which reagent is preferably added during the course of the reaction, e.g. when there is no more starting material present and/or a thiourea intermediate has been formed) that may enhance the reactivity of any intermediate that may be formed (e.g. a thiourea intermediate such of formulae IIIA, IIIB, IIIC and/or IIID described hereinafter) between the reaction of the compound of formula II with the compound of formula III, for instance a carbodiimide based compound such as dicyclohexylcarbodiimide (DCC), 1-ethyl-3-(3-dimethylaminopropyl) carbodiimide (or salt, e.g. hydrochloride, thereof) or, preferably N,N-diisopropylcarbodiimide (DIC), which reaction may proceed at any suitable temperature (e.g. one between about 0° C. to about 200° C.), and which may also be performed in the presence of an additive (such as 2,2,2-trifluoro-N,O-bis-(trimethylsilyl)-acetamide).

Alternatively, this reaction may be performed in the presence of a suitable base or mixture of bases, such as those described hereinafter (process step (ii)), for example by reaction in the presence of triethylamine and/or DMAP (optionally in the presence of a suitable solvent such as dichloromethane), after which any intermediate so formed may be protected, optionally isolated and reacted in the presence of an aqueous basic solution (e.g. aqueous NaOH; optionally mixed with a further suitable solvent such as an alcoholic solvent), which reaction may take place at ambient temperature or up to reflux. The skilled person will appreciate that the reaction between compounds of formulae II and III may proceed via intermediates of formulae IIIA or IIIB (as appropriate),

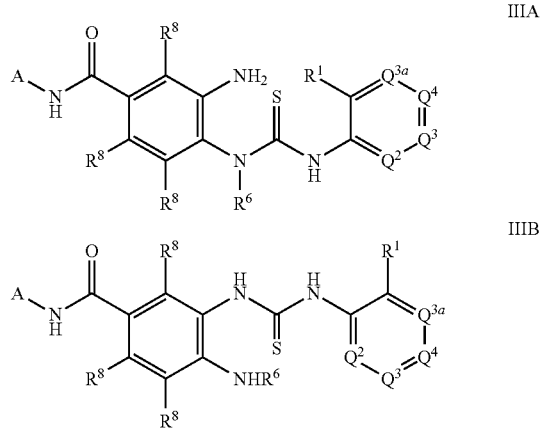

wherein $R^1$, $R^6$, $R^8$, $Q^2$, $Q^3$, $Q^{3a}$, $Q^4$ and A are as hereinbefore defined. Such intermediates may be isolated or may be produced in situ in the reaction to form a compound of formula I. When such intermediates are produced separately, then they may be reacted in the presence of solvent (e.g. acetonitrile and/or methanol) and that the intermediate so formed may be then reacted under the conditions set out above;
(ii) for compounds of formula I, reaction of a compound of formula IV,

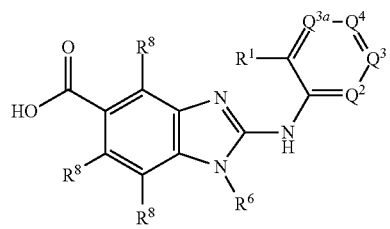

or a derivative thereof (e.g. an ester derivative, such as a methyl ester), wherein $R^1$, $Q^2$, $Q^3$, $Q^{3a}$, $Q^4$, $R^6$ and $R^8$ are as hereinbefore defined, with a compound of formula V,

A-$NH_2$    V wherein A is as hereinbefore defined, under coupling reaction conditions, for example at around room temperature or above (e.g. up to 40-180° C.), optionally in the presence of a suitable base (e.g. sodium hydride, sodium bicarbonate, potassium carbonate, pyrrolidinopyridine, pyridine, triethylamine, tributylamine, trimethylamine, dimethylaminopyridine, diisopropylamine, 1,8-diazabicyclo[5.4.0]undec-7-ene, sodium hydroxide, N-ethyldiisopropylamine, N-(methylpolystyrene)-4-(methylamino)pyridine, butyllithium (e.g. n-, s- or t-butyllithium) or mixtures thereof), an appropriate solvent (e.g. tetrahydrofuran, pyridine, toluene, dichloromethane, chloroform, acetonitrile, dimethylformamide, dimethylsulfoxide, trifluoromethylbenzene, triethylamine or water) and a suitable coupling agent (e.g. 1,1'-carbonyldiimidazole, N,N'-dicyclohexylcarbodiimide, N,N-diisopropylcarbodiimide, 1-(3-dimethylamino-propyl)-3-ethylcarbodiimide (or salt, e.g. hydrochloride thereof), N,N'-disuccinimidyl carbonate, benzotriazol-1-yloxytris (dimethylamino)phosphonium hexafluorophosphate, 2-(1H-benzotriazol-1-yl)-1,1,3,3-tetramethyluronium hexafluorophosphate, benzotriazol-1-yloxytrispyrrolidino-phosphonium hexafluorophosphate, bromo-tris-pyrrolidino-phosphonium hexafluorophosphate, 2-(1H-benzotriazol-1-yl)-1,1,3,3-tetramethyluronium tetrafluorocarbonate, 1-cyclohexyl-carbodiimide-3-propyloxymethyl polystyrene, O-(7-azabenzotriazol-1-yl)-N,N,N',N'-tetra-methyluronium hexafluorophosphate, O-pentafluorophenyl-N,N,N',N'-tetra-methyluronium hexafluorophosphate, O-(benzotriazol-1-yl)-N,N,N',N'-tetra-methyluronium tetrafluoroborate or mixtures thereof). Alternatively, compounds of formula III may first be activated by treatment with a suitable reagent (e.g. oxalyl chloride, thionyl chloride, phosphorous pentachloride, phosphorous oxychloride, (1-chloro-2-methyl-propenyl)-dimethyl-amine or the like, or mixtures thereof) optionally in the presence of an appropriate solvent (e.g. dichloromethane, THF, toluene or benzene) and a suitable catalyst (e.g. DMF), resulting in the formation of the respective acyl chloride. This activated intermediate may then be reacted with a compound of formula V under standard conditions, such as those described above. An alternative way of performing this step, includes the reaction of an ester derivative of a compound of formula IV (e.g. an ethyl or, preferably, a methyl ester) with a compound of formula V, in the presence of, e.g. trimethyla-luminium, optionally in the presence of a suitable solvent (e.g. dichloromethane or tetrahydrofuran) under an inert atmosphere;

Compounds of formula II in which both B and E represent —C=, one of $Y^1$ and $X^1$ represents —N(H)—, and the other represents —O—, —S— or —N($R^6$)—, may be prepared by reduction of a compound of formula XX,

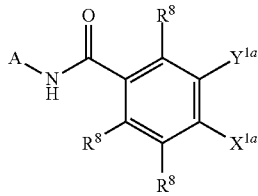

XX wherein $Y^{1a}$ represents —$NO_2$ (or an azido group), and $X^{1a}$ represents —N($R^6$)H or, in the case where the compound of formula II to be formed is one in which both $X^1$ and $Y^1$ represent —N(H)—, then both of $X^{1a}$ and $Y^{1a}$ may represent —$NO_2$ (or an azido group), and $R^8$ and A are as hereinbefore defined, under standard conditions known to those skilled in the art, for example, under hydrogenation reaction conditions, including catalytic hydrogenation reaction conditions (e.g. employing a precious metal catalyst such as a platinum group catalyst, e.g. platinum or, preferably, palladium, which latter may be employed as 10%-20% Pd/C, or employing a non-precious metal catalyst such as one based on nickel, e.g. Raney nickel), for example in the presence of a suitable solvent such as diethyl ether or, preferably, ethyl acetate, tetrahydrofuran or an alcoholic solvent (e.g. EtOH or MeOH), or mixtures thereof. Alternatively, the reduction may be performed in the presence of other suitable conditions, such as employing a mixture of Sn/HCl or Fe powder in EtOH and/or acetic acid and $NH_4Cl$. Compounds of formula IIIA and IIIB (the latter with $R^6$=H) may be prepared by reduction of a corresponding compound of formula XXA or XXB,

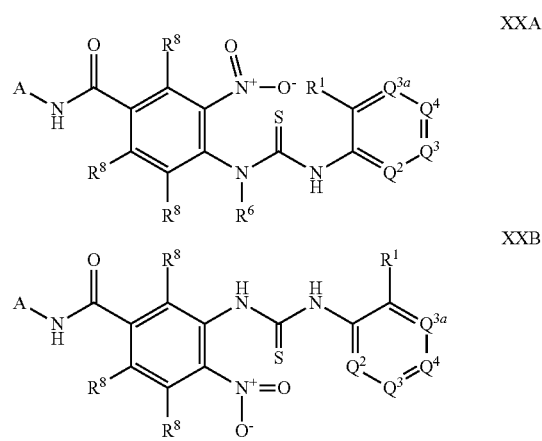

wherein $R^1$, $R^6$, $R^8$, $Q^2$, $Q^3$, $Q^{3a}$, $Q^4$ and A are as hereinbefore defined, under reduction reaction conditions for example such as those hereinbefore described in respect of preparation of compounds of formula II. The skilled person will appreciate that a similar reaction may be performed on compounds in which the nitro group is replaced with an azido group.

Compounds of formula XX may be prepared by nitration of a compound of formula XXIII,

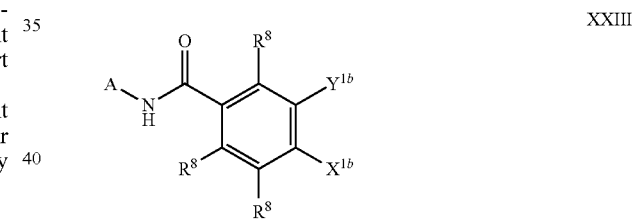

XXIII wherein $X^{1b}$ represents —N($R^6$)H and $Y^{1b}$ represents hydrogen, or $X^{1b}$ represents hydrogen and $Y^{1b}$ represents —$NH_2$, and $R^8$ and A are as hereinbefore defined, under standard nitration reaction conditions, for example in the presence of a mixture of nitric acid and sulfuric acid (e.g. conc. sulfuric acid) which may be mixed at low temperatures (e.g. at about 0° C.), thereby forming a nitronium ion in situ, which may then react with the compound of formula XXIII.

Alternatively, compounds of formula XX in which one of $X^{1a}$ and $Y^{1a}$ represents
—$NO_2$ and the other represents —$NH_2$ or —N($R^6$)H may be prepared by reaction of a compound of formula XXIIIA,

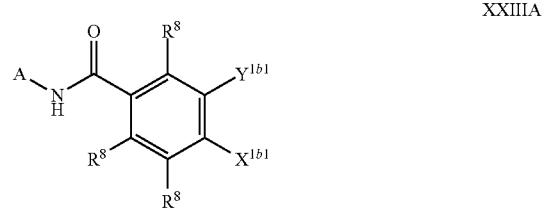

XXIIIA wherein one of $X^{1b1}$ and $Y^{1b1}$ represents —$NO_2$ and the other represents a suitable leaving group, such as hereinbefore defined in respect of $L^{yb}$ (and preferably represents a halo group, such as chloro), and A and $R^8$ are as hereinbefore defined, with either: ammonia (or a suitable source thereof; for example, methanolic ammonia, or the like); or, for the introduction of the appropriate —N($R^6$)H (e.g. when $R^6$ is hydrogen), the corresponding amine $R^6$—NH$_2$, under standard nucleophilic aromatic substitution reaction conditions.

Compounds of formula XXA and XXB in which $X^1$ and $Y^1$ preferably represent
—N(H)— may be prepared by reaction of a compound of formula XXIIIB or XXIIIC,

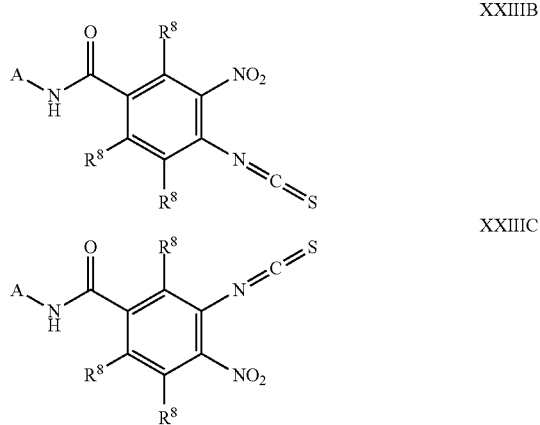

respectively, wherein $R^8$ and A are as hereinbefore defined, with a compound of formula X as hereinbefore defined, under standard reaction conditions, for example such as those hereinbefore described in respect of preparation of compounds of formula I (process step (iv) above).

Compounds of formulae III, IIIA, IIIB, IV, V, VI, VII, VIII, X, XI, XII, XIII, XIV, XV, XVII, XVIII, XIX, XXIIB, XXIIC, XXIII, XXIIIB, XXIIIC, XXIIIA, XXV, XXVI, XXVIA, XXVII and XXVIII are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991. The substituents $R^1$, $Q^2$, $Q^3$, $Q^{3a}$, $Q^4$, $R^6$, $R^8$ and A in final compounds of formula I or relevant intermediates may be modified one or more times, after or during the processes described above by way of methods that are well known to those skilled in the art. Examples of such methods include substitutions, reductions (e.g. of double bonds to single bonds by hydrogenation), oxidations, alkylations, acylations, hydrolyses, esterifications, etherifications and nitrations. The precursor groups can be changed to a different such group, or to the groups defined in formula I, at any time during the reaction sequence. In this respect, the skilled person may also refer to "*Comprehensive Organic Functional Group Transformations*" by A. R. Katritzky, O. Meth-Cohn and C. W. Rees, Pergamon Press, 1995. For example, in the case where $R^1$ or $R^2$ represents a halo group, such groups may be inter-converted one or more times, after or during the processes described above for the preparation of compounds of formula I. Appropriate reagents include NiCl$_2$ (for the conversion to a chloro group). Further, oxidations that may be mentioned include oxidations of sulfanyl groups to sulfoxide and sulfonyl groups, for example employing standard reagents (e.g. meta-chloroperbenzoic acid, KMnO$_4$ or a solution of Oxone® in ethylenediaminetetraacetic acid).

Other transformations that may be mentioned include the conversion of a halo group (preferably iodo or bromo) to a —CN or 1-alkynyl group (e.g. by reaction with a compound which is a source of cyano anions (e.g. sodium, potassium, copper (I) or zinc cyanide) or with a 1-alkyne, as appropriate). The latter reaction may be performed in the presence of a suitable coupling catalyst (e.g. a palladium and/or a copper based catalyst) and a suitable base (e.g. a tri-($C_{1-6}$ alkyl)amine such as triethylamine, tributylamine or ethyldiisopropylamine).

Further, amino groups and hydroxy groups may be introduced in accordance with standard conditions using reagents known to those skilled in the art.

Compounds of formula I may be isolated from their reaction mixtures using conventional techniques.

It will be appreciated by those skilled in the art that, in the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", 3$^{rd}$ edition, T. W. Greene & P. G. M. Wutz, Wiley-Interscience (1999).

Medical and Pharmaceutical Uses

Compounds of the invention are indicated as pharmaceuticals. According to a further aspect of the invention there is provided a compound of the invention, as hereinbefore defined but without the provisos for use as a pharmaceutical.

Although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention. By "prodrug of a compound of the invention", we include compounds that form a compound of the invention, in an experimentally-detectable amount, within a predetermined time (e.g. about 1 hour), following oral or parenteral administration. All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds (e.g. compounds of the invention) that possess pharmacological activity as such. Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds which possess pharmacological activity (e.g. similar or pronounced pharmacological activity as compared to the compounds of the invention from which they are formed).

Compounds of the invention are particularly useful because they may inhibit the activity of a member of the MAPEG family.

Compounds of the invention are particularly useful because they may inhibit (for example selectively) the activity of prostaglandin E synthases (and particularly microsomal prostaglandin E synthase-1 (mPGES-1)), i.e. they prevent the action of mPGES-1 or a complex of which the mPGES-1 enzyme forms a part, and/or may elicit a mPGES-1 modulating effect, for example as may be demonstrated in the test described below.

Compounds of the invention may thus be useful in the treatment of those conditions in which inhibition of a PGES, and particularly mPGES-1, is required.

Compounds of the invention are thus expected to be useful in the treatment of inflammation. Further, as the compounds of the invention may be of use as mPGES inhibitors (e.g. mPGES-1 inhibitors), they may also be useful in preventing or treating benign or malignant neoplasias (as they may reduce the production of PGE2).

Hence, the compounds of the invention may also be useful in treating cancers.

The term "inflammation" will be understood by those skilled in the art to include any condition characterised by a localised or a systemic protective response, which may be elicited by physical trauma, infection, chronic diseases, such as those mentioned hereinbefore, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow, invasion of the affected area by white blood cells, loss of function and/or any other symptoms known to be associated with inflammatory conditions.

The term "inflammation" will thus also be understood to include any inflammatory disease, disorder or condition per se, any condition that has an inflammatory component associated with it, and/or any condition characterised by inflammation as a symptom, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Where a condition has an inflammatory component associated with it, or a condition characterised by inflammation as a symptom, the skilled person will appreciate that compounds of the invention may be useful in the treatment of the inflammatory symptoms and/or the inflammation associated with the condition.

Accordingly, compounds of the invention may be useful in the treatment of asthma, chronic obstructive pulmonary disease, pulmonary fibrosis, inflammatory bowel disease, irritable bowel syndrome, inflammatory pain, fever, migraine, headache, low back pain, fibromyalgia, myofascial disorders, viral infections (e.g. influenza, common cold, herpes zoster, hepatitis C and AIDS), bacterial infections, fungal infections, dysmenorrhea, burns, surgical or dental procedures, malignancies (e.g. breast cancer, colon cancer, and prostate cancer), hyperprostaglandin E syndrome, classic Bartter syndrome, atherosclerosis, gout, arthritis, osteoarthritis, juvenile arthritis, rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, psoriasis, stroke, diabetes mellitus, neurodegenerative disorders such as Alzheimer's disease and multiple sclerosis, autoimmune diseases, allergic disorders, rhinitis, ulcers, coronary heart disease, sarcoidosis and any other disease with an inflammatory component.

Compounds of the invention may also have effects that are not linked to inflammatory mechanisms, such as in the reduction of bone loss in a subject. Conditions that may be mentioned in this regard include osteoporosis, osteoarthritis, Paget's disease and/or periodontal diseases. Compounds the invention may thus also be useful in increasing bone mineral density, as well as the reduction in incidence and/or healing of fractures, in subjects. Compounds of the invention are indicated both in the therapeutic and/or prophylactic treatment of the above-mentioned conditions.

According to a further aspect of the present invention, there is provided a method of treatment of a disease which is associated with, and/or which can be modulated by inhibition of, a member of the MAPEG family such as a PGES (e.g. mPGES-1), $LTC_4$ synthase and/or FLAP and/or a method of treatment of a disease in which inhibition of the activity of a member of the MAPEG family such as PGES (and particularly mPGES-1), $LTC_4$ synthase and/or FLAP is desired and/or required (e.g. inflammation), which method comprises administration of a therapeutically effective amount of a compound of the invention, as hereinbefore defined but without the provisos, to a patient suffering from, or susceptible to, such a condition.

"Patients" include mammalian (including human) patients.

The term "effective amount" refers to an amount of a compound, which confers a therapeutic effect on the treated patient. The effect may be objective (i.e. measurable by some test or marker) or subjective (i.e. the subject gives an indication of or feels an effect).

Compounds of the invention will normally be administered orally, intravenously, subcutaneously, buccally, rectally, dermally, nasally, tracheally, bronchially, sublingually, by any other parenteral route or via inhalation, in a pharmaceutically acceptable dosage form. Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like.

Such formulations may be prepared in accordance with standard and/or accepted pharmaceutical practice.

According to a further aspect of the invention there is thus provided a pharmaceutical formulation including a compound of the invention, as hereinbefore defined but without the provisos, in admixture with a pharmaceutically acceptable adjuvant, diluent or carrier. Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The invention further provides a process for the preparation of a pharmaceutical formulation, as hereinbefore defined, which process comprises bringing into association a compound of the invention, as hereinbefore defined but without the provisos, or a pharmaceutically acceptable salt thereof with a pharmaceutically-acceptable adjuvant, diluent or carrier. Compounds of the invention may also be combined with other therapeutic agents that are useful in the treatment of inflammation (e.g. NSAIDs and coxibs).

According to a further aspect of the invention, there is provided a combination product comprising:
(A) a compound of the invention, as hereinbefore defined but without the provisos; and
(B) another therapeutic agent that is useful in the treatment of inflammation, wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined but without the provisos, another therapeutic agent that is useful in the treatment of inflammation, and a pharmaceutically-acceptable adjuvant, diluent or carrier; and
(2) a kit of parts comprising components:
(a) a pharmaceutical formulation including a compound of the invention, as hereinbefore defined but without the provisos, in admixture with a pharmaceutically-acceptable adjuvant, diluent or carrier; and
(b) a pharmaceutical formulation including another therapeutic agent that is useful in the treatment of inflammation in admixture with a pharmaceutically-acceptable adjuvant, diluent or carrier,
which components (a) and (b) are each provided in a form that is suitable for administration in conjunction with the other.

The invention further provides a process for the preparation of a combination product as hereinbefore defined, which process comprises bringing into association a compound of the invention as hereinbefore defined but without the provisos with another therapeutic agent that is useful in the treatment of inflammation, and a pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Compounds of the invention may be administered at varying doses. Oral, pulmonary and topical dosages may range from between about 0.01 mg/kg of body weight per day (mg/kg/day) to about 100 mg/kg/day, preferably about 0.01 to about 100 mg/kg/day, and more preferably about 0.1 to about 25 mg/kg/day. For e.g. oral administration, the compositions typically contain between about 0.01 mg to about 5000 mg, and preferably between about 1 mg to about 2000 mg, of the active ingredient. Intravenously, the most preferred doses will range from about 0.001 to about 10 mg/kg/hour during constant rate infusion. Advantageously, compounds may be administered in a single daily dose, or the total daily dosage may be administered in divided doses of two, three or four times daily. In any event, the physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

Compounds of the invention may have the advantage that they are effective, and preferably selective, inhibitors of a member of MAPEG family, e.g. inhibitors of prostaglandin E synthases (PGES) and particularly microsomal prostaglandin E synthase-1 (mPGES-1). The compounds of the invention may reduce the formation of the specific arachidonic acid metabolite $PGE_2$ without reducing the formation of other COX generated arachidonic acid metabolites, and thus may not give rise to the associated side-effects mentioned hereinbefore.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

Biological Test

Microsomes from Rosetta *E. coli* bacteria expressing recombinant human mPGES-1 is dissolved in 0.1 M $KP_i$ pH 7.4 buffer containing 2.5 mM GSH. 50 µl of the enzyme is subsequently dispensed in a 384-well plate. 0.5 µl of the inhibitor dissolved in DMSO at is thereafter added to each well and incubated for 25 minutes at room temperature. Subsequently, 2 µl of PGH2 dissolved in an appropriate solvent is added to each well and after one minute the acidified stop solution containing $FeCl_2$ is added. 4 µl of the total volume is transferred to a separate plate and diluted 750-fold in two separate steps before HTRF detection of PGE2.

The HTRf detection is performed by the use of a commercially available kit from CisBio essentially according to the manufacturer's protocol. Briefly, 10 µl of the diluted sample is transferred to a white 384-well plate. 5 µl of d2 and 5 µl Eu3+-Cryptate labeled anti-$PGE_2$ is added to each well containing samples by the use of a Multidrop. The plate is covered with a plastic self-adhesive film, centrifuged at 1200 rpm for 1 minute and subsequently stored at +4° C. over night.

After over night incubation the fluorescence is measured by the use of an appropriate microplate reader. The fluorescence of europium cryptate, and d2 are measured using the following excitation and emission wavelength, europium cryptate: $\lambda_{max}^{ex}=307$ nm, $\lambda_{max}^{em}=620$ nm and d2: $\lambda_{max}^{ex}=620$ nm, $\lambda_{max}^{em}=665$ nm), respectively. The extent of the specific FRET is measured as a ratio of the emission intensity at 665 nm vs. that at 620 nm. A standard curve using synthetic PGE2 is used to quantify the amount of PGE2 in unknown samples.

EXAMPLES

Unless otherwise stated, one or more tautomeric forms of compounds of the examples described hereinafter may be prepared in situ and/or isolated. All tautomeric forms of compounds of the examples described hereinafter should be considered to be disclosed. The invention is illustrated by way of the following examples, in which the following abbreviations may be employed:
AIBN Azo-bis-isobutyronitrile
aq. aquaeous solution
Boc tert.-butoxycarbonyl
DIC diisopropyl-carbodiimide
DIPEA N-ethyl-diisopropylamine
DMSO dimethylsulphoxide
DMF N,N-dimethylformamide
sat. saturated
h hour(s)
HATU O-(7-azabenzotriazol-1-yl)-N,N,N',N'-tetramethyluronium-hexafluorophosphate
HBTU O-Benzotriazole-1-yl-N,N,N',N'-tetramethyluronium-hexafluorophosphate
DPPA Diphenylphosphoryl azide
HPLC high performance liquid chromatography
i.vac. in vacuo
conc. concentrated
KHMDS potassium hexamethyl disilazide
min minute(s)
MS mass spectrometry
NBS N-bromo-succinimide
NMM N-methyl-morpholine
NMP N-methyl-pyrrolidin-2-one
o ortho
PfTU O-pentafluorophenyl-N,N,N',N'-tetramethyluronium-hexafluorophosphate
PPA propanephosphonic acid cycloanhydride
quant. quantitative
$R_f$ retention factor
$R_t$ retention time
mp melting point
rac. Racemic
M mol/L
TBME tert.-butyl-methyl-ether
TBTU O-(benzotriazol-1-yl)-N,N,N',N'-tetramethyluronium tetrafluoroborate
TEA triethylamine
TFA trifluoroacetic acid
THF tetrahydrofuran
tert. tertiary
TLC Thin layer chromatography
Σ yield over all the steps carried out analogously as described
KHCO$_3$ potassium-hydrogen-carbonate
K$_2$CO$_3$ potassium carbonate
Na$_2$SO$_4$ sodium sulfate
NaOH sodium hydroxide
HCl hydrochloric acid
DCC N,N-Dicyclohexylcarbodiimide
DIBAL-H Diisobutylaluminium hydride
DMAP 4-Dimethylaminopyridine
EDC 3-(3-Dimethylaminopropyl)-1-ethyl-carbodiimide
EDCI 3-(3-Dimethylaminopropyl)-1-ethyl-carbodiimide hydrochloride The HPLC/MS data, where specified, were obtained under the following conditions:
Agilent 1100 with quarternary pump, Gilson G215 Autosampler, HP diode array detector.
The following was used as the mobile phase:
E1: water with 0.15% formic acid
E2: acetonitrile
E3: water with 0.1% acetic acid
Eluent Gradient A (Polar):

| time in min | % E1 | % E2 | flow rate in mL/min |
|---|---|---|---|
| 0.0 | 95 | 5 | 1.6 |
| 4.00 | 50 | 50 | 1.6 |
| 4.50 | 10 | 90 | 1.6 |
| 5.00 | 10 | 90 | 1.6 |
| 5.50 | 90 | 10 | 1.6 |

Eluent Gradient B (Standard):

| time in min | % E1 | % E2 | flow rate in mL/min |
|---|---|---|---|
| 0.0 | 95 | 5 | 1.6 |
| 4.50 | 10 | 90 | 1.6 |
| 5.00 | 10 | 90 | 1.6 |
| 5.50 | 90 | 10 | 1.6 |

Eluent Gradient C (Unpolar):

| time in min | % E1 | % E2 | flow rate in mL/min |
|---|---|---|---|
| 0.0 | 95 | 5 | 1.6 |
| 2.00 | 10 | 90 | 1.6 |
| 5.00 | 10 | 90 | 1.6 |
| 5.50 | 90 | 10 | 1.6 |

Eluent Gradient D (Ultrakurz-Polar):

| time in min | % E1 | % E2 | flow rate in mL/min |
|---|---|---|---|
| 0.0 | 95 | 5 | 1.6 |
| 2.00 | 50 | 50 | 1.6 |
| 2.25 | 10 | 90 | 1.6 |
| 2.5 | 10 | 90 | 1.6 |
| 2.75 | 95 | 5 | 1.6 |

Eluent Gradient E (Ultrakurz-Standard):

| time in min | % E1 | % E2 | flow rate in mL/min |
|---|---|---|---|
| 0.0 | 95 | 5 | 1.6 |
| 2.25 | 10 | 90 | 1.6 |
| 2.5 | 10 | 90 | 1.6 |
| 2.75 | 95 | 5 | 1.6 |

Eluent Gradient F (Ultakurz-Unpolar):

| time in min | % E1 | % E2 | flow rate in mL/min |
|---|---|---|---|
| 0.0 | 95 | 5 | 1.6 |
| 1.00 | 10 | 90 | 1.6 |

-continued

| time in min | % E1 | % E2 | flow rate in mL/min |
| --- | --- | --- | --- |
| 2.5 | 10 | 90 | 1.6 |
| 2.75 | 95 | 5 | 1.6 |

Eluent Gradient G:

| time in min | % E3 | % E2 | flow rate in mL/min |
| --- | --- | --- | --- |
| 0.0 | 95 | 5 | 3 |
| 0.3 | 95 | 5 | 3 |
| 2 | 2 | 98 | 3 |
| 2.4 | 2 | 98 | 3 |
| 2.45 | 95 | 5 | 3 |
| 2.8 | 95 | 5 | 3 |

The following was used as the stationary phase: (column temperature: constant at 25° C.)
1: Zorbax StableBond C18, 3.5 µm, 4.6×75 mm
2: Waters Symmetry C18, 3.5 µm, 4.6×75 mm
3: Zorbax Bonus-RP C18, 3.5 µm, 4.6×75 mm
4: YMC-Pack ODS-AQ, 3 µm, 4.6×75 mm
5: XBridge O18, 3.5 µm, 4.6×75 mm
7: Zobrax Stable Bond C18, 1.8 µm, 3.0×30 mm
8: Sunfire C18, 2.5 µm, 3.0×30 mm
9: Xbridge C1, 2.5 µm, 3.0×30 mm
12: Zorbax Stable Bond O18, 3.5 µm, 4.6×75 mm The following was used as the stationary phase: (column temperature: constant at 20° C.)
10: Interchim Strategy C18, 5 µm, 4.6×50 mm
11: XRS C18, 5 µm, 4.6×50 mm The method is abbreviated using the above descriptions (eg. A1 for Eluent gradient A with stationary phase 1).

The diode array detection took place in a wavelength range from 210-550 nm

Range of mass-spectrometric detection: m/z 120 to m/z 1000

Alternatively, the following method was used, abbreviated CC:
HP1100 HPLC+DAD (Wavelength range: 210 nm to 500 nm), and Gilson 215 Autosampler
RP-HPLC MS analyses were performed on a Waters ZQ2000 mass spectrometer.

The following was used as the mobile phase:
E1: water with 0.1% trifluoracetic acid
E2: acetonitrile with 0.1% trifluoracetic acid
Eluent Gradient:

| time in min | % E1 | % E2 | flow rate in mL/min |
| --- | --- | --- | --- |
| 0.0 | 95 | 5 | 1.5 |
| 2.00 | 0 | 100 | 1.5 |
| 2.50 | 0 | 100 | 1.5 |
| 2.60 | 95 | 5 | 1.5 |

The following was used as the stationary phase:
Sunfire C18 4.6×50 mm, 3.5 µm (column temperature: constant at 40° C.)
The diode array detection took place in a wavelength range from 210-500 nm
Range of mass-spectrometric detection: m/z 120 to m/z 820.

Alternatively, the following method was used, abbreviated EX1:
Column: Atlantis dC18 5 mm, 2.1×50 mm.
Mobile phase: 10-95% MeCN in 0.01% TFA.
Flow rate: 0.2 mL/min.
Detection: UV 254 nm.

Alternatively, the following method was used, abbreviated EX2:
Column: Acquity HPLC BEH SHIELD RP18 1.7 mm, 2.1× 100 mm.
Mobile phase: 5-100% MeCN in 0.1% HCOOH.
Flow rate: 0.2 mL/min.
Detection: UV 254 nm/211 nm.

The following compounds are accompanied by structural drawings. The skilled person will appreciate that the rules of valency must be adhered to and hence there must be a certain number of bonds attached to each atom, which may not necessarily be depicted on the drawings. For example, in the case where a nitrogen heteroatom is depicted with only one or two bonds attached to it, the skilled person will realise that it should be attached to an additional one or two bonds (a total of three), in which such bonds are normally attached to one or two hydrogen atoms (so forming a —$NH_2$ or —N(H)— moiety).

Example 1

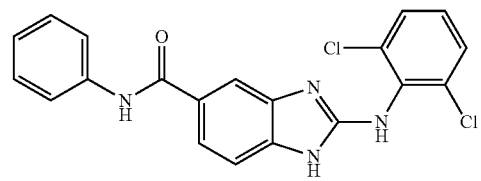 [SMILES: O=C(Nc1ccccc1)c1ccc2[nH]c(Nc3c(Cl)cccc3Cl)nc2c1]

2-(2,6-Dichloro-phenylamino)-1H-benzimidazole-5-carboxylic acid phenylamide (1a) 3,4-Dinitro-N-phenyl-benzamide A mixture of 3,4-dinitro-benzoylchloride (24 g, 93.7 mmol) in 80 mL THF was added to a stirred mixture of aniline (10.4 mL, 112 mmol) and TEA (15.6 mL, 112 mmol) in 300 mL THF under nitrogen. After stirring for 5 days, the mixture was filtrated, washed with THF and evaporated to dryness. The residue was taken up in diethyl ether, filtrated and dried at 55° C.

The residue is further reacted directly without any further purification.
Yield: 26.1 g (73%) slightly contaminated
$R_t$ value: 2.76 min (C2)
$C_{13}H_9N_3O_5$ (287.23)
Mass spectrum: (M−H)=286
$R_f$ value: 0.28 (silica gel; petrol ether/ethyl acetate=8:2)

(1b) 3,4-Diamino-N-phenyl-benzamide

A mixture of the product obtained at (1a) (19.0 g, 46.3 mmol) in 200 mL of THF was combined with 10% palladium on charcoal (3.0 g) and hydrogenated in a Parr apparatus at ambient temperature for 20 h at 3.5 bar hydrogen pressure. Then the mixture is filtered and the filtrate is concentrated i.vac. The residue is purified by chromatography on silica gel (eluent gradient: dichloromethane/(methanol/conc. ammonia=95:5)=100:0->92:8).

Yield: 3.60 g (31%) slightly contaminated
$R_t$ value: 2.48 min (A4)
$C_{13}H_{13}N_3O$ (227.26)
Mass spectrum: (M+H)$^+$=228

(1c) 2-(2,6-Dichloro-phenylamino)-1H-benzimidazole-5-carboxylic acid phenyl-amide A mixture of the product obtained at (1b) (250 mg, 0.99 mmol) in 5.0 mL of THF was combined with 1,3-dichloro-2-isothiocyanato-benzene (222 mg, 1.09 mmol) and stirred for 5 h at ambient temperature under nitrogen. DIC (166 μL, 1.04 mmol) was added and the stirred mixture was heated to 55° C. for 16 h. The mixture was filtrated and concentrated i.vac., the residue purified by HPLC (Symmetry C18, 7 μM, eluent gradient: (H$_2$O+0.15% HCOOH)/acetonitrile=95:5->5:95).

Yield: 80 mg (20%)
$R_t$ value: 1.93 min (C2)
$C_{20}H_{14}Cl_2N_4O$ (397.26)
$R_f$ value: 0.59 (silica gel; dichloromethane/ethanol=9:1+0.5% conc. ammonia)

In analogy with the above described example, the following compounds were prepared:

| No. | Structural formula Name | Yield | Mass peak(s) | $R_f$-value or $R_t$ |
|---|---|---|---|---|
| 6 | 2-(2-Trifluoromethyl-phenylamino)-1H-benzimidazole-5-carboxylic acid-phenylamide | Σ: 8.1% | (M + H)$^+$ = 397 | 1.95 min (C2) |
| 7 | 2-(2,5-Dichloro-phenylamino)-1H-benzimidazole-5-carboxylic acid-phenylamide | Σ: 2.7% | (M + H)$^+$ = 397/399/401 (chlorine isotopes) | 3.03 min (B2) |
| 9 | 2-(2-Chloro-phenylamino)-1H-benzimidazole-5-carboxylic acid-phenylamide | Σ: 2.9% | (M + H)$^+$ = 363/365 (chlorine isotope) | 2.31 min (B2) |
| 10 | 2-(o-Tolyl-amino)-1H-benzimidazole-5-carboxylic acid-phenylamide | Σ: 7.7% | (M + H)$^+$ = 343 | 1.85 min (C2) |
| 11 | 2-(2-Methoxy-phenylamino)-1H-benzimidazole-5-carboxylic acid-phenylamide | Σ: 5.0% | (M + H)$^+$ = 359 | 1.87 min (C2) |

| Structural formula No. Name | Yield | Mass peak(s) | $R_f$ value or $R_t$ |
|---|---|---|---|
| 12 ![structure 12] 2-(2-Chloro-6-methyl-phenylamino)-1H-benzimidazole-5-carboxylic acid-phenylamide | Σ: 6.3% | $(M + H)^+ =$ 377/379 (chlorine isotope) | 1.88 min (B2) |
| 19 ![structure 19] 2-(2-Chloro-6-fluoro-phenylamino)-1H-benzimidazole-5-carboxylic acid-phenylamide | Σ: 3.6% | $(M + H)^+ =$ 381/383 (chlorine isotope) | 0.42 (silica gel, dichloromethane/ ethanol = 9:1 + 0.5% conc. ammonia) |

Example 3

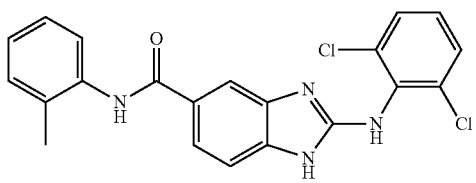 [SMILES: Cc1ccccc1NC(=O)c1ccc2[nH]c(Nc3c(Cl)cccc3Cl)nc2c1]

2-(2,6-Dichloro-phenylamino)-1H-benzimidazole-5-carboxylic acid o-tolylamide (3a) 2-(2,6-Dichloro-phenylamino)-1H-benzimidazole-5-carboxylic acid ethyl ester Prepared analogously to example 1c from 3,4-diaminobenzoic acid ethyl ester and 1,3-dichloro-2-thioisocyanato-benzene with DIC in DMF.
Yield: 63% slightly contaminated
$C_{16}H_{13}Cl_2N_3O_2$ (350.20)

(3b) 2-(2,6-Dichloro-phenylamino)-1H-benzimidazole-5-carboxylic acid

A mixture of the product obtained at (3a) (4.91 g, 12.6 mmol) in 30 mL of ethanol with 5N aqueous NaOH (10 mL, 50 mmol) was stirred at ambient temperature for 16 h, then heated to reflux for 1 h. The mixture was concentrated i.vac., poured into water at 0° C. and acidified to pH 2-3 using formic acid. The formed solid was filtered off, washed with little water and diethyl ether and dried i.vac.
Yield: 3.11 g (77%)
$C_{14}H_9Cl_2N_3O_2$ (322.15)
Mass spectrum: $(M+H)^+=322/324/326$ (chlorine isotopes)

(3c) 2-(2,6-Dichloro-phenylamino)-1H-benzimidazole-5-carboxylic acid N-methyl-phenylamide A mixture of the product obtained at (3b) (322 mg, 1.00 mmol) in 3.0 mL of DMF with TEA (550 μL, 4.0 mmol) and TBTU (328 mg, 1.02 mmol) was combined with 2-Methylaniline (107 μL, 1.00 mmol) and stirred for 3 days at ambient temperature. 2.0 mL of formic acid were added, the mixture was concentrated i.vac. and the residue purified by HPLC (Symmetry C18, 7 μM, eluent gradient: ($H_2O$+0.15% HCOOH)/acetonitrile=95:5->5:95).
Yield: 140 mg (34%)
$R_t$ value: 2.62 min (B2)
$C_{21}H_{16}Cl_2N_4O$ (411.28)
Mass spectrum: $(M+H)^+=411/413/415$ (chlorine isotopes)
In analogy with the above described example, the following compounds were prepared:

| Structural formula No. Name | Yield | Mass peak(s) | $R_f$ value or $R_t$ |
|---|---|---|---|
| 4 ![structure 4] 2-(2,6-Dichloro-phenylamino)-1H-benzimidazole-5-carboxylic acid m-tolylamide | Σ: 24% | $(M + H)^+ =$ 411/413/415 (chlorine isotopes) | 2.85 min (B2) |

-continued

| No. | Structural formula Name | Yield | Mass peak(s) | $R_f$ value or $R_t$ |
|---|---|---|---|---|
| 5 | 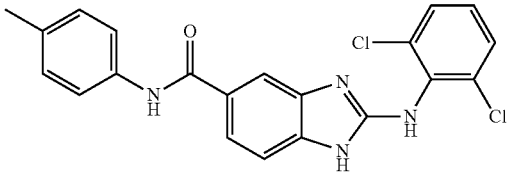 [SMILES: Cc1ccc(NC(=O)c2ccc3[nH]c(Nc4c(Cl)cccc4Cl)nc3c2)cc1]<br>2-(2,6-Dichloro-phenylamino)-1H-benzimidazole-5-carboxylic acid p-tolylamide | Σ: 25% | (M + H)⁺ = 411/413/415 (chlorine isotopes) | 2.83 min (B2) |
| 13 | 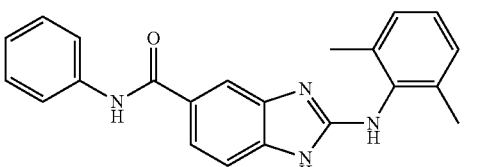<br>2-(2,6-Dimethyl-phenylamino)-1H-benzimidazole-5-carboxylic acid-phenylamide | Σ: 32% | (M + H)⁺ = 357 | 2.56 min (B2) |
| 20 | 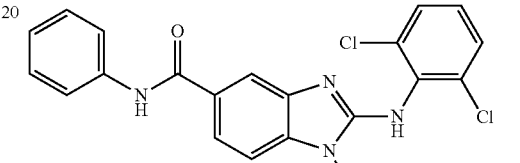<br>2-(2,6-Dichloro-phenylamino)-1-methyl-1H-benzimidazole-5-carboxylic acid phenylamide | Σ: 34% | (M + H)⁺ = 411/413/415 (chlorine isotopes) | 2.72 min (B2) |
| 51 | 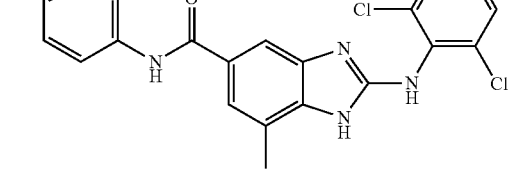<br>2-(2,6-Dichloro-phenylamino)-7-methyl-1H-benzimidazole-5-carboxylic acid (4-bromo-phenyl)-amide | Σ: 11.2% | (M + H)⁺ = 489/491/ 493/495 (chlorine and bromine isotopes) | 2.48 min (C1) |
| 52 | 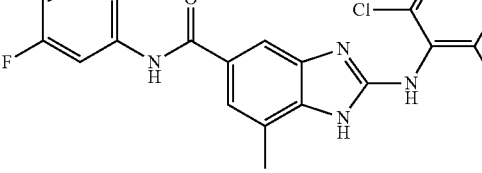<br>2-(2,6-Dichloro-phenylamino)-7-methyl-1H-benzimidazole-5-carboxylic acid (4-chloro-3-fluoro-phenyl)-amide | Σ: 8.4% | (M + H)⁺ = 463/465/ 467/469 (chlorine isotopes) | 2.37 min (C1) |
| 64 | 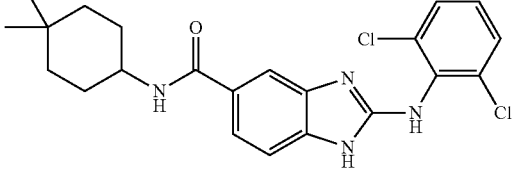<br>2-(2,6-Dichloro-phenylamino)-1H-benzimidazole-5-carboxylic acid (4,4-dimethyl-cyclohexyl)-amide | Σ: 35% | (M + H)⁺ = 431/433/435 (chlorine isotopes) | 3.29 min (B6) |
| 66 | 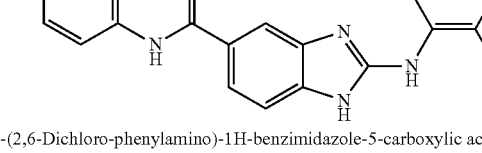<br>2-(2,6-Dichloro-phenylamino)-1H-benzimidazole-5-carboxylic acid (4-bromo-phenyl)-amide | Σ: 20% | (M + H)⁺ = 475/477/ 479/481 (bromine and chlorine isotopes) | 2.07 min (C2) |

| No. | Structural formula Name | Yield | Mass peak(s) | $R_f$ value or $R_t$ |
|---|---|---|---|---|
| 67 | 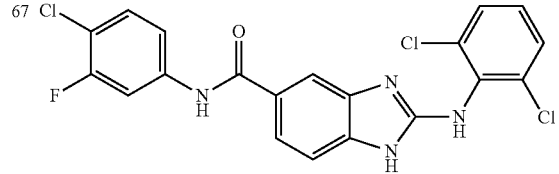<br>2-(2,6-Dichloro-phenylamino)-1H-benzimidazole-5-carboxylic acid (4-chloro-3-fluoro-phenyl)-amide | Σ: 7.3% | (M + H)⁺ = 449/451/ 453/455 (chlorine isotopes) | 2.11 min (C2) |
| 68 | 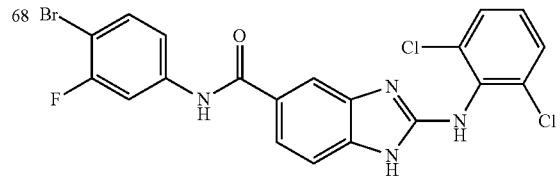<br>2-(2,6-Dichloro-phenylamino)-1H-benzimidazole-5-carboxylic acid (4-bromo-3-fluoro-phenyl)-amide | Σ: 10.2% | (M + H)⁺ = 493/495/ 497/499 (bromine and chlorine isotopes) | 2.14 min (C2) |
| 69 | 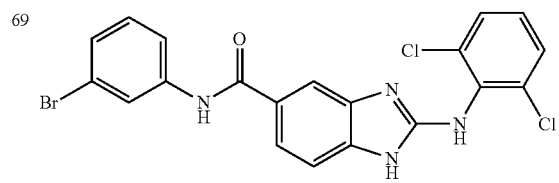<br>2-(2,6-Dichloro-phenylamino)-1H-benzimidazole-5-carboxylic acid (3-bromo-phenyl)-amide | Σ: 12.1% | (M + H)⁺ = 475/477/ 479/481 (bromine and chlorine isotopes) | 2.08 in (C2) |
| 70 | 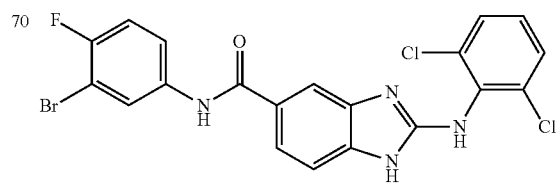<br>2-(2,6-Dichloro-phenylamino)-1H-benzimidazole-5-carboxylic acid (3-bromo-4-fluoro-phenyl)-amide | Σ: 12.1% | (M + H)⁺ = 493/495/ 497/499 (bromine and chlorine isotopes) | 2.09 min (C2) |
| 71 | 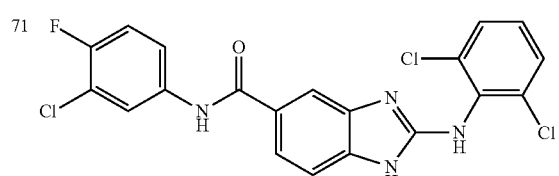<br>2-(2,6-Dichloro-phenylamino)-1H-benzimidazole-5-carboxylic acid (3-chloro-4-fluoro-phenyl)-amide | Σ: 19.9% | (M + H)⁺ = 449/451/ 453/455 (chlorine isotopes) | 2.09 min (C2) |
| 84 | 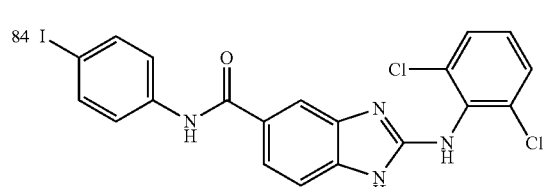<br>2-(2,6-Dichloro-phenylamino)-1H-benzimidazole-5-carboxylic acid (4-iodo-phenyl)-amide | Σ: 5.3% | (M + H)⁺ = 523/535/527 (chlorine isotopes) | 3.40 min (B6) |
| 420 | 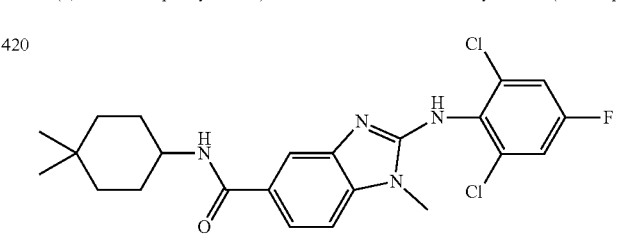<br>2-(2,6-Dichloro-4-fluorophenylamino)-N-(4,4-dimethylcyclohexyl)-1-methyl-1H-benzimidazole-5-carboxamide | Σ: 47% | (M + H)⁺ = 463/465/467 (chlorine isotopes) | 3.90 min (B1) |

| No. | Structural formula Name | Yield | Mass peak(s) | $R_f$ value or $R_t$ |
|---|---|---|---|---|
| 426 | 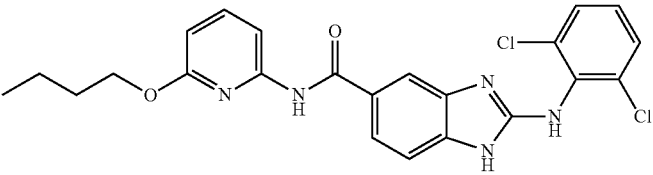 [SMILES: CCCCOc1cccc(NC(=O)c2ccc3[nH]c(Nc4c(Cl)cccc4Cl)nc3c2)n1]<br>N-(6-Butoxypyridin-2-yl)-2-(2,6-dichlorophenylamino)-1H-benzimidazole-5-carboxamide | Σ: 13% | (M + H)$^+$ = 470/472/474 (chlorine isotopes) | 0.3 (silica gel, petrolether/ ethylacetate = 1:1) |
| 571 | 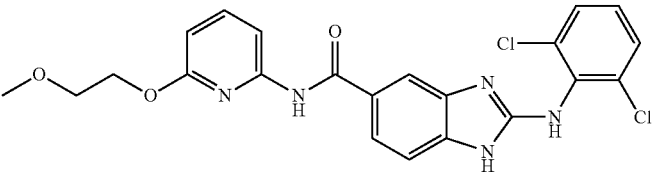 [SMILES: COCCOc1cccc(NC(=O)c2ccc3[nH]c(Nc4c(Cl)cccc4Cl)nc3c2)n1]<br>2-(2,6-Dichlorophenylamino)-N-(6-(2-methoxyethoxy)pyridin-2-yl)-1H-benzimidazole-5-carboxamide | Σ: 40% | (M + H)$^+$ = 472/474/476 (chlorine isotopes) | 0.34 (silica gel, dichloromethane/ methanol = 25:1) |
| 578 | 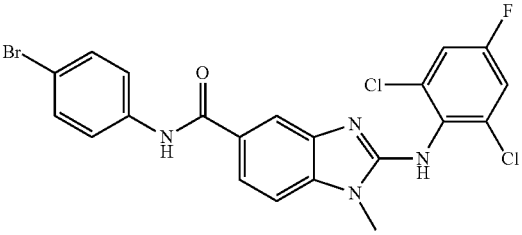 [SMILES: Cn1c(Nc2c(Cl)cc(F)cc2Cl)nc2cc(C(=O)Nc3ccc(Br)cc3)ccc21]<br>2-(2,6-Dichloro-4-fluoro-phenylamino)-N-(4-bromo-phenyl)-1-methyl-1H-benzimidazole-5-carboxamide | Σ: 31% | (M + H)$^+$ = 507/509/ 511/513 (bromine and chlorine isotopes) | 2.68 min (C3) |
| 596 | 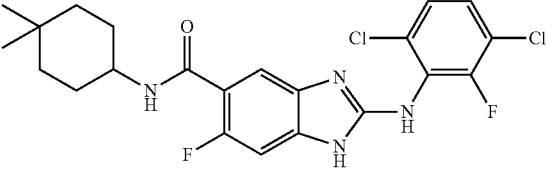 [SMILES: CC1(C)CCC(NC(=O)c2cc3nc(Nc4c(Cl)ccc(Cl)c4F)[nH]c3cc2F)CC1]<br>2-(3,6-Dichloro-2-fluoro-phenylamino)-N-(4,4-dimethyl-cyclohex-1-yl)-6-fluoro-1H-benzimidazole-5-carboxamide | Σ: 26% | (M + H)$^+$ = 467/469/471 (chlorine isotopes) | 1.40 min (F7) |
| 597 | 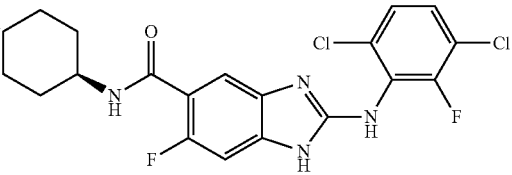<br>2-(3,6-Dichloro-2-fluoro-phenylamino)-N-(trans-4-trifluoromethyl-cyclohex-1-yl)-6-fluoro-1H-benzimidazole-5-carboxamide | Σ: 53% | (M + H)$^+$ = 507/509/511 (chlorine isotopes) | 1.36 min (F7) |
| 598 | 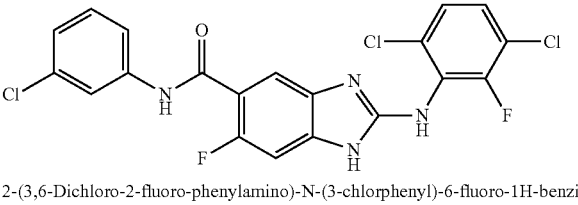<br>2-(3,6-Dichloro-2-fluoro-phenylamino)-N-(3-chlorphenyl)-6-fluoro-1H-benzimidazole-5-carboxamide | Σ: 3.8% | (M + H)$^+$ = 467/469/ 471/473 (chlorine isotopes) | 1.38 min (F7) |
| 608 | 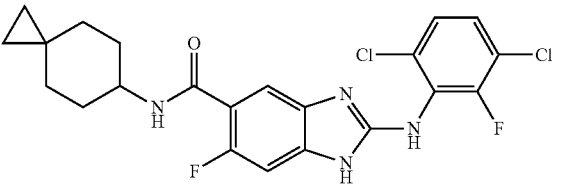 [SMILES: O=C(NC1CCC2(CC1)CC2)c1cc2nc(Nc3c(Cl)ccc(Cl)c3F)[nH]c2cc1F]<br>2-(3,6-Dichloro-2-fluoro-phenylamino)-N-(spiro[2.5]oct-6-yl)-6-fluoro-1H-benzimidazole-5-carboxamide | Σ: 18% | (M + H)$^+$ = 465/467/469 (chlorine isotopes) | 1.36 min (F7) |

-continued

| No. | Structural formula Name | Yield | Mass peak(s) | $R_f$-value or $R_t$ |
|---|---|---|---|---|
| 649 | 2-(6-Chloro-2-fluoro-3-methyl-phenylamino)-N-cyclohexyl-6-fluoro-1H-benzimidazole-5-carboxamide | Σ: 11.2% | $(M + H)^+ =$ 419/421 (chlorine isotopes) | 2.90 min (C5) |
| 653 | 2-(6-Chloro-2-fluoro-3-methyl-phenylamino)-N-(trans-4-trifluoromethyl-cyclohex-1-yl)-6-fluoro-1H-benzimidazole-5-carboxamide | Σ: 22% | $(M + H)^+ =$ 487/489 (chlorine isotopes) | 2.93 min (C4) |

Example 22

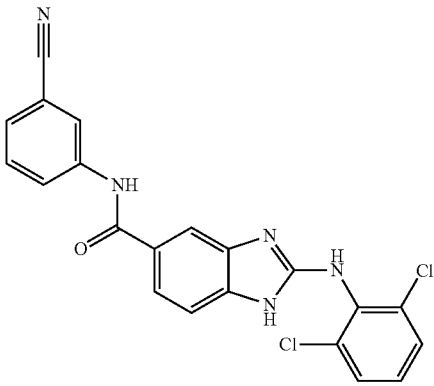 [SMILES: N#Cc1cccc(NC(=O)c2ccc3[nH]c(Nc4c(Cl)cccc4Cl)nc3c2)c1]

2-(2,6-Dichloro-phenylamino)-1H-benzimidazole-5-carboxylic acid (3-cyano-phenyl)-amide (22a) 2-(2,6-Dichloro-phenylamino)-1H-benzimidazole-5-carboxylic acid To 3,4-diamino-benzoic acid ethyl ester (4.0 g, 22.2 mmol) in 100 mL dichloromethane was added 1,3-dichloro-2-isothiocyanato-benzene (4.5 g, 22 mmol) in 50 mL dichloromethane. After stirring overnight and refluxing for another 6 hrs, the solvent was evaporated. After adding 200 mL dichloromethane, triethylamine (7 mL, 50 mmol) and 4-dimethylaminopyridine (100 mg, 0.82 mmol) have been added, methanesulfonyl chloride (1.7 mL, 22 mmol) in 50 mL dichloromethane was added to the reaction mixture. After stirring for 2 h, another portion of methanesulfonyl chloride (1.7 mL, 22 mmol) was added. After stirring at room temperature overnight, the solvent was evaporated. The residue was mixed with 150 mL methanol and 40 mL 4N NaOH (aq), stirred over night, another 20 mL 4N NaOH (aq) added and refluxed for 2 h. The solvent was removed, the residue mixed with water and methanol and the mixture neutralized with 4 N HCl (aq). The mixture was filtered, washed with water and dried.

Yield 5.2 g (73%).
$C_{14}H_9Cl_2N_3O_2$ (322.15)
Mass spectroscopy: $[M+H]^+=322/324/326$ (22b) 2-(2,6-Dichloro-phenylamino)-1H-benzimidazole-5-carboxylic acid (3-cyano-phenyl)-amide To 2-(2,6-dichloro-phenylamino)-1H-benzimidazole-5-carboxylic acid (32 mg, 0.1 mmol) in DMF TEA (50 µL, 0.36 mmol) and TBTU (32.1 mg, 0.1 mmol) were added, followed by 3-amino-benzonitrile (11.8 mg, 0.1 mmol). After shaking overnight at room temperature, the solvent was removed i.vac. and the residue purified by preparative reverse phase chromatography (gradient $H_2O/AcCN=90:10$ to 35:65; both solvents containing 0.1% TFA).
$C_{21}H_{13}Cl_2N_5O$ (422.28)
Mass spectroscopy: $[M+H]^+=422/424/426$

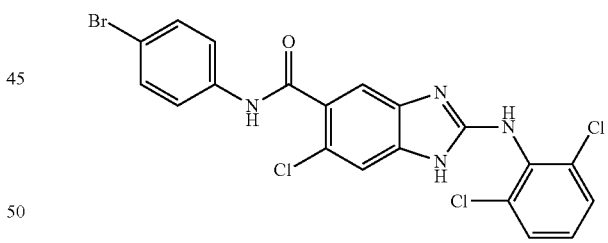

2-(2,6-Dichloro-phenylamino)-6-chloro-1H-benzimidazole-5-carboxylic acid (4-bromo-phenyl)-amide (53a) 4-Amino-2-chloro-5-nitro-benzoyl chloride A mixture of 4-amino-2-chloro-5-nitro-benzoic acid (2.60 g, 12.0 mmol) in 200 mL dichloromethane with 20 mL thionyl chloride was refluxed for 4 h, cooled to ambient temperature, filtrated and concentrated to dryness i.vac. The residue was further reacted without further purification.
Yield: 2.70 g (96%)
$C_7H_4Cl_2N_2O_3$ (235.02)

(53b) 4-Amino-2-chloro-5-nitro-benzoic acid (4-bromo-phenyl)-amide

Prepared analogously to example 1a from the product obtained in 53a and 4-bromo-aniline using TEA in THF.

Yield: 95%

$R_f$ value: 0.30 (silica gel; dichloromethane/methanol=50:1)

$C_{13}H_9BrClN_3O_3$ (370.59)

Mass spectrum: $(m-H)^-$=368/370/372 (bromine and chlorine isotopes)

(53c) 4,5-Diamino-2-chloro-benzoic acid (4-bromo-phenyl)-amide

Prepared analogously to example 14b by hydrogenation of the product obtained in 53b using Raney nickel in THF.

Yield: 97%

$R_f$ value: 0.20 (silica gel; dichloromethane/methanol=19:1)

$C_{13}H_{11}BrClN_3O$ (340.60)

(53d) 2-(2,6-Dichloro-phenylamino)-6-chloro-1H-benzimidazole-5-carboxylic acid (4-bromo-phenyl)-amide Prepared analogously to example 1c from the product obtained in 53c with 1,3-dichloro-2-isocyanato-benzene and DIC in ACN under reflux.

Yield: 53%

$R_f$ value: 0.21 (silica gel; dichloromethane/methanol=19:1)

$C_{20}H_{12}BrCl_3N_4O$ (510.60)

Mass spectrum: $(M+H)^+$=509/511/513/515 (bromine and chlorine isotopes)

In analogy with the above described example, the following compounds were prepared:

| No. | Structural formula / Name | Yield | Mass peak(s) | $R_f$ value or $R_t$ |
|---|---|---|---|---|
| 54 | 2-(2,6-Dichloro-phenylamino)-6-chloro-1H-benzimidazol-5-carboxylic acid (4-bromo-3-fluoro-phenyl)-amide | Σ: 15.0% | $(M+H)^+$ = 527/529/531/533/535 (chlorine and bromine isotopes) | 0.11 (silica gel, dichloromethane/methanol = 19:1) |
| 55 | 2-(2,6-Dichloro-phenylamino)-6-chloro-1H-benzimidazol-5-carboxylic acid (4-chloro-3-fluoro-phenyl)-amide | Σ: 14.3% | $(M+H)^+$ = 483/485/487/489 (chlorine isotopes) | 0.23 (silica gel, dichloromethane/methanol = 19:1) |
| 56 | 2-(2,6-Dichloro-phenylamino)-6-chloro-1H-benzimidazol-5-carboxylic acid (3-chloro-phenyl)-amide | Σ: 33% | $(M+H)^+$ = 465/467/469/471 (chlorine isotopes) | 0.12 (silica gel, dichloromethane/methanol = 19:1) |
| 57 | 2-(2,6-Dichloro-phenylamino)-6-chloro-1H-benzimidazol-5-carboxylic acid (4-iodo-phenyl)-amide | Σ: 17.2% | $(M+H)^+$ = 557/559/561/563 (chlorine isotopes) | 0.10 (silica gel, dichloromethane/methanol = 19:1) |

-continued

| No. | Structural formula Name | Yield | Mass peak(s) | $R_f$ value or $R_t$ |
|---|---|---|---|---|
| 58 | 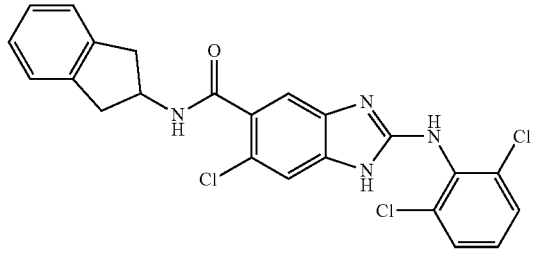 [SMILES: O=C(NC1Cc2ccccc2C1)c1cc2nc(Nc3c(Cl)cccc3Cl)[nH]c2cc1Cl]<br>2-(2,6-Dichloro-phenylamino)-6-chloro-1H-benzimidazol-5-carboxylic acid indan-2-yl-amide | Σ: 15.2% | $(M + H)^+ =$ 471/473/ 475/477 (chlorine isotopes) | 0.25 (silica gel, dichloromethane/ methanol = 19:1) |
| 89 | 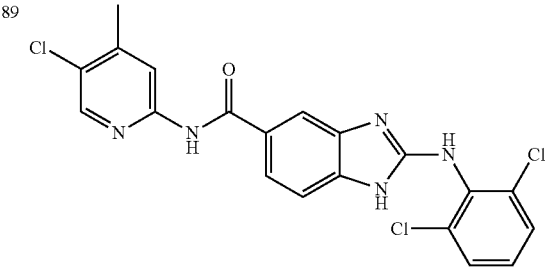<br>2-(2,6-Dichloro-phenylamino)-1H-benzimidazol-5-carboxylic acid (5-chloro-4-methyl-pyridin-2-yl)-amide | Σ: 13.1% | $(M + H)^+ =$ 446/448/ 450/452 (chlorine isotopes) | 2.08 min (C2) |
| 121 | 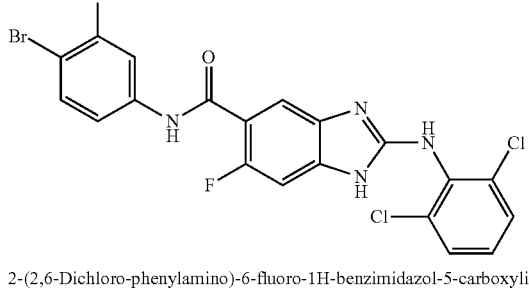<br>2-(2,6-Dichloro-phenylamino)-6-fluoro-1H-benzimidazol-5-carboxylic acid (4-bromo-3-fluoro-phenyl)-amide | Σ: 41% | $(M + H)^+ =$ 511/513/ 515/517 (bromine and chlorine isotopes) | 0.32 (silica gel, dichloromethane/ ethanol = 19:1) |
| 122 | 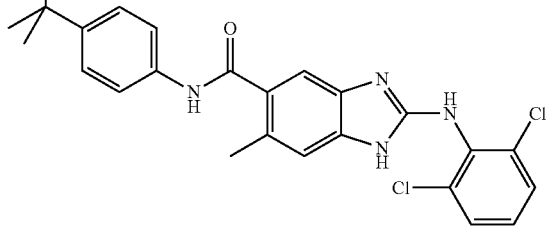<br>2-(2,6-Dichloro-phenylamino)-6-methyl-1H-benzimidazol-5-carboxylic acid (4-tert.-butyl-phenyl)-amide | Σ: 21% | $(M + H)^+ =$ 467/469/471 (chlorine isotopes) | 0.30 (silica gel, petrol ether/ethyl acetate = 1:1) |
| 123 | 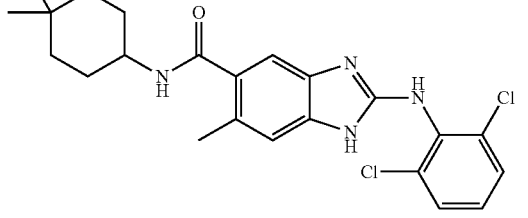<br>2-(2,6-Dichloro-phenylamino)-6-methyl-1H-benzimidazol-5-carboxylic acid (4,4-dimethyl-cyclohexyl)-amide | Σ: 32% | $(M + H)^+ =$ 445/447/449 (chlorine isotopes) | 2.08 min (C1) |

| No. | Structural formula Name | Yield | Mass peak(s) | $R_f$ value or $R_t$ |
|---|---|---|---|---|
| 124 | 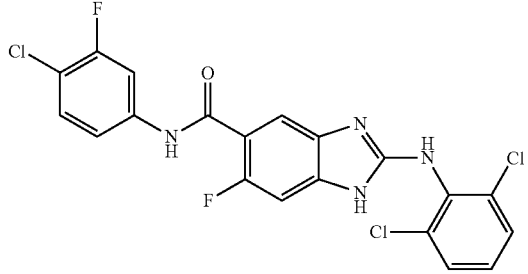 [SMILES: O=C(Nc1ccc(Cl)c(F)c1)c1cc2nc(Nc3c(Cl)cccc3Cl)[nH]c2cc1F]<br>2-(2,6-Dichloro-phenylamino)-6-fluoro-1H-benzimidazol-5-carboxylic acid (4-chloro-3-fluoro-phenyl)-amide | Σ: 41% | $(M + H)^+$ = 467/469/ 471/473 (chlorine isotopes) | 2.65 min (C1) |
| 125 | 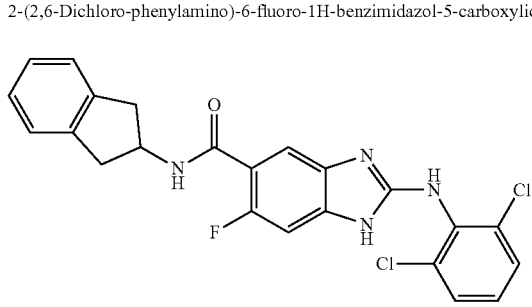<br>2-(2,6-Dichloro-phenylamino)-6-fluoro-1H-benzimidazol-5-carboxylic acid indan-2-yl-amide | Σ: 41% | $(M + H)^+$ = 455/457/459 (chlorine isotopes) | 0.36 (silica gel, dichloromethane/ methanol = 19:1) |
| 639 | 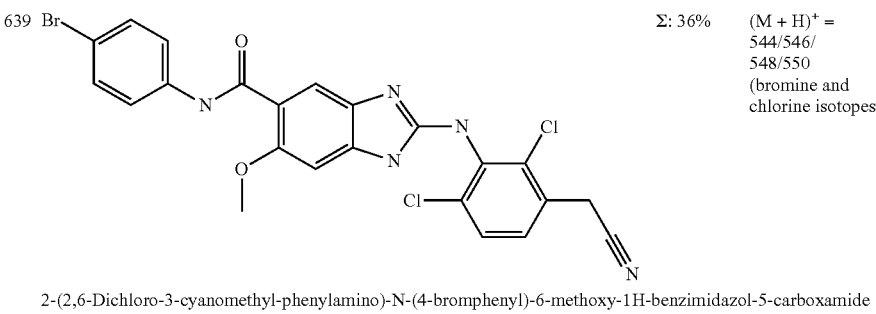<br>2-(2,6-Dichloro-3-cyanomethyl-phenylamino)-N-(4-bromphenyl)-6-methoxy-1H-benzimidazol-5-carboxamide | Σ: 36% | $(M + H)^+$ = 544/546/ 548/550 (bromine and chlorine isotopes) | 2.01 min (E9) |
| 640 | 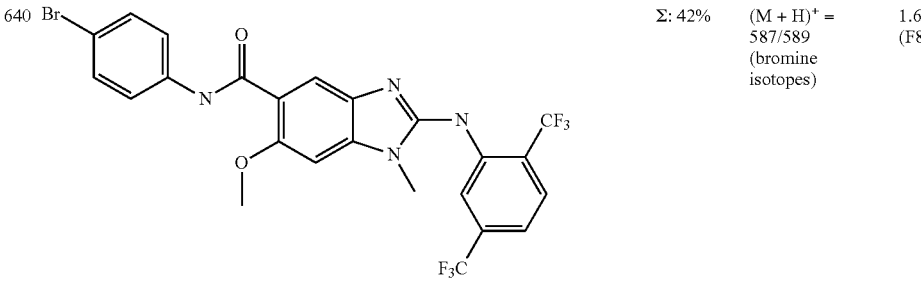<br>2-(2,5-Di-(trifluoromethyl)-phenylamino)-N-(4-bromphenyl)-6-methoxy-1-methyl-1H-benzimidazol-5-carboxamide | Σ: 42% | $(M + H)^+$ = 587/589 (bromine isotopes) | 1.63 min (F8) |
| 641 | 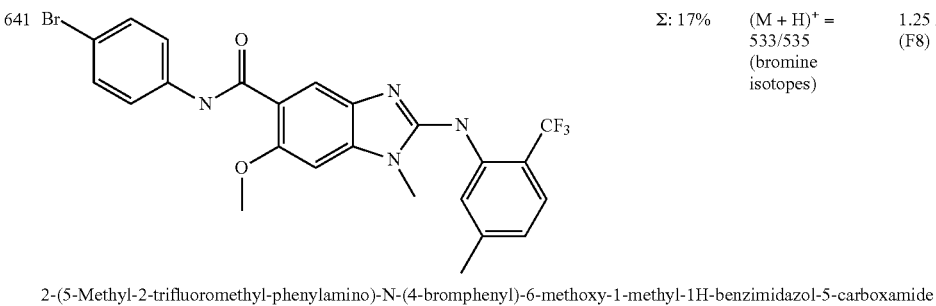<br>2-(5-Methyl-2-trifluoromethyl-phenylamino)-N-(4-bromphenyl)-6-methoxy-1-methyl-1H-benzimidazol-5-carboxamide | Σ: 17% | $(M + H)^+$ = 533/535 (bromine isotopes) | 1.25 min (F8) |

-continued

| No. | Structural formula Name | Yield | Mass peak(s) | $R_f$ value or $R_t$ |
|---|---|---|---|---|
| 642 | 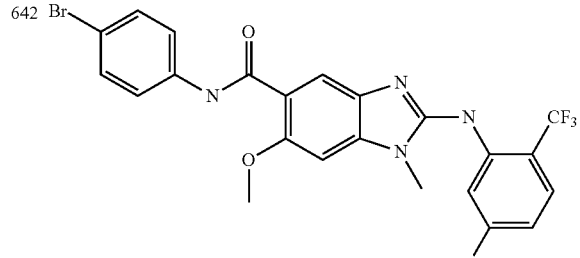<br>2-(5-Fluoro-2-trifluoromethyl-phenylamino)-N-(4-bromphenyl)-6-methoxy-1-methyl-1H-benzimidazol-5-carboxamide | Σ: 11.0% | $(M + H)^+$ = 537/539 (bromine isotopes) | 1.47 min (F7) |
| 654 | 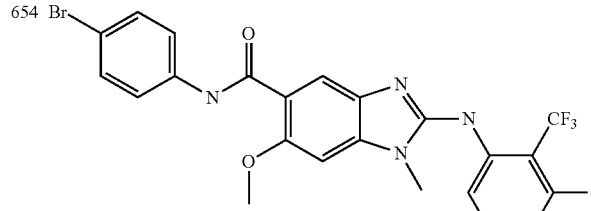<br>2-(5-Fluoro-2-trifluoromethyl-phenylamino)-N-(4-bromphenyl)-6-methoxy-1-methyl-1H-benzimidazol-5-carboxamide | Σ: 19% | $(M + H)^+$ = 553/555/557 (bromine and chlorine isotopes) | 1.41 min (F7) |

Example 74

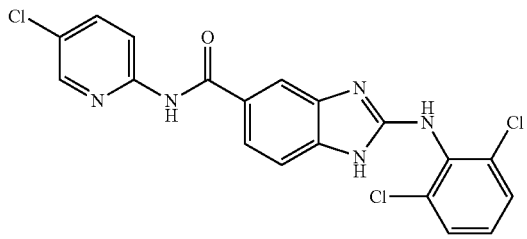 [SMILES: O=C(Nc1ccc(Cl)cn1)c1ccc2[nH]c(Nc3c(Cl)cccc3Cl)nc2c1]

2-(2,6-Dichloro-phenylamino)-1H-benzimidazole-5-carboxylic acid (5-chloro-pyridin-2-yl)-amide

(74a) 3,4-Bis-tert.-butoxycarbonylamino-benzoic acid methyl ester

Di-tert.-butyl-dicarbonate (20.0 g, 91.6 mmol) in 25 mL THF was added to 3,4-diamino-benzoic acid methyl ester and stirred for 45 h at ambient temperature, for 2 h at reflux, for 7 days at ambient temperature and 2 h at reflux. Di-tert.-butyl-dicarbonat (1.0 g, 4.5 mmol) and 4-dimethylamino-pyridine (75 mg, 0.61 mmol) were added and refluxed for 1 h. The mixture was concentrated i.vac. and reacted further without further purification.
Yield: 16.5 g (quant.), slightly contaminated
$C_{18}H_{26}N_2O_6$ (366.41)

(74b) 3,4-Bis-tert.-butoxycarbonylamino-benzoic acid

Prepared analogously to example 3b with the product obtained in 74a and 1N NaOH (aq) in ethanol.
Yield: 57%
$R_t$ value: 2.78 min (C2); $C_{17}H_{24}N_2O_6$ (366.41).

(74c) 3,4-Bis-tert.-butoxycarbonylamino-benzoic acid (5-chloro-pyridine-2-yl) amide (1-Chloro-2-methyl-propenyl)-dimethyl-amine (150 µL, 1.13 mmol) was added to the product obtained in 74b (350 mg, 0.99 mmol) in dichloromethane and stirred at ambient temperature for 45 min. Then pyridine (100 µL, 1.26 mmol) and 2-amino-5-chloro-pyridine (140 mg, 1.09 mmol) were added and stirred at ambient temperature for 1.5 h. Then methanol was added, the mixture was concentrated i.vac. and the residue was purified by HPLC (0-18 symmetry, eluent gradient: (water+0.15% HCOOH)/acetonitrile=85:15->0:100).
Yield: 350 mg (76%); $R_t$ value: 3.28 min (C2); $C_{22}H_{27}ClN_4O_5$ (462.93).

(74d) 3,4-Diamino-benzoic acid (5-chloro-pyridine-2-yl) amide

A mixture of the product obtained in 74c (540 mg, 1.17 mmol) in 3 mL dichloromethane with TFA (3.0 mL, 38.9 mmol) was stirred at ambient temperature for 1 h. The mixture was poured into water and washed with diethylether. 10N sodium hydroxide (aq) and ice were added to the aqueous layer and extracted with dichloromethane/methanol=9:1. The organic layers were dried over $MgSO_4$ and concentrated i.vac.
Yield: 210 mg (69%)
$R_t$ value: 1.98 min (C2)
$C_{12}H_{11}ClN_4O$ (262.70)
Mass spectrum: $(M+H)^+$=263/265 (chlorine isotopes)

(74e) [5-(4-tert.-Butyl-benzyloxy)-1H-benzimidazol-2-yl]-(2,6-dichloro-phenyl)-amine Prepared analogously to example 1c from the product obtained in 74d with 1,3-dichloro-2-isocyanato-benzene and DIC in DMF at 60° C.
Yield: 72%
$R_t$ value: 2.00 min (C2)
$C_{19}H_{12}Cl_3N_5O$ (432.69)
Mass spectrum: $(M+H)^+$=432/434/436/438 (chlorine isotopes)

In analogy with the above described example, the following compounds were prepared:

| No. | Structural formula Name | Yield | Mass peak(s) | $R_f$ value or $R_t$ |
|---|---|---|---|---|
| 75 | 2-(2,6-Dichloro-phenylamino)-1H-benzimidazole-5-carboxylic acid (4-chloro-pyridin-2-yl)-amide | Σ: 8.9% | $(M+H)^+$ = 432/434/436/438 (chlorine isotopes) | 1.98 min (C2) |
| 76 | 2-(2,6-Dichloro-phenylamino)-1H-benzimidazole-5-carboxylic acid (5-bromo-6-methyl-pyridin-2-yl)-amide | Σ: 16.1% | $(M+H)^+$ = 490/492/494/496 (bromine and chlorine isotopes) | 2.12 min (C2) |

Example 77

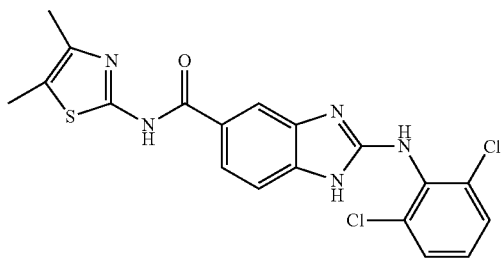 [SMILES: Cc1nc(NC(=O)c2ccc3[nH]c(Nc4c(Cl)cccc4Cl)nc3c2)sc1C]

2-(2,6-Dichloro-phenylamino)-1H-benzimidazole-5-carboxylic acid (4,5-dimethyl-thiazol-2-yl)-amide (77a) 4-Amino-3-nitro-benzoic acid (4,5-dimethyl-thiazol-2-yl) amide Prepared analogously to example 3c with 4-amino-3-nitro-benzoic acid and 2-amino-4,5-dimethyl-thiazole using TBTU and TEA in DMF.
Yield: 45%
$R_t$ value: 3.68 min (B6)
$C_{12}H_{12}N_4O_3S$ (292.32)
Mass spectrum: $(M+H)^+$=293

(77b) 3,4-Diamino-benzoic acid (4,5-dimethyl-thiazol-2-yl) amide

Prepared analogously to example 14b by hydrogenation of the product obtained in 77a using Raney nickel in methanol.
Yield: 69%
$R_t$ value: 2.55 min (B6)
$C_{12}H_{14}N_4OS$ (262.33)
Mass spectrum: $(M+H)^+$=263

(77c) 2-(2,6-Dichloro-phenylamino)-1H-benzimidazole-5-carboxylic acid (4,5-dimethyl-thiazol-2-yl)-amide Prepared analogously to example 1c with from the product obtained in 77b with 1,3-dichloro-2-isocyanato-benzene and DIC in DMF at ambient temperature.
Yield: 54%
$R_t$ value: 2.11 min (C6)
$C_{19}H_{15}Cl_2N_5OS$ (432.33)
Mass spectrum: $(M+H)^+$=432/434/436 (chlorine isotopes)

In analogy with the above described example, the following compounds were prepared:

| No. | Structural formula Name | Yield | Mass peak(s) | $R_f$ value or $R_t$ |
|---|---|---|---|---|
| 78 | 2-(2,6-Dichloro-phenylamino)-1H-benzimidazole-5-carboxylic acid (5,6-dihydro-4H-cyclopentathiazol-2-yl)-amide | Σ: 17.7% | $(M+H)^+$ = 444/446/448 (chlorine isotopes) | 2.16 min (C6) |

-continued

| No. | Structural formula Name | Yield | Mass peak(s) | R$_f$ value or R$_t$ |
|---|---|---|---|---|
| 79 | 2-(2,6-Dichloro-phenylamino)-1H-benzimidazole-5-carboxylic acid (4,5,6,7-tetrahydro-benzothiazol-2-yl)-amide | Σ: 37% | (M + H)$^+$ = 458/460/462 (chlorine isotopes) | 2.23 min (C6) |
| 80 | 2-(2,6-Dichloro-phenylamino)-1H-benzimidazole-5-carboxylic acid (benzimidazol-2-yl)-amide | Σ: 11.1% | (M + H)$^+$ = 437/439/441 (chlorine isotopes) | 1.90 min (C6) |
| 81 | 2-(2,6-Dichloro-phenylamino)-1H-benzimidazole-5-carboxylic acid (1-methyl-benzimidazol-2-yl)-amide | Σ: 20% | (M + H)$^+$ = 451/453/455 (chlorine isotopes) | 2.10 min (C6) |

Example 106

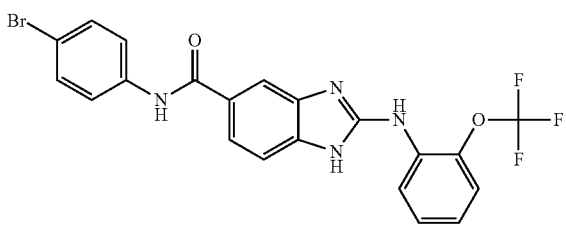 [SMILES: O=C(Nc1ccc(Br)cc1)c1ccc2[nH]c(Nc3ccccc3OC(F)(F)F)nc2c1]

2-(2-Trifluoromethoxy-phenylamino)-1H-benzimidazole-5-carboxylic acid (4-bromo-phenyl)-amide (106a) 2-(2-Trifluoromethoxy-phenylamino)-1H-benzimidazole-5-carboxylic acid (4-bromo-phenyl)-amide A mixture of 3,4-diamino-N-(4-bromo-phenyl)-benzamide (300 mg, 1.0 mmol) and 1-isothiocyanato-2-trifluoromethoxy-benzene (215.0 mg, 1.0 mmol) was stirred in 5 mL DMF. After stirring for 2 h DCC (202.2 mg, 1.0 mmol) was added and stirred overnight. The mixture was heated to 80° C. for 30 min, then cooled. Water was added and the mixture was concentrated i.vac. The residue was purified by chromatography on silica gel (eluent: dichloromethane/methanol=40:1).

Yield: 200 mg slightly contaminated

Mass spectrum: (N–H)$^-$=489/91 (bromine isotopes); mp: 241-243° C.

In analogy with the above described example, the following compounds were prepared:

| No. | Structural formula Name | Yield | Mass peak(s) | $R_f$-value or $R_t$ |
|---|---|---|---|---|
| 107 | 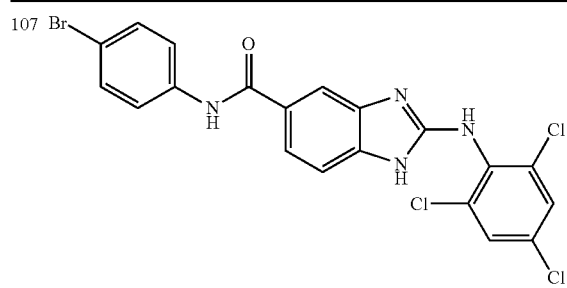<br>2-(2,4,6-Trichloro-phenylamino)-1H-benzimidazole-5-carboxylic acid (4-bromo-phenyl)-amide | Σ: 22% | $(M - H)^- =$ 506/508/ 510/512 (chlorine and bromine isotopes) | 0.6 (silica gel dichloromethane/ methanol 25:1) |
| 108 | 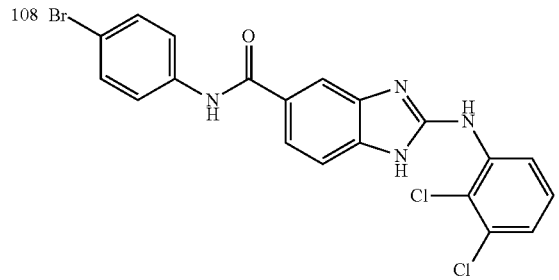<br>2-(2,3-Dichloro-phenylamino)-1H-benzimidazole-5-carboxylic acid (4-bromo-phenyl)-amide | Σ: 12.9% | $(M - H)^- =$ 473/475/477 (chlorine and bromine isotopes) | 0.65 (silica gel dichloromethane/ methanol 25:1) |
| 109 | 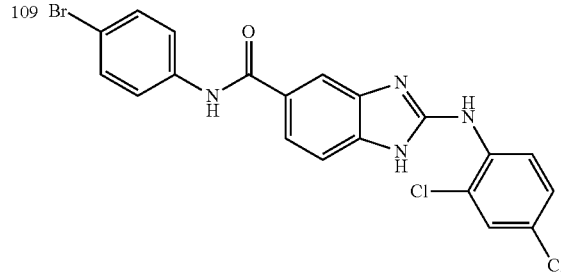<br>2-(2,4-Dichloro-phenylamino)-1H-benzimidazole-5-carboxylic acid (4-bromo-phenyl)-amide | Σ: 17% | $(M - H)^- =$ 473/475/ 477/479 (chlorine and bromine isotopes) | 0.62 (silica gel dichloromethane/ methanol 25:1) |
| 279 | 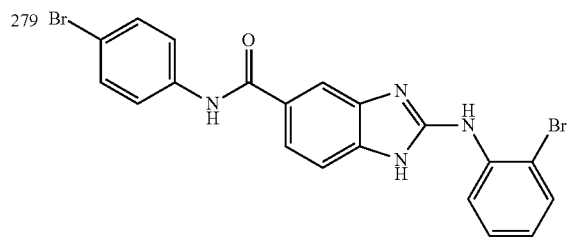<br>2-(2-Bromo-phenylamino)-1H-benzimidazole-5-carboxylic acid (4-bromo-phenyl)-amide | Σ: 25% | $(M - H)^- =$ 483/485/487 (bromine isotopes) | 0.54 (silica gel dichloromethane/ methanol 50:1) |
| 291 | 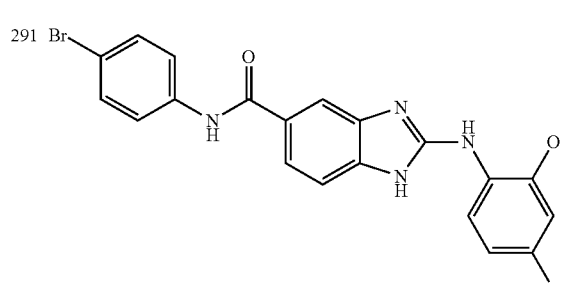<br>2-(5-Chloro-2-trifluoromethoxy-phenylamino)-1H-benzimidazole-5-carboxylic acid (4-bromo-phenyl)-amide | Σ: 25% | $(M + H)+ =$ 525/527/529 (chlorine and bromine isotopes) | 0.63 (silica gel dichloromethane/ methanol 25:1) |

| Structural formula No. Name | Yield | Mass peak(s) | $R_f$ value or $R_t$ |
|---|---|---|---|
| 456 N-(4-Bromophenyl)-2-(2-chloro-4-fluorophenylamino)-1-methyl-1H-benzimidazole-5-carboxamide | Σ: 96% | (M + H)+ = 473/475/477 (chlorine and bromine isotopes) | 12.19 min (EX1) |

Example 110

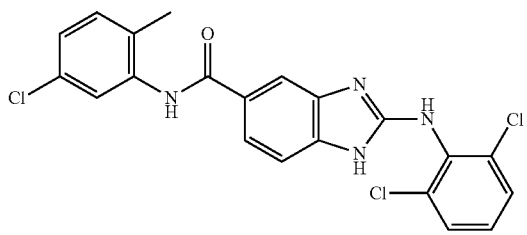 [SMILES: Cc1ccc(Cl)cc1NC(=O)c1ccc2[nH]c(Nc3c(Cl)cccc3Cl)nc2c1]

2-(2,6-Dichloro-phenylamino)-1H-benzimidazole-5-carboxylic acid (5-chloro-2-methyl-phenyl)-amide (110a) 2-(2,6-Dichloro-phenylamino)-1H-benzimidazole-5-carboxylic acid (5-chloro-2-methyl-phenyl)-amide Prepared analogously to Example 113b from 2-(2,6-dichloro-phenylamino)-1H-benzimidazole-5-carboxylic acid and 1-chloro-N,N-2-trimethyl-1-propenylamin with 5-chloro-2-methyl-phenylamine in dichloromethane.

Yield: 32 mg (8%)

mp: 178-180° C.

mass spectrum: $(M+H)^+$=445/47/49/51 (chlorine isotopes)

In analogy with the above described example, the following compounds were prepared:

| Structural formula No. Name | Yield | Mass peak(s) | $R_f$ value or $R_t$ |
|---|---|---|---|
| 111 2-(2,6-Dichloro-phenylamino)-1H-benzimidazole-5-carboxylic acid (3,4-dichloro-phenyl)-amide | Σ: 13.0% | $(M + H)^+$ = 465/467/ 469/471 (chlorine isotopes) | 0.14 (silica gel petrol ether/ethyl acetate = 1/1) |
| 112 2-(2,6-Dichloro-phenylamino)-1H-benzimidazole-5-carboxylic acid (3,5-dichloro-phenyl)-amide | Σ: 12.0% | $(M + H)^+$ = 465/467/ 469/471 (chlorine isotopes) | 0.32 (silica gel petrol ether/ethyl acetate = 1/1) |

Example 113

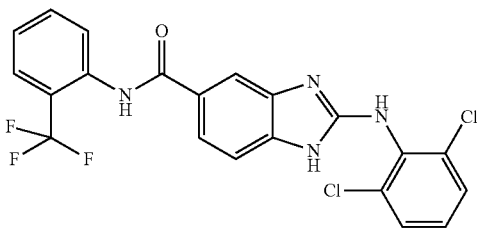 [SMILES: O=C(Nc1ccccc1C(F)(F)F)c1ccc2[nH]c(Nc3c(Cl)cccc3Cl)nc2c1]

2-(2,6-Dichloro-phenylamino)-1H-benzimidazole-5-carboxylic acid (2-trifluoromethyl-phenyl)-amide

(113a) 2-(2,6-Dichloro-phenylamino)-1H-benzimidazole-5-carboxylic acid

A mixture of 3,4-diamino-benzoic acid ethyl ester (5.00 g, 27.8 mmol) and 1,3-dichloro-2-isothiocyanato-benzene (5.66 g, 27.8 mmol) in 40 mL DMF was stirred for 2 h under argon. DCC (5.72 g, 27.8 mmol) was added and mixture heated to 80° C. for 45 min. After stirring the mixture was diluted with water and concentrated i.vac. The residue was diluted with ethanol and 1 M NaOH (aq). The mixture was heated to 100° C. and stirred overnight. Then ethanol was evaporated and the aq. phase was cooled, acidified with acetic acid, filtered and the solid washed with water.

Yield: 8 g (90%)

(113b) 2-(2,6-Dichloro-phenylamino)-1H-benzimidazole-5-carboxylic acid (2-trifluoromethyl-phenyl)-amide A mixture of 2-(2,6-dichloro-phenylamino)-1H-benzimidazole-5-carboxylic acid (600 mg, 1.86 mmol) and 1-chloro-N,N-2-trimethyl-1-propenylamin (420 µL, 3.2 mmol) in 8 mL dichloromethane was stirred for 45 min. 2-Trifluoromethyl-aniline (2.3 mL, 18.6 mmol) in pyridine was added. After stirring overnight, the mixture was diluted with ethyl acetate, washed with water and brine, dried and concentrated i.vac.

Yield: 68 mg (8%) (slightly contaminated)
mp: 143-145° C.
mass spectrum: $(M+H)^+$=465/467/469 (chlorine isotopes)
$R_f$ value: 0.54 (silica gel; petrol ether/ethyl acetate=1/1)

In analogy with the above described example, the following compounds were prepared:

| | Structural formula<br>Name | Yield | Mass peak(s) | $R_f$ value or $R_t$ |
|---|---|---|---|---|
| 111 | 2-(2,6-Dichloro-phenylamino)-1H-benzimidazole-5-carboxylic acid (3,4-dichloro-phenyl)-amide | Σ: 12% | $(M + H)^+$ = 465/467/469/471 (chlorine isotopes) | 0.14 (silica gel petrol ether/ethyl acetate = 1/1) |
| 112 | 2-(2,6-Dichloro-phenylamino)-1H-benzimidazole-5-carboxylic acid (3,5-dichloro-phenyl)-amide | Σ: 11.0% | $(M + H)^+$ = 465/467/469/471 (chlorine isotopes) | 0.32 (silica gel petrol ether/ethyl acetate = 1/1) |
| 110 | 2-(2,6-Dichloro-phenylamino)-1H-benzimidazole-5-carboxylic acid (5-chloro-2-methyl-phenyl)-amide | Σ: 3.0% | $(M + H)^+$ = 445/447/449/451 (chlorine isotopes) | mp: 178-180° C. |

-continued

| Structural formula Name | Yield | Mass peak(s) | $R_f$-value or $R_t$ |
|---|---|---|---|
| 281 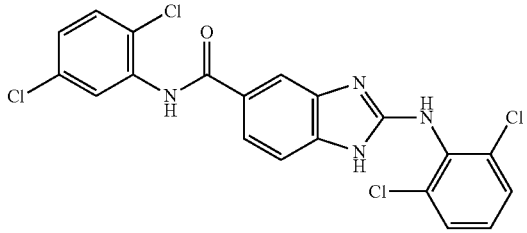 [SMILES: O=C(Nc1cc(Cl)ccc1Cl)c1ccc2[nH]c(Nc3c(Cl)cccc3Cl)nc2c1]<br>2-(2,6-Dichloro-phenylamino)-1H-benzimidazole-5-carboxylic acid (2,5-dichloro-phenyl)-amide | Σ: 5% | (M + H)$^+$ = 465/467/ 469/471 (chlorine isotopes) | 0.29 (silica gel petrol ether/ethyl acetate 1:1) |
| 282 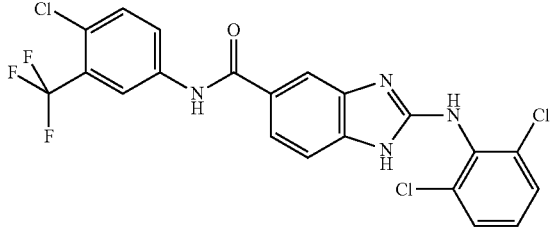 [SMILES: O=C(Nc1ccc(Cl)c(C(F)(F)F)c1)c1ccc2[nH]c(Nc3c(Cl)cccc3Cl)nc2c1]<br>2-(2,6-Dichloro-phenylamino)-1H-benzimidazole-5-carboxylic acid (4-chloro-3-trifluoromethyl-phenyl)-amide | Σ: 3% | (M + H)$^+$ = 499/401/ 403/405 (chlorine isotopes) | 0.24 (silica gel petrol ether/ethyl acetate 1:1) |
| 283 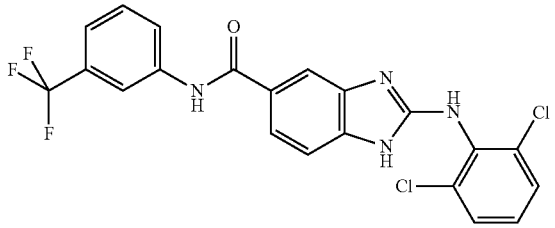 [SMILES: O=C(Nc1cccc(C(F)(F)F)c1)c1ccc2[nH]c(Nc3c(Cl)cccc3Cl)nc2c1]<br>2-(2,6-Dichloro-phenylamino)-1H-benzimidazole-5-carboxylic acid (3-trifluoromethyl-phenyl)-amide | Σ: 21% | (M + H)$^+$ = 465/467/469 (chlorine isotopes) | 0.27 (silica gel petrol ether/ethyl acetate 1:1) |
| 284 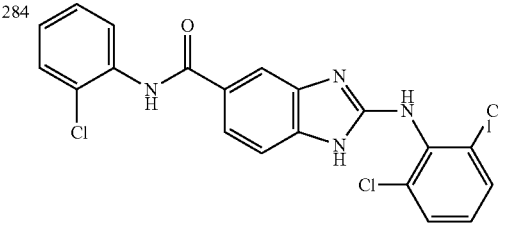<br>2-(2,6-Dichloro-phenylamino)-1H-benzimidazole-5-carboxylic acid (2-chloro-phenyl)-amide | Σ: 12% | (M + H)$^+$ = 431/433/ 435/437 (chlorine isotopes) | 0.31 (silica gel petrol ether/ethyl acetate 1:1) |
| 285 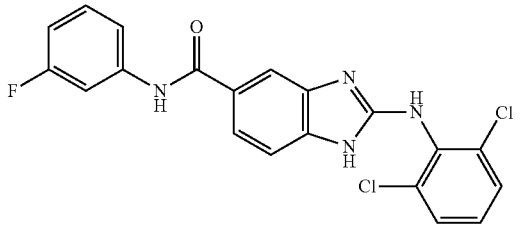 [SMILES: O=C(Nc1cccc(F)c1)c1ccc2[nH]c(Nc3c(Cl)cccc3Cl)nc2c1]<br>2-(2,6-Dichloro-phenylamino)-1H-benzimidazole-5-carboxylic acid (3-fluoro-phenyl)-amide | Σ: 16% | (M + H)$^+$ = 415/417/419 (chlorine isotopes) | 0.54 (silica gel petrol ether/ethyl acetate 1:1) |
| 286 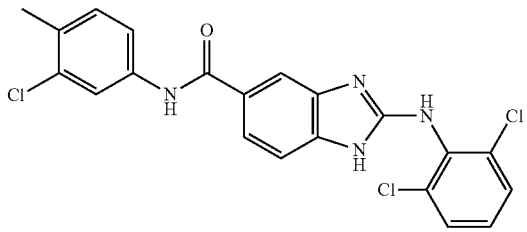 [SMILES: Cc1ccc(NC(=O)c2ccc3[nH]c(Nc4c(Cl)cccc4Cl)nc3c2)cc1Cl]<br>2-(2,6-Dichloro-phenylamino)-1H-benzimidazole-5-carboxylic acid (3-chloro-4-methyl-phenyl)-amide | Σ: 6% | (M + H)$^+$ = 445/447/ 49/451 (chlorine isotopes) | 0.19 (silica gel petrol ether/ethyl acetate 1:1) |

-continued

| Structural formula Name | Yield | Mass peak(s) | $R_f$-value or $R_t$ |
|---|---|---|---|
| 287 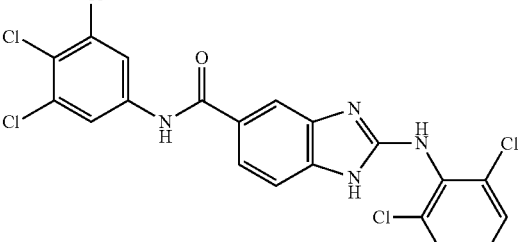 2-(2,6-Dichloro-phenylamino)-1H-benzimidazole-5-carboxylic acid (3,4,5-trichloro-phenyl)-amide | Σ: 12% | $(M + H)^+ =$ 499/401/ 403/405 407 (chlorine isotopes) | 0.31 (silica gel petrol ether/ethyl acetate 1:1) |
| 288 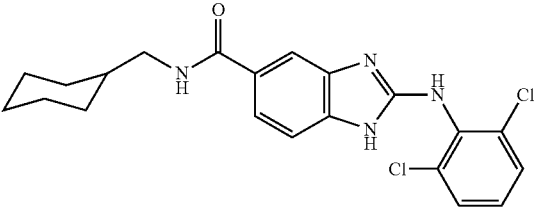 [SMILES: O=C(NCC1CCCCC1)c1ccc2[nH]c(Nc3c(Cl)cccc3Cl)nc2c1] 2-(2,6-Dichloro-phenylamino)-1H-benzimidazole-5-carboxylic acid cyclohexylmethyl-amide | Σ: 5% | $(M + H)^+ =$ 417/419/421 (chlorine isotopes) | 0.12 (silica gel petrol ether/ethyl acetate 1:1) |
| 292 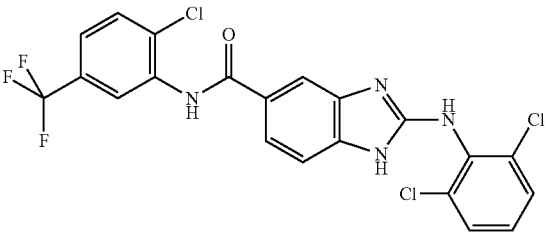 [SMILES: O=C(Nc1cc(C(F)(F)F)ccc1Cl)c1ccc2[nH]c(Nc3c(Cl)cccc3Cl)nc2c1] 2-(2,6-Dichloro-phenylamino)-1H-benzimidazole-5-carboxylic acid (2-chloro-5-trifluoromethyl-phenyl)-amide | Σ: 5% | $(M + H)^+ =$ 499/401/403 (chlorine isotopes) | 0.42 (silica gel petrol ether/ethyl acetate 1:1) |
| 280 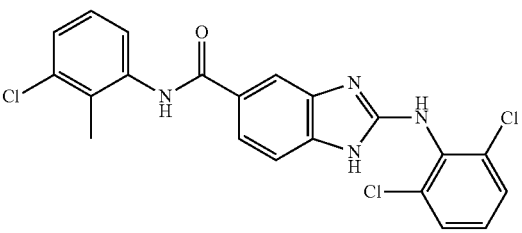 [SMILES: Cc1c(Cl)cccc1NC(=O)c1ccc2[nH]c(Nc3c(Cl)cccc3Cl)nc2c1] N-(3-Chloro-2-methylphenyl)-2-(2,6-dichlorophenylamino)-1H-benzimidazole-5-carboxamide | Σ: 6% | $(M + H)^+ =$ 445/447/449 (chlorine isotopes) | 0.18 (silica gel petrol ether/ethyl acetate 1:1) |
| 498 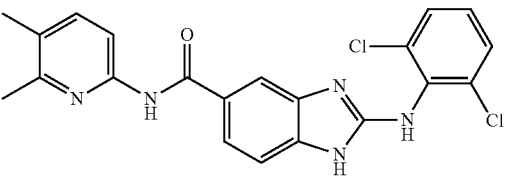 [SMILES: Cc1ccc(NC(=O)c2ccc3[nH]c(Nc4c(Cl)cccc4Cl)nc3c2)nc1C] 2-(2,6-Dichlorophenylamino)-N-(5,6-dimethylpyridin-2-yl)-1H-benzimidazole-5-carboxamide | Σ: 10% | $(M + H)^+ =$ 426/428/430 (chlorine isotopes) | 9.53 min (EX1) |
| 539 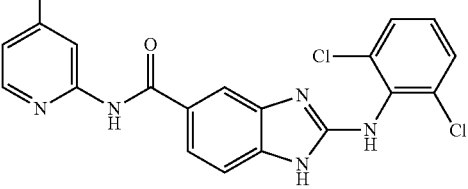 N-(4-Cyanopyridin-2-yl)-2-(2,6-dichlorophenylamino)-1H-benzimidazole-5-carboxamide | Σ: 4% | $(M + H)^+ =$ 423/425/427 (chlorine isotopes) | 9.97 min (EX2) |

| Structural formula Name | Yield | Mass peak(s) | $R_f$-value or $R_t$ |
|---|---|---|---|
| 558 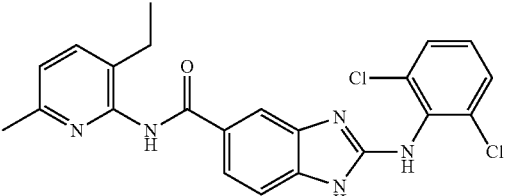  2-(2,6-Dichlorophenylamino)-N-(3-ethyl-6-methylpyridin-2-yl)-1H-benzimidazole-5-carboxamide | Σ: 4% | (M + H)⁺ = 440/442/444 (chlorine isotopes) | 9.32 min (EX1) |

Example 114

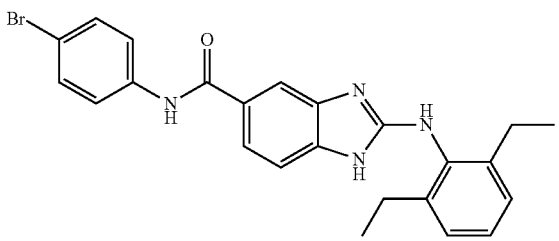 [SMILES: CCc1cccc(CC)c1Nc1nc2cc(C(=O)Nc3ccc(Br)cc3)ccc2[nH]1]

2-(2,6-Diethyl-phenylamino)-1H-benzimidazole-5-carboxylic acid (4-bromo-phenyl)-amide A mixture of 2,6-diethyl-phenylamine (243 mg, 1.6 mmol) and N,N-thiocarbonyl diimidazole (290 mg, 1.6 mmol) in 10 mL dichloromethane was stirred overnight at 0° C. under argon. This resulting mixture was added to (4-bromo-phenylamino)-(3,4-diamino-phenyl)-methanol (500 mg, 1.63 mmol) in 6 mL DMF. After stirring for 2 h DCC (336 mg, 1.6 mmol) was added and stirred overnight. The mixture was concentrated i.vac. The residue was purified by chromatography on silica gel (eluent: dichloromethane/methanol=50:1).

Yield: 50 mg (5.5%) (slightly contaminated)
mass spectrum: (M+H)⁺=463/65 (bromine isotopes)

Example 116

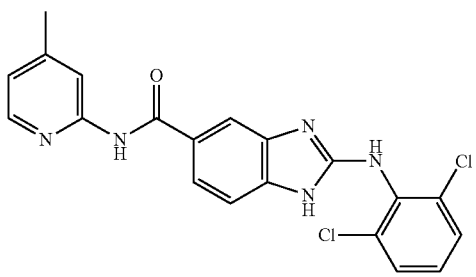 [SMILES: Cc1ccnc(NC(=O)c2ccc3[nH]c(Nc4c(Cl)cccc4Cl)nc3c2)c1]

2-(2,6-Dichloro-phenylamino)-1H-benzimidazole-5-carboxylic acid (4-methyl-pyridin-2-yl)-amide (116a) 4-Amino-3-nitro-benzoyl-chloride Prepared analogously to example 53a from 4-amino-3-nitro-benzoic acid with thionyl chloride and DMF in dichloromethane at reflux.

Yield: quant.
$C_7H_5ClN_2O_3$ (200.58)

(116b) 4-Amino-3-nitro-benzoic acid (4-methyl-pyridin-2-yl) amide

The product obtained in 116a (550 mg, 2.74 mmol) in 5 mL THF was added to a mixture of 2-amino-4-methyl-pyridine (750 mg, 6.94 mmol) in 10 mL THF under stirring at ambient temperature. The mixture was stirred for 20 min at ambient temperature, then 1 mL methanol was added and the mixture was concentrated i.vac. The residue was purified by HPLC (C18 symmetry, eluent-gradient: (water+0.15% HCOOH)/acetonitrile=90:10->0:100). Conc. ammonia (aq) was added to the product containing fractions until alkaline, and acetonitrile was removed by evaporation. The aqueous mixture was extracted with dichloromethane/methanol 9:1, the combined organic layers dried over $MgSO_4$ and concentrated to dryness i. vac. and the residue triturated with methanol. After filtration, the solid was washed with methanol and dried at 55° C.

Yield: 150 mg (20%)
$R_t$ value: 1.87 min (C2)
$C_{13}H_{12}N_4O_3$ (272.26)
Mass spectrum: (M+H)⁺=273

(116c) 3,4-Diamino-benzoic acid (4-methyl-pyridin-2-yl) amide

Prepared analogously to example 14b from the product obtained in 116b by hydrogenation using Raney nickel in THF at 3.5 bar.

Yield: 86%
$R_t$ value: 1.34 min (B2)
$C_{13}H_{14}N_4O$ (242.28)
Mass spectrum: (M+H)⁺=243

(116d) 2-(2,6-Dichloro-phenylamino)-1H-benzimidazole-5-carboxylic acid (4-methyl-pyridin-2-yl)-amide Prepared analogously to example 1c from the product obtained in (116c) and 1,3-dichloro-2-isothiocyanato-benzene using DIC in acetonitrile.

Yield: 39%
$R_t$ value: 2.19 min (B2)
$C_{20}H_{15}Cl_2N_5O$ (412.27)
Mass spectrum: (M+H)⁺=412/414/416 (chlorine isotopes)

In analogy with the above described example, the following compounds were prepared:

| No. | Structural formula Name | Yield | Mass peak(s) | $R_f$ value or $R_t$ |
|---|---|---|---|---|
| 117 | 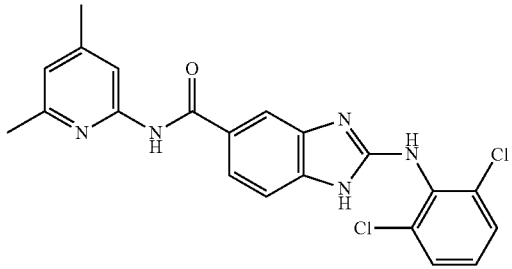 [SMILES: Cc1cc(C)nc(NC(=O)c2ccc3[nH]c(Nc4c(Cl)cccc4Cl)nc3c2)c1] 2-(2,6-Dichloro-phenylamino)-1H-benzimidazole-5-carboxylic acid (4,6-dimethyl-pyridin-2-yl)-amide | Σ: 40% | (M + H)⁺ = 426/428/430 (chlorine isotopes) | 2.28 min (B2) |
| 118 | 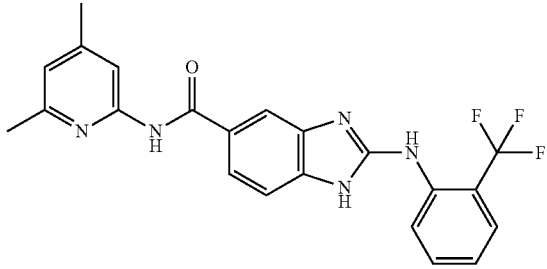 [SMILES: Cc1cc(C)nc(NC(=O)c2ccc3[nH]c(Nc4ccccc4C(F)(F)F)nc3c2)c1] 2-(2-Trifluoromethyl-phenylamino)-1H-benzimidazole-5-carboxylic acid (4,6-dimethyl-pyridin-2-yl)-amide | Σ: 32% | (M + H)⁺ = 426 | 2.36 min (B2) |

Example 120

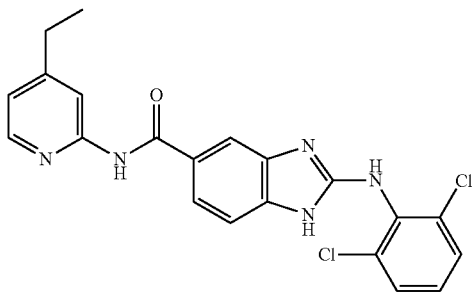 [SMILES: CCc1ccnc(NC(=O)c2ccc3[nH]c(Nc4c(Cl)cccc4Cl)nc3c2)c1]

2-(2,6-Dichloro-phenylamino)-1H-benzimidazole-5-carboxylic acid (4-ethyl-pyridin-2-yl)-amide (120a) 2-(2,6-Dichloro-phenylamino)-1H-benzimidazole-5-carboxylic acid methyl-ester Prepared analogously to example 1c from methyl 3,4-diamino-benzoate and 2,6-dichloro-1-isothiocyanato-benzene with DIC in acetonitrile. Yield: 56%
$R_t$ value: 1.88 min (C2)
$C_{15}H_{11}Cl_2N_3O_2$ (336.17)
Mass spectrum: (M+H)⁺=370/372/374 (chlorine isotopes)

(120b) 2-(2,6-Dichloro-phenylamino)-1H-benzimidazole-5-carboxylic acid (4-ethyl-pyridin-2-yl)-amide 2-Amino-4-ethyl-pyridine (140 mg, 1.15 mmol) and trimethyl-aluminium (2N in hexane, 700 µL, 1.4 mmol) were stirred in 5 mL THF at ambient temperature for 5 min. The product obtained in 120a (350 mg, 1.04 mmol) was added and the mixture stirred at ambient temperature for 3 d. 50 mL Dichloromethane were added and the mixture was poured into 0.5N NaOH (aq). The aqueous layer was extracted with dichloromethane, the organic layers dried over MgSO₄ and concentrated i.vac. The residue was triturated with acetonitrile, the solid filtered off, washed with acetonitrile and dried at 60° C.

Yield: 120 mg (27%)
$R_t$ value: 2.39 min (B2)
$C_{21}H_{17}Cl_2N_5O$ (426.30)
Mass spectrum: (M+H)⁺=426/428/430 (chlorine isotopes)

Example 126

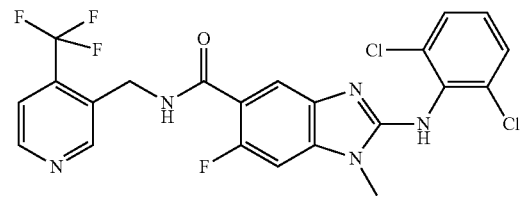 [SMILES: Cn1c(Nc2c(Cl)cccc2Cl)nc2cc(C(=O)NCc3cnccc3C(F)(F)F)c(F)cc21]

2-(2,6-Dichloro-phenylamino)-6-fluoro-1-methyl-1H-benzimidazole-5-carboxylic acid (4-trifluoromethyl-pyridin-3-ylmethyl)-amide (126a) 2,4-Difluoro-5-nitro-benzoic acid ethyl ester Prepared analogously to example 156a from 2,4-difluoro-5-nitro-benzoyl chloride and ethanol with TEA in THF.
Yield: 5.08 g (97%)
$R_t$ value: 2.80 min (C2)

(126b) 2-Fluoro-4-methylamino-5-nitro-benzoic acid ethyl ester

Prepared analogously to example 156b from 2,4-difluoro-5-nitro-benzoic acid ethyl ester and 2 M methylamine solution in THF.

Yield: 1.72 g (66%)

$R_t$ value: 3.92 min (B2)

(126c) 5-Amino-2-fluoro-4-methylamino-benzoic acid ethyl ester

Prepared analogously to example 156c from 2-fluoro-4-methylamino-5-nitro-benzoic acid ethyl ester and Raney nickel in THF.

Yield: 11.08 g (99%)

$R_t$ value: 2.19 min (C2)

(126d) 5-[3-(2,6-Dichloro-phenyl)-thioureido]-2-fluoro-4-methylamino-benzoic acid ethyl ester Prepared analogously to example 131d from 5-amino-2-fluoro-4-methylamino-benzoic acid ethyl ester and 1,3-dichloro-2-isothiocyanato-benzene in methanol and acetonitrile.

Yield: 2.70 g (93%)

$R_t$ value: 2.73 min (C2)

(126e) 5-[3-(2,6-Dichloro-phenyl)-thioureido]-2-fluoro-4-methylamino-benzoic acid ethyl ester DIC (1.50 mL, 9.6 mmol) was added to the product obtained in 126d (2.70 g, 6.5 mmol) in 25 mL acetonitrile and stirred for 1 h at reflux. The mixture was concentrated i.vac. The residue was taken up in ethanol and 1 M NaOH (aq) was added. After stirring for 40 min at reflux, the mixture was concentrated i.vac. and the residue was taken up in water and filtered. The filtrate was acidified with hydrochloric acid, stirred and filtered.

Yield: 1.72 g (75%)

$R_t$ value: 1.98 min (C2)

(126f) 2-(2,6-Dichloro-phenylamino)-6-fluoro-1-methyl-1H-benzimidazole-5-carboxylic acid (4-trifluoromethyl-pyridin-3-ylmethyl)-amide Prepared analogously to example 3c from 5-[3-(2,6-dichloro-phenyl)-thioureido]-2-fluoro-4-methylamino-benzoic acid ethyl ester, (4-trifluoromethyl-pyridin-3-yl)-methylamine hydrochloride, TBTU and TEA in DMF.

Yield: 245 mg (85%)

$R_t$ value: 3.34 min (B6)

mass spectrum: (M+H)$^+$=512/514/516 (chlorine isotopes)

Example 127

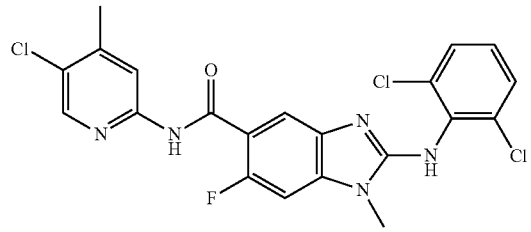 [SMILES: Cc1cc(NC(=O)c2cc3nc(Nc4c(Cl)cccc4Cl)n(C)c3cc2F)ncc1Cl]

2-(2,6-Dichloro-phenylamino)-6-fluoro-1-methyl-1H-benzimidazole-5-carboxylic acid (5-chloro-4-methyl-pyridin-2-yl)-amide

(127a) 2,4-Difluoro-5-nitro-benzoic acid ethyl ester

Prepared analogously to example 156a from 2,4-difluoro-5-nitro-benzoyl chloride and ethanol with TEA in THF.

Yield: 5.08 g (97%)

$R_t$ value: 2.80 min (C2)

(127b) 2-Fluoro-4-methylamino-5-nitro-benzoic acid ethyl ester

Prepared analogously to example 156b from 2,4-difluoro-5-nitro-benzoic acid ethyl ester and 2 M methylamine solution in THF.

Yield: 12.78 g (69%)

(127c) 5-Amino-2-fluoro-4-methylamino-benzoic acid ethyl ester

Prepared analogously to example 156c from 2-fluoro-4-methylamino-5-nitro-benzoic acid ethyl ester and Raney nickel in THF.

Yield: 11.08 g (99%)

$R_t$ value: 2.11 min (C2)

(127d) 5-[3-(2,6-Dichloro-phenyl)-thioureido]-2-fluoro-4-methylamino-benzoic acid ethyl ester Prepared analogously to example 131d from 5-amino-2-fluoro-4-methylamino-benzoic acid ethyl ester and 1,3-dichloro-2-isothiocyanato-benzene in methanol and acetonitrile.

Yield: 19.44 g (89%)

$R_t$ value: 4.28 min (B2)

(127e) 2-(2,6-Dichloro-phenylamino)-6-fluoro-1-methyl-1H-benzimidazole-5-carboxylic acid ethyl ester DIC (8.0 mL, 51.1 mmol) was added to a solution of the product obtained in 127d (19.4 g, 46.7 mmol) in 200 mL acetonitrile. After stirring for 10 min at reflux the mixture was cooled to ambient temperature and filtered. The organic phase was concentrated i.vac. The residue was taken up in acetonitrile and filtered. Both residues were combined.

Yield: 13.4 g (75%)

mass spectrum: (M+H)$^+$=382/384/386 (chlorine isotopes)

$R_t$ value: 3.68 min (B2)

(127f) 2-(2,6-Dichloro-phenylamino)-6-fluoro-1-methyl-1H-benzimidazole-5-carboxylic acid (5-chloro-4-methyl-pyridin-2-yl)-amide 2 M Trimethyl aluminium solution in hexane (300 μL, 0.6 mmol) was added to a stirred solution of 5-chloro-4-methyl-pyridin-2-ylamine (70 mg, 0.5 mmol) in 3 mL THF. After stirring for 10 min 2-(2,6-dichloro-phenylamino)-6-fluoro-1-methyl-1H-benzimidazole-5-carboxylic acid ethyl ester (150 mg, 0.4 mmol) was added and stirred for 10 days at 60° C. The mixture was diluted with methanol and acetic acid and concentrated i.vac. The residue was purified by RP-HPLC (Symmetry C 18-Symmetry, eluent-gradient ($H_2O$+0.15% HCOOH)/acetonitrile=9:1->0:1). The product containing fractions were concentrated i.vac., the residue taken up in acetonitrile, filtered and dried at 60° C.

Yield: 75 mg (40%)

mass spectrum: $(M+H)^+$=478/480/482/484 (chlorine isotopes)

$R_f$ value: 4.28 min (B6)

In analogy with the above described example, the following compounds were prepared:

Example 131

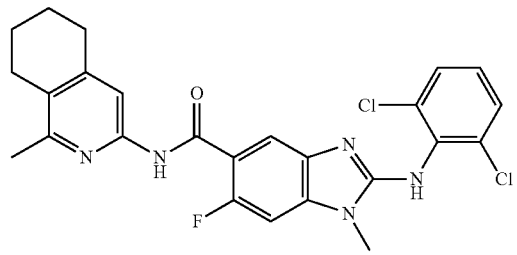 [SMILES: Cc1nc(NC(=O)c2cc3nc(Nc4c(Cl)cccc4Cl)n(C)c3cc2F)cc2c1CCCC2]

2-(2,6-Dichloro-phenylamino)-6-fluoro-1-methyl-1H-benzimidazole-5-carboxylic acid (1-methyl-5,6,7,8-tetrahydro-isoquinolin-3-yl)-amide

(131a) 2,4-Difluoro-5-nitro-benzoic acid ethyl ester

Prepared analogously to example 156a from 2,4-difluoro-5-nitro-benzoyl chloride and ethanol with TEA in THF.

| No. | Structural formula Name | Yield | Mass peak(s) | $R_f$-value or $R_t$ |
|---|---|---|---|---|
| 128 | 2-(2,6-Dichloro-phenylamino)-6-fluoro-1-methyl-1H-benzimidazole-5-carboxylic acid (4,6-dimethyl-pyridin-2-yl)-amide | Σ: 7.2% | $(M + H)^+$ = 458/460/462 (chlorine isotopes) | 3.28 min (B6) |
| 129 | 2-(2,6-Dichloro-phenylamino)-6-fluoro-1-methyl-1H-benzimidazole-5-carboxylic acid (4-chloro-pyridin-2-yl)-amide | Σ: 6.9% | $(M + H)^+$ = 464/466/468/470 (chlorine isotopes) | 3.95 min (B6) |
| 130 | 2-(2,6-Dichloro-phenylamino)-6-fluoro-1-methyl-1H-benzimidazole-5-carboxylic acid (4-trifluoromethyl-pyridin-2-yl)-amide | Σ: 1.3% | $(M + H)^+$ = 498/500/502 (chlorine isotopes) | 4.25 min (B6) |

Yield: 97%
R$_t$ value: 2.80 min (C2)

(131b) 2-Fluoro-4-methylamino-5-nitro-benzoic acid ethyl ester

Prepared analogously to example 156b from 2,4-difluoro-5-nitro-benzoic acid ethyl ester and 2 M methylamine solution in THF. Yield: 69%.

(131c) 5-Amino-2-fluoro-4-methylamino-benzoic acid ethyl ester

Prepared analogously to example 156c from 2-fluoro-4-methylamino-5-nitro-benzoic acid ethyl ester and Raney nickel in THF.
Yield: 99%
R$_t$ value: 2.11 min (C2)

(131d) 5-[3-(2,6-Dichloro-phenyl)-thioureido]-2-fluoro-4-methylamino-benzoic acid ethyl ester A mixture of 5-amino-2-fluoro-4-methylamino-benzoic acid ethyl ester (11.1 g, 52.2 mmol) and 1,3-dichloro-2-isothiocyanato-benzene (10.7 g, 52.5 mmol) in 100 mL acetonitrile was for 1.5 h at ambient temperature. The mixture was filtered, washed with THF. The filtrate was concentrated i.vac. The residue was taken up in acetonitrile, filtered and washed with acetonitrile. Both precipitates were combined and dried.
Yield: 19.4 g (89%)
mass spectrum: (M+H)$^+$=416/418/420 (chlorine isotopes)
R$_t$ value: 4.28 min (B2)

(131e) 2-(2,6-Dichloro-phenylamino)-6-fluoro-1-methyl-1H-benzimidazole-5-carboxylic acid ethyl ester Prepared analogously to example 127e from 5-[3-(2,6-dichloro-phenyl)-thioureido]-2-fluoro-4-methylamino-benzoic acid ethyl ester and DIC in acetonitrile.
Yield: 75%
R$_t$ value: 3.68 min (B2)
mass spectrum: (M+H)$^+$=382/384/386 (chlorine isotopes)

(131f) 2-(2,6-Dichloro-phenylamino)-6-fluoro-1-methyl-1H-benzimidazole-5-carboxylic acid (1-methyl-5,6,7,8-tetrahydro-isoquinolin-3-yl)-amide 2 M Trimethyl aluminium solution in hexane (0.60 mL, 1.2 mmol) was added to a stirred solution of 1-methyl-5,6,7,8-tetrahydro-isoquinolin-3-ylamine (0.14 g, 0.9 mmol) in 2 mL THF. After stirring for 1 h 2-(2,6-dichloro-phenylamino)-6-fluoro-1-methyl-1H-benzimidazole-5-carboxylic acid ethyl ester (0.33 g, 0.9 mmol) in 1 mL THF was added and stirred for 3 days at 60° C. The mixture was poured in 0.1 M NaOH (aq) and filtered. The residue was purified by RP-HPLC (Symmetry C 18, 8 µm, eluent eluent-gradient (H$_2$O+0.15% HCOOH)/acetonitrile=9:1->0:1).
Yield: 0.06 g (13.8%)
mass spectrum: (M+H)$^+$=498/500/502 (chlorine isotopes).

In analogy with the above described example, the following compounds were prepared:

| No. | Structural formula Name | Yield | Mass peak(s) | R$_f$-value or R$_t$ |
|---|---|---|---|---|
| 132 | 2-(2,6-Dichloro-phenylamino)-1H-benzimidazole-5-carboxylic acid (1-methyl-5,6,7,8-tetrahydro-isoquinolin-3-yl)-amide | Σ: 7.714.5% | (M + H)$^+$ = 466/468/470 (chlorine isotopes) | 1.86 min (C2) |
| 138 | 2-(2,6-Dichloro-phenylamino)-6-fluoro-1H-benzimidazole-5-carboxylic acid (1-methyl-5,6,7,8-tetrahydro-isoquinolin-3-yl)-amide | Σ: 7.324% | (M + H)$^+$ = 484/486/488 (chlorine isotopes) | 3.04 min (C2) |
| 139 | 2-(2,6-Dichloro-phenylamino)-1-methyl-1H-benzimidazole-5-carboxylic acid (1-methyl-5,6,7,8-tetrahydro-isoquinolin-3-yl)-amide | Σ: 917% | (M + H)$^+$ = 480/482/484 (chlorine isotopes) | 2.71 min (B2) |

-continued

| Structural formula No. Name | Yield | Mass peak(s) | $R_f$-value or $R_t$ |
|---|---|---|---|
| 372 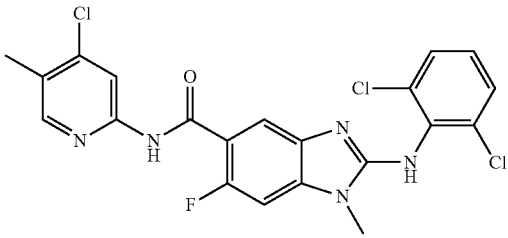 [SMILES: Cc1cnc(NC(=O)c2cc3nc(Nc4c(Cl)cccc4Cl)n(C)c3cc2F)cc1Cl] N-(4-Chloro-5-methylpyridin-2yl)-2-(2,6-dichlorophenylamino)-6-fluoro-1-methyl-1H-benzimidazole-5-carboxamide | Σ: 7.4% | (M + H)⁺ = 478/480/482 (chlorine isotopes) | 3.04 min (C2) |

Example 135

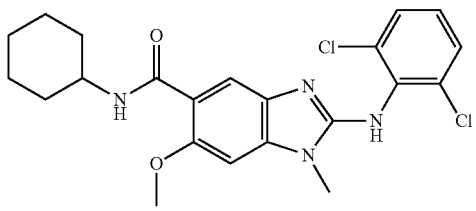 [SMILES: COc1cc2c(cc1C(=O)NC1CCCCC1)nc(Nc1c(Cl)cccc1Cl)n2C]

2-(2,6-Dichloro-phenylamino)-6-methoxy-1-methyl-1H-benzimidazole-5-carboxylic acid cyclohexylamide (135a) 4-(Acetyl-methyl-amino)-2-methoxy-5-nitro-benzoic acid methyl ester A mixture of 4-acetylamino-2-methoxy-5-nitro-benzoic acid methyl ester (4.0 g, 14.9 mmol), methanesulfonic acid methyl ester (1.3 mL, 15.4 mmol) and K₂CO₃ (4.0 g, 28.9 mmol) in 40 mL DMF was stirred overnight at ambient temperature. The mixture was poured onto ice water and diluted with dichloromethane. The organic phase was separated, dried and concentrated i.vac.

Yield: 4.68 g (89%)
$R_t$ value: 2.53 min (C2)

(135b) 2-Methoxy-4-methylamino-5-nitro-benzoic acid

Prepared analogously to example 3b from 4-(Acetyl-methyl-amino)-2-methoxy-5-nitro-benzoic acid methyl ester and NaOH in ethanol.
Yield: 93%
mass spectrum: (M+H)⁺=227
$R_t$ value: 2.26 min (B2)

(135c) 5-Amino-2-methoxy-4-methylamino-benzoic acid

Prepared analogously to example 1b by hydrogenation of 2-methoxy-4-methylamino-5-nitro-benzoic acid using palladium/charcoal 10% in THF and methanol.

Yield: 36%
$R_t$ value: 1.00 min (C2)

(135d) 5-Amino-4-[3-(2,6-dichloro-phenyl)1-methyl-thioureido]-2-methoxy-benzoic acid Prepared analogously to example 131d from 5-amino-2-methoxy-4-methylamino-benzoic acid methyl ester and 1,3-dichloro-2-isothiocyanato-benzene in methanol.

Yield: 40%
$R_t$ value: 2.32 min (C2); mass spectrum: (M+H)⁺=400/402/404 (chlorine isotopes).

(135e) 2-(2,6-Dichloro-phenylamino)-6-methoxy-1-methyl-1H-benzimidazole-5-carboxylic acid A mixture of DIC (275 µL, 1.8 mmol) and 2,2,2-trifluoro-N,O-bis-(trimethylsilyl)-acetamide (450 µL, 1.7 mmol) was added to a refluxed mixture of the product obtained in 135d (610 mg, 1.5 mmol) in 25 mL acetonitrile. After 1 h of stirring the mixture glacial acetic acid was added and the mixture was concentrated i.vac. The residue was taken up in water and diluted with NaOH (aq). The mixture was filtered. The filtrate was acidified with HCl (aq), filtered and washed with water and acetonitrile.

Yield: 470 mg (84%)
$R_t$ value: 1.83 min (C2)
mass spectrum: (M+H)⁺=366/368/370 (chlorine isotopes)

(135f) 2-(2,6-Dichloro-phenylamino)-6-methoxy-1-methyl-1H-benzimidazole-5-carboxylic acid cyclohexylamide Prepared analogously to example 3c from 2-(2,6-dichloro-phenylamino)-6-methoxy-1-methyl-1H-benzimidazole-5-carboxylic acid, cyclohexylamine, TBTU and TEA in DMF.

Yield: 66%
$R_t$ value: 3.27 min (B6)
mass spectrum: (M+H)⁺=447/449/451 (chlorine isotopes)
In analogy with the above described example, the following compounds were prepared:

| No. | Structural formula Name | Yield | Mass peak(s) | $R_f$ value or $R_t$ |
|---|---|---|---|---|
| 136 | 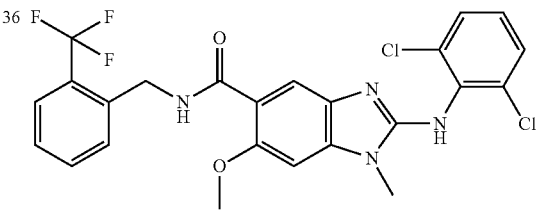<br>2-(2,6-Dichloro-phenylamino)-6-methoxy-1-methyl-1H-benzimidazole-5-carboxylic acid 2-trifluoromethyl-benzylamide | Σ: 6.7% | (M + H)⁺ = 523/525/527 (chlorine isotopes) | 3.53 min (B6) |
| 359 | 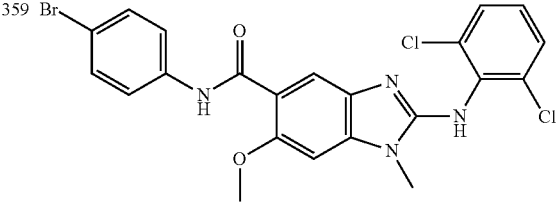<br>2-(2,6-Dichlorophenylamino)-6-methoxy-1-methyl-N-(4-bromo-phenyl)-1H-benzimidazole-5-carboxamide | Σ: 13% | (M + H)⁺ = 519/521/523 (chlorine isotopes) | 1.83 min (E7) |
| 367 | 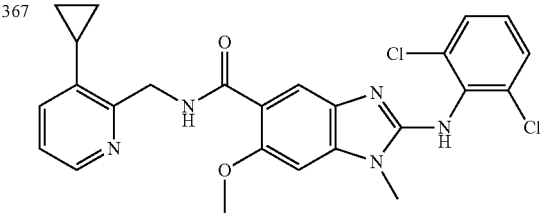<br>N-((3-Cyclopropylpyridin-2-yl)-methyl)-2-(2,6-dichlorophenylamino)-6-methoxy-1-methyl-1H-benzimidazole-5-carboxamide | Σ: 16% | (M + H)⁺ = 496/498/500 (chlorine isotopes) | 1.03 min (F8) |
| 369 | 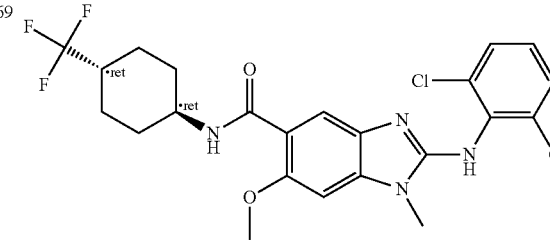<br>2-(2,6-Dichlorophenylamino)-6-methoxy-1-methyl-N-((1r,4r)-4-trifluoromethyl-cyclohexyl)-1H-benzimidazole-5-carboxamide | Σ: 4% | (M + H)⁺ = 515/517/519 (chlorine isotopes) | 1.7 min (F8) |
| 370 | 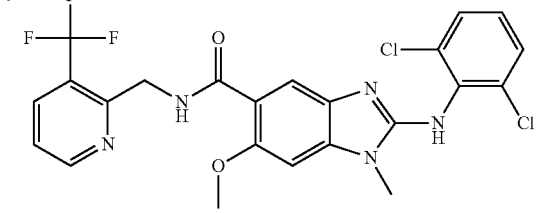<br>2-(2,6-Dichlorophenylamino)-6-methoxy-1-methyl-N-((3-trifluoromethyl-pyridin-2-yl)methyl)-1H-benzimidazole-5-carboxamide | Σ: 17% | (M + H)⁺ = 524/526/528 (chlorine isotopes) | 1.59 min (F8) |
| 465 | 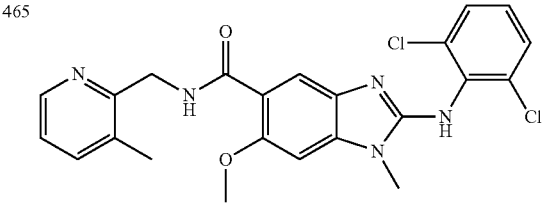<br>2-(2,6-Dichlorophenylamino)-6-methoxy-1-methyl-N-((3-methylpyridin-2-yl)methyl)-1H-benzimidazole-5-carboxamide | Σ: 5.2% | (M + H)⁺ = 470/472/474 (chlorine isotopes) | 0.98 min (F8) |

| Structural formula No. Name | | Yield | Mass peak(s) | $R_f$ value or $R_t$ |
|---|---|---|---|---|
| 491 | 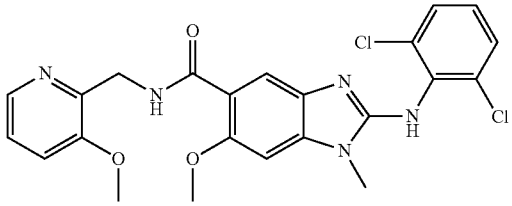 [SMILES: COc1cc2c(cc1C(=O)NCc1ncccc1OC)nc(Nc1c(Cl)cccc1Cl)n2C] 2-(2,6-Dichlorophenylamino)-6-methoxy-N-((3-methoxypyridin-2-yl)-methyl)-1-methyl-1H-benzimidazole-5-carboxamide | Σ: 6% | $(M + H)^+ =$ 486/488/490 (chlorine isotopes) | 1.04 min (F8) |
| 577 | 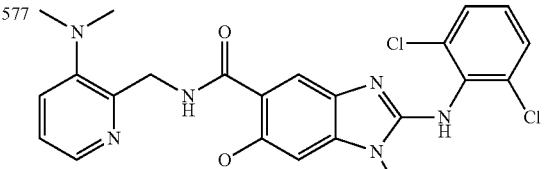 2-(2,6-Dichlorophenylamino)-6-methoxy-N-((3-methylpyridin-2-yl)-methyl)-1H-benzimidazole-5-carboxamide | Σ: 9% | $(M + H)^+ =$ 456/458/460 (chlorine isotopes) | 0.94 min (F8) |
| 631 | 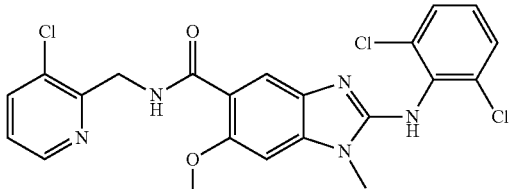 2-(2,6-Dichlorophenylamino)-6-methoxy-N-((3-chlorpyridin-2-yl)-methyl)-1H-benzimidazole-5-carboxamide | Σ: 5.3% | $(M + H)^+ =$ 490/492/ 494/496 (chlorine isotopes) | 2.05 min (F7) |

Example 140

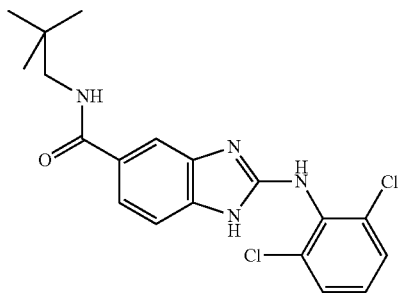 [SMILES: CC(C)(C)CNC(=O)c1ccc2[nH]c(Nc3c(Cl)cccc3Cl)nc2c1]

2-(2,6-Dichloro-phenylamino)-1H-benzimidazole-5-carboxylic acid (2,2-dimethyl-propyl)-amide (140a) 2-(2,6-Dichloro-phenylamino)-1H-benzimidazole-5-carboxylic acid A mixture of 1,3-dichloro-2-isothiocyanato-benzene (4.50 g, 22.1 mmol) in 50 mL dichloromethane was added to a stirred solution of 3,4-diamino-benzoic acid ethyl ester (4.00 g, 22.2 mmol) in 100 mL dichloromethane. After stirring for 2 days the mixture was concentrated i.vac. The residue was taken up in 200 mL dichloromethane. TEA (7.0 mL, 49.9 mmol) and DMAP (100 mg, 0.8 mmol) were added. A mixture of methanesulfonyl chloride (1.70 mL, 22.0 mmol) in 50 mL dichloromethane was added to the solution and stirred overnight. The mixture was concentrated i.vac. The residue was taken up in methanol and 4 M NaOH (aq) was added. After stirring overnight at ambient temperature the mixture was heated to reflux for 2 h and concentrated i.vac. The residue was taken up in water and methanol and neutralized with HCl (aq). The mixture was filtered and washed with water.

Yield: 5.22 g (74%); mass spectrum: $(M+H)^+=322$ (140b) 2-(2,6-Dichloro-phenylamino)-1H-benzimidazole-5-carboxylic acid (2,2-dimethyl-propyl)-amide Prepared analogously to example 3c from 2-(2,6-dichloro-phenylamino)-1H-benzimidazole-5-carboxylic acid, 2,2-dimethyl-propylamine, TEA and TBTU in DMF.

Yield: 88% mass spectrum: $(M+H)^+=363/65/67$ $R_t$ value: 1.68 min (CC)

In analogy with the above described example, the following compounds were prepared:

| No. | Structural formula Name | Yield | Mass peak(s) | $R_f$ value or $R_t$ |
|---|---|---|---|---|
| 141 | 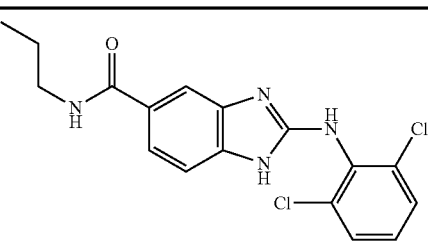<br>2-(2,6-Dichloro-phenylamino)-3H-benzimidazole-5-carboxylic acid propylamide | Σ: 44% | (M + H)⁺ = 391/393/395 (chlorine isotopes) | 1.85 min (CC) |

Example 142

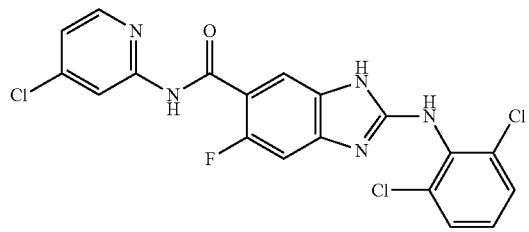 [SMILES: O=C(Nc1cc(Cl)ccn1)c1cc2[nH]c(Nc3c(Cl)cccc3Cl)nc2cc1F]

2-(2,6-Dichloro-phenylamino)-6-fluoro-3H-benzimidazole-5-carboxylic acid (4-chloro-pyridin-2-yl)-amide (142a) 4-Amino-2-fluoro-benzoic acid A solution of 2-fluoro-4-nitro-benzoic acid (2.8 g, 15.1 mmol) in 100 mL THF was combined with palladium/charcoal 10% (250 mg) and hydrogenated for 6.5 h in a Parr apparatus at ambient temperature at 3 bar hydrogen pressure. Then the mixture is filtered.
Yield: 2.33 g (99%)
$R_t$ value: 2.07 min (B1)

(142b) 4-Acetylamino-2-fluoro-benzoic acid

A mixture of 4-amino-2-fluoro-benzoic acid (5.61 g, 36.2 mmol) and acetic anhydride (5.13 mL, 54.3 mmol) in 60 mL acetic acid was stirred at 60° C. overnight. The mixture was taken up in 250 mL water and stirred for 30 min. The precipitate was filtered and washed with water. The filtrate was washed with ethyl acetate. The organic phase was neutralized with sat. $K_2CO_3$ (aq) and concentrated i.vac. A small volume was left, the precipitate was filtered and combined with the first isolated precipitate.
Yield: 6.7 g (94%)
mass spectrum: (M+H)⁺=198
$R_t$ value: 2.40 min (B1)

(142c) 4-Acetylamino-2-fluoro-5-nitro-benzoic acid

Prepared analogously to example 83b from 4-acetylamino-2-fluoro-benzoic acid, conc. sulphuric acid and conc. nitric acid.
Yield: 72%
mass spectrum: (M−H)⁻=241
$R_t$ value: 2.84 min (B1)

(142d) 4-Amino-5-nitro-2-fluoro-benzoic acid

A solution of the product obtained at 142c (5.95 g, 24.6 mmol) in 100 mL dioxane and 100 mL half-conc. hydrochloric acid was heated to 110° C. for 1.5 h. The mixture was cooled in an ice bath, filtered and washed with water.
Yield: 4.04 g (82%)
mass spectrum: (M−H)⁻=199
$R_t$ value: 2.73 min (B1)

(142e) 4-Amino-5-nitro-2-fluoro-benzoyl chloride

Prepared analogously to example 53a from 4-amino-5-nitro-2-fluoro-benzoic acid and thionyl chloride in 1,2-dichloroethane. Yield: 99%

(142f) 4-Amino-N-(4-chloro-pyridin-2-yl)-2-fluoro-5-nitro-benzamide

The product obtained at 142e (0.40 g, 1.8 mmol) was added to a stirred solution of 4-chloro-pyridin-2-ylamine (0.24 g, 1.8 mmol) and pyridine (0.29 mL, 3.7 mmol) in 30 mL dichloromethane. After stirring overnight the mixture was concentrated i.vac. The residue was taken up in water, filtered and washed with water. The residue was taken up in ethyl acetate and aq. $NaHCO_3$ solution (5%). The organic phase was dried and concentrated i.vac.
Yield: 0.32 g (56%)
mass spectrum: (M+H)⁺=311
$R^f$ value: 0.48 (silica gel; dichloromethane/ethanol=19:1)

(142g) 4,5-Diamino-N-(4-chloro-pyridin-2-yl)-2-fluoro-benzamide

A solution of the product obtained at 142f (320 mg, 1.0 mmol) in 20 mL THF was combined with Raney nickel (70 mg) and hydrogenated in a Parr apparatus at ambient temperature for 1.5 days at 3 bar hydrogen pressure. Then the mixture is filtered and concentrated i.vac. The residue is purified by chromatography on RP-HPLC (stable bond C18, 5 µm). The mixture was concentrated i.vac., taken up in water and treated with $K_2CO_3$. The aq. phase is diluted with ethyl acetate. The organic phase is dried, filtered and concentrated i.vac.
Yield: 40 mg (13.8%)
$R_f$ value: 2.21 min (C1)

(142h) 2-(2,6-Dichloro-phenylamino)-6-fluoro-3H-benzimidazole-5-carboxylic acid (4-chloro-pyridin-2-yl)-amide Prepared analogously to example 1c from 4,5-diamino-N-(4-chloro-pyridin-2-yl)-2-fluoro-benzamide and 1,3-dichloro-2-isothiocyanato-benzene in acetonitrile with DIC.

Yield: 39 mg (61%)

mass spectrum: (M+H)⁺=450/452/454/456 (chlorine isotopes)

$R_t$ value: 2.51 min (C1)

In analogy with the above described example, the following compounds were prepared:

Yield: 36%

$R_f$ value: 0.55 (silica gel; dichloromethane/ethanol=9:1)

(145b) 4-Amino-2-methyl-5-nitro-benzoic acid

A mixture of 4-acteylamino-2-methyl-3-nitro-benzoic acid (4.8 g, 20.2 mmol) and 6 M HCl (aq) (150 mL) in 120 mL dioxane was stirred for 15 min at 105° C. The mixture was cooled, filtered and washed with water.

Yield: 3.6 g (91%)

$R_t$ value: 3.70 min (A1)

| No. | Structural formula Name | Yield | Mass peak(s) | $R_f$ value or $R_t$ |
|---|---|---|---|---|
| 143 | ![structure] 2-(2,6-Dichloro-phenylamino)-6-fluoro-3H-benzimidazole-5-carboxylic acid (3-chloro-phenyl)-amide | Σ: 45% | (M + H)⁺ = 449/451/453/455. (chlorine isotopes) | 2.57 min (C1) |
| 144 | ![structure] 2-(2,6-Dichloro-phenylamino)-6-fluoro-3H-benzimidazole-5-carboxylic acid (4-bromo-phenyl)-amide | Σ: 88% | (M + H)⁺ = 491/493/495/497 (chlorine and bromine isotopes) | 2.57 min (C1) |

Example 145

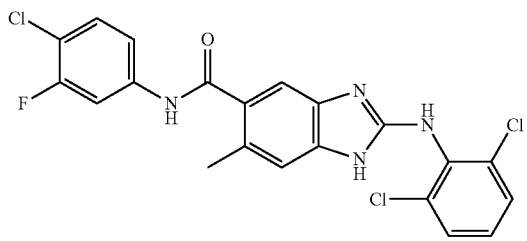 [SMILES: Cc1cc2[nH]c(Nc3c(Cl)cccc3Cl)nc2cc1C(=O)Nc1ccc(Cl)c(F)c1]

2-(2,6-Dichloro-phenylamino)-6-methyl-1H-benzimidazole-5-carboxylic acid (4-chloro-3-fluorophenyl)-amide

(145a) 4-Acteylamino-2-methyl-3-nitro-benzoic acid

Prepared analogously to example 83b from 4-acetylamino-2-methyl-benzoic acid, conc. sulphuric acid and conc. nitric acid.

(145c) 4-Amino-2-methyl-5-nitro-benzoylchloride

Prepared analogously to example 53a from 4-amino-2-methyl-5-nitro-benzoic acid and thionyl chloride in dichloroethane.

Yield: 99%

(145d) 4-Amino-N-(4-chloro-3-fluoro-phenyl)-2-methyl-5-nitro-benzamide

4-Amino-2-methyl-5-nitro-benzoylchloride (950 mg, 4.4 mmol) was added to a stirred mixture of 4-chloro-3-fluoroaniline (644 mg, 4.4 mmol) and TEA (0.74 mL, 5.3 mmol) in 80 mL THF. After stirring for 2 h the mixture was concentrated i.vac. The residue was taken up in water and filtrated.

Yield: 1.40 g (98%)

mass spectrum: (M+H)⁺=324/326 (chlorine isotopes)

(145e) 4,5-Diamino-N-(4-chloro-3-fluoro-phenyl)-2-methyl-benzamide

Prepared analogously to example 14b from 4-amino-N-(4-chloro-3-fluoro-phenyl)-2-methyl-5-nitro-benzamide and Raney nickel in THF.

Yield: 87%

$R_f$ value: 0.2 (silica gel; dichloromethane/ethanol=19:1)

(145f) 2-(2,6-Dichloro-phenylamino)-6-methyl-1H-benzimidazole-5-carboxylic acid (4-chloro-3-fluoro-phenyl)-amide Prepared analogously to example 1c from 4,5-diamino-N-(4-chloro-3-fluoro-phenyl)-2-methyl-benzamide and 1,3-dichloro-2-isothiocyanato-benzene with DIC in acetonitrile.
Yield: 58%
mass spectrum: (M+H)⁺=463/65/67 (chlorine isotopes)
$R_f$ value: 2.53 min (C1)
In analogy with the above described example, the following compounds were prepared:

| No. | Structural formula Name | Yield | Mass peak(s) | $R_f$ value or $R_t$ |
|---|---|---|---|---|
| 148 | 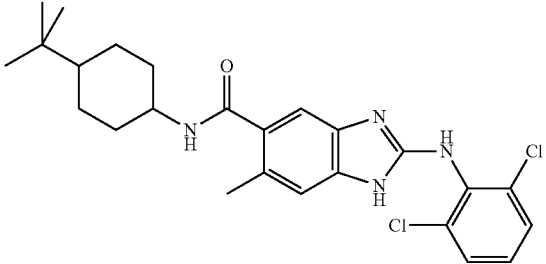 [SMILES: Cc1cc2[nH]c(Nc3c(Cl)cccc3Cl)nc2cc1C(=O)NC1CCC(C(C)(C)C)CC1] 2-(2,6-Dichloro-phenylamino)-6-methyl-1H-benzimidazole-5-carboxylic acid (4-tert.-butyl-cyclohexyl)-amide | Σ: 8.5% | (M + H)⁺= 473/475/477 (chlorine isotopes) | 2.71 min (C1) |

Example 146

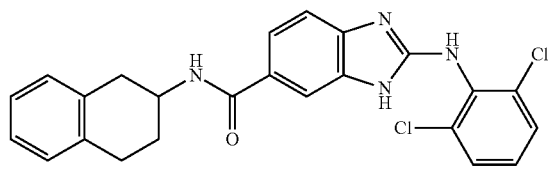 [SMILES: O=C(NC1CCc2ccccc2C1)c1ccc2nc(Nc3c(Cl)cccc3Cl)[nH]c2c1]

2-(2,6-Dichloro-phenylamino)-3H-benzimidazole-5-carboxylic acid (1,2,3,4-tetrahydro-naphthalen-2-yl)-amide (146a) 2-(2,6-Dichloro-phenylamino)-3H-benzimidazole-5-carboxylic acid A mixture of 3,4-diamino-benzoic acid ethyl ester (5.0 g, 27.8 mmol) and 1,3-dichloro-2-isothiocyanato-benzene (5.66 g, 27.8 mmol) in 40 mL DMF was stirred for 2 h. DIC (4.40 mL, 28.2 mmol) was added and the mixture stirred overnight. After 30 min stirring at 80° C. water was added and the mixture was concentrated i.vac. The residue was taken up in ethanol and 1 M aq. NaOH. The mixture stirred overnight at reflux. Ethanol was evaporated and the aq. phase diluted with water. The precipitate was filtered and washed with water. The filtrate was acidified with formic acid and cooled. The mixture was filtered and washed with water.
Yield: 8.58 g (96%)

(146b) 2-(2,6-Dichloro-phenylamino)-3H-benzimidazole-5-carboxylic acid (1,2,3,4-tetrahydro-naphthalen-2-yl)-amide Prepared analogously to example 3c from 2-(2,6-dichloro-phenylamino)-3H-benzimidazole-5-carboxylic acid, 1,2,3,4-tetrahydro-naphthalen-2-ylamin hydrochloride, TBTU and TEA in DMF and THF.
Yield: 50%
$R_t$ value: 2.35 min (C1)
mass spectrum: (M+H)⁺=451/453/455 (chlorine isotopes)
In analogy with the above described example, the following compounds were prepared:

| No. | Structural formula Name | Yield | Mass peak(s) | $R_f$ value or $R_t$ |
|---|---|---|---|---|
| 147 | 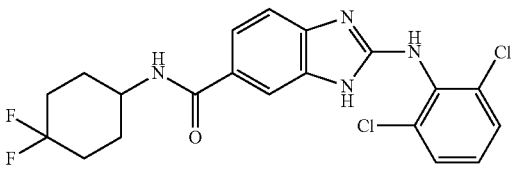 [SMILES: O=C(NC1CCC(F)(F)CC1)c1ccc2nc(Nc3c(Cl)cccc3Cl)[nH]c2c1] 2-(2,6-Dichloro-phenylamino)-3H-benzimidazole-5-carboxylic acid (4,4-difluoro-cyclohexyl)-amide | Σ: 4128% | (M + H)⁺= 473/475/477 (chlorine isotopes) | 2.71 min (C1) |

-continued

| No. | Structural formula Name | Yield | Mass peak(s) | $R_f$ value or $R_t$ |
|---|---|---|---|---|
| 153 | 2-(2,6-Dichloro-phenylamino)-1H-benzimidazole-5-carboxylic acid chroman-3-ylamide | Σ: 245% | (M + H)⁺ = 453/455/457 (chlorine isotopes) | 2.19 min (C5) |
| 161 | 2-(2,6-Dichloro-phenylamino)-1H-benzimidazole-5-carboxylic acid (trans-4-trifluoromethyl-cyclohexyl)-amide | Σ: 446% | (M + H)⁺ = 471/473/475 (chlorine isotopes) | 2.23 min (C5) |
| 168 | 2-(2,6-Dichloro-phenylamino)-1H-benzimidazole-5-carboxylic acid (cis-4-trifluoromethyl-cyclohexyl)-amide | Σ: 3925% | (M + H)⁺ = 453/455/457 (chlorine isotopes) | 2.19 min (C5) |
| 418 | 4-Chloro-2-(2-(2,6-dichlorophenylamino)-1H-benzimidazole-6-carboxamido)-5-methylpyridine 1-oxide | Σ: 25% | (M + H)⁺ = 462/464/466 (chlorine isotopes) | 0.51 (silica gel, dichlormethan/methanol = 9:1) |

| No. | Structural formula Name | Yield | Mass peak(s) | $R_f$-value or $R_t$ |
|---|---|---|---|---|
| 432 | 2-(2,6-Dichloro-4-fluorophenylamino)-1-methyl-N-((1R,4R)-4-trifluoromethyl-cyclohexyl)-1H-benzimidazole-5-carboxamide | Σ: 33% | $(M + H)^+$ = 503/505/507 (chlorine isotopes) | 3.66 min (B1) |
| 214 | 2-(2,6-Dichloro-phenylamino)-1H-benzimidazole-5-carboxylic acid cycloheptyl-amide | Σ: 52% | $(M + H)+$ = 417/419/421 (chlorine isotopes) | 1.72 min (CC) |
| 215 | 2-(2,6-Dichloro-phenylamino)-1H-benzimidazole-5-carboxylic acid (4-methyl-cyclohexyl)-amide | Σ: 51% | $(M + H)+$ = 417/419/421 (chlorine isotopes) | 1.74 min (CC) |
| 216 | 2-(2,6-Dichloro-phenylamino)-1H-benzimidazole-5-carboxylic acid ((1R,4R)-4-methoxy-cyclohexyl)-amide | Σ: 16% | $(M + H)+$ = 433/435/437 (chlorine isotopes) | 1.51 min (CC) |

| No. | Structural formula Name | Yield | Mass peak(s) | $R_f$-value or $R_t$ |
|---|---|---|---|---|
| 217 | 2-(2,6-Dichloro-phenylamino)-1H-benzimidazole-5-carboxylic acid (tetrahydro-pyran-4-ylmethyl)-amide | Σ: 41% | (M + H)+ = 419/421/423 (chlorine isotopes) | 1.46 min (CC) |
| 218 | 2-(2,6-Dichloro-phenylamino)-1H-benzimidazole-5-carboxylic acid (3,3,5-trimethyl-cyclohexyl)-amide | Σ: 53% | (M + H)+ = 445/447/449 (chlorine isotopes) | 1.87 min (CC) |
| 219 | 2-(2,6-Dichloro-phenylamino)-1H-benzimidazole-5-carboxylic acid cyclopentylmethyl-amide | Σ: 40% | (M + H)+ = 403/405/407 (chlorine isotopes) | 1.68 min (CC) |
| 220 | 2-(2,6-Dichloro-phenylamino)-1H-benzimidazole-5-carboxylic acid (3-trifluoromethyl-pyridin-2-ylmethyl)-amide | Σ: 42% | (M + H)+ = 480/482/484 (chlorine isotopes) | 1.62 min (CC) |

| No. | Structural formula Name | Yield | Mass peak(s) | $R_f$-value or $R_t$ |
|---|---|---|---|---|
| 221 | 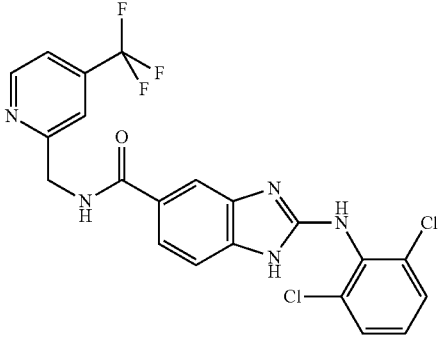 [SMILES: O=C(NCc1cc(C(F)(F)F)ccn1)c1ccc2[nH]c(Nc3c(Cl)cccc3Cl)nc2c1]<br>2-(2,6-Dichloro-phenylamino)-1H-benzimidazole-5-carboxylic acid (4-trifluoromethyl-pyridin-2-ylmethyl)-amide | Σ:<br>26% | (M + H)+ = 480/482/484 (chlorine isotopes) | 1.62 min (CC) |
| 222 | 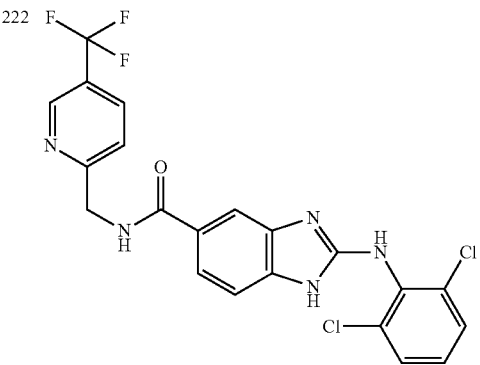<br>2-(2,6-Dichloro-phenylamino)-1H-benzimidazole-5-carboxylic acid (5-trifluoromethyl-pyridin-2-ylmethyl)-amide | Σ:<br>26% | (M + H)+ = 480/482/484 (chlorine isotopes) | 1.62 min (CC) |
| 223 | 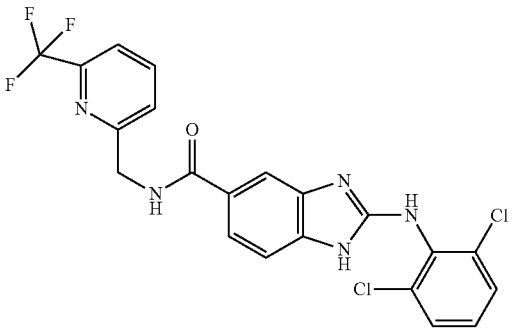 [SMILES: O=C(NCc1cccc(C(F)(F)F)n1)c1ccc2[nH]c(Nc3c(Cl)cccc3Cl)nc2c1]<br>2-(2,6-Dichloro-phenylamino)-1H-benzimidazole-5-carboxylic acid (6-trifluoromethyl-pyridin-2-ylmethyl)-amide | Σ:<br>53% | (M + H)+ = 480/482/484 (chlorine isotopes) | 1.67 min (CC) |
| 224 | 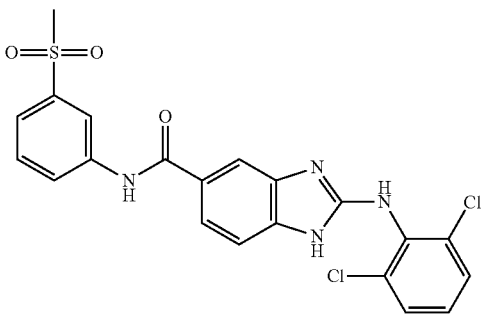 [SMILES: CS(=O)(=O)c1cccc(NC(=O)c2ccc3[nH]c(Nc4c(Cl)cccc4Cl)nc3c2)c1]<br>2-(2,6-Dichloro-phenylamino)-1H-benzimidazole-5-carboxylic acid (3-methanesulfonyl-phenyl)-amide | Σ:<br>7% | (M + H)+ = 475/477/479 (chlorine isotopes) | 1.57 min (CC) |

-continued

| No. | Structural formula Name | Yield | Mass peak(s) | $R_f$-value or $R_t$ |
|---|---|---|---|---|

225 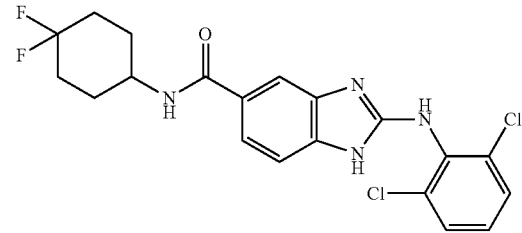 [SMILES: O=C(NC1CCC(F)(F)CC1)c1ccc2[nH]c(Nc3c(Cl)cccc3Cl)nc2c1]

2-(2,6-Dichloro-phenylamino)-1H-benzimidazole-5-carboxylic acid (4,4-difluoro-cyclohexyl)-amide

Σ: 64%

(M + H)+ = 439/441/443 (chlorine/ isotopes)

1.65 min (CC)

226 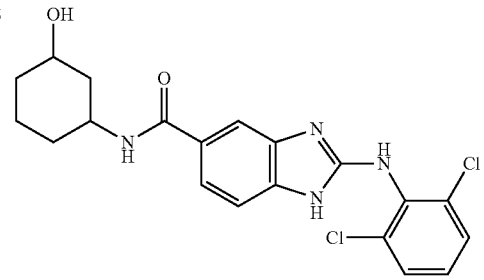

2-(2,6-Dichloro-phenylamino)-1H-benzimidazole-5-carboxylic acid (3-hydroxy-cyclohexyl)-amide

Σ: 48%

(M + H)+ = 419/421/423 (chlorine isotopes)

1.44 min (CC)

227 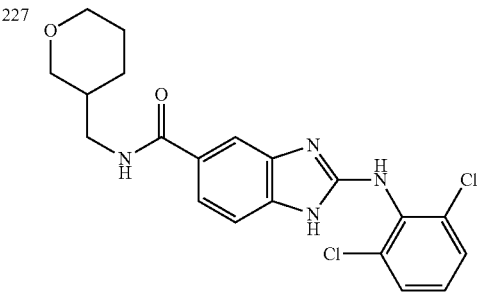

2-(2,6-Dichloro-phenylamino)-1H-benzimidazole-5-carboxylic acid (tetrahydro-pyran-3-ylmethyl)-amide

Σ: 53%

(M + H)+ = 419/421/423 (chlorine isotopes)

1.49 min (CC)

228 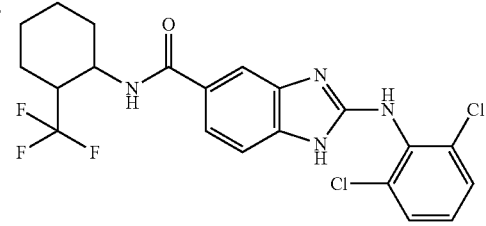

2-(2,6-Dichloro-phenylamino)-1H-benzimidazole-5-carboxylic acid (2-trifluoromethyl-cyclohexyl)-amide

Σ: 47%

(M + H)+ = 471/473/475 (chlorine isotopes)

1.73 min (CC)

| No. | Structural formula / Name | Yield | Mass peak(s) | $R_f$ value or $R_t$ |
|---|---|---|---|---|
| 229 | 2-(2,6-Dichloro-phenylamino)-1H-benzimidazole-5-carboxylic acid (3-trifluoromethyl-cyclohexyl)-amide | Σ: 50% | (M + H)+ = 471/473/475 (chlorine isotopes) | 1.77 min (CC) |
| 230 | 2-(2,6-Dichloro-phenylamino)-1H-benzimidazole-5-carboxylic acid (4-trifluoromethyl-cyclohexyl)-amide | Σ: 64% | (M + H)+ = 471/473/475 (chlorine isotopes) | 1.75 min (CC) |
| 231 | 2-(2,6-Dichloro-phenylamino)-1H-benzimidazole-5-carboxylic acid (1-cyano-cyclohexyl)-amide | Σ: 8% | (M + H)+ = 428/430/432 (chlorine isotopes) | 1.66 min (CC) |
| 232 | 2-(2,6-Dichloro-phenylamino)-1H-benzimidazole-5-carboxylic acid (2-pyridin-3-yl-ethyl)-amide | Σ: 60% | (M + H)+ = 426/428/430 (chlorine isotopes) | 1.30 min (CC) |

| No. | Structural formula Name | Yield | Mass peak(s) | $R_f$-value or $R_t$ |
|---|---|---|---|---|
| 233 | 2-(2,6-Dichloro-phenylamino)-1H-benzimidazole-5-carboxylic acid (2-pyridin-4-yl-ethyl)-amide | Σ: 55% | (M + H)+ = 426/428/430 (chlorine isotopes) | 1.30 min (CC) |
| 234 | 2-(2,6-Dichloro-phenylamino)-1H-benzimidazole-5-carboxylic acid (tetrahydro-furan-2-ylmethyl)-amide | Σ: 55% | (M + H)+ = 405/407/409 (chlorine isotopes) | 1.47 min (CC) |
| 235 | 2-(2,6-Dichloro-phenylamino)-1H-benzimidazole-5-carboxylic acid (pyridin-2-ylmethyl)-amide | Σ: 42% | (M + H)+ = 412/414/416 (chlorine isotopes) | 1.30 min (CC) |
| 236 | 2-(2,6-Dichloro-phenylamino)-1H-benzimidazole-5-carboxylic acid (pyridin-4-ylmethyl)-amide | Σ: 43% | (M + H)+ = 412/414/416 (chlorine isotopes) | 1.29 min (CC) |

| No. | Structural formula Name | Yield | Mass peak(s) | $R_f$-value or $R_t$ |
|---|---|---|---|---|
| 237 | 2-(2,6-Dichloro-phenylamino)-1-methyl-1H-benzimidazole-5-carboxylic acid (2-hydroxy-cyclohexyl)-amide | Σ: 64% | (M + H)+ = 433/435/437 (chlorine isotopes) | 1.49 min (CC) |
| 238 | 2-(2,6-Dichloro-phenylamino)-1-methyl-1H-benzimidazole-5-carboxylic acid cycloheptylamide | Σ: 64% | (M + H)+ = 431/433/435 (chlorine isotopes) | 1.70 min (CC) |
| 239 | 2-(2,6-Dichloro-phenylamino)-1-methyl-1H-benzimidazole-5-carboxylic acid (4-methyl-cyclohexyl)-amide | Σ: 62% | (M + H)+ = 431/433/435 (chlorine isotopes) | 1.72 min (CC) |
| 240 | 2-(2,6-Dichloro-phenylamino)-1-methyl-1H-benzimidazole-5-carboxylic acid (trans-4-methoxy-cyclohexyl)-amide | Σ: 32% | (M + H)+ = 447/449/451 (chlorine isotopes) | 1.50 min (CC) |
| 241 | 2-(2,6-Dichloro-phenylamino)-1-methyl-1H-benzimidazole-5-carboxylic acid (3,3,5-trimethyl-cyclohexyl)-amide | Σ: 62% | (M + H)+ = 459/461/463 (chlorine isotopes) | 1.83 min (CC) |

| No. | Structural formula Name | Yield | Mass peak(s) | $R_f$-value or $R_t$ |
|---|---|---|---|---|
| 242 | 2-(2,6-Dichloro-phenylamino)-1-methyl-1H-benzimidazole-5-carboxylic acid (1-pyridin-2-yl-ethyl))-amide | Σ: 81% | (M + H)+ = 440/442/444 (chlorine isotopes) | 1.30 min (CC) |
| 243 | 2-(2,6-Dichloro-phenylamino)-1-methyl-1H-benzimidazole-5-carboxylic acid cyclopentylmethyl-amide | Σ: 46% | (M + H)+ = 417/419/421 (chlorine isotopes) | 1.66 min (CC) |
| 244 | 2-(2,6-Dichloro-phenylamino)-1-methyl-1H-benzimidazole-5-carboxylic acid (3-trifluoromethyl-pyridin-2-ylmethyl)-amide | Σ: 58% | (M + H)+ = 494/496/498 (chlorine isotopes) | 1.61 min (CC) |
| 245 | 2-(2,6-Dichloro-phenylamino)-1-methyl-1H-benzimidazole-5-carboxylic acid (4-trifluoromethyl-pyridin-2-ylmethyl)-amide | Σ: 41% | (M + H)+ = 494/496/498 (chlorine isotopes) | 1.61 min (CC) |

| No. | Structural formula Name | Yield | Mass peak(s) | $R_f$-value or $R_t$ |
|---|---|---|---|---|
| 246 | 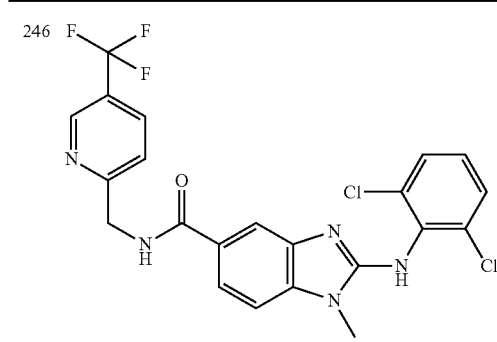<br>2-(2,6-Dichloro-phenylamino)-1-methyl-1H-benzimidazole-5-carboxylic acid (5-trifluoromethyl-pyridin-2-ylmethyl)-amide | Σ: 55% | (M + H)+ = 494/496/498 (chlorine isotopes) | 1.62 min (CC) |
| 247 | 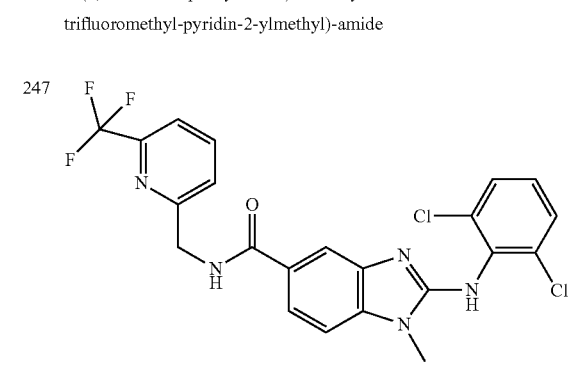<br>2-(2,6-Dichloro-phenylamino)-1-methyl-1H-benzimidazole-5-carboxylic acid (6-trifluoromethyl-pyridin-2-ylmethyl)-amide | Σ: 60% | (M + H)+ = 494/496/498 (chlorine isotopes) | 1.65 min (CC) |
| 248 | 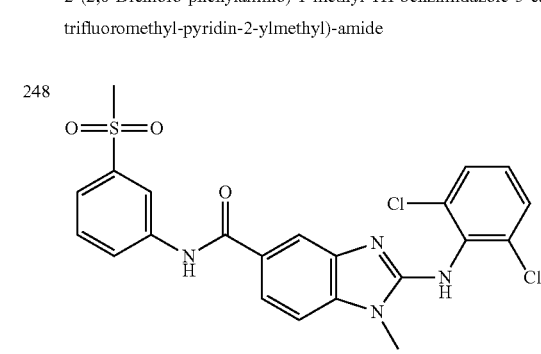<br>2-(2,6-Dichloro-phenylamino)-1-methyl-1H-benzimidazole-5-carboxylic acid (3-methanesulfonyl-phenyl)-amide | Σ: 25% | (M + H)+ = 489/491/493 (chlorine isotopes) | 1.56 min (CC) |
| 249 | 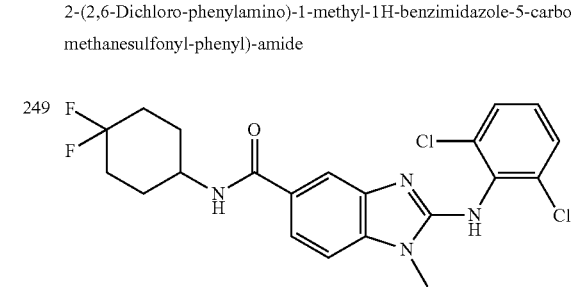<br>2-(2,6-Dichloro-phenylamino)-1-methyl-1H-benzimidazole-5-carboxylic acid (4,4-difluoro-cyclohexyl)-amide | Σ: 67% | (M + H)+ = 453/455/457 (chlorine/ isotopes) | 1.63 min (CC) |

-continued

| No. | Structural formula Name | Yield | Mass peak(s) | $R_f$ value or $R_t$ |
|---|---|---|---|---|
| 250 | 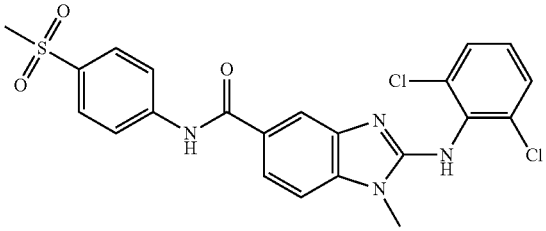 [SMILES: Cn1c(Nc2c(Cl)cccc2Cl)nc2cc(C(=O)Nc3ccc(S(C)(=O)=O)cc3)ccc21]<br>2-(2,6-Dichloro-phenylamino)-1-methyl-1H-benzimidazole-5-carboxylic acid (4-methanesulfonyl-phenyl)-amide | Σ: 5% | (M + H)+ = 489/491/493 (chlorine isotopes) | 1.56 min (CC) |
| 251 | 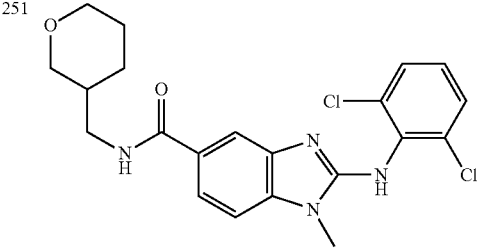<br>2-(2,6-Dichloro-phenylamino)-1-methyl-1H-benzimidazole-5-carboxylic acid (tetrahydro-pyran-3-ylmethyl)-amide | Σ: 57% | (M + H)+ = 433/435/437 (chlorine isotopes) | 1.48 min (CC) |
| 252 | 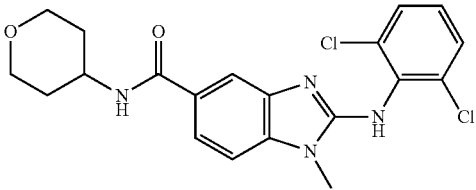<br>2-(2,6-Dichloro-phenylamino)-1-methyl-1H-benzimidazole-5-carboxylic acid (tetrahydro-pyran-4-yl)-amide | Σ: 61% | (M + H)+ = 433/435/437 (chlorine isotopes) | 1.45 min (CC) |
| 253 | 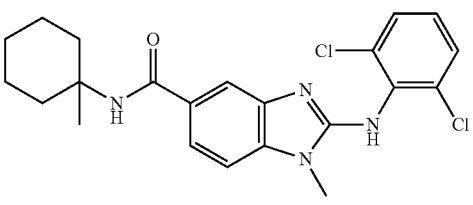 [SMILES: Cn1c(Nc2c(Cl)cccc2Cl)nc2cc(C(=O)NC3(C)CCCCC3)ccc21]<br>2-(2,6-Dichloro-phenylamino)-1-methyl-1H-benzimidazole-5-carboxylic acid (1-methyl-cyclohexyl)-amide | Σ: 38% | (M + H)+ = 431/433/435 (chlorine isotopes) | 1.74 min (CC) |
| 254 | 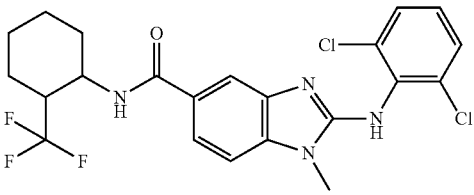 [SMILES: Cn1c(Nc2c(Cl)cccc2Cl)nc2cc(C(=O)NC3CCCCC3C(F)(F)F)ccc21]<br>2-(2,6-Dichloro-phenylamino)-1-methyl-1H-benzimidazole-5-carboxylic acid (2-trifluoromethyl-cyclohexyl)-amide | Σ: 57% | (M + H)+ = 485/487/489 (chlorine isotopes) | 1.71 min (CC) |

| No. | Structural formula Name | Yield | Mass peak(s) | $R_f$-value or $R_t$ |
|---|---|---|---|---|
| 255 | 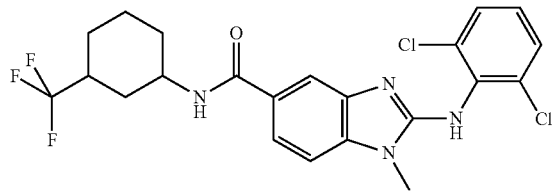 [SMILES: Cn1c(Nc2c(Cl)cccc2Cl)nc2cc(C(=O)NC3CCCC(C(F)(F)F)C3)ccc21]<br>2-(2,6-Dichloro-phenylamino)-1-methyl-1H-benzimidazole-5-carboxylic acid (3-trifluoromethyl-cyclohexyl)-amide | Σ: 62% | (M + H)+ = 485/487/489 (chlorine isotopes) | 1.75 min (CC) |
| 256 | 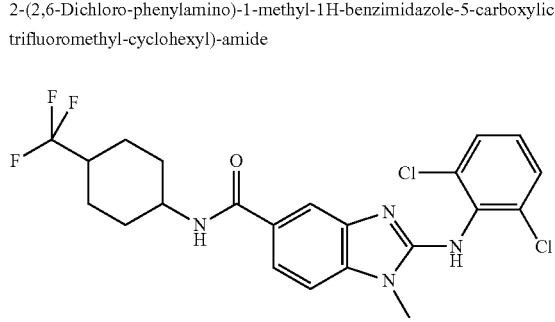<br>2-(2,6-Dichloro-phenylamino)-1-methyl-1H-benzimidazole-5-carboxylic acid (4-trifluoromethyl-cyclohexyl)-amide | Σ: 62% | (M + H)+ = 485/487/489 (chlorine isotopes) | 1.73 min (CC) |
| 257 | 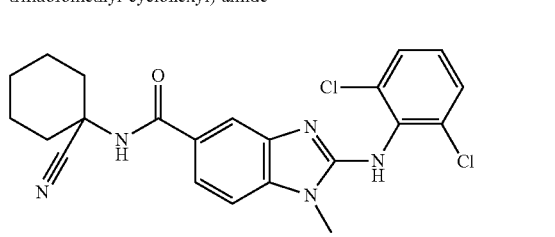<br>2-(2,6-Dichloro-phenylamino)-1-methyl-1H-benzimidazole-5-carboxylic acid (1-cyano-cyclohexyl)-amide | Σ: 19% | (M + H)+ = 442/444/446 (chlorine isotopes) | 1.64 min (CC) |
| 258 | 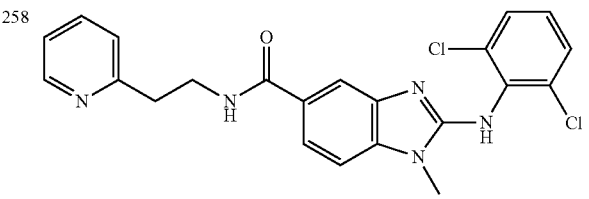<br>2-(2,6-Dichloro-phenylamino)-1-methyl-1H-benzimidazole-5-carboxylic acid (2-pyridin-2-yl-ethyl)-amide | Σ: 68% | (M + H)+ = 440/442/444 (chlorine isotopes) | 1.28 min (CC) |
| 259 | 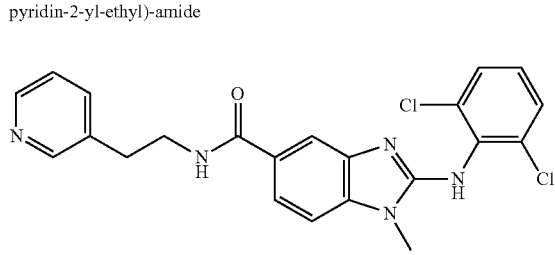<br>2-(2,6-Dichloro-phenylamino)-1-methyl-1H-benzimidazole-5-carboxylic acid (2-pyridin-3-yl-ethyl)-amide | Σ: 70% | (M + H)+ = 440/442/444 (chlorine isotopes) | 1.28 min (CC) |

| No. | Structural formula Name | Yield | Mass peak(s) | $R_f$-value or $R_t$ |
|---|---|---|---|---|
| 260 | 2-(2,6-Dichloro-phenylamino)-1-methyl-1H-benzimidazole-5-carboxylic acid (2-pyridin-4-yl-ethyl)-amide | Σ: 72% | (M + H)+ = 440/442/444 (chlorine isotopes) | 1.28 min (CC) |
| 261 | 2-(2,6-Dichloro-phenylamino)-1-methyl-1H-benzimidazole-5-carboxylic acid (tetrahydro-furan-2-ylmethyl)-amide | Σ: 54% | (M + H)+ = 419/421/423 (chlorine isotopes) | 1.46 min (CC) |
| 262 | 2-(2,6-Dichloro-phenylamino)-1-methyl-1H-benzimidazole-5-carboxylic acid (2-pyridin-4-yl-methyl)-amide | Σ: 65% | (M + H)+ = 426/428/430 (chlorine isotopes) | 1.27 min (CC) |
| 213 | 2-(2,6-Dichloro-phenylamino)-1H-benzimidazole-5-carboxylic acid cyclohexylamide | Σ: 54% | (M + H)+ = 419/421/423 (chlorine isotopes) | 1.5 min (CC) |
| 436 | 2-(2,6-Dichlorophenylamino)-1-methyl-N-(spiro[2.4]heptan-5-yl)-1H-benzimidazole-5-carboxamide | Σ: 59% | (M + H)+ = 429/431/433 (chlorine isotopes) | 1.5 min (G11) |

| No. | Structural formula Name | Yield | Mass peak(s) | $R_f$-value or $R_t$ |
|---|---|---|---|---|
| 488 | 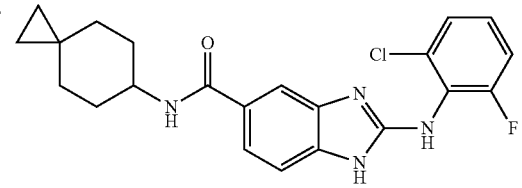<br>2-(2-Chloro-6-fluorophenylamino)-N-(spiro[2.5]octan-6-yl)-1H-benzimidazole-5-carboxamide | Σ:<br>8% | (M + H)+ = 413/415/417<br>(chlorine isotopes) | 2.21 min (C4) |
| 483 | 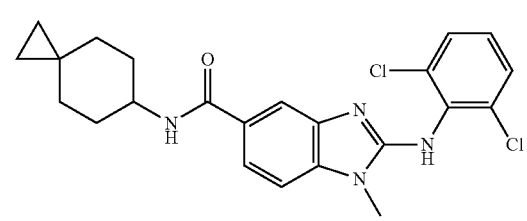 [SMILES: Cn1c(Nc2c(Cl)cccc2Cl)nc2cc(C(=O)NC3CCC4(CC3)CC4)ccc21]<br>2-(2,6-Dichlorophenylamino)-1-methyl-N-(spiro[2.5]octan-6-yl)-1H-benzimidazole-5-carboxamide | Σ:<br>7.2% | (M + H)+ = 443/445/447<br>(chlorine isotopes) | 1.61 min (G10) |
| 542 | 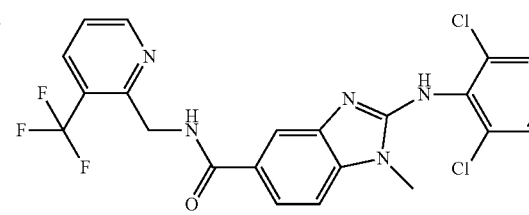<br>2-(2,6-Dichloro-4-fluorophenylamino)-1-methyl-N-((3-trifluoromethyl-pyridin-2-yl)methyl)-1H-benzimidazole-5-carboxamide | Σ:<br>9.5% | (M + H)+ = 512/414/416<br>(chlorine isotopes) | 3.27 min (B1) |

Example 149

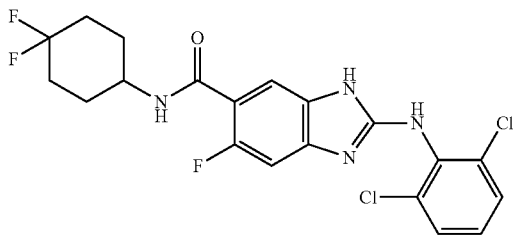 [SMILES: O=C(NC1CCC(F)(F)CC1)c1cc2[nH]c(Nc3c(Cl)cccc3Cl)nc2cc1F]

2-(2,6-Dichloro-phenylamino)-6-fluoro-3H-benzimidazole-5-carboxylic acid (4,4-difluoro-cyclohexyl)-amide (149a) 4-Amino-2-fluoro-benzoic acid Prepared analogously to example 1b by hydrogenation of 2-fluoro-4-nitro-benzoic acid using palladium/charcoal 10% in THF.
Yield: 99%; $R_t$ value: 2.07 min (B1).

(149b) 4-Acetylamino-2-fluoro-benzoic acid

A mixture of 4-amino-2-fluoro-benzoic acid (5.61 g, 36.2 mmol) and acetic anhydride (5.13 mL, 54.3 mmol) in 60 mL acetic acid was stirred at 60° C. overnight. The mixture was taken up in 250 mL water and stirred for 30 min. The precipitate was filtered and washed with water. The filtrate was washed with ethyl acetate. The organic phase was neutralized with sat. $K_2CO_3$ (aq) and concentrated i.vac. The precipitate was filtered and combined with the first isolated precipitate.
Yield: 6.7 g (94%)
mass spectrum: $(M+H)^+ = 198$
$R_t$ value: 2.40 min (B1)

(149c) 4-Acetylamino-2-fluoro-5-nitro-benzoic acid

Prepared analogously to example 83b from 4-acetylamino-2-fluoro-benzoic acid, conc. sulphuric acid and conc. nitric acid
Yield: 72%
mass spectrum: $(M-H)^- = 241$
$R_t$ value: 2.84 min (B1)

(149d) 4-Amino-5-nitro-2-fluoro-benzoic acid

Prepared analogously to example 145b from 4-acetylamino-2-fluoro-5-nitro-benzoic acid and half-conc. hydrochloric acid in dioxane.
Yield: 82%, mass spectrum: $(M-H)^- = 199$, $R_t$ value: 2.73 min (B1).

(149e) 4-Amino-5-nitro-2-fluoro-benzoyl chloride

Prepared analogously to example 53a from 4-amino-5-nitro-2-fluoro-benzoic acid and thionyl chloride in 1,2-dichloroethane.
Yield: 99%

(149f) 4-Amino-5-nitro-2-fluoro-benzoic acid ethyl ester

A solution of the product obtained at 149e (1.4 g, 6.4 mmol) in 50 mL ethanol was heated to reflux for 2 h. The mixture was filtered and the filtrate concentrated i.vac. The residue is reacted without any further purification. Yield: 89%.

(149g) 4,5-Diamino-2-fluoro-benzoic acid ethyl ester

Prepared analogously to example 1b by hydrogenation of 4-amino-5-nitro-2-fluoro-benzoic acid ethyl ester using palladium/charcoal 10% in methanol.
Yield: 97%

(149h) 2-(2,6-Dichloro-phenylamino)-6-fluoro-3H-benzimidazole-pyridine-5-carboxylic acid ethyl ester Prepared analogously to example 1c from 4,5-diamino-2-fluoro-benzoic acid ethyl ester and 1,3-dichloro-2-isothiocyanato-benzene with DIC in acetonitrile.

Yield: 56%
mass spectrum: $(M+H)^+=368/70/72$ (chlorine isotopes)

(149i) 2-(2,6-Dichloro-phenylamino)-6-fluoro-3H-benzimidazole-pyridine-5-carboxylic acid A mixture of 2-(2,6-dichloro-phenylamino)-6-fluoro-3H-benzimidazole-pyridine-5-carboxylic acid ethyl ester (1.1 g, 3.0 mmol) and 2 M LiOH (aq) (10.0 mL, 20.0 mmol) in 40 mL ethanol was stirred overnight at ambient temperature. The mixture was acidified with HCl (aq) and stirred. The precipitate was filtered, washed with water and dried.
Yield: 0.90 g (89%)
mass spectrum: $(M+H)^+=340/42/44$ (chlorine isotopes)

(149j) 2-(2,6-Dichloro-phenylamino)-6-fluoro-3H-benzimidazole-5-carboxylic acid (4,4-difluoro-cyclohexyl)-amide Prepared analogously to example 3c from 2-(2,6-dichloro-phenylamino)-6-fluoro-3H-benzimidazole-pyridine-5-carboxylic acid, 4,4-difluoro-cyclohexylamine hydrochloride, TBTU and TEA in DMF
Yield: 52%
mass spectrum: $(M+H)^+=457/59/61$ (chlorine isotopes)
$R_t$ value: 2.23 min (C1)
In analogy with the above described example, the following compounds were prepared:

| No. | Structural formula / Name | Yield | Mass peak(s) | $R_f$-value or $R_t$ |
|---|---|---|---|---|
| 150 | 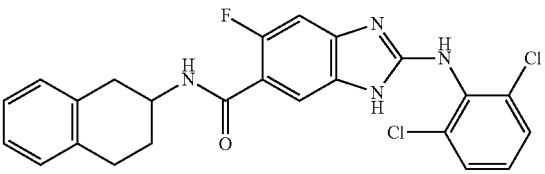 [SMILES: O=C(NC1CCc2ccccc2C1)c1cc2[nH]c(Nc3c(Cl)cccc3Cl)nc2cc1F] 2-(2,6-Dichloro-phenylamino)-6-fluoro-3H-benzimidazole-5-carboxylic acid (1,2,3,4-tetrahydro-naphthalen-2-yl)-amide | Σ: 6.424% | $(M+H)^+=$ 467/69/71 (chlorine isotopes) | 2.44 min (C5) |
| 152 | 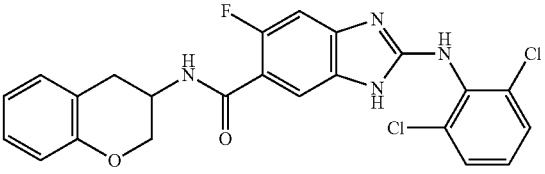 [SMILES: O=C(NC1COc2ccccc2C1)c1cc2[nH]c(Nc3c(Cl)cccc3Cl)nc2cc1F] 2-(2,6-Dichloro-phenylamino)-6-fluoro-1H-benzimidazole-5-carboxylic acid chroman-3-ylamide | Σ: 6.625% | $(M+H)^+=$ 471/73/75 (chlorine isotopes) | 2.37 min (C5) |
| 155 | 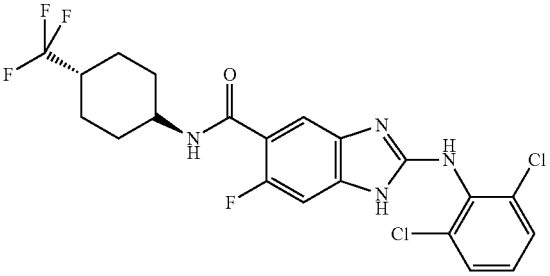 2-(2,6-Dichloro-phenylamino)-6-fluoro-1H-benzimidazole-5-carboxylic acid (trans-4-trifluoromethyl-cyclohexyl)-amide | Σ: 12.446% | $(M+H)^+=$ 489/91/93 (chlorine isotopes) | 2.39 min (C5) |

-continued

| No. | Structural formula Name | Yield | Mass peak(s) | $R_f$-value or $R_t$ |
|---|---|---|---|---|
| 169 | 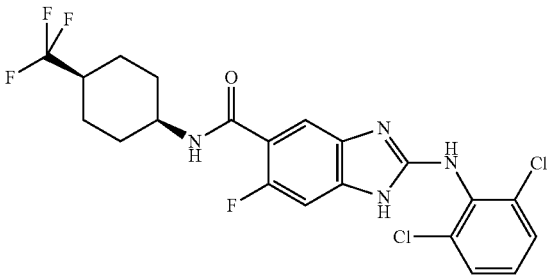 [SMILES: O=C(N[C@H]1CC[C@@H](C(F)(F)F)CC1)c1cc2nc(Nc3c(Cl)cccc3Cl)[nH]c2cc1F] 2-(2,6-Dichloro-phenylamino)-6-fluoro-1H-benzimidazole-5-carboxylic acid (cis-4-trifluoromethyl-cyclohexyl)-amide | Σ: 12.848% | $(M + H)^+$ = 489/91/93 (chlorine isotopes) | 2.42 min (C5) |
| 356 | 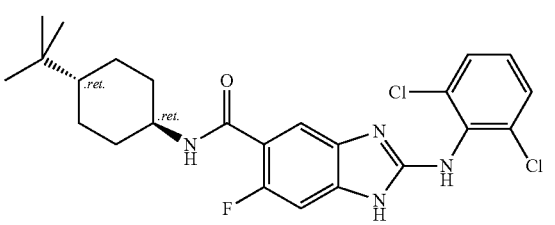 [SMILES: CC(C)(C)[C@H]1CC[C@H](NC(=O)c2cc3nc(Nc4c(Cl)cccc4Cl)[nH]c3cc2F)CC1] N-((1r,4r)-4-tert.-Butylcyclohexyl)-2-(2,6-dichlorophenylamino)-6-fluoro-1H-benzimidazole-5-carboxamide | Σ: 9.4% | $(M + H)+$ = 477/479/481 (chlorine isotopes) | 2.87 min (C4) |
| 357 | 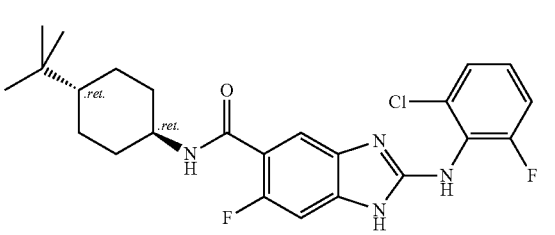 [SMILES: CC(C)(C)[C@H]1CC[C@H](NC(=O)c2cc3nc(Nc4c(F)cccc4Cl)[nH]c3cc2F)CC1] N-((1r,4r)-4-tert.-Butylcyclohexyl)-2-(2-chloro-6-fluorophenylamino)-6-fluoro-1H-benzimidazole-5-carboxamide | Σ: 18.6% | $(M + H)+$ = 461/463/465 | 2.76 min (C4) |
| 374 | 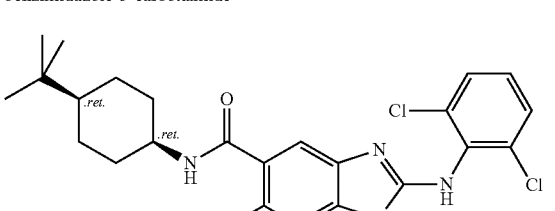 N-((1s,4s)-4-tert.-Butylcyclohexyl)-2-(2,6-dichlorophenylamino)-6-fluoro-1H-benzimidazole-5-carboxamide | Σ: 10.8% | $(M + H)+$ = 477/479/481 (chlorine isotopes) | 2.78 min (C4) |
| 375 | 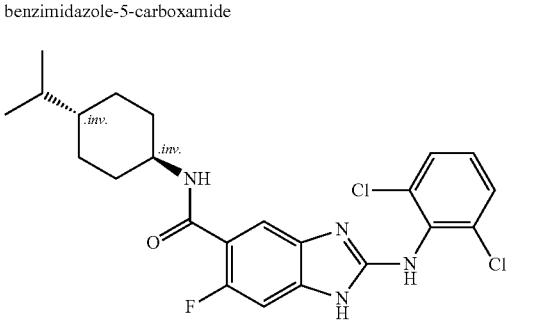 2-(2,6-Dichlorophenylamino)-6-fluoro-N-(1r,4r)-4-isopropylcyclohexyl)-1H-benzimidazole-5-carboxamide | Σ: 3.8% | $(M + H)+$ = 463/465/467 (chlorine isotopes) | 2.70 min (C3) |

| No. | Structural formula Name | Yield | Mass peak(s) | $R_f$-value or $R_t$ |
|---|---|---|---|---|
| 378 | N-((1s,4s)-4-tert.-Butylcyclohexyl)-2-(2-chloro-6-fluorophenylamino)-6-fluoro-1H-benzimidazole-5-carboxamide | Σ: 5.8% | (M + H)+ = 461/463/465 (chlorine isotopes) | 2.74 min (C4) |
| 387 | 2-(2,6-Dichlorophenylamino)-6-fluoro-N-(spiro[2.5]octan-6-yl)-1H-benzimidazole-5-carboxamide | Σ: 19% | (M + H)+ = 447/449/451 (chlorine isotopes) | 3.43 min (C4) |
| 399 | 2-(2-Chloro-6-fluorophenylamino)-6-fluoro-N-(spiro[2.5]octan-6-yl)-1H-benzimidazole-5-carboxamide | Σ: 13.8% | (M + H)+ = 431/433/435 (chlorine isotopes) | 3.58 min (B4) |
| 443 | (S)-2-(2,6-Dichlorophenylamino)-6-fluoro-N-(hexan-2-yl)-1H-benzimidazole-5-carboxamide | Σ: 8.2% | (M + H)+ = 423/425/427 (chlorine isotopes) | 3.44 min (B3) |
| 457 | (R)-2-(2,6-Dichlorophenylamino)-6-fluoro-N-(hexan-2-yl)-1H-benzimidazole-5-carboxamide | Σ: 9.8% | (M + H)+ = 423/425/427 (chlorine isotopes) | 3.46 min (B3) |

-continued

| No. | Structural formula Name | Yield | Mass peak(s) | $R_f$-value or $R_t$ |
|---|---|---|---|---|
| 496 | 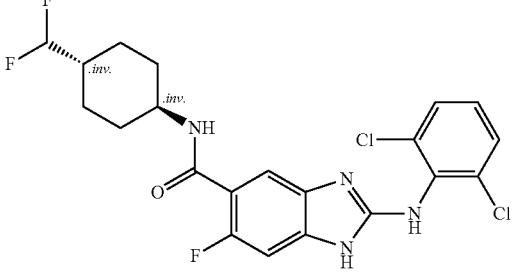<br>2-(2,6-Dichlorophenylamino)-N-((1r,4r)-4-(difluoromethyl)cyclohexyl)-6-fluoro-1H-benzimidazole-5-carboxamide | Σ: 10.7% | (M + H)+ = 471/473/475 (chlorine isotopes) | 3.27 min (B3) |

Example 156

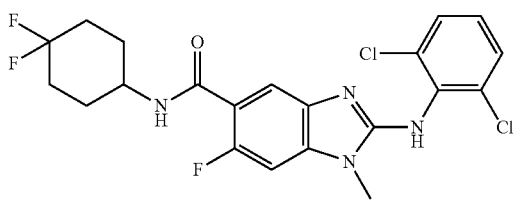 [SMILES: Cn1c(Nc2c(Cl)cccc2Cl)nc2cc(C(=O)NC3CCC(F)(F)CC3)c(F)cc21]

2-(2,6-Dichloro-phenylamino)-6-fluoro-1-methyl-1H-benzimidazole-5-carboxylic acid (4,4-difluoro-cyclohexyl)-amide (156a) 2,4-Difluoro-5-nitro-benzoic acid ethyl ester Ethanol (1.50 mL, 26.0 mmol) was added to a stirred mixture of 2,4-difluoro-5-nitro-benzoyl chloride (5.0 g, 22.6 mmol) and TEA (3.50 mL, 25.2 mmol) in 50 mL THF. After 30 min of stirring the precipitate was filtered and washed with THF. The filtrate was concentrated i.vac.
Yield: 5.08 g (97%)
$R_t$ value: 2.80 min (C2)

(156b) 2-Fluoro-4-methylamino-5-nitro-benzoic acid ethyl ester

A solution of the product obtained at 156a (2.50 g, 10.8 mmol) in 20 mL THF was cooled. 2 M methylamine (solution in THF) (11.5 mL, 23.0 mmol) was added. The mixture was allowed to stir at ambient temperature for 15 min. The mixture was concentrated i.vac. The residue was taken up in water and dichloromethane. The aq. phase was washed with dichloromethane. The combined organic phases were dried and concentrated i.vac. The residue was taken up in ethanol, filtered and washed with ethanol.
Yield: 1.72 g (66%)
$R_t$ value: 3.92 min (B2)
mass spectrum: $(M+H)^+=243$ (156c) 5-Amino-2-fluoro-4-methylamino-benzoic acid ethyl ester Prepared analogously to example 14b by hydrogenation of 2-fluoro-4-methylamino-5-nitro-benzoic acid ethyl ester using Raney nickel in THF.

Yield: 98%
mass spectrum: $(M+H)^+=213$
$R_t$ value: 2.19 min (C2)

(156d) 5-[3-(2,6-Dichloro-phenyl)-thioureido]-2-fluoro-4-methylamino-benzoic acid ethyl ester A mixture of 5-amino-2-fluoro-4-methylamino-benzoic acid ethyl ester (1.48 g, 7.0 mmol) and 1,3-dichloro-2-isothiocyanato-benzene (1.42 g, 7.0 mmol) in 20 mL acetonitrile and 5 mL methanol was stirred for 5 h at ambient temperature. The mixture was concentrated i.vac., taken up in acetonitrile and filtered.
Yield: 2.70 g (93%)
mass spectrum: $(M+H)^+=416/18/20$ (chlorine isotopes)
$R_t$ value: 2.73 min (C2)

(156e) 2-(2,6-Dichloro-phenylamino)-6-fluoro-1-methyl-1H-benzimidazole-5-carboxylic acid DIC (1.50 mL, 9.6 mmol) was added to a stirred mixture of 5-[3-(2,6-dichloro-phenyl)-thioureido]-2-fluoro-4-methylamino-benzoic acid ethyl ester (2.70 g, 6.5 mmol) in acetonitrile. After stirring for 1 h the mixture was concentrated i.vac. The residue was taken up in ethanol and 1 M aq. NaOH and stirred for further 40 min at reflux. Ethanol was evaporated, the mixture was diluted with water and filtered. The filtrate was acidified with hydrochloric acid, stirred and filtered. Both residues were combined and dried.
Yield: 1.72 g (75%)
$R_t$ value: 1.98 min (C2)

(156f) 2-(2,6-Dichloro-phenylamino)-6-fluoro-1-methyl-1H-benzimidazole-5-carboxylic acid (4,4-difluoro-cyclohexyl)-amide Prepared analogously to example 3c from 2-(2,6-dichloro-phenylamino)-6-fluoro-1-methyl-1H-benzimidazole-5-carboxylic acid and 4,4-difluoro-cyclohexylamine hydrochloride with TBTU in DMF.
Yield: 61%
mass spectrum: $(M+H)^+=471/73/75$ (chlorine isotopes)
$R_t$ value: 2.45 min (C5)

In analogy with the above described example, the following compounds were prepared:

| No. | Structural formula / Name | Yield | Mass peak(s) | R_f value or R_t |
|---|---|---|---|---|
| 157 | 2-(2,6-Dichloro-phenylamino)-6-fluoro-1-methyl-1H-benzimidazole-5-carboxylic acid (4,4-dimethyl-cyclohexyl)-amide | Σ: 10.243% | (M + H)+ = 463/65/67 (chlorine isotopes) | 2.82 min (C5) |
| 158 | 2-(2,6-Dichloro-phenylamino)-6-fluoro-1-methyl-1H-benzimidazole-5-carboxylic acid (trans-4-trifluoromethyl-cyclohexyl)-amide | Σ: 12.351% | (M + H)+ = 503/05/07 (chlorine isotopes) | 2.64 min (C5) |
| 159 | 2-(2,6-Dichloro-phenylamino)-6-fluoro-1-methyl-1H-benzimidazole-5-carboxylic acid cyclohexylamide | Σ: 7.833% | (M + H)+ = 435/37/39 (chlorine isotopes) | 2.54 min (C5) |
| 160 | 2-(2,6-Dichloro-phenylamino)-6-fluoro-1-methyl-1H-benzimidazole-5-carboxylic acid chroman-3-ylamide | Σ: 938% | (M + H)+ = 485/87/89 (chlorine isotopes) | 2.54 min (C5) |
| 162 | 2-(2,6-Dichloro-phenylamino)-6-fluoro-1-methyl-1H-benzimidazole-5-carboxylic acid (1,2,3,4-tetrahydro-naphthalen-2-yl)-amide | Σ: 5.623% | (M + H)+ = 483/85/87 (chlorine isotopes) | 2.63 min (C5) |

| No. | Structural formula Name | Yield | Mass peak(s) | $R_f$ value or $R_t$ |
|---|---|---|---|---|
| 163 | 2-(2,6-Dichloro-phenylamino)-6-fluoro-1-methyl-1H-benzimidazole-5-carboxylic acid (octahydro-inden-2-yl)-amide | Σ: 10.745% | (M + H)+ = 475/77/79 (chlorine isotopes) | 2.89 min (C5) |
| 164 | 2-(2,6-Dichloro-phenylamino)-6-fluoro-1-methyl-1H-benzimidazole-5-carboxylic acid (1-methyl-cyclohexyl)-amide | Σ: 833% | (M + H)+ = 449/51/53 (chlorine isotopes) | 2.73 min (C5) |
| 165 | 2-(2,6-Dichloro-phenylamino)-6-fluoro-1-methyl-1H-benzimidazole-5-carboxylic acid adamantan-1-ylamide | Σ: 14.661% | (M + H)+ = 487/89/91 (chlorine isotopes) | 2.98 min (C5) |
| 166 | 2-(2,6-Dichloro-phenylamino)-6-fluoro-1-methyl-1H-benzimidazole-5-carboxylic acid octylamide | Σ: 1042% | (M + H)+ = 465/67/69 (chlorine isotopes) | 2.5 min (C5) |
| 167 | 2-(2,6-Dichloro-phenylamino)-6-fluoro-1-methyl-1H-benzimidazole-5-carboxylic acid (4-bromo-phenyl)-amide | Σ: 8.119% | (M + H)+ = 507/09/11/13 (chlorine and bromine isotopes) | 2.82 min (C5) |

-continued

| No. | Structural formula Name | Yield | Mass peak(s) | R_f value or R_t |
|---|---|---|---|---|
| 170 | 2-(2,6-Dichloro-phenylamino)-6-fluoro-1-methyl-1H-benzimidazole-5-carboxylic acid (cis-4-trifluoromethyl-cyclohexyl)-amide | Σ: 2433% | (M + H)+ = 503435/537/739 (chlorine isotopes) | 2.54 min (C5) |
| 175 | 2-(2,6-Dichloro-phenylamino)-6-fluoro-1-methyl-1H-benzimidazole-5-carboxylic acid ((3R)-3-methyl-cyclopentyl)-amide  Chiral | Σ: 14.259% | (M + H)+ = 435/37/39 (chlorine isotopes) | 2.52 min (C5) |
| 354 | N-(4-tert.-Butylcyclohexyl)-2-(2-chloro-6-fluorophenylamino)-6-fluoro-1-methyl-1H-benzimidazole-5-carboxamide | Σ: 21% | (M + H)+ = 474/476/478 (chlorine isotopes) | 2.87 min (C4) |
| 362 | N-(4-Ethylcyclohexyl)-2-(2-chloro-6-fluorophenylamino)-6-fluoro-1-methyl-1H-benzimidazole-5-carboxamide | Σ: 9% | (M + H)+ = 477/479/481 (chlorine isotopes) | 2.72 min (C4) |
| 363 | 2-(2-Chloro-6-fluorophenylamino-N-(4-isopropylcyclohexyl)-6-fluoro-1-methyl-1H-benzimidazole-5-carboxamide | Σ: 11% | (M + H)+ = 446/448/450 (chlorine isotopes) | 3.04 min (C4) |

| No. | Structural formula Name | Yield | Mass peak(s) | R$_f$ value or R$_t$ |
|---|---|---|---|---|
| 368 | 2-(2-Chloro-6-fluorophenylamino-N-(4-isopropylcyclohexyl)-6-fluoro-1-methyl-1H-benzimidazole-5-carboxamide | Σ: 17.8% | (M + H)+ = 460/62/64 (chlorine isotopes) | 2.86 min (C4) |
| 373 | 2-(2,6-Dichlorophenylamino)-6-fluoro-N-hexyl-1-methyl-1H-benzimidazole-5-carboxamide | Σ: 13.9% | (M + H)+ = 437/39/41 (chlorine isotopes) | 2.67 min (C4) |
| 384 | 2-(2-Chloro-6-fluorophenylamino)-6-fluoro-1-methyl-N-(spiro[2.5]octan-6-yl-1H-benzimidazole-5-carboxamide | Σ: 23% | (M + H)+ = 445/47/49 (chlorine isotopes) | 2.57 min (C4) |
| 390 | 2-(2-Chloro-6-fluorophenylamino)-N-(3-cyclopropylpropyl)-6-fluoro-1-methyl-1H-benzimidazole-5-carboxamide | Σ: 23% | (M + H)+ = 419/21/23 (chlorine isotopes) | 2.43 min (C4) |
| 391 | 2-(2,6-Dichlorophenylamino)-6-fluoro-1-methyl-N-pentyl-1H-benzimidazole-5-carboxamide | Σ: 14.7% | (M + H)+ = 423/25/27 (chlorine isotopes) | 2.52 min (C4) |

| No. | Structural formula / Name | Yield | Mass peak(s) | R_f value or R_t |
|---|---|---|---|---|
| 392 | 2-(2-Chloro-6-fluorophenylamino)-N-(3-ethylcyclopentyl)-6-fluoro-1-methyl-1H-benzimidazole-5-carboxamide | Σ: 27% | (M + H)+ = 433/35/37 (chlorine isotopes) | 2.59 min (C4) |
| 397 | N-(2-Cyclobutylethyl)-2-(2,6-dichlorophenylamino)-6-fluoro-1-methyl-1H-benzimidazole-5-carboxamide | Σ: 9.6% | (M + H)+ = 435/37/39 (chlorine isotopes) | 1.81 min (G10) |
| 398 | N-(3-Cyclopropylpropyl)-2-(2,6-dichlorophenylamino)-6-fluoro-1-methyl-1H-benzimidazole-5-carboxamide | Σ: 10.9% | (M + H)+ = 435/37/39 (chlorine isotopes) | 2.59 min (C4) |
| 404 | 2-(2-Chloro-6-fluorophenylamino)-N-(3,3-dimethylcyclohexyl)-6-fluoro-1-methyl-1H-benzimidazole-5-carboxamide | Σ: 28.2% | (M + H)+ = 447/49/51 (chlorine isotopes) | 2.70 min (C4) |
| 408 | 2-(2,6-Dichlorophenylamino)-6-fluoro-1-methyl-N-(4-methylpentyl)-1H-benzimidazole-5-carboxamide | Σ: 13.7% | (M + H)+ = 437/39/41 (chlorine isotopes) | 2.65 min (C4) |

| No. | Structural formula Name | Yield | Mass peak(s) | R_f value or R_t |
|---|---|---|---|---|
| 412 | 2-(2,6-Dichlorophenylamino)-N-(3-ethylcyclopentyl)-6-fluoro-1-methyl-1H-benzimidazole-5-carboxamide | Σ: 17% | (M + H)+ = 437/39/41 (chlorine isotopes) | 2.73 min (C4) |
| 415 | 2-(2,6-Dichlorophenylamino)-6-fluoro-1-methyl-N-(spiro[2.4]heptan-5-yl)-1H-benzimidazole-5-carboxamide | Σ: 19.8% | (M + H)+ = 447/49/51 (chlorine isotopes) | 1.82 min (G11) |
| 416 | (R)-2-(2,6-Dichlorophenylamino)-6-fluoro-N-(hexan-2-yl)-1-methyl-1H-benzimidazole-5-carboxamide | Σ: 10% | (M + H)+ = 437/39/41 (chlorine isotopes) | 2.63 min (C4) |
| 419 | 2-(2,6-Dichlorophenylamino)-6-fluoro-1-methyl-N-(spiro[2.5]octan-6-yl)-1H-benzimidazole-5-carboxamide | Σ: 11.6% | (M + H)+ = 435/37/39 (chlorine isotopes) | 1.91 min (G10) |
| 422 | N-((3-Cyclopropylpyridin-2-yl)methyl)-2-(2,6-dichlorophenylamino)-6-fluoro-1-methyl-1H-benzimidazole-5-carboxamide | Σ: 14.6% | (M + H)+ = 484/86/89 (chlorine isotopes) | 1.19 min (F7) |

-continued

| No. | Structural formula Name | Yield | Mass peak(s) | $R_f$ value or $R_t$ |
|---|---|---|---|---|
| 428 | 2-(2,6-Dichlorophenylamino)-6-fluoro-N-isopentyl-1-methyl-1H-benzimidazole-5-carboxamide | Σ: 11.7% | (M + H)+ = 423/25/27 (chlorine isotopes) | 2.50 min (C4) |
| 430 | 2-(2-Chloro-6-fluorophenylamino)-N-(4,4-dimethylcyclohexyl)-6-fluoro-1-methyl-1H-benzimidazole-5-carboxamide | Σ: 10.5% | (M + H)+ = 447/49/51 (chlorine isotopes) | 2.67 min (C4) |
| 355 | 2-(2,6-Dichlorophenylamino)-N-(3,3-dimethylcyclohexyl)-6-fluoro-1-methyl-1H-benzimidazole-5-carboxamide | Σ: 16% | (M + H)+ = 463/65/67 (chlorine isotopes) | 2.78 min (C4) |
| 437 | 2-(2,6-Dichlorophenylamino)-N-(4-ethylcyclohexyl)-6-fluoro-1-methyl-1H-benzimidazole-5-carboxamide | Σ: 16.3% | (M + H)+ = 463/465/467 (chlorine isotopes) | 2.84 min (C4) |
| 442 | Chiral<br>2-(2,6-Dichlorophenylamino)-6-fluoro-1-methyl-N-((1R,3R)-3-methylcyclohexyl)-1H-benzimidazole-5-carboxamide | Σ: 16.5% | (M + H)+ = 449/451/453 (chlorine isotopes) | 2.73 min (C4) |

| No. | Structural formula Name | Yield | Mass peak(s) | $R_f$ value or $R_t$ |
|---|---|---|---|---|
| 447 | 2-(2,6-Dichlorophenylamino)-N-(3,3-dimethylcyclobutyl)-6-fluoro-1-methyl-1H-benzimidazole-5-carboxamide | Σ: 21% | (M + H)+ = 435/437/439 (chlorine isotopes) | 3.81 min (C4) |
| 450 | (S)-2-(2,6-Dichlorophenylamino)-6-fluoro-N-(hexan-2-yl)-1-methyl-1H-benzimidazole-5-carboxamide | Σ: 20% | (M + H)+ = 437/439/441 (chlorine isotopes) | 2.64 min (C4) |
| 452 | N-((3-Chloropyridin-2-yl)methyl)-2-(2,6-dichlorophenylamino)-6-fluoro-1-methyl-1H-benzimidazole-5-carboxamide | Σ: 2.7% | (M + H)+ = 478/480/482 (chlorine isotopes) | 1.23 min (F8) |
| 458 | 2-(2-Chloro-6-fluorophenylamino)-6-fluoro-N-hexyl-1-methyl-1H-benzimidazole-5-carboxamide | Σ: 20% | (M + H)+ = 421/423/425 (chlorine isotopes) | 2.58 min (C4) |
| 470 | 2-(2,6-Dichlorophenylamino)-N-((3,5-dimethylpyridin-2-yl)methyl)-6-fluoro-1-methyl-1H-benzimidazole-5-carboxamide | Σ: 17% | (M + H)+ = 472/474/476 (chlorine isotopes) | 1.09 min (F7) |

| No. | Structural formula Name | Yield | Mass peak(s) | $R_f$ value or $R_t$ |
|---|---|---|---|---|
| 475 | 2-(2,6-Dichlorophenylamino)-N-((1r,4r)-4-(difluoromethyl)cyclohexyl)-6-fluoro-1-methyl-1H-benzimidazole-5-carboxamide | Σ: 12.3% | (M + H)+ = 485/487/489 (chlorine isotopes) | 2.58 min (B3) |
| 476 | 2-(2-Chloro-6-fluorophenylamino)-N-((1r,4r)-4-(difluoromethyl)cyclohexyl)-6-fluoro-1-methyl-1H-benzimidazole-5-carboxamide | Σ: 15.9% | (M + H)+ = 468/470/472 (chlorine isotopes) | 2.40 min (C4) |
| 484 | N-(2-Cyclopropylethyl)-2-(2,6-dichlorophenylamino)-6-fluoro-1-methyl-1H-benzimidazole-5-carboxamide | Σ: 20% | (M + H)+ = 421/423/425 (chlorine isotopes) | 2.4 min (C4) |
| 501 | Chiral 2-(2-Chloro-6-fluorophenylamino)-6-fluoro-1-methyl-N-((3R)-3-methylcyclopentyl)-1H-benzimidazole-5-carboxamide | Σ: 19% | (M + H)+ = 419/421/423 (chlorine isotopes) | 2.43 min (C4) |
| 502 | 2-(2-Chloro-6-fluorophenylamino)-N-(2-cyclopropylethyl)-6-fluoro-1-methyl-1H-benzimidazole-5-carboxamide | Σ: 23% | (M + H)+ = 404/406/408 (chlorine isotopes) | 2.31 min (C4) |

-continued

| No. | Structural formula Name | Yield | Mass peak(s) | $R_f$ value or $R_t$ |
|---|---|---|---|---|
| 510 | 2-(2,6-Dichlorophenylamino)-6-fluoro-1-methyl-N-((3-methylpyridin-2-yl)methyl)-1H-benzimidazole-5-carboxamide | Σ: 23% | (M + H)+ = 458/460/462 (chlorine isotopes) | 0.99 min (F8) |
| 513 | 2-(2-Chloro-6-fluorophenylamino)-6-fluoro-1-methyl-N-(pent-2-ynyl)-1H-benzimidazole-5-carboxamide | Σ: 19% | (M + H)+ = 403/405/407 (chlorine isotopes) | 2.31 min (C4) |
| 516 | N-(Cyclobutylmethyl)-2-(2,6-dichlorophenylamino)-6-fluoro-1-methyl-1H-benzimidazole-5-carboxamide | Σ: 37% | (M + H)+ = 421/423/425 (chlorine isotopes) | 1.69 min (G10) |
| 529 | 2-(2,6-Dichlorophenylamino)-6-fluoro-N-((3-methoxypyridin-2-yl)methyl)-1-methyl-1H-benzimidazole-5-carboxamide | Σ: 28% | (M + H)+ = 474/476/478 (chlorine isotopes) | 1.16 min (F7) |
| 534 | 2-(2,6-Dichlorophenylamino)-6-fluoro-1-methyl-N-((4-methylpyridin-2-yl)methyl)-1H-benzimidazole-5-carboxamide | Σ: 19% | (M + H)+ = 458/460/462 (chlorine isotopes) | 1.45 min (F8) |

| No. | Structural formula / Name | Yield | Mass peak(s) | $R_f$ value or $R_t$ |
|---|---|---|---|---|
| 536 | 2-(2,6-Dichlorophenylamino)-6-fluoro-N-((3-fluoropyridin-2-yl)methyl)-1-methyl-1H-benzimidazole-5-carboxamide | Σ: 21% | (M + H)+ = 462/464/466 (chlorine isotopes) | 1.22 min (F7) |
| 546 | 2-(2-Chloro-6-fluorophenylamino)-N-(cyclopropylmethyl)-6-fluoro-1-methyl-1H-benzimidazole-5-carboxamide | Σ: 24% | (M + H)+ = 391/393/395 (chlorine isotopes) | 2.22 min (C4) |
| 548 | 2-(2,6-Dichlorophenylamino)-6-fluoro-1-methyl-N-(pyridin-2-ylmethyl)-1H-benzimidazole-5-carboxamide | Σ: 10.4% | (M + H)+ = 478/480/482 (chlorine isotopes) | 2.18 min (C2) |
| 552 | 2-(2,6-Dichlorophenylamino)-6-fluoro-1-methyl-N-(pyridin-2-ylmethyl)-1H-benzimidazole-5-carboxamide | Σ: 5.3% | (M + H)+ = 444/446/448 (chlorine isotopes) | 0.98 min (F8) |
| 561 | N-(1-Cyclopropylpiperidin-4-yl)-2-(2,6-dichlorophenylamino)-6-fluoro-1-methyl-1H-benzimidazole-5-carboxamide | Σ: 21% | (M + H)+ = 476/478/480 (chlorine isotopes) | 2.26 min (G10) |

-continued

| No. | Structural formula Name | Yield | Mass peak(s) | R_f value or R_t |
|---|---|---|---|---|
| 563 | 2-(2,6-Dichlorophenylamino)-6-fluoro-1-methyl-N-((1-methyl-1H-benzo[d]imidazol-2-yl)methyl)-1H-benzimidazole-5-carboxamide | Σ: 12% | (M + H)+ = 497/499/501 (chlorine isotopes) | 1.50 min (E7) |
| 564 | N-((6-Chloroimidazo[1,2-a]pyridin-2-yl)methyl)-2-(2,6-dichlorophenylamino)-6-fluoro-1-methyl-1H-benzimidazole-5-carboxamide | Σ: 32% | (M + H)+ = 517/519/521 (chlorine isotopes) | 1.03 min (F8) |
| 568 | 2-((2-(2,6-Dichlorophenylamino)-6-fluoro-1-methyl-1H-benzimidazole-5-carboxamido)methyl)-3-trifluoromethyl-pyridine 1-oxide | Σ: 28% | (M + H)+ = 528/530/532 (chlorine isotopes) | 1.6 min (E7) |
| 569 | 2-(2,6-Dichlorophenylamino)-6-fluoro-N-((4-methoxypyridin-2-yl)methyl)-1-methyl-1H-benzimidazole-5-carboxamide | Σ: 18% | (M + H)+ = 474/476/478 (chlorine isotopes) | 0.95 min (F8) |
| 601 | 2-(3,6-Dichloro-2-fluoro-phenylamino)-6-fluoro-N-(trans-4-trifluoromethyl-cyclohex-1-yl)-1-methyl-1H-benzimidazole-5-carboxamide | Σ: 14.1% | (M + H)+ = 521/523/525 (chlorine isotopes) | 1.46 min (F7) |

-continued

| No. | Structural formula / Name | Yield | Mass peak(s) | R_f value or R_t |
|---|---|---|---|---|
| 606 | 2-(3,6-Dichloro-2-fluoro-phenylamino)-6-fluoro-N-(spiro[2.5]oct-6-yl)-1-methyl-1H-benzimidazole-5-carboxamide | Σ: 14.9% | (M + H)+ = 479/481/483 (chlorine isotopes) | 1.51 min (F7) |
| 623 | 2-(6-Chloro-2-fluoro-3-methyl-phenylamino)-6-fluoro-N-cyclohexyl-1-methyl-1H-benzimidazole-5-carboxamide | Σ: 21% | (M + H)+ = 433/435 (chlorine isotopes) | 2.91 min (C5) |
| 627 | 2-(6-Chloro-2-fluoro-3-methyl-phenylamino)-6-fluoro-N-(4,4-dimethyl-cyclohex-1-yl)-1-methyl-1H-benzimidazole-5-carboxamide | Σ: 20% | (M + H)+ = 461/463 (chlorine isotopes) | 3.12 min (C5) |
| 629 | 2-(6-Chloro-2-fluoro-3-methyl-phenylamino)-6-fluoro-N-(trans-4-trifluoromethyl-cyclohex-1-yl)-1-methyl-1H-benzimidazole-5-carboxamide | Σ: 18% | (M + H)+ = 501/503 (chlorine isotopes) | 2.97 min (C5) |

Example 171

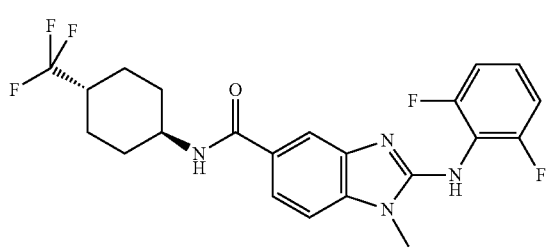 [SMILES: Cn1c(Nc2c(F)cccc2F)nc2cc(C(=O)N[C@H]3CC[C@H](C(F)(F)F)CC3)ccc21]

2-(2,6-Difluoro-phenylamino)-1-methyl-1H-benzimidazole-5-carboxylic acid (trans-4-trifluoromethyl-cyclohexyl)-amide

(171a) 3-Amino-4-aminomethyl-benzoic acid ethyl ester

Prepared analogously to example 1b by hydrogenation of 4-methylamino-3-nitro-benzoic acid ethyl ester using palladium/charcoal 10% in methanol.

Yield: 98%

(171b) 2-(2,6-Difluoro-phenylamino)-1-methyl-1H-benzimidazole-5-carboxylic acid ethyl ester Prepared analogously to example 1c from 3-amino-4-aminomethyl-benzoic acid ethyl ester and 1,3-dichloro-2-isothiocyanato-benzene with DIC in acetonitrile.

Yield: 65% mass spectrum: (M+H)$^+$=332

(171c) 2-(2,6-Difluoro-phenylamino)-1-methyl-1H-benzimidazole-5-carboxylic acid Prepared analogously to example 3b from 2-(2,6-difluoro-phenylamino)-1-methyl-1H-benzimidazole-5-carboxylic acid ethyl ester and NaOH in ethanol.
Yield: 70%
mass spectrum: $(M+H)^+=304$

(171d) 2-(2,6-Difluoro-phenylamino)-1-methyl-1H-benzimidazole-5-carboxylic acid (trans-4-trifluoromethyl-cyclohexyl)-amide Prepared analogously to example 3c from 2-(2,6-difluoro-phenylamino)-1-methyl-1H-benzimidazole-5-carboxylic acid and trans-4-trifluoromethyl-cyclohexylamine hydrochloride with TBTU in DMF.
Yield: 52%
mass spectrum: $(M+H)^+=453$
$R_t$ value: 2.23 min (C5)
In analogy with the above described example, the following compounds were prepared:

| No. | Structural formula Name | Yield | Mass peak(s) | $R_f$ value or $R_t$ |
|---|---|---|---|---|
| 172 | ![structure] <br> 2-(2,6-Difluoro-phenylamino)-1-methyl-1H-benzimidazole-5-carboxylic acid (4,4-dimethyl-cyclohexyl)-amide | Σ: 2146% | (M + H)+ = 413 | 2.11 min (C5) |
| 441 | ![structure] <br> 2-(2-Chloro-6-fluorophenylamino)-1-methyl-N-(spiro[2.5]octan-6-yl)-1H-benzimidazole-5-carboxamide | Σ: 19% | (M + H)+ = 427/429/431 (chlorine isotopes) | 2.36 min (C4) |

Example 173

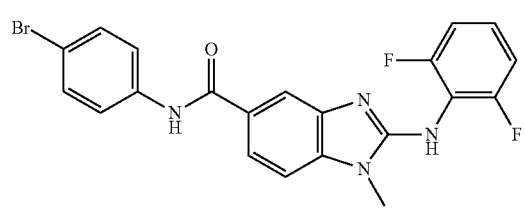 [SMILES: Cn1c(Nc2c(F)cccc2F)nc2cc(C(=O)Nc3ccc(Br)cc3)ccc21]

2-(2,6-Difluoro-phenylamino)-1-methyl-1H-benzimidazole-5-carboxylic acid (4-bromo-phenyl)-amide

(173a) 3-Amino-4-aminomethyl-benzoic acid ethyl ester

Prepared analogously to example 1b by hydrogenation of 4-methylamino-3-nitro-benzoic acid ethyl ester using palladium/charcoal 10% in methanol.
Yield: 98%

(173b) 2-(2,6-Difluoro-phenylamino)-1-methyl-1H-benzimidazole-5-carboxylic acid ethyl ester Prepared analogously to example 1c from 3-amino-4-aminomethyl-benzoic acid ethyl ester and 1,3-dichloro-2-isothiocyanato-benzene with DIC in acetonitrile and DMF.
Yield: 65%
mass spectrum: $(M+H)^+=332$

(173c) 2-(2,6-Difluoro-phenylamino)-1-methyl-1H-benzimidazole-5-carboxylic acid Prepared analogously to example 3b from 2-(2,6-difluoro-phenylamino)-1-methyl-1H-benzimidazole-5-carboxylic acid ethyl ester and NaOH in ethanol and water.
Yield: 70%
mass spectrum: $(M+H)^+=304$

(173d) 2-(2,6-Difluoro-phenylamino)-1-methyl-1H-benzimidazole-5-carboxylic acid (4-bromo-phenyl)-amide Prepared analogously to example 8c from 2-(2,6-difluoro-phenylamino)-1-methyl-1H-benzimidazole-5-carboxylic acid, HATU and TEA in NMP
Yield: 15%
$R_t$ value: 2.34 min (C5)
mass spectrum: $(M+H)^+=457$

Example 179

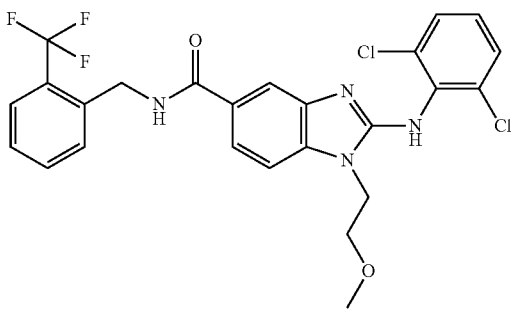 [SMILES: COCCn1c(Nc2c(Cl)cccc2Cl)nc2cc(C(=O)NCc3ccccc3C(F)(F)F)ccc21]

2-(2,6-Difluoro-phenylamino)-1-(2-methoxy-ethyl)-
1H-benzimidazole-5-carboxylic acid 2-trifluorom-
ethyl-benzylamide

(179a) 4-(2-Methoxy-ethylamino)-3-nitro-benzoic acid ethyl ester

2-Methoxy-ethylamine (1.55 mL, 17.8 mmol) was added to a stirred solution of 4-fluoro-3-nitro-benzoic acid ethyl ester (3.60 g, 16.9 mmol) and $K_2CO_3$ (4.67 g, 33.8 mmol) in 50 mL DMF. After stirring for 4 h the mixture was poured onto ice water, stirred for 10 min, filtered and dried.
Yield: 4.27 g (94%)
mass spectrum: $(M+H)^+ = 269$

(179b) 3-Amino-4-(2-methoxy-ethyl)-benzoic acid ethyl ester

Prepared analogously to example 1b by hydrogenation of 4-(2-methoxy-ethylamino)-3-nitro-benzoic acid ethyl ester using palladium/charcoal 10% in ethanol.
Yield: 98%

(179c) 2-(2,6-Difluoro-phenylamino)-1-(2-methoxy-ethyl)-1H-benzimidazole-5-carboxylic acid ethyl ester Prepared analogously to example 1c from 3-amino-4-(2-methoxy-ethyl)-benzoic acid ethyl ester and 1,3-dichloro-2-isothiocyanato-benzene with DIC in THF.
Yield: 73%
mass spectrum: $(M+H)^+ = 408/10/12$ (chlorine isotopes)
$R_t$ value: 2.68 min (C2)

(179d) 2-(2,6-Difluoro-phenylamino)-1-(2-methoxy-ethyl)-1H-benzimidazole-5-carboxylic acid Prepared analogously to example 3b from 2-(2,6-difluoro-phenylamino)-1-(2-methoxy-ethyl)-1H-benzimidazole-5-carboxylic acid ethyl ester and aq. NaOH in ethanol.
Yield: 63%
mass spectrum: $(M+H)^+ = 378/80/82$ (chlorine isotopes)
$R_t$ value: 2.07 min (C2)

(179e) 2-(2,6-Difluoro-phenylamino)-1-(2-methoxy-ethyl)-1H-benzimidazole-5-carboxylic acid 2-trifluoromethyl-benzylamide Prepared analogously to example 8c from 2-(2,6-difluoro-phenylamino)-1-(2-methoxy-ethyl)-1H-benzimidazole-5-carboxylic acid and 2-trifluoromethyl-benzylamine with HATU in NMP.
Yield: 37%
mass spectrum: $(M+H)^+ = 537/39/41$ (chlorine isotopes)
$R_t$ value: 2.54 min (C2)
In analogy with the above described example, the following compounds were prepared:

| No. | Structural formula Name | Yield | Mass peak(s) | $R_f$ value or $R_t$ |
|---|---|---|---|---|
| 180 | 2-(2,6-Dichloro-phenylamino)-1-(2-methoxy-ethyl)-1H-benzimidazole-5-carboxylic acid (4,4-dimethyl-cyclohexyl)-amide | Σ: 1831% | (M+H)+ = 489/91/93 (chlorine isotopes) | 2.58 min (C2) |

| Structural formula No. Name | Yield | Mass peak(s) | $R_f$-value or $R_t$ |
|---|---|---|---|
| 181 ![structure] 2-(2,6-Dichloro-phenylamino)-1-(2-methoxy-ethyl)-1H-benzimidazole-5-carboxylic acid (3-chloro-phenyl)-amide | Σ: 1628% | (M + H)+ = 489/91/93/95 (chlorine isotopes) | 2.66 min (C2) |

Example 182

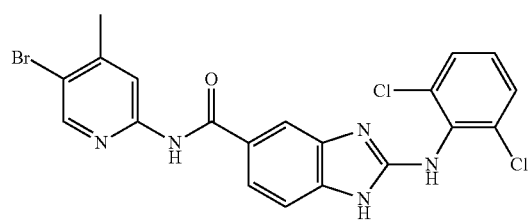 [SMILES: Cc1cc(NC(=O)c2ccc3[nH]c(Nc4c(Cl)cccc4Cl)nc3c2)ncc1Br]

2-(2,6-Dichloro-phenylamino)-1H-benzimidazole-5-carboxylic acid (5-bromo-4-methyl-pyridin-2-yl)-amide (182a) 2-(2,6-Dichloro-phenylamino)-1H-benzimidazole-5-carboxylic acid A mixture of 1,3-dichloro-2-isothiocyanato-benzene (5.66 g, 27.8 mmol) and 3,4-diamino-benzoic acid ethyl ester (5.00 g, 27.8 mmol) in 40 mL DMF was stirred for 2 h. DIC (4.40 mL, 28.2 mmol) was added and stirred overnight at ambient temperature. The mixture was stirred for 30 min at 80° C., diluted with water and concentrated i.vac. The residue was taken up in ethanol and 60 mL 1 M aq. NaOH was added and stirred overnight at reflux. Ethanol was evaporated and the aq. phase was filtered. The filtrate was acidified with formic acid, cooled, filtered and dried.

Yield: 8.58 g (96%)

(182b) 2-(2,6-Dichloro-phenylamino)-1H-benzimidazole-5-carboxylic acid ethyl ester Prepared analogously to example 174b from 2-(2,6-dichloro-phenylamino)-1H-benzimidazole-5-carboxylic acid and ethanol in conc. sulphuric acid.

Yield: 86% mass spectrum: (M+H)$^+$=350/52/54 (chlorine isotopes)

$R_t$ value: 2.68 min (B2)

(182c) 2-(2,6-Dichloro-phenylamino)-1H-benzimidazole-5-carboxylic acid (5-bromo-4-methyl-pyridin-2-yl)-amide Prepared analogously to example 131f from 2-(2,6-dichloro-phenylamino)-1H-benzimidazole-5-carboxylic acid ethyl ester and 2 M solution of trimethyl aluminium in hexane in THF.

Yield: 59% mass spectrum: (M+H)$^+$=490/92/94/96 (chlorine isotopes)

$R_t$ value: 3.08 min (B2)

In analogy with the above described example, the following compounds were prepared:

| Structural formula No. Name | Yield | Mass peak(s) | $R_f$-value or $R_t$ |
|---|---|---|---|
| 183 ![structure] 2-(2,6-Dichloro-phenylamino)-1H-benzimidazole-5-carboxylic acid (5-bromo-3-methyl-pyridin-2-yl)-amide | Σ: 409% | (M + H)+ = 490/92/94/96 (chlorine and bromine isotopes) | 2.67 min (B2) |

| No. | Structural formula Name | Yield | Mass peak(s) | $R_f$ value or $R_t$ |
|---|---|---|---|---|
| 184 | 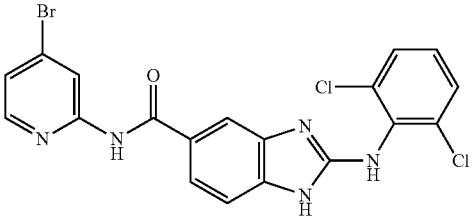 [SMILES: O=C(Nc1cc(Br)ccn1)c1ccc2[nH]c(Nc3c(Cl)cccc3Cl)nc2c1]<br>2-(2,6-Dichloro-phenylamino)-1H-benzimidazole-5-carboxylic acid (4-bromo-pyridin-2-yl)-amide | Σ: 238% | (M + H)+ = 476/78/80/82 (chlorine and bromine isotopes) | 2.92 min (B2) |
| 185 | 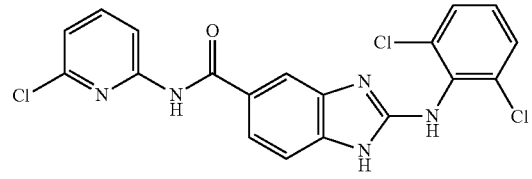 [SMILES: O=C(Nc1cccc(Cl)n1)c1ccc2[nH]c(Nc3c(Cl)cccc3Cl)nc2c1]<br>2-(2,6-Dichloro-phenylamino)-1H-benzimidazole-5-carboxylic acid (6-chloro-pyridin-2-yl)-amide | Σ: 238% | (M + H)+ = 432/34/36/38 (chlorine isotopes) | 2.89 min (B2) |
| 186 | 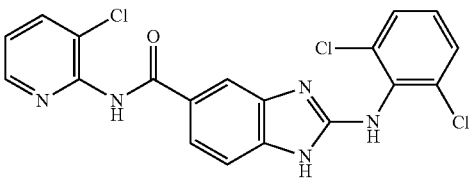 [SMILES: O=C(Nc1ncccc1Cl)c1ccc2[nH]c(Nc3c(Cl)cccc3Cl)nc2c1]<br>2-(2,6-Dichloro-phenylamino)-1H-benzimidazole-5-carboxylic acid (3-chloro-pyridin-2-yl)-amide | Σ: 307% | (M + H)+ = 432/34/36/38 (chlorine isotopes) | 2.48 min (B2) |
| 187 | 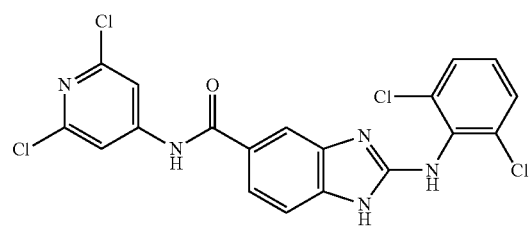 [SMILES: O=C(Nc1cc(Cl)nc(Cl)c1)c1ccc2[nH]c(Nc3c(Cl)cccc3Cl)nc2c1]<br>2-(2,6-Dichloro-phenylamino)-1H-benzimidazole-5-carboxylic acid (2,6-dichloro-pyridin-4-yl)-amide | Σ: 15% | (M + H)+ = 466/68/70/72 (chlorine isotopes) | 3.20 min (B2) |
| 188 | 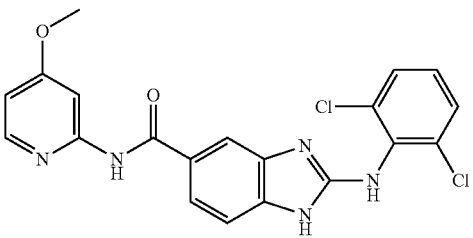 [SMILES: COc1ccnc(NC(=O)c2ccc3[nH]c(Nc4c(Cl)cccc4Cl)nc3c2)c1]<br>2-(2,6-Dichloro-phenylamino)-1H-benzimidazole-5-carboxylic acid (4-methoxy-pyridin-2-yl)-amide | Σ: 39% | (M + H)+ = 428/30/32 (chlorine isotopes) | 2.06 min (B2) |

| Structural formula No. Name | | Yield | Mass peak(s) | $R_f$ value or $R_t$ |
|---|---|---|---|---|
| 189 | 2-(2,6-Dichloro-phenylamino)-1H-benzimidazole-5-carboxylic acid (5-fluoro-4-methyl-pyridin-2-yl)-amide | Σ: 55% | (M + H)+ = 430/32/34 (chlorine isotopes) | 2.78 min (B2) |
| 190 | 2-(2,6-Dichloro-phenylamino)-1H-benzimidazole-5-carboxylic acid (3-trifluoromethyl-pyridin-2-yl)-amide | Σ: 0.6% | (M + H)+ = 466/68/70 (chlorine isotopes) | 2.49 min (C2) |
| 191 | 2-(2,6-Dichloro-phenylamino)-1H-benzimidazole-5-carboxylic acid (5-trifluoromethyl-pyridin-2-yl)-amide | Σ: 6.0% | (M + H)+ = 466/68/70 (chlorine isotopes) | 3.13 min (C2) |

Example 192

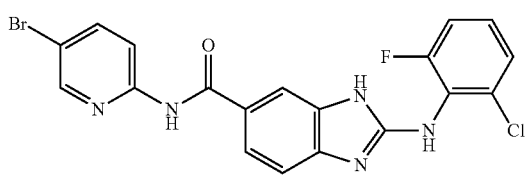 [SMILES: O=C(Nc1ccc(Br)cn1)c1ccc2nc(Nc3c(F)cccc3Cl)[nH]c2c1]

2-(2-Chloro-6-fluoro-phenylamino)-3H-benzimidazole-5-carboxylic acid (5-bromo-pyridin-2-yl)-amide (192a) 1-Chloro-3-fluoro-2-isothiocyanato-benzene A mixture of 2-chloro-6-fluoro-phenylamine (400 mg, 2.8 mmol), thiocarbonic acid O,O-dipyridin-2-yl ester (650 mg, 2.8 mmol) and TEA (840 μL, 6.0 mmol) in 5 mL THF was stirred overnight at 50° C. The mixture was heated to 65° C. and stirred for further 5 h. The mixture was concentrated i.vac. The residue was purified by chromatography on HPLC (C-18 Symmetry, eluent gradient: water+0.15% HCOOH+ 15-100% acetonitrile).

Yield: 270 mg (52%)

$R_t$ value: 3.57 min (C2)

(192b) 4-Amino-N-(5-bromo-pyridin-2-yl)-3-nitro-benzamide

4-Amino-3-nitro-benzoic acid (350 mg, 1.9 mmol) and (1-chloro-2-methyl-propenyl)-dimethyl-amine (300 μL, 2.3 mmol) in 5 mL dichloromethane were stirred for 1.5 h. A mixture of 5-bromo-pyridin-2-ylamine (335 mg, 1.9 mmol) and 300 μL pyridine in 5 mL dichloromethane was added and stirred for further 30 min. Methanol was added and the mixture was concentrated i.vac. The residue was taken up in methanol, filtered, washed and dried.

Yield: 460 mg (71%)

mass spectrum: $(M+H)^+$=337/39 (bromine isotopes)

$R_t$ value: 2.74 min (C2)

(192c) 3,4-Diamino-N-(5-bromo-pyridin-2-yl)-benzamide

Prepared analogously to example 14b by hydrogenation of 4-amino-N-(5-bromo-pyridin-2-yl)-3-nitro-benzamide using Raney nickel in THF.

Yield: 95% mass spectrum: $(M+H)^+$=307/09 (bromine isotopes)

$R_t$ value: 2.78 min (B2)

(192d) 4-Amino-N-(5-bromo-pyridin-2-yl)-3-[3-(2-chloro-6-fluoro-phenyl)-thioureido]-benzamide A mixture of the product obtained in 192c (400 mg, 1.3 mmol) and the product obtained in 192a (245 mg, 1.3 mmol) in 20 mL DMF was stirred for 2 days at ambient temperature. The mixture was concentrated i.vac. The residue was purified by chromatography on HPLC (C-18 Symmetry, eluent gradient: water+0.15% HCOOH+15-100% acetonitrile).

Yield: 440 mg (68%)
mass spectrum: (M+H)$^+$=494/96/98 (chlorine and bromine isotopes)
R$_t$ value: 2.71 min (C2)

(192e) 2-(2-Chloro-6-fluoro-phenylamino)-3H-benzimidazole-5-carboxylic acid (5-bromo-pyridin-2-yl)-amide Prepared analogously to example 127e from 4-amino-N-(5-bromo-pyridin-2-yl)-3-[3-(2-chloro-6-fluoro-phenyl)-thioureido]-benzamide with DIC in acetonitrile.

Yield: 34%
mass spectrum: (M+H)$^+$=460/62/64 (chlorine and bromine isotopes)
R$_t$ value: 2.89 min (B2)

In analogy with the above described example, the following compounds were prepared:

| No. | Structural formula / Name | Yield | Mass peak(s) | R$_f$ value or R$_t$ |
|---|---|---|---|---|
| 133 | 2-(2,6-Dichloro-phenylamino)-6-methoxy-3H-benzimidazole-5-carboxylic acid (4-chloro-pyridin-4-yl)-amide | Σ: 88% | (M + H)+ = 462/64/66/68 (chlorine isotopes) | 2.08 min (C2) |
| 134 | 2-(2,6-Dichloro-phenylamino)-6-methoxy-1-methyl-3H-benzimidazole-5-carboxylic acid (6-methoxy-pyridin-2-yl)-amide | Σ: 86% | (M + H)+ = 476/78/80/82 (chlorine isotopes) | 2.34 min (C2) |
| 137 | 2-(2,6-Dichloro-phenylamino)-3H-benzimidazole-5-carboxylic acid cyclohexylamide | Σ: 96% | (M + H)+ = 404/06/08 (chlorine isotopes) | 2.13 min (C2) |
| 193 | 2-(2,6-Dichloro-phenylamino)-3H-benzimidazole-5-carboxylic acid (2-methyl-pyridin-4-yl)-amide | Σ: 87% | (M + H)+ = 412/14/16 (chlorine isotopes) | 1.92 min (B2) |

-continued

| Structural formula No. Name | Yield | Mass peak(s) | $R_f$ value or $R_t$ |
|---|---|---|---|
| 194 2-(2,6-Dichloro-phenylamino)-3H-benzimidazole-5-carboxylic acid (6-methoxy-pyridin-2-yl)-amide | Σ: 38% | (M + H)+ = 428/30/32 (chlorine isotopes) | 2.80 min (B2) |
| 195 2-(2,6-Dichloro-phenylamino)-3H-benzimidazole-5-carboxylic acid (5-methoxy-pyridin-2-yl)-amide | Σ: 68% | (M + H)+ = 428/30/32 (chlorine isotopes) | 2.50 min (B2) |
| 197 2-(2,6-Dichloro-phenylamino)-6-methoxy-3H-benzimidazole-5-carboxylic acid (4-chloro-3-fluoro-pyridin-4-yl)-amide | Σ: 85% | (M + H)+ = 479/81/83/85 (chlorine isotopes) | 2.22 min (C2) |
| 198 2-(2,6-Dichloro-phenylamino)-3H-benzimidazole-5-carboxylic acid (2-chloro-6-methyl-pyridin-4-yl)-amide | Σ: 72% | (M + H)+ = 480/82/84/86 (chlorine isotopes) | 1.98 min (C2) |
| 201 2-(2,6-Dichloro-phenylamino)-1-methyl-1H-benzimidazole-5-carboxylic acid (4,6-dimethyl-pyridin-2-yl)-amide | Σ: 85% | (M + H)+ = 440/42/44 (chlorine isotopes) | 1.89 min (C2) |

-continued

| Structural formula No. Name | Yield | Mass peak(s) | $R_f$-value or $R_t$ |
|---|---|---|---|
| 202 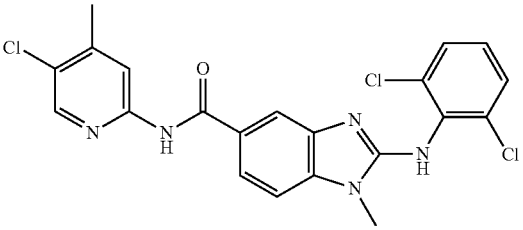 [SMILES: Cc1cc(NC(=O)c2ccc3c(c2)nc(Nc2c(Cl)cccc2Cl)n3C)ncc1Cl]<br>2-(2,6-Dichloro-phenylamino)-1-methyl-1H-benzimidazole-5-carboxylic acid (5-chloro-4-methyl-pyridin-2-yl)-amide | Σ: 86% | (M + H)+ = 460/62/64/66 (chlorine isotopes) | 2.35 min (C2) |
| 203 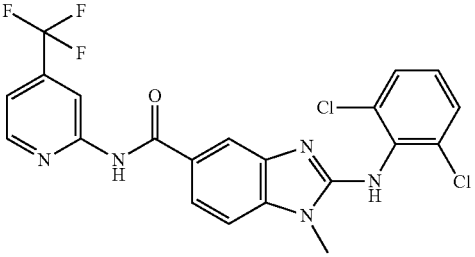 [SMILES: Cn1c(Nc2c(Cl)cccc2Cl)nc2cc(C(=O)Nc3cc(C(F)(F)F)ccn3)ccc21]<br>2-(2,6-Dichloro-phenylamino)-1-methyl-1H-benzimidazole-5-carboxylic acid (4-trifluoromethyl-pyridin-2-yl)-amide | Σ: 70% | (M + H)+ = 480/82/84 (chlorine isotopes) | 2.40 min (C2) |

Example 199

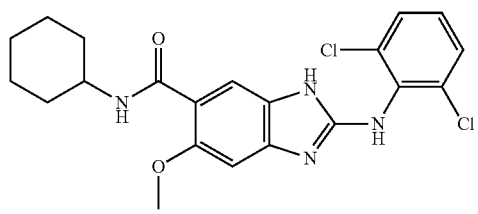 [SMILES: COc1cc2nc(Nc3c(Cl)cccc3Cl)[nH]c2cc1C(=O)NC1CCCCC1]

N-(Cyclohexyl)-2-(2,6-dichlorophenylamino)-6-methoxy-1H-benzimidazole-5-carboxamide (199a) 4-Amino-2-methoxy-5-nitro-benzoic acid Prepared analogously to example 3b from methyl 4-acetylamino-2-methoxy-5-nitro-benzoate with NaOH in ethanol.
Yield: 92%
mass spectrum: (M+H)$^+$=213
$R_t$ value: 1.99 min (C5)

(199b) 4,5-Diamino-2-methoxy-bezoic acid

Prepared analogously to example 1b by hydrogenation of the product obtained in example 199a using palladium/charcoal 10% in methanol.
Yield: 92%

(199c) 4-Amino-5-(3-(2,6-dichlorophenyl)-thioureido)-2-methoxybenzoic acid

Prepared analogously to example 156d from the product obtained in example 199b and 1,3-dichloro-2-isothiocyanato-benzene in acetonitrile and methanol.
Yield: 72%, mass spectrum: (M+H)$^+$=386/388/390 (chlorine isotopes), $R_t$ value: 2.22 min (C2)

(199d) 2-(2,6-Dichloro-phenylamino)-6-methoxy-1H-benzimidazole-5-carboxylic acid Prepared analogously to example 135f from the product obtained from 199c with 2,2,2-trifluoro-N-(trimethylsilyl) acetimidate) and DIC in acetonitrile.
Yield: 650 mg (71%)
mass spectrum: (M+H)$^+$=352/354/356 (chlorine isotopes)

(199e) N-Cyclohexyl-2-(2,6-dichlorophenylamino)-6-methoxy-1H-benzimidazole-5-carboxamide Prepared analogously to example 3c from the product obtained from 199d and cyclohexylamine with TBTU and TEA in DMF.
Yield: 49%
mass spectrum: (M+H)$^+$=433/435/437 (chlorine isotopes)
$R_t$ value: 2.86 min (B2)

In analogy with the above described example, the following compounds were prepared:

| No. | Structural formula Name | Yield | Mass peak(s) | $R_f$ value or $R_t$ |
|---|---|---|---|---|
| 200 | 2-(2,6-Dichloro-phenylamino)-6-methoxy-3H-benzimidazole-5-carboxylic acid 2-trifluoromethyl-benzamide | Σ: 2.9% | $(M + H)^+ =$ 509/511/513 (chlorine isotopes) | 3.11 min (B2) |
| 371 | N-(4-Bromophenyl)-2-(2,6-dichlorophenylamino)-6-methoxy-1H-benzimidazole-5-carboxamide | Σ: 8% | $(M + H)^+ =$ 524/526/28 (chlorine and bromine isotopes)isotopes | 2.03 min (E7) |
| 376 | 2-(2,6-Dichlorophenylamino)-6-methoxy-N-((1r,4r)-4-trifluoromethyl-cyclohexyl)-1H-benzimidazole-5-carboxamide | Σ: 5% | $(M + H)^+ =$ 501/03/05 (chlorine isotopes) | 1.98 min (E7) |
| 383 | 2-(2,6-Dichlorophenylamino)-6-methoxy-N-((3-trifluoromethyl-pyridin-2-yl)-methyl)-1H-benzimidazole-5-carboxamide | Σ: 10% | $(M + H)^+ =$ 510/12/17 (chlorine isotopes) | 1.8 min (E7) |
| 407 | N-((3-Cyclopropylpyridin-2-yl)-methyl)-2-(2,6-dichlorophenylamino)-6-methoxy-1H-benzimidazole-5-carboxamide | Σ: 19% | $(M + H)^+ =$ 482/84/86 (chlorine isotopes) | 1.0 min (F7) |

-continued

| No. | Structural formula Name | Yield | Mass peak(s) | R_f value or R_t |
|---|---|---|---|---|
| 507 | 2-(2,6-Dichlorophenylamino)-6-methoxy-N-((3-methylpyridin-2-yl)-methyl)-1H-benzimidazole-5-carboxamide | Σ: 9% | (M + H)⁺ = 456/458/460 (chlorine isotopes) | 0.94 min (F8) |
| 525 | 2-(2,6-Dichlorophenylamino)-6-methoxy-N-((3-methoxypyridin-2-yl)methyl)-1H-benzimidazole-5-carboxamide | Σ: 14.5% | (M + H)⁺ = 472/474/476 (chlorine isotopes) | 1.0 min (F8) |
| 579 | 2-(2,6-Dichloro-4-fluoro-phenylamino)-6-methoxy-N-(trans-4-trifluoromethyl-cyclohex-1-yl)-1H-benzimidazole-5-carboxamide | Σ: 16% | (M + H)⁺ = 519/521/523 (chlorine isotopes) | 3.84 min (B1) |
| 580 | 2-(2,6-Dichloro-4-fluoro-phenylamino)-6-methoxy-N-((3-trifluoromethyl-pyridin-2-yl)-methyl)-1H-benzimidazole-5-carboxamide | Σ: 19% | (M + H)⁺ = 528/530/532 (chlorine isotopes) | 3.51 min (B1) |
| 581 | 2-(2,6-Dichloro-4-fluoro-phenylamino)-6-methoxy-N-(4-bromo-phenyl)-1H-benzimidazole-5-carboxamide | Σ: 16% | (M + H)⁺ = 523/525/527/529 (chlorine and bromine isotopes) | 4.05 min (B1) |

-continued

| Structural formula No. Name | Yield | Mass peak(s) | $R_f$ value or $R_t$ |
|---|---|---|---|
| 630 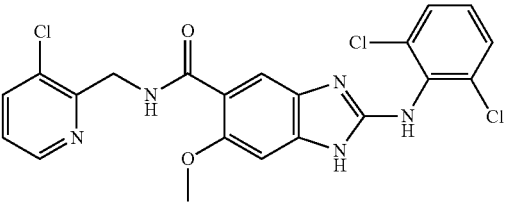 [SMILES: COc1cc2[nH]c(Nc3c(Cl)cccc3Cl)nc2cc1C(=O)NCc1ncccc1Cl] 2-(6-Chloro-2-fluoro-3-methyl-phenylamino)-6-methoxy-N-(3-chlor-pyridin-2-yl-methyl)-1H-benzimidazole-5-carboxamide | Σ: 37% | (M + H)+ = 476/478/480/482 (chlorine isotopes) | 1.94 min (C2) |

Example 205

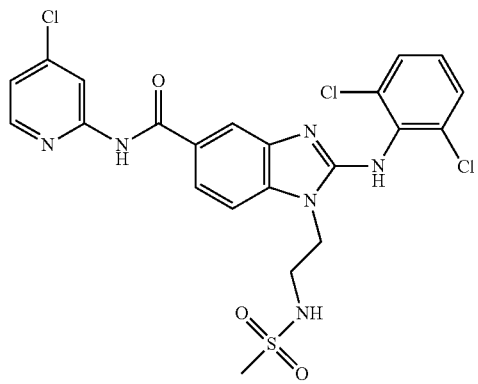 [SMILES: CS(=O)(=O)NCCn1c(Nc2c(Cl)cccc2Cl)nc2cc(C(=O)Nc3cc(Cl)ccn3)ccc21]

2-(2,6-Dichloro-phenylamino)-1-(2-methanesulfony-lamino-ethyl)-1H-benzimidazole-5-carboxylic acid (4-chloro-pyridin-2-yl)-amide (205a) 2-(2,6-Dichloro-phenylamino)-1-(2-methane-sulfonylamino-ethyl)-1H-benzimidazole-5-carboxylic acid (4-chloro-pyridin-2-yl)-amide A mixture of methanesulfonyl chloride (8 μL, 0.1 mmol) and TEA (49 μL, 0.4 mmol) was added to a stirred solution of the product obtained in example 211 (59 mg, 0.1 mmol) in 2 mL acetonitrile. After stirring for 2 h the mixture was concentrated i.vac. The residue was purified by chromatography on RP-HPLC.

Yield: 10 mg (18%)

mass spectrum: $(M+H)^+$=553/55/57/59 (chlorine isotopes)

$R_t$ value: 1.87 min (CC)

In analogy with the above described example, the following compounds were prepared:

| Structural formula No. Name | Yield | Mass peak(s) | $R_f$ value or $R_t$ |
|---|---|---|---|
| 206 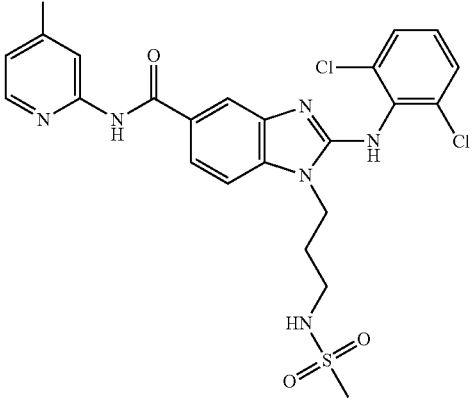 2-(2,6-Dichloro-phenylamino)-1-(3-methanesulfonylamino-propyl)-1H-benzimidazole-5-carboxylic acid (4-chloro-pyridin-2-yl)-amide | Σ: 53% | (M + H)+ = 567/69/71 (chlorine isotopes) | 1.89 min (CC) |

Example 207

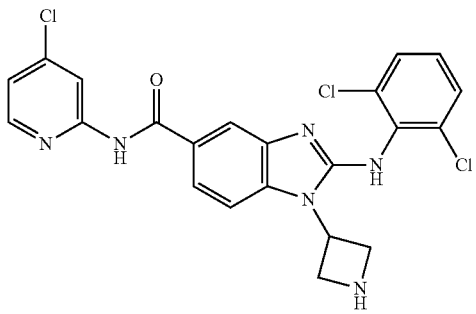 [SMILES: O=C(Nc1cc(Cl)ccn1)c1ccc2c(c1)nc(Nc1c(Cl)cccc1Cl)n2C1CNC1]

2-(2,6-Dichloro-phenylamino)-1-azetidin-3-yl-1H-benzimidazole-5-carboxylic acid (4-chloro-pyridin-2-yl)-amide(trifluoro-acetate)

(207a) N-(4-Chloro-pyridin-2-yl)-4-fluoro-3-nitro-benzamide

A mixture of 4-fluoro-3-nitro-benzoic acid (5.55 g, 30.0 mmol) and (1-chloro-2-methyl-propenyl)-dimethyl-amine (4.37 mL, 33.0 mmol) in 100 mL dichloromethane was stirred for 40 min. A mixture of 4-chloro-pyridin-2-ylamine (3.86 g, 30.0 mmol) and 3.56 mL pyridine in 100 mL was added and stirred overnight. The mixture was concentrated i.vac. The residue was taken up in warm methanol, a precipitate formed after cooling which was filtered and taken up in a mixture of dichloromethane, methanol and water. The organic solvents were evaporated. The aq. phase was filtered and the solid dried.

Yield: 5.10 g (58%)

mass spectrum: $(M+H)^+=296/98$ (chlorine isotopes)

(207b) 2-(2,6-Dichloro-phenylamino)-1-azetidin-3-yl-1H-benzimidazole-5-carboxylic acid (4-chloro-pyridin-2-yl)-amide(trifluoro-acetate)

To a stirred mixture of azetidin-3-yl-amine (18 mg, 0.3 mmol) and $K_2CO_3$ (52 mg, 0.4 mmol) in 1 mL DMF, N-(4-chloro-pyridin-2-yl)-4-fluoro-3-nitro-benzamide (74 mg, 0.3 mmol) in 1 mL DMF was added and stirred overnight at ambient temperature. The mixture was filtered with Alox B, washed with DMF/methanol and concentrated i.vac. The residue was taken up in THF and methanol. Raney nickel (50 mg) was added. The mixture was hydrogenated for 4 h at ambient temperature in a Parr apparatus at 3.5 bar hydrogen pressure. Then the mixture was filtered over silica gel and concentrated i.vac. The residue was taken up in acetonitrile. 1,3-Dichloro-2-thioisocyanato-benzene (41 mg, 0.2 mmol) was added and stirred. After stirring for 2 days DIC (27 mg, 0.2 mmol) was added and stirred overnight. The mixture was concentrated i.vac. and taken up in dichloromethane. TFA was added and stirred overnight. The mixture was concentrated i.vac. and purified by chromatography on RP-HPLC.

Yield: 10 mg (21%)

mass spectrum: $(M+H)^+=487/89/91$ (chlorine isotopes)

Example 208

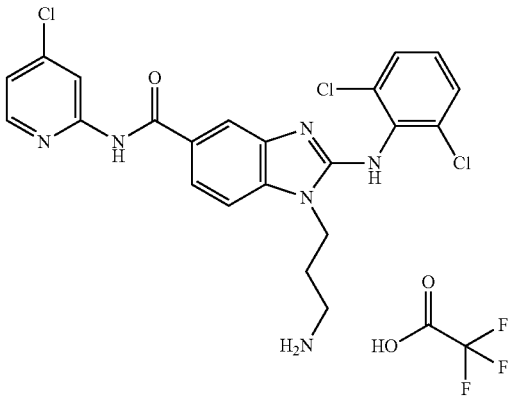 [SMILES: NCCCn1c(Nc2c(Cl)cccc2Cl)nc2cc(C(=O)Nc3cc(Cl)ccn3)ccc21 ; O=C(O)C(F)(F)F]

2-(2,6-Dichloro-phenylamino)-1-(3-amino-propyl)-1H-benzimidazole-5-carboxylic acid (4-chloro-pyridin-2-yl)-amide(trifluoro-acetate)

(208a) N-(4-Chloro-pyridin-2-yl)-4-fluoro-3-nitro-benzamide

A mixture of 4-fluoro-3-nitro-benzoic acid (5.6 g, 30.0 mmol) and (1-chloro-2-methyl-propenyl)-dimethyl-amine (4.4 mL, 33.0 mmol) in 100 mL dichloromethane was stirred for 40 min. A mixture of 4-chloro-pyridin-2-ylamine (3.86 g, 30.0 mmol) and 3.6 mL pyridine in 100 mL dichoromethane was added and stirred overnight. The mixture was concentrated i.vac. The residue was taken up in methanol, dichloromethane and water. The organic solvents were evaporated. The aq. phase was filtered and the solid dried.

Yield: 5.10 g (58%)

mass spectrum: $(M+H)^+=296/98$ (chlorine isotopes)

(208b) {3-[4-(4-Chloro-pyridin-2-ylcarbamoyl)-2-nitro-phenylamino]-propyl}-carbamic acid tert.-butyl ester A mixture of the product obtained in 208a (89 mg, 0.3 mmol), (3-amino-propyl)-carbamic acid tert.-butyl ester (52 mg, 0.3 mmol) and $K_2CO_3$ (83 mg, 0.6 mmol) in 4 mL DMF was stirred overnight at ambient temperature. The mixture was filtered with Alox B, washed with DMF and concentrated i.vac. The residue was reacted without any further purification.

Yield: 122 mg (90%); $R_t$ value: 2.36 min (CC).

(208c) {3-[2-Amino-4-(4-chloro-pyridin-2-ylcarbamoyl)-phenylamino]-propyl}-carbamic acid tert.-butyl ester Prepared analogously to example 1b by hydrogenation of {3-[4-(4-chloro-pyridin-2-ylcarbamoyl)-2-nitro-phenylamino]-propyl}-carbamic acid tert.-butyl ester using Pt/charcoal 5% in methanol and THF.

Yield: 74%

$R_t$ value: 1.75 min (CC)

(208d) 2-(2,6-Dichloro-phenylamino)-1-(3-amino-propyl)-1H-benzimidazole-5-carboxylic acid (4-chloro-pyridin-2-yl)-amide(trifluoro-acetate)

A mixture of the product obtained in 208c (84 mg, 0.2 mmol) and 1,3-dichloro-2-isothiocyanato-benzene (41 mg, 0.2 mmol) in 7 mL acetonitrile was stirred overnight at ambient temperature. EDC (31 mg, 0.2 mmol) was added and stirred for 2 days. The mixture was concentrated i.vac. The residue was taken up in dichloromethane and trifluoro-acetic acid and stirred for 1 h. The mixture was concentrated i.vac. and purified by chromatography on RP-HPLC.

Yield: 10 mg (8.3%)

mass spectrum: (M+H)$^+$=489/91/93/95 (chlorine isotopes)

In analogy with the above described example, the following compounds were prepared:

| No. | Structural formula Name | Yield | Mass peak(s) | $R_f$ value or $R_t$ |
|---|---|---|---|---|
| 209 | 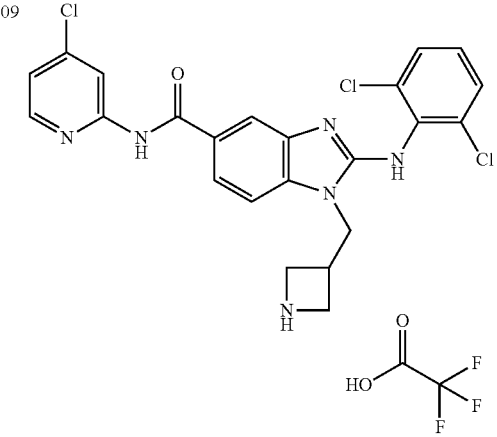 2-(2,6-Dichloro-phenylamino)-(1-azetidin-3-ylmethyl)-1H-benzimidazole-5-carboxylic acid (4-chloro-pyridin-2-yl)-amide (trifluoroacetate) | Σ: 24% | (M + H)+ = 501/03/05/07 (chlorine isotopes) | |
| 210 | 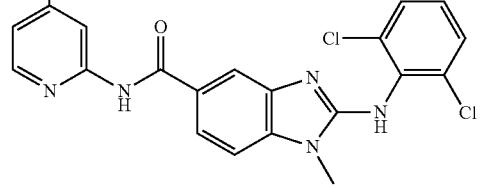 2-(2,6-Dichloro-phenylamino)-1-methyl-1H-benzimidazole-5-carboxylic acid (4-chloro-pyridin-2-yl)-amide | Σ: 32% | (M + H)+ = 444/46/48/50 (chlorine isotopes) | |
| 211 | 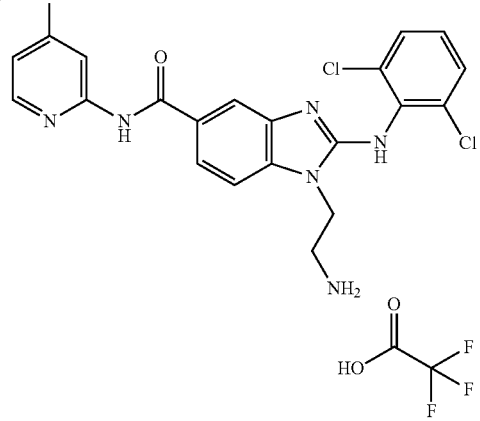 2-(2,6-Dichloro-phenylamino)-1-(2-amino-ethyl)-1H-benzimidazole-5-carboxylic acid (4-chloro-pyridin-2-yl)-amide (trifluoroacetate) | Σ: 63% | (M + H)+ = 475/77/781 (chlorine isotopes) | 1.73 min (CC) |

| No. | Structural formula Name | Yield | Mass peak(s) | $R_f$-value or $R_t$ |
|---|---|---|---|---|
| 212 | ![structure] 2-(2,6-Dichloro-phenylamino)-1-(2-methylamino-ethyl)-1H-benzimidazole-5-carboxylic acid (4-chloro-pyridin-2-yl)-amide (trifluoroacetate) | Σ: 30% | (M + H)+ = 489/91/93/35 (chlorine isotopes) | 1.78 min (CC) |

Example 213

2-(2,6-Dichloro-phenylamino)-1H-benzimidazole-5-carboxylic acid cyclohexyl-amide (213a) 2-(2,6-Dichloro-phenylamino)-1H-benzimidazole-5-carboxylic acid Prepared analogously to Example 113a from 3,4-diamino-benzoic acid ethyl ester and 1,3-dichloro-2-isothiocyanato-benzene with DCC in DMF and NaOH in ethanol.

Yield: 8.0 g (90%)

(213b) 2-(2,6-Dichloro-phenylamino)-1H-benzimidazole-5-carboxylic acid cyclohexylamide Prepared analogously to Example 3c from 2-(2,6-dichloro-phenylamino)-1H-benzimidazole-5-carboxylic acid, 2-amino-cyclohexanol, TEA and TBTU in DMF.

Yield: 25 mg (60%)

mass spectrum: (M+H)+=419/21/23 (chlorine isotopes)

$R_t$ value: 1.5 min (CC)

In analogy with the above described example, the following compounds were prepared:

Example 263

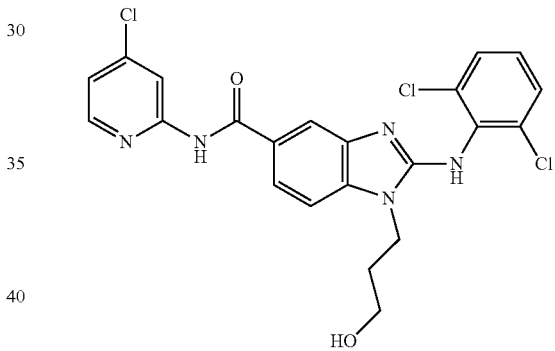

2-(2,6-Dichloro-phenylamino)-1-(3-hydroxy-propyl)-1H-benzimidazole-5-carboxylic acid (4-chloro-pyridin-2-yl)-amide (263a) N-(4-Chloro-pyridin-2-yl)-4-fluoro-3-nitro-benzamide Prepared analogous to example 113b from 4-fluoro-3-nitro-benzoic acid (5.55 g, 30.0 mmol) and 1-chloro-N,N-2-trimethyl-1-propenylamin in dichloromethane.

Yield: 5.10 g (58%)

mass spectrum: (M+H)+=296/98 (chlorine isotopes)

(263b) 2-(2,6-Dichloro-phenylamino)-1-(3-hydroxy-propyl)-1H-benzimidazole-5-carboxylic acid (4-chloro-pyridin-2-yl)-amide Prepared analogous to example 207b from N-(4-chloro-pyridin-2-yl)-4-fluoro-3-nitro-benzamide, 3-amino-propan-1-ol and $K_2CO_3$ in DMF, hydrogen and Pt/charcoal 5% and 1,3-dichloro-2-isothiocyanato-benzene and EDC in acetonitrile.

Yield: 28% mass spectrum: (M+H)+=490/92/94 (chlorine isotopes)

$R_t$ value: 1.71 min (CC)

In analogy with the above described example, the following compounds were prepared:

| No. | Structural formula / Name | Yield | Mass peak(s) | $R_f$-value or $R_t$ |
|---|---|---|---|---|
| 264 | 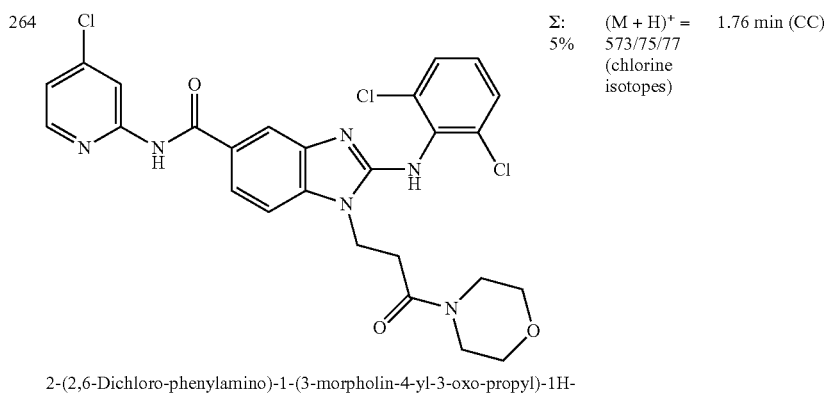<br>2-(2,6-Dichloro-phenylamino)-1-(3-morpholin-4-yl-3-oxo-propyl)-1H-benzimidazole-5-carboxylic acid (4-chloro-pyridin-2-yl)-amide | Σ: 5% | $(M+H)^+ =$ 573/75/77 (chlorine isotopes) | 1.76 min (CC) |
| 265 | 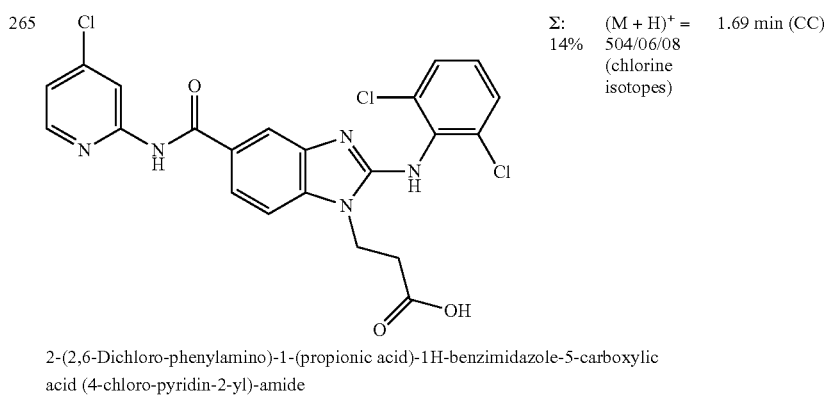<br>2-(2,6-Dichloro-phenylamino)-1-(propionic acid)-1H-benzimidazole-5-carboxylic acid (4-chloro-pyridin-2-yl)-amide | Σ: 14% | $(M+H)^+ =$ 504/06/08 (chlorine isotopes) | 1.69 min (CC) |
| 266 | 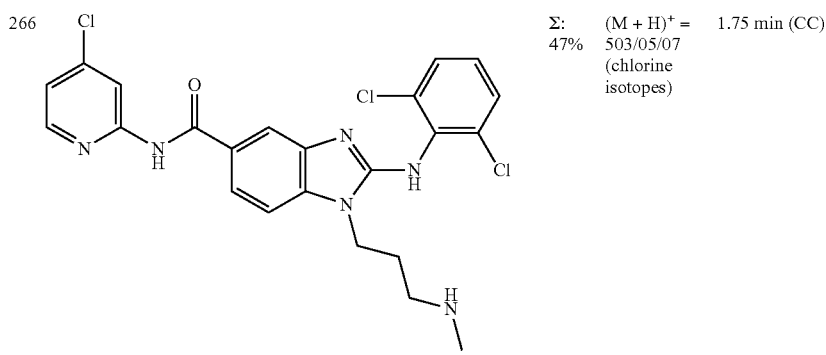<br>2-(2,6-Dichloro-phenylamino)-1-(3-methylamino-propyl)-1H-benzimidazole-5-carboxylic acid (4-chloro-pyridin-2-yl)-amide | Σ: 47% | $(M+H)^+ =$ 503/05/07 (chlorine isotopes) | 1.75 min (CC) |

| No. | Structural formula Name | Yield | Mass peak(s) | $R_f$ value or $R_t$ |
|---|---|---|---|---|
| 267 | 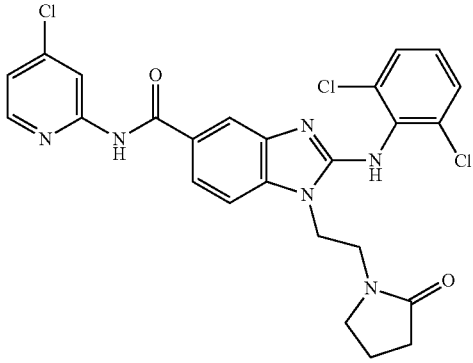 [SMILES: O=C(Nc1cc(Cl)ccn1)c1ccc2c(c1)nc(Nc1c(Cl)cccc1Cl)n2CCN1CCCC1=O]<br>2-(2,6-Dichloro-phenylamino)-1-[2-(2-oxo-pyrrolidin-1-yl)-ethyl]-1H-benzimidazole-5-carboxylic acid (4-chloro-pyridin-2-yl)-amide | Σ: 39% | $(M + H)^+$ = 543/45/47 (chlorine isotopes) | 1.71 min (CC) |
| 268 | 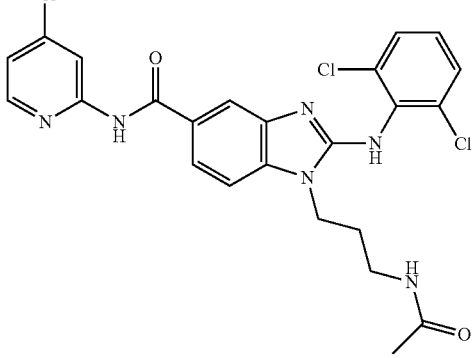<br>2-(2,6-Dichloro-phenylamino)-1-(3-acetylamino-propyl)-1H-benzimidazole-5-carboxylic acid (4-chloro-pyridin-2-yl)-amide | Σ: 57% | $(M + H)^+$ = 531/33/35 (chlorine isotopes) | 1.69 min (CC) |
| 269 | 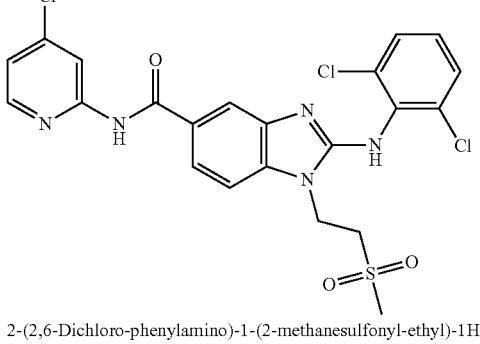<br>2-(2,6-Dichloro-phenylamino)-1-(2-methanesulfonyl-ethyl)-1H-benzimidazole-5-carboxylic acid (4-chloro-pyridin-2-yl)-amide | Σ: 6% | $(M + H)^+$ = 538/40/42 (chlorine isotopes) | 1.80 min (CC) |
| 270 | 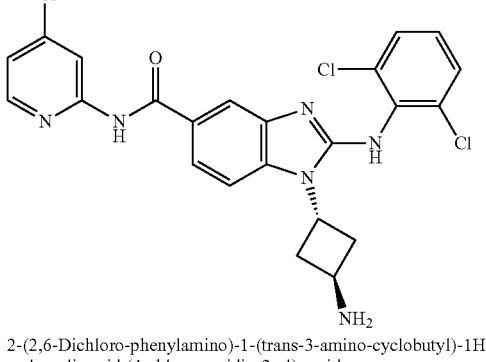<br>2-(2,6-Dichloro-phenylamino)-1-(trans-3-amino-cyclobutyl)-1H-benzimidazole-5-carboxylic acid (4-chloro-pyridin-2-yl)-amide | Σ: 43% | $(M + H)^+$ = 501/03/05 (chlorine isotopes) | 1.58 min (CC) |

| No. | Structural formula Name | Yield | Mass peak(s) | $R_f$-value or $R_t$ |
|---|---|---|---|---|
| 271 | 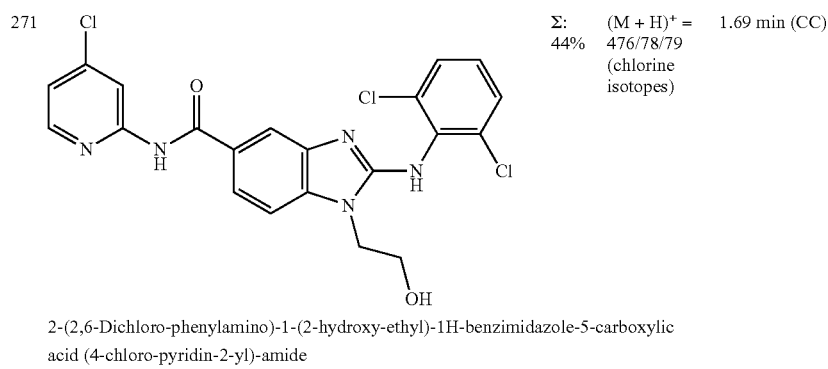<br>2-(2,6-Dichloro-phenylamino)-1-(2-hydroxy-ethyl)-1H-benzimidazole-5-carboxylic acid (4-chloro-pyridin-2-yl)-amide | Σ: 44% | $(M+H)^+ =$ 476/78/79 (chlorine isotopes) | 1.69 min (CC) |
| 272 | 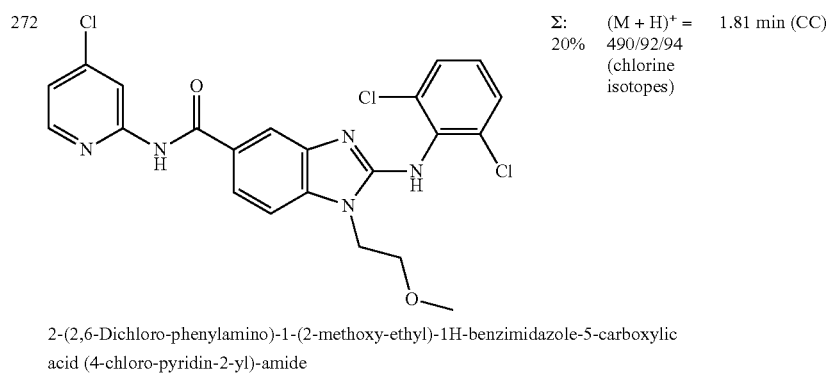<br>2-(2,6-Dichloro-phenylamino)-1-(2-methoxy-ethyl)-1H-benzimidazole-5-carboxylic acid (4-chloro-pyridin-2-yl)-amide | Σ: 20% | $(M+H)^+ =$ 490/92/94 (chlorine isotopes) | 1.81 min (CC) |
| 273 | 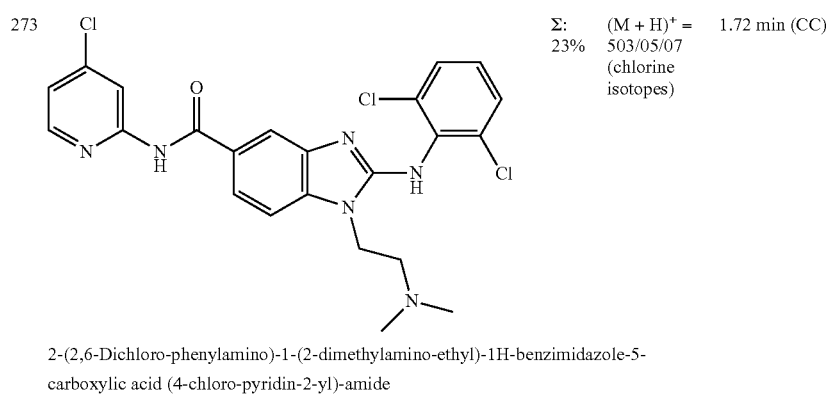<br>2-(2,6-Dichloro-phenylamino)-1-(2-dimethylamino-ethyl)-1H-benzimidazole-5-carboxylic acid (4-chloro-pyridin-2-yl)-amide | Σ: 23% | $(M+H)^+ =$ 503/05/07 (chlorine isotopes) | 1.72 min (CC) |
| 274 | 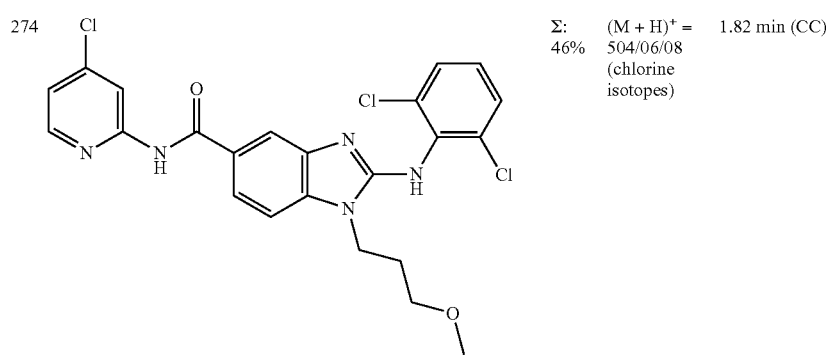<br>2-(2,6-Dichloro-phenylamino)-1-(3-methoxy-propyl)-1H-benzimidazole-5-carboxylic acid (4-chloro-pyridin-2-yl)-amide | Σ: 46% | $(M+H)^+ =$ 504/06/08 (chlorine isotopes) | 1.82 min (CC) |

-continued

| No. | Structural formula Name | Yield | Mass peak(s) | $R_f$-value or $R_t$ |
|---|---|---|---|---|
| 275 | 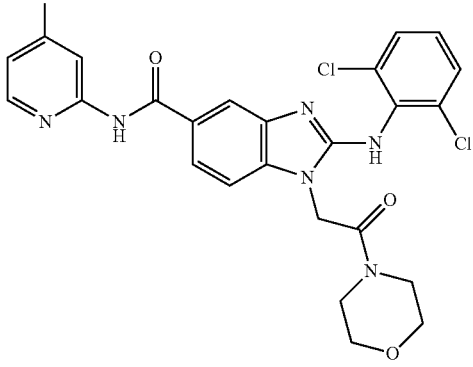 2-(2,6-Dichloro-phenylamino)-1-(2-morpholin-4-yl-2-oxo-ethyl)-1H-benzimidazole-5-carboxylic acid (4-chloro-pyridin-2-yl)-amide | Σ: 24% | $(M+H)^+$ = 559/61/63 (chlorine isotopes) | 1.70 min (CC) |
| 276 | 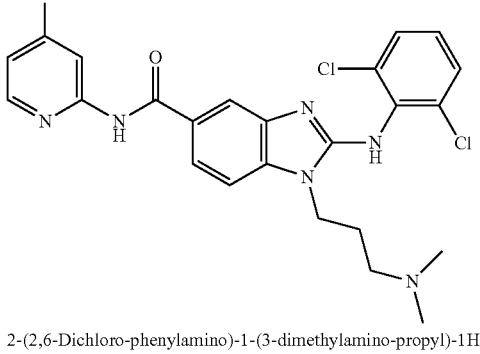 2-(2,6-Dichloro-phenylamino)-1-(3-dimethylamino-propyl)-1H-benzimidazole-5-carboxylic acid (4-chloro-pyridin-2-yl)-amide | Σ: 2% | $(M+H)^+$ = 517/19/21 (chlorine isotopes) | 1.54 min (CC) |
| 277 | 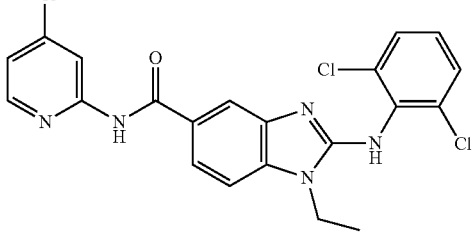 2-(2,6-Dichloro-phenylamino)-1-ethyl-1H-benzimidazole-5-carboxylic acid (4-chloro-pyridin-2-yl)-amide | Σ: 73% | $(M+H)^+$ = 460/62/64 (chlorine isotopes) | 1.77 min (CC) |
| 278 | 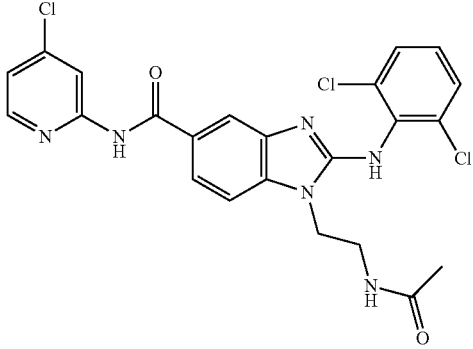 [SMILES: CC(=O)NCCn1c(Nc2c(Cl)cccc2Cl)nc2cc(C(=O)Nc3cc(Cl)ccn3)ccc21] 2-(2,6-Dichloro-phenylamino)-1-(2-acetylamino-ethyl)-1H-benzimidazole-5-carboxylic acid (4-chloro-pyridin-2-yl)-amide | Σ: 12% | $(M+H)^+$ = 517/19/21 (chlorine isotopes) | 1.66 min (CC) |

Example 280

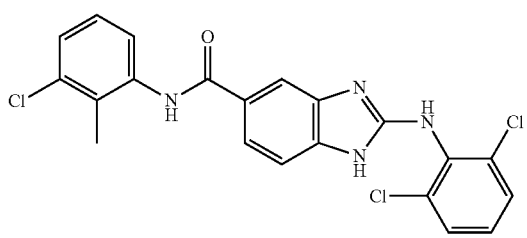 [SMILES: Cc1c(Cl)cccc1NC(=O)c1ccc2[nH]c(Nc3c(Cl)cccc3Cl)nc2c1]

2-(2,6-Dichloro-phenylamino)-1H-benzimidazole-5-carboxylic acid (3-chloro-2-methyl-phenyl)-amide (280a) 2-(2,6-Dichloro-phenylamino)-1H-benzimidazole-5-carboxylic acid (3-chloro-2-methyl-phenyl)-amide Prepared analogously to Example 113b from 2-(2,6-dichloro-phenylamino)-1H-benzimidazole-5-carboxylic acid, 3-chloro-2-methyl-aniline and 1-chloro-N,N-2-trimethyl-1-propenylamin in dichloromethane.

Yield: 7% slightly contaminated mass spectrum: (M+H)$^+$=445/47/49/51 (chlorine isotopes)

mp=267-269° C.

$R_f$ value: 0.18 (silica gel; petrol ether/ethyl acetate=1/1)

In analogy with the above described example, the following compounds were prepared:

| No. | Structural formula Name | Yield | Mass peak(s) | $R_f$ value or $R_t$ |
|---|---|---|---|---|
| 281 | 2-(2,6-Dichloro-phenylamino)-1H-benzimidazole-5-carboxylic acid (2,5-dichlorophenyl)-amide | Σ: 5% | (M + H)+ = 465/67/69/71 (chlorine isotopes) | 0.29 (silica gel petrol ether/ethyl acetate 1:1) |
| 282 | 2-(2,6-Dichloro-phenylamino)-1H-benzimidazole-5-carboxylic acid (4-chloro-3-trifluoromethyl-phenyl)-amide | Σ: 3% | (M + H)+ = 499/01/03/05 (chlorine isotopes) | 0.24 (silica gel petrol ether/ethyl acetate 1:1) |
| 283 | 2-(2,6-Dichloro-phenylamino)-1H-benzimidazole-5-carboxylic acid (3-trifluoromethyl-phenyl)-amide | Σ: 23% | (M + H)+ = 465/67/69 (chlorine isotopes) | 0.27 (silica gel petrol ether/ethyl acetate 1:1) |
| 284 | 2-(2,6-Dichloro-phenylamino)-1H-benzimidazole-5-carboxylic acid (2-chlorophenyl)-amide | Σ: 13% | (M + H)+ = 431/33/35/37 (chlorine isotopes) | 0.31 (silica gel petrol ether/ethyl acetate 1:1) |

| No. | Structural formula Name | Yield | Mass peak(s) | R_f value or R_t |
|---|---|---|---|---|
| 285 | 2-(2,6-Dichloro-phenylamino)-1H-benzimidazole-5-carboxylic acid (3-fluoro-phenyl)-amide | Σ: 18% | (M + H)+ = 415/17/19 (chlorine isotopes) | 0.54 (silica gel petrol ether/ethyl acetate 1:1) |
| 286 | 2-(2,6-Dichloro-phenylamino)-1H-benzimidazole-5-carboxylic acid (3-chloro-4-methyl-phenyl)-amide | Σ: 7% | (M + H)+ = 445/47/49/51 (chlorine isotopes) | 0.19 (silica gel petrol ether/ethyl acetate 1:1) |
| 287 | 2-(2,6-Dichloro-phenylamino)-1H-benzimidazole-5-carboxylic acid (3,4,5-trichloro-phenyl)-amide | Σ: 13% | (M + H)+ = 499/01/03/05/07 (chlorine isotopes) | 0.31 (silica gel petrol ether/ethyl acetate 1:1) |
| 288 | 2-(2,6-Dichloro-phenylamino)-1H-benzimidazole-5-carboxylic acid cyclohexylmethyl-amide | Σ: 5% | (M + H)+ = 417/19/21 (chlorine isotopes) | 0.12 (silica gel petrol ether/ethyl acetate 1:1) |
| 292 | 2-(2,6-Dichloro-phenylamino)-1H-benzimidazole-5-carboxylic acid (2-chloro-5-trifluoromethyl-phenyl)-amide | Σ: 5% | (M + H)+ = 499/01/03/05 (chlorine isotopes) | 0.42 (silica gel petrol ether/ethyl acetate 1:1) |

Example 293

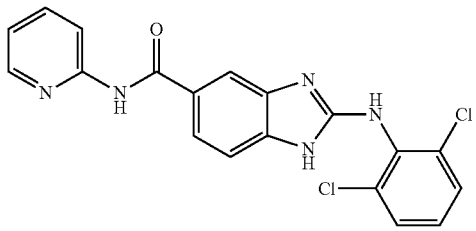 [SMILES: O=C(Nc1ccccn1)c1ccc2[nH]c(Nc3c(Cl)cccc3Cl)nc2c1]

2-(2,6-Dichloro-phenylamino)-1H-benzimidazole-5-carboxylic acid pyridin-2-ylamide

(293a) 3,4-Diamino-N-pyridin-2-yl-benzamid

A mixture of 3,4-dinitro-N-pyridin-2-yl-benzamid (725 mg, 2.5 mmol) and $SnCl_2 \times 2H_2O$ (5.7 g, 25.2 mmol) was stirred in 20 mL ethanol under argon. After stirring for 1 h the mixture was cooled and diluted with sat. $NaHCO_3$ (aq). The aq. phase was extracted with ethyl acetate, dried over $Na_2SO_4$ and concentrated i.vac. The residue was purified by chromatography on silica gel (eluent gradient: dichloromethane/methanol=50:1->10:1)

Yield: 468 mg (82%)

(293b) 2-(2,6-Dichloro-phenylamino)-1H-benzimidazole-5-carboxylic acid pyridin-2-ylamide Prepared analogously to example 106a from 3,4-diamino-N-pyridin-2-yl-benzamide and 1,3-dichloro-2-isothiocyanato-benzene with DCC in DMF.

Yield: 3.6% (slightly contaminated)

mp: 245-247° C.

mass spectrum: $(M+H)^+ = 398/400/402$ (chlorine isotopes)

$R_f$ value: 0.07 (silica gel; dichloromethane/methanol=95/5)

Example 297

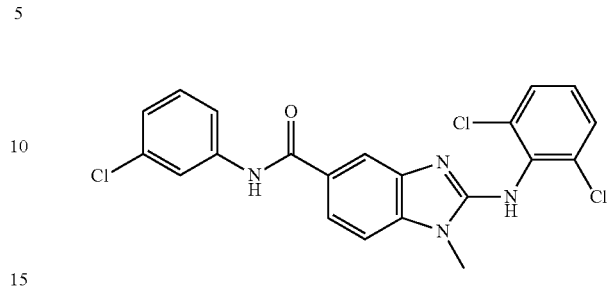

2-(2,6-Dichloro-phenylamino)-1-methyl-1H-benzimidazole-5-carboxylic acid (3-chloro-phenyl)-amide

(297a) 2-(2,6-Dichloro-phenylamino)-1-methyl-1H-benzimidazole-5-carboxylic acid Prepared analogously to example 113a from 3-amino-4-methylamino-benzoic acid methyl ester and 1,3-dichloro-2-isothiocyanato-benzene with DCC in DMF and NaOH in ethanol.

Yield: 77%

(297b) 2-(2,6-Dichloro-phenylamino)-1-methyl-1H-benzimidazole-5-carboxylic acid (3-chloro-phenyl)-amide Prepared analogously to example 113b from 2-(2,6-dichloro-phenylamino)-1-methyl-1H-benzimidazole-5-carboxylic acid and 1-chloro-N,N-2-trimethyl-1-propenylamin with 3-chloro-phenylamine in acetonitrile.

Yield: 11% mass spectrum: $(M+H)^+ = 445/47/49$ (chlorine isotopes)

$R_f$ value: 0.59 (silica gel; petrol ether/ethyl acetate=2/1)

mp: 175-176° C.

In analogy with the above described example, the following compounds were prepared:

| No. | Structural formula Name | Yield | Mass peak(s) | $R_f$ value or $R_t$ |
|---|---|---|---|---|
| 298 | ![structure] 2-(2,6-Dichloro-phenylamino)-1-methyl-1-H-benzimidazole-5-carboxylic acid (4-bromo-phenyl)-amide | Σ: 16% | $(M + H)^+ =$ 489/91/93 (chlorine and bromine isotopes) | 0.71 (silica gel petrol ether/ethyl acetate 2:1) |

Example 302

2-(2,6-Dichloro-phenylamino)-1-methyl-1H-benz-imidazole-5-carboxylic acid [6-(2-methoxy-ethoxy)-pyridin-2-yl]-amide (302a) 2-(2,6-Dichloro-phenylamino)-1-methyl-1H-benzimidazole-5-carboxylic acid benzotriazol-1-yl ester A mixture of 2-(2,6-dichloro-phenylamino)-1-methyl-1H-benzimidazole-5-carboxylic acid (1.0 g, 3.0 mmol), TBTU (955 mg, 3.0 mmol) and TEA (835 μL, 5.9 mmol) in 15 mL DMF was stirred for 72 h. The mixture was poured onto water, the solid filtered off, washed with water and dried.

Yield: 1.0 g (77%)

(302b) 2-(2,6-Dichloro-phenylamino)-1-methyl-1H-benzimidazole-5-carboxylic acid [6-(2-methoxy-ethoxy)-pyridin-2-yl]-amide A mixture of the product obtained in 302a (300 mg, 0.7 mmol) and 6-(2-methoxy-ethoxy)-pyridin-2-ylamine (334 mg, 2.0 mmol) in acetonitrile was stirred for 4 h at 130° C. The mixture was concentrated i.vac. The residue was purified by chromatography on silica gel (eluent gradient: hexane/ethyl acetate=7:93->0:1).

Yield: 100 mg (29%)
$R_f$ value: 0.21 (silica gel; petrol ether/ethyl acetate=1/1)
mp: 185-187° C.
mass spectrum: $(M+H)^+$=486/88/490 (chlorine isotopes)

In analogy with the above described example, the following compounds were prepared:

Example 303

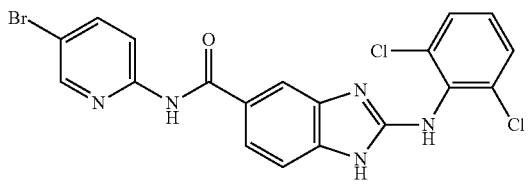 [SMILES: O=C(Nc1ccc(Br)cn1)c1ccc2[nH]c(Nc3c(Cl)cccc3Cl)nc2c1]

2-(2,6-Dichloro-phenylamino)-1H-benzimidazole-5-carboxylic acid (5-bromo-pyridin-2-yl)-amide (303a) N-(5-Bromo-pyridin-2-yl)-3,4-dinitro-benzamide A mixture 3,4-dinitro-benzoyl chloride (1.78 g, 7.8 mmol) and 5-bromo-2-amino-pyridine (1.35 g, 7.8 mmol) in 20 mL DMF was stirred overnight. After evaporation of the solvent, the residue was purified by chromatography on silica gel (eluent gradient: dichloromethane/methanol 100:0->75:1).

Yield: 500 mg (20%)
$R_f$ value: 0.78 (silica gel; petrol ether/ethyl acetate=1:1)

(303b) 3,4-Diamino-N-(5-bromo-pyridin-2-yl)-benzamide

To a mixture of the product obtained in 303a (560 mg, 1.5 mmol) in ethanol tin(II)chloride dihydrate (3.4 g, 15.3 mmol) was added and refluxed for 1 h. The mixture was cooled and sat. $NaHCO_3$ (aq) was added. The aq. phase was washed with ethyl acetate and dichloromethane. The combined organic layers were washed with water, dried and concentrated i.vac. The residue was purified by chromatography on silica gel (eluent gradient: dichloromethane/methanol 50:1->10:1).

Yield: 123 mg (26%)
$R_f$ value: 0.05 (silica gel; dichloromethane/methanol=20:1)

| No. | Structural formula Name | Yield | Mass peak(s) | $R_f$ value or $R_t$ |
|---|---|---|---|---|
| 341 | ![structure] <br> 2-(2,6-Dichloro-phenylamino)-1-methyl-1-H-benzimidazole-5-carboxylic acid (3-methyl-pyridin-2-yl)-amide | Σ: 52% | $(M + H)^+$ = 426/28/30 (chlorine isotopes) | 3.35 min (EX2) |
| 349 | ![structure] <br> 2-(2,6-Dichloro-phenylamino)-1-methyl-1-H-benzimidazole-5-carboxylic acid (6-butoxy-pyridin-2-yl)-amide | Σ: 19% | $(M + H)^+$ = 484/86/88 (chlorine isotopes) | 0.79 (silica gel petrol ether/ethyl acetate = 1:1) |

(303c) 2-(2,6-Dichloro-phenylamino)-1H-benzimidazole-5-carboxylic acid (5-bromo-pyridin-2-yl)-amide Prepared analogously to example 106a from 3,4-diamino-N-(5-bromo-pyridin-2-yl)-benzamide and 1,3-dichloro-2-isothiocyanato-benzene with DCC in DMF.

Yield: 77% (slightly contaminated)
mass spectrum: (M+H)$^+$=476/78/80/82 (chlorine and bromine isotopes)
mp: 183-185° C.
R$_f$ value: 0.06 (silica gel; dichloromethane/methanol=20:1; 2x)

In analogy with the above described example, the following compounds were prepared:

Example 304

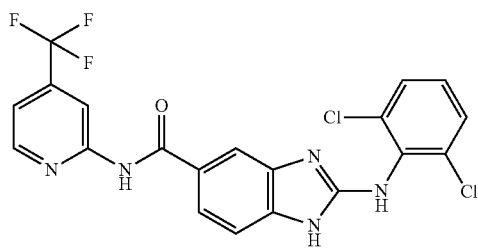 [SMILES: O=C(Nc1cc(C(F)(F)F)ccn1)c1ccc2[nH]c(Nc3c(Cl)cccc3Cl)nc2c1]

2-(2,6-Dichloro-phenylamino)-1H-benzimidazole-5-carboxylic acid (4-trifluoromethyl-pyridin-2-yl)-amide

| No. | Structural formula Name | Yield | Mass peak(s) | R$_f$ value or R$_t$ |
|---|---|---|---|---|
| 312 | 2-(2,6-Dichloro-phenylamino)-1H-benzimidazole-5-carboxylic acid (2,3,4-trichloro-phenyl)-amide | Σ: 47% | (M + H)$^+$ = 499/01/03/05 (chlorine isotopes) | 0.36 (silica gel dichloromethane/methanol = 20:1) |
| 313 | 2-(2,6-Dichloro-phenylamino)-1H-benzimidazole-5-carboxylic acid (2,4,6-trichloro-phenyl)-amide | Σ: 64% | (M + H)$^+$ = 499/01/03/05 (chlorine isotopes) | 0.16 (silica gel dichloromethane/methanol = 20:1) |
| 314 | 2-(2,6-Dichloro-phenylamino)-1H-benzimidazole-5-carboxylic acid (5,6-dimethyl-1H-benzimidazol-2-yl)-amide | Σ: 29% | (M + H)$^+$ = 465/67 (chlorine isotopes) | 0.26 (silica gel dichloromethane/methanol = 10:1) |
| 322 | 2-(2,6-Dichloro-3-methyl-phenylamino)-1H-benzimidazole-5-carboxylic acid (4-bromo-phenyl)-amide | Σ: 31% | (M + H)$^+$ = 489/91/93 (chlorine and bromine isotopes) | 0.32 (silica gel petrol ether/ethyl acetate = 1:1) |

(304a) 3,4-Dinitro-N-(4-trifluoromethyl-pyridin-2-yl)-benzamide

Prepared analogously to example 303a from 3,4-dinitro-benzoyl chloride and 2-amino-4-trifluoromethyl-pyridine.
Yield: 28%
$R_f$ value: 0.70 (silica gel; petrol ether/ethyl acetate=1:1)

(304b) 3,4-Diamino-N-(4-trifluoromethyl-pyridin-2-yl)-benzamide

Prepared analogously to example 1b by hydrogenation of 3,4-dinitro-N-(4-trifluoromethyl-pyridin-2-yl)-benzamide using palladium/charcoal 10% in methanol.
Yield: 44%

(304c) 2-(2,6-Dichloro-phenylamino)-1H-benzimidazole-5-carboxylic acid (4-trifluoromethyl-pyridin-2-yl)-amide Prepared analogously to example 106a from 3,4-diamino-N-(4-trifluoromethyl-pyridin-2-yl)-benzamide and 1,3-dichloro-2-isothiocyanato-benzene with DCC in DMF.
Yield: 60%
mp: 179-182° C.
mass spectrum: (M+H)$^+$=466/68/70 (chlorine isotopes)
$R_f$ value: 0.22 (silica gel; dichloromethane/methanol=20:1)

In analogy with the above described example, the following compounds were prepared:

Example 308

2-(2,6-Dichloro-phenylamino)-1-methyl-1H-benzimidazole-6-carboxylic acid (4,4-dimethyl-cyclohexyl)-amide

(306a) 2-(2,6-Dichloro-phenylamino)-1-methyl-1H-benzimidazole-5-carboxylic acid Prepared analogously to example 3b from 2-(2,6-Dichloro-phenylamino)-1-methyl-1H-benzimidazole-5-carboxylic acid-methyl ester and NaOH in ethanol.
Yield: 77%

(306b) 2-(2,6-Dichloro-phenylamino)-1-methyl-1H-benzimidazole-5-carboxylic acid (4,4-dimethyl-cyclohexyl)-amide Prepared analogously to example 3c from 2-(2,6-dichloro-phenylamino)-1-methyl-1H-benzimidazole-6-carboxylic acid, 4,4-dimethyl-cyclohexylamine hydrochloride, TBTU and NMM in DMF; mp: 189-190° C., $R_f$ value: 0.56 (silica gel; petrol ether/ethyl acetate=2:1).

In analogy with the above described example, the following compound was prepared:

| No. | Structural formula Name | Yield | Mass peak(s) | $R_f$ value or $R_t$ |
|---|---|---|---|---|
| 305 | 2-(2,6-Dichloro-phenylamino)-1H-benzimidazole-5-carboxylic acid (6-trifluoromethyl-pyridin-2-yl)-amide | Σ: 56% | (M + H)$^+$ = 466/68/70 (chlorine isotopes) | 0.32 (silica gel dichloromethane/ methanol = 20:1) |
| 321 | 2-(2,6-Dichloro-phenylamino)-1H-benzimidazole-5-carboxylic acid (5-methyl-pyridin-2-yl)-amide | Σ: 66% | (M + H)$^+$ = 412/14/16 (chlorine isotopes) | 0.54 (silica gel dichloromethane/ methanol = 200:1) |

| Structural formula No. Name | Yield | Mass peak(s) | $R_f$ value or $R_t$ |
|---|---|---|---|
| 317 2-(2,6-Dichloro-phenylamino)-1-methyl-1H-benzimidazole-5-carboxylic acid cyclohexylamide | Σ: 52% | $(M+H)^+$ = 416/18/20 (chlorine isotopes) | 0.29 (silica gel petrol ether/ethyl acetate = 2:1) |

Example 309

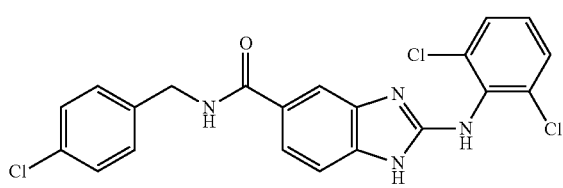 [SMILES: O=C(NCc1ccc(Cl)cc1)c1ccc2[nH]c(Nc3c(Cl)cccc3Cl)nc2c1]

2-(2,6-Dichloro-phenylamino)-1H-benzimidazole-5-carboxylic acid 4-chloro-benzylamide

(309a) 2-(2,6-Dichloro-phenylamino)-1H-benzimidazole-5-carboxylic acid

Prepared analogously to example 113a from 3-amino-4-methylamino-benzoic acid methyl ester, 1,3-dichloro-2-isothiocyanato-benzene with DCC and NaOH in DMF.
Yield: 77%

(309b) 2-(2,6-Dichloro-phenylamino)-1H-benzimidazole-5-carboxylic acid 4-chloro-benzylamide Prepared analogously to example 280a from 3-amino-4-methylamino-benzoic acid, (1-chloro-2-methyl-propenyl)-dimethyl-amine and 4-chloro-benzylamine in acetonitrile.
Yield: 67%
$R_f$ value: 0.71 (silica gel; petrol ether/ethyl acetate=2:1)
mp: 195-196° C.
mass spectrum: $(M+H)^+$=493/95/97 (chlorine isotopes)

Example 316

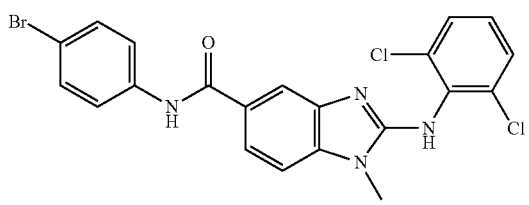 [SMILES: Cn1c(Nc2c(Cl)cccc2Cl)nc2cc(C(=O)Nc3ccc(Br)cc3)ccc21]

2-(2,6-Dichloro-phenylamino)-1-methyl-1H-benzimidazole-5-carboxylic acid (4-bromo-phenyl)-amide

(316a) N-(4-Bromo-phenyl)-4-methylamino-3-nitro-benzamide 40 mL liquid methylamine was added to a stirred mixture of N-(4-bromo-phenyl)-4-fluoro-3-nitro-benzamide (1.5 g, 4.4 mmol) in a pressure tube. The mixture was stirred for 20 h at 60° C. The mixture was cooled and concentrated i.vac. The residue was taken up in ethyl acetate, filtered with celite and silica gel and dried.
Yield: 1.21 g (78%)

(316b) 3-Amino-N-(4-bromo-phenyl)-4-methylamino-benzamide

Prepared analogously to example 91a from N-(4-bromo-phenyl)-4-methylamino-3-nitro-benzamide and iron powder in acetic acid.

(316c) 2-(2,6-Dichloro-phenylamino)-1-methyl-1H-benzimidazole-5-carboxylic acid (4-bromo-phenyl)-amide A mixture of the product obtained in 316b (160 mg, 0.5 mmol) and 1,3-dichloro-2-isothiocyanato-benzene (85 mg, 0.5 mmol) in 5 mL DMF was stirred for 2 h. EDC (96 mg, 0.5 mmol) was added and stirred overnight. The mixture was heated to 80° C. and stirred for 30 min. The mixture was cooled, water added and concentrated i.vac. The residue was taken up in ethyl acetate and washed with water and brine, dried and concentrated i.vac.
Yield: 12 mg (5%)
mp: 255-257° C.
$R_t$ value: 7.05 min (EX2)
mass spectrum: $(M+H)^+$=455/57/59 (chlorine and bromine isotopes)

In analogy with the above described example, the following compounds were prepared:

| No. | Structural formula Name | Yield | Mass peak(s) | $R_f$ value or $R_t$ |
|---|---|---|---|---|
| 318 | 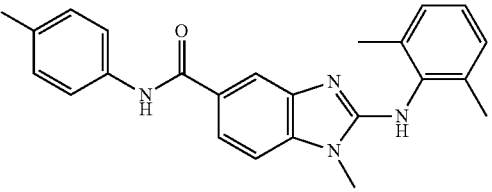 2-(2,6-Dimethyl-phenylamino)-1-methyl-1H-benzimidazole-5-carboxylic acid (4-bromo-phenyl)-amide | Σ: 13% | (M + H)⁺ = 449/51 (bromine isotopes) | 49.92 min (EX2) |

Example 319

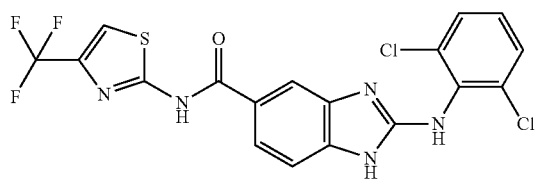 [SMILES: O=C(Nc1nc(C(F)(F)F)cs1)c1ccc2[nH]c(Nc3c(Cl)cccc3Cl)nc2c1]

2-(2,6-Dichloro-phenylamino)-1H-benzimidazole-5-carboxylic acid (4-trifluoro-methyl-thiazol-2-yl)-amide

(319a) 3,4-Dinitro-N-(4-trifluoromethyl-thiazol-2-yl)-benzamide

A mixture of 3,4-dinitrobenzoic acid (1.78 g, 8.4 mmol) and thionyl chloride was stirred for 2 h at reflux. The mixture was concentrated i.vac., toluene and 4-trifluoromethyl-thiazol-2-ylamine (1.49 g, 8.4 mmol) were added and the mixture was stirred at 120° C. for 3 days. Then the mixture was filtered and dried i.vac.

Yield: 890 mg (29%)

(319b) 3,4-Diamino-N-(4-trifluoromethyl-thiazol-2-yl)-benzamide

Prepared analogously to example 1b by hydrogenation of 3,4-dinitro-N-(4-trifluoromethyl-thiazol-2-yl)-benzamide using 10% palladium on charcoal in methanol.

Yield: 19%

(319c) 2-(2,6-Dichloro-phenylamino)-1H-benzimidazole-5-carboxylic acid (4-trifluoromethyl-thiazol-2-yl)-amide Prepared analogously to example 106a from 3,4-diamino-N-(4-trifluoromethyl-thiazol-2-yl)-benzamide, 1,3-dichloro-2-isothiocyanato-benzene and DCC in DMF.

Yield: 37% (slightly contaminated)

mp: 301-303° C.

mass spectrum: (M+H)⁺=472/74/76 (chlorine isotopes)

$R_f$ value: 0.19 (silica gel; dichloromethane/methanol=20:1)

Example 320

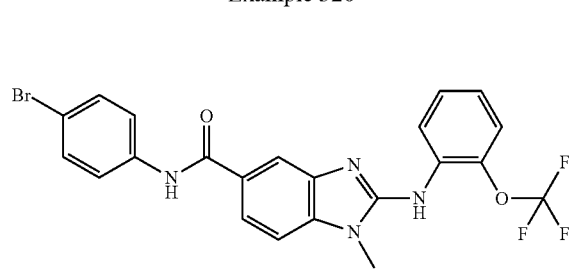

1-Methyl-2-(2-trifluoromethoxy-phenylamino)-1H-benzimidazole-5-carboxylic acid (4-bromo-phenyl)-amide

(320a) N-(4-Bromo-phenyl)-4-methylamino-3-nitro-benzamide

A mixture of N-(4-bromo-phenyl)-4-fluoro-3-nitro-benzamide (1.5 g, 4.4 mmol) and 40 mL liquid methyl amine was stirred for 20 h at 60° C. The mixture was cooled to −78° C., diluted with ethyl acetate and filtered with celite and silica gel. The filtrate was concentrated i.vac.

Yield: 1.21 g (78%)

(320b) 3-Amino-N-(4-bromo-phenyl)-4-methylamino-benzamide

Prepared analogously to example 303b from N-(4-bromo-phenyl)-4-methylamino-3-nitro-benzamide and tin(II)chloride in ethanol.

Yield: 86%

(320c) 1-Methyl-2-(2-trifluoromethoxy-phenylamino)-1H-benzimidazole-5-carboxylic acid (4-bromo-phenyl)-amide Prepared analogously to example 208d from 3-amino-N-(4-bromo-phenyl)-4-methylamino-benzamide, 1,3-dichloro-2-isothiocyanato-benzene and EDC in DMF.

Yield: 8% mass spectrum: (M+H)⁺=505/07 (bromine isotopes)

$R_t$ value: 5.3 min (EX2)

Example 326

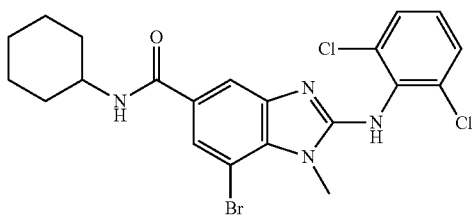 [SMILES: Cn1c(Nc2c(Cl)cccc2Cl)nc2cc(C(=O)NC3CCCCC3)cc(Br)c21]

7-Bromo-2-(2,6-dichloro-phenylamino)-1-methyl-1H-benzimidazole-5-carboxylic acid cyclohexylamide (326a) 7-Bromo-2-(2,6-dichloro-phenylamino)-1-methyl-1H-benzimidazole-5-carboxylic acid cyclohexylamide Prepared analogously to example 3c from 7-bromo-2-(2,6-dichloro-phenylamino)-1-methyl-1H-benzimidazole-5-carboxylic acid, cyclohexylamine, TBTU and TEA in DMF.
Yield: 100 mg
$R_f$-value: 0.60 (silica gel; petrol ether/ethyl acetate=1:1)
mass spectrum: (M+H)$^+$=495/97/99 (chlorine and bromine isotopes)
In analogy with the above described example, the following compounds were prepared:

(327a) 2-(2,6-Dichloro-phenylamino)-1-methyl-1H-benzimidazole-5-carboxylic acid benzotriazol-1-yl ester A mixture of 2-(2,6-dichloro-phenylamino)-1-methyl-1H-benzimidazole-5-carboxylic acid (0.50 g, 1.5 mmol), HBTU (0.56 g, 1.5 mmol) and TEA (0.42 mL, 3.0 mmol) in 8 mL DMF was stirred for 3 days at ambient temperature. The mixture was diluted with water and ethyl acetate. The organic phase was washed with water and brine, dried and concentrated i.vac.

Yield: 0.56 g (84%)

(327b) 2-(2,6-Dichloro-phenylamino)-1-methyl-1H-benzimidazole-5-carboxylic acid (5-methyl-pyridin-2-yl)-amide A mixture of the product obtained in 327a (0.30 g, 0.7 mmol) and 5-methyl-pyridin-2-yl-amine (0.09 g, 0.8 mmol) in 25 mL acetonitrile was stirred at 110° C. for 59 h. The mixture was concentrated i.vac. The residue was purified by

| No. | Structural formula Name | Yield | Mass peak(s) | $R_f$-value or $R_t$ |
|---|---|---|---|---|
| 352 | ![structure] 7-Bromo-2-(2,6-dichloro-phenylamino)-1-methyl-1H-benzimidazole-5-carboxylic acid ethylamide | Σ: 38% | (M + H)$^+$ = 441/43/45 (chlorine and bromine isotopes) | 0.29 (silica gel petrol ether/ethyl acetate = 1:1) |
| 353 | ![structure] 7-Bromo-2-(2,6-dichloro-phenylamino)-1-methyl-1H-benzimidazole-5-carboxylic acid isopropylamide | Σ: 40% | (M + H)$^+$ = 455/57/59 (chlorine and bromine isotopes) | 0.42 (silica gel petrol ether/ethyl acetate = 1:1) |

Example 327

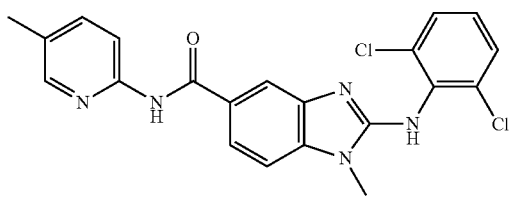 [SMILES: Cc1ccc(NC(=O)c2ccc3c(c2)nc(Nc2c(Cl)cccc2Cl)n3C)nc1]

2-(2,6-Dichloro-phenylamino)-1-methyl-1H-benzimidazole-5-carboxylic acid (5-methyl-pyridin-2-yl)-amide chromatography on silica gel (eluent gradient: dichloromethane/ethanol=100:0->100:2).

Yield: 0.22 g (79%)

mass spectrum (M+H)$^+$=426/28/30 (chlorine isotopes)

$R_t$ value: 3.65 min (Acquity UPLC™ BEH SHIELD RP 18 1.7μ, 2.1×100 mm; eluent: acetonitrile in 0.1% formic acid=5%->100%; flow rate 0.2 mL/min; detection: UV 248 nm)

In analogy with the above described example, the following compounds were prepared:

| No. | Structural formula Name | Yield | Mass peak(s) | $R_f$ value or $R_t$ |
|---|---|---|---|---|
| 328 | 2-(2,6-Dichloro-phenylamino)-1-methyl-1H-benzimidazole-5-carboxylic acid (6-methyl-pyridin-2-yl)-amide | Σ: 90% | $(M+H)^+ =$ 426/28/30 (chlorine isotopes) | 3.79 min (EX2) |

Example 329

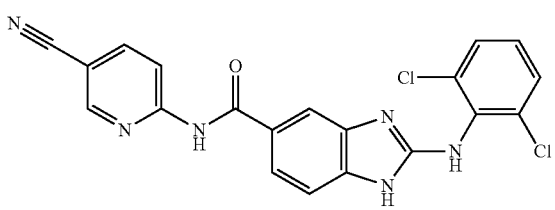 [SMILES: N#Cc1ccc(NC(=O)c2ccc3[nH]c(Nc4c(Cl)cccc4Cl)nc3c2)nc1]

2-(2,6-Dichloro-phenylamino)-1H-benzimidazole-5-carboxylic acid (5-cyano-pyridin-2-yl)-amide (329a) N-(5-Cyano-pyridin-2-yl)-3,4-dinitro-benzamide 3,4-Dinitro-benzoyl chloride (0.69 g, 3.0 mmol) in 2 mL toluene was added to a stirred mixture of 2-amino-5-cyanopyridine (0.357 g, 3.0 mmol) and 5 mL pyridine. After stirring overnight at ambient temperature the mixture was concentrated i.vac. The residue was taken up in ethyl acetate and 5% NaHCO₃ (aq). The organic layer was washed with water and brine, separated, dried and concentrated i.vac. The residue was purified by chromatography on silica gel (eluent gradient: dichloromethane/ethanol=100:0->100:2).

Yield: 329 mg (35%)

(329b) 3,4-Diamino-N-(5-cyano-pyridin-2-yl)-benzamide

Prepared analogously to example 91a from N-(5-cyano-pyridin-2-yl)-3,4-dinitro-benzamide, iron powder and glacial acetic acid in ethanol.

Yield: 41%

(329c) 2-(2,6-Dichloro-phenylamino)-1H-benzimidazole-5-carboxylic acid (4-trifluoromethyl-pyridin-2-yl)-amide Prepared analogously to example 106a from 3,4-diamino-N-(5-cyano-pyridin-2-yl)-benzamide, 1,3-dichloro-2-isothiocyanato-benzene and DCC in DMF.

Yield: 56% mass spectrum: $(M+H)^+=423/25/27$ (chlorine isotopes)

$R_t$ value: 3.81 min (Acquity UPLC™ BEH SHIELD RP 18 1.7μ, 2.1×100 mm; eluent: acetonitrile in 0.1% formic acid=5%->100%; flow rate 0.2 mL/min; detection: UV 254 nm)

In analogy with the above described example, the following compounds were prepared:

| No. | Structural formula Name | Yield | Mass peak(s) | $R_f$ value or $R_t$ |
|---|---|---|---|---|
| 336 | 2-(2,6-Dichloro-phenylamino)-1H-benzimidazole-5-carboxylic acid (6-methyl-pyridin-2-yl)-amide | Σ: 65% | $(M+H)^+ =$ 412/14/15 (chlorine isotopes) | 3.11 min (EX2) |

Example 333

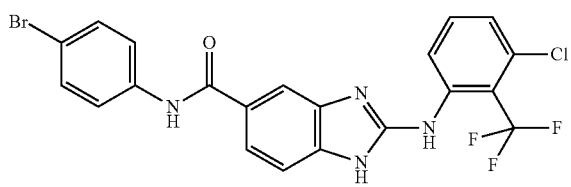 [SMILES: O=C(Nc1ccc(Br)cc1)c1ccc2[nH]c(Nc3cccc(Cl)c3C(F)(F)F)nc2c1]

2-(3-Chloro-2-trifluoromethyl-phenylamino)-1H-benzimidazole-5-carboxylic acid (4-bromo-phenyl)-amide

(333a) 1-Chloro-3-isothiocyanato-2-trifluoromethyl-benzene

Prepared analogously to example 192a from 3-chloro-2-trifluoromethyl-phenylamine, thiocarbonic acid O,O-dipyridin-2-yl ester and TEA in THF.
Yield: 21%
GC-MS: M=237

(333b) 2-(3-Chloro-2-trifluoromethyl-phenylamino)-1H-benzimidazole-5-carboxylic acid (4-bromo-phenyl)-amide Prepared analogously to example 106a from 3,4-diamino-N-(4-bromo-phenyl)-benzamide, 1-chloro-3-isothiocyanato-2-trifluoromethyl-benzene and DCC in DMF.
Yield: 22%
$R_f$ value: 0.39 (silica gel; petrol ether/ethyl acetate=5:2)
mass spectrum: $(M+H)^+=509/11/13$
In analogy with the above described example, the following compounds were prepared:

| No. | Structural formula Name | Yield | Mass peak(s) | $R_f$-value or $R_t$ |
|---|---|---|---|---|
| 334 | 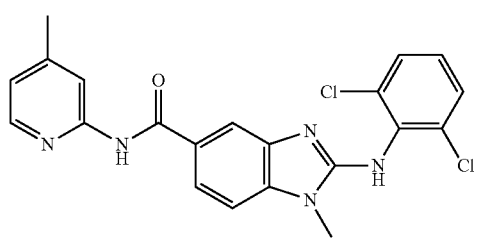<br>2-(2-Chloro-6-fluoro-phenylamino)-1H-benzimidazole-5-carboxylic acid (4-bromo-phenyl)-amide | Σ: 27% | $(M+H)^+=$ 459/61/63 (chlorine and bromine isotopes) | 0.50 (silica gel dichloromethane/ methanol = 10:1) |

Example 335

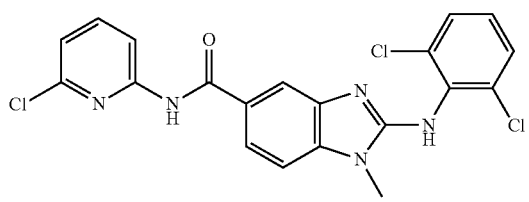 [SMILES: Cn1c(Nc2c(Cl)cccc2Cl)nc2cc(C(=O)Nc3cccc(Cl)n3)ccc21]

2-(2,6-Dichloro-phenylamino)-1-methyl-1H-benzimidazole-5-carboxylic acid (4-methyl-pyridin-2-yl)-amide

(335a) 2-(2,6-Dichloro-phenyl)-1-methyl-1H-benzimidazole-5-carboxylic acid benzotriazol-1-yl ester Prepared analogously to example 327a from benzimidazole-5-carboxylic acid, HBTU and TEA in DMF.
Yield: 95%

(335b) 2-(2,6-Dichloro-phenylamino)-1-methyl-1H-benzimidazole-5-carboxylic acid (4-methyl-pyridin-2-yl)-amide Prepared analogously to example 302b from 2-(2,6-dichloro-phenyl)-1-methyl-1H-benzimidazole-5-carboxylic acid benzotriazol-1-yl ester and 4-methyl-pyridin-2-ylamine in acetonitrile.
Yield: 72%; mp: 157-159° C.;
mass spectrum: $(M+H)^+=426/28/29$ (chlorine isotopes)
$R_t$ value: 3.06 min (EX2).

Example 347

2-(2,6-Dichloro-phenylamino)-1-methyl-1H-benzimidazole-5-carboxylic acid (6-chloro-pyridin-2-yl)-amide

(347a) N-(6-Chloro-pyridin-2-yl)-4-methylamino-3-nitro-benzamide

Prepared analogously to example 316a from N-(6-chloropyridin-2-yl)-4-fluoro-3-nitro-benzamide and methylamine.
Yield: 400 mg
$R_f$ value: 0.20 (silica gel; petrol ether/ethyl acetate=1:2)

(347b) 3-Amino-N-(6-chloro-pyridin-2-yl)-4-methylamino-benzamide

Prepared analogously to example 323c from N-(6-chloro-pyridin-2-yl)-4-methylamino-3-nitro-benzamide, iron powder and sat. NH₄Cl solution in ethanol.
Yield: 120 mg
$R_f$ value: 0.48 (silica gel; petrol ether/ethyl acetate=1:1)

(347c) 2-(2,6-Dichloro-phenylamino)-1-methyl-1H-benzimidazole-5-carboxylic acid (6-chloro-pyridin-2-yl)-amide Prepared analogously to example 106a from 3-amino-N-(6-chloro-pyridin-2-yl)-4-methylamino-benzamide, 1,3-dichloro-2-isothiocyanato-benzene and DCC in DMF.
Yield: 6 mg
$R_f$ value: 0.71 (silica gel; petrol ether/ethyl acetate=1:1)
mass spectrum: $(M+H)^+$=446/48/50 (chlorine isotopes)

Example 350

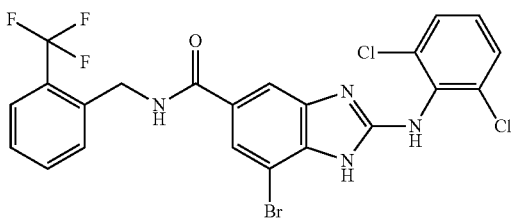 [SMILES: O=C(NCc1ccccc1C(F)(F)F)c1cc(Br)c2[nH]c(Nc3c(Cl)cccc3Cl)nc2c1]

7-Bromo-2-(2,6-dichloro-phenylamino)-1H-benzimidazole-5-carboxylic acid 2-trifluoromethyl-benzylamide (350a) 7-Bromo-2-(2,6-dichloro-phenylamino)-1H-benzimidazole-5-carboxylic acid 2-trifluoromethyl-benzylamide A mixture of 7-bromo-2-(2,6-dichloro-phenylamino)-1H-benzimidazole-5-carboxylic acid (100 mg, 0.2 mmol) and CDI (42 mg, 0.3 mmol) in 3 mL acetonitrile was stirred for 1 h at reflux. 2-Trifluoromethyl-benzylamine (87 mg, 0.5 mmol) was added and the mixture was stirred for further 2 h at 40° C. The mixture was diluted with brine and ethyl acetate. The organic phase was washed with brine, 1% aq. $NaHCO_3$, water and 1 M HCl (aq). The organic layer was separated, dried and concentrated i.vac. The residue was purified by chromatography on silica gel (eluent gradient: petrol ether/ethyl acetate=9:1->0:1).
Yield: 25 mg (18%)
mp: 176-178° C.
$R_f$ value: 0.65 (silica gel; dichloromethane/methanol=9:1)
mass spectrum: $(M+H)^+$=557/59/561/62 (chlorine and bromine isotopes)
In analogy with the above described example, the following compounds were prepared:

Example 358

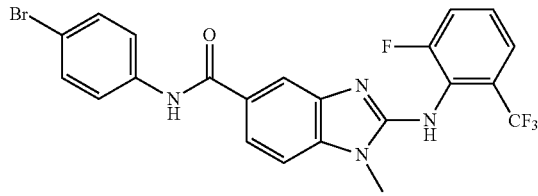 [SMILES: Cn1c(Nc2c(F)cccc2C(F)(F)F)nc2cc(C(=O)Nc3ccc(Br)cc3)ccc21]

N-(4-Bromophenyl)-2-(2-fluoro-6-trifluoromethyl-phenylamino)-1-methyl-1H-benzimidazole-5-carboxamide (358a)
N-(4-Bromophenyl)-4-fluoro-3-nitrobenzamide To 4-fluoro-3-nitrobenzoic (20 g, 108 mmol) acid in thionylchloride (40 mL, 540 mmol) was added 2 drops of DMF. The mixture was refluxed for 2.5 h hours. Then remaining thionylchloride was removed i.vac., 100 mL methylenechloride were added and the mixture added to p-bromaniline (18.6 g, 108 mmol) in 50 mL dichloromethane at 0° C. The reaction was left to warm in 1 hour, poured into water and extracted with ethylacetate. The organic extract was washed with brine, dried over $Na_2SO_4$ and the solvent was removed i.vac. The residue was crystallized from ethylacetate/petrol ether.
$R_f$ value: 0.65 (silica gel; petrolether/ethylacetate=1:1)
Yield: 30 g (69%)

(358b) N-(4-bromophenyl)-4-(methylamino)-3-nitrobenzamide

Prepared analogously to example 156b from the product obtained in example 358a and 2 M methylamine (solution in THF) in THF
Yield: 83%

(358c) 3-Amino-N-(4-bromophenyl)-4-(methylamino)benzamide

Prepared analogously to example 91a from N-(4-bromophenyl)-4-(methylamino)-3-nitrobenzamide and iron powder in acetic acid and DMF.
Yield: 44%
$R_f$ value: 0.52 (silica gel; petrolether/ethylacetate=10:1)

| No. | Structural formula Name | Yield | Mass peak(s) | $R_f$ value or $R_t$ |
|---|---|---|---|---|
| 351 | 7-Bromo-2-(2,6-dichloro-phenylamino)-1H-benzimidazole-5-carboxylic acid (3-chloro-phenyl)-amide | Σ: 23% | $(M + H)^+$ = 509/11/13/15 (chlorine and bromine isotopes) | 0.7 (silica gel dichloromethane/ methanol = 9:1) |

(358d) N-(4-Bromophenyl)-2-(2-fluoro-6-trifluoromethyl-phenylamino)-1-methyl-1H-benzimidazole-5-carboxamide Prepared analogously to example 316c from 3-amino-N-(4-bromophenyl)-4-(methylamino)benzamide and EDC in DMF.

Yield: 15%; mass spectrum: (M+H)$^+$=507/509/511; $R_f$ value: 0.55 (silica gel; petrol-ether/ethylacetate=1:1)

In analogy with the above described example, the following compounds were prepared:

| No. | Structural formula / Name | Yield | Mass peak(s) | $R_f$ value or $R_t$ |
|---|---|---|---|---|
| 380 | N-(4-Bromophenyl)-2-(2,5-dichlorophenylamino)-1-methyl-1H-benzimidazole-5-carboxamide | Σ: 3.3% | (M + H)$^+$ = 489/491/493 (chlorine isotopes and bromine isotopes) | 13.55 min (EX1) |
| 381 | N-(4-Bromophenyl)-2-(2-chloro-6-fluorophenylamino)-1-methyl-1H-benzimidazole-5-carboxamide | Σ: 1.9% | (M + H)$^+$ = (chlorine and bromine isotopes) | 12.17 min (EX1) |
| 382 | N-(4-Bromophenyl)-2-(2-chloro-6-methylphenylamino)-1-methyl-1H-benzimidazole-5-carboxamide | Σ: 5.7% | (M + H)$^+$ = 473/475/477 (chlorine and bromine isotopes) | 12.17 min (EX1) |
| 402 | N-(4-Bromophenyl)-2-(2,4-dichloro-6-methylphenylamino)-1-methyl-1H-benzimidazole-5-carboxamide | Σ: 2.6% | (M + H)$^+$ = 503/505/507 (chlorine and bromine isotopes) | 12.78 min (EX1) |
| 423 | N-(4-Bromophenyl)-2-(2-chloro-5-trifluoromethyl-phenylamino)-1-methyl-1H-benzimidazole-5-carboxamide | Σ: 2.5% | (M + H)$^+$ = 523/525/527 (chlorine and bromine isotopes) | 14.35 min (EX1) |

| No. | Structural formula Name | Yield | Mass peak(s) | $R_f$-value or $R_t$ |
|---|---|---|---|---|
| 433 | N-(4-Bromophenyl)-2-(4-chloro-2-trifluoromethyl-phenylamino)-1-methyl-1H-benzimidazole-5-carboxamide | Σ: 2% | (M + H)⁺ = 523/525/527 (chlorine and bromine isotopes) | 0.46 (silica gel, petrolether/ ethylacetate = 1:1) |
| 385 | N-(4-Bromophenyl)-2-(4-fluoro-2-trifluoromethyl-phenylamino)-1-methyl-1H-benzimidazole-5-carboxamide | Σ: 0.7% | (M + H)⁺ = 507/509/510 (chlorine and bromine isotopes) | 12.55 min (EX1) |
| 489 | N-(4-Bromophenyl)-2-(2-chloro-4,6-dimethylphenylamino)-1-methyl-1H-benzimidazole-5-carboxamide | Σ: 2% | (M + H)⁺ = 483/485/487 (chlorine and bromine isotopes) | 12.65 min (EX1) |
| 499 | N-(4-Bromophenyl)-2-(2-chloro-6-(dimethylamino)phenylamino)-1-methyl-1H-benzimidazole-5-carboxamide | Σ: 0.3% | (M + H)⁺ = 498/500/502 (chlorine and bromine isotopes) | 11.77 min (EX1) |
| 512 | N-(4-Bromophenyl)-2-(2-chloro-4-methylphenylamino)-1-methyl-1H-benzimidazole-5-carboxamide | Σ: 1.4% | (M + H)⁺ = 469/471/473 (chlorine and bromine isotopes) | 12.62 min (EX1) |

| No. | Structural formula Name | Yield | Mass peak(s) | $R_f$ value or $R_t$ |
|---|---|---|---|---|
| 519 | 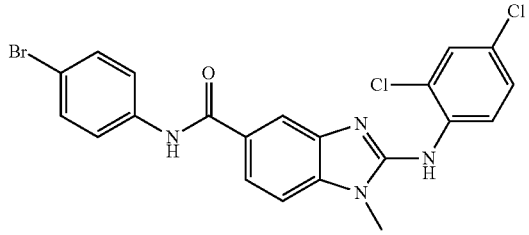 [SMILES: Cn1c(Nc2ccc(Cl)cc2Cl)nc2cc(C(=O)Nc3ccc(Br)cc3)ccc21]<br>N-(4-Bromophenyl)-2-(2,4-dichlorophenylamino)-1-methyl-1H-benzimidazole-5-carboxamide | Σ: 0.9% | (M + H)⁺ = 489/491/493 (chlorine and bromine isotopes) | 0.27 (silica gel, petrolether/ ethylacetate = 1:1) |
| 526 | 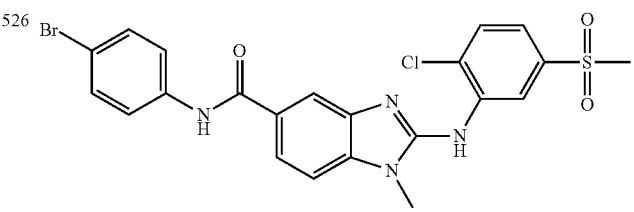<br>N-(4-Bromophenyl)-2-(2-chloro-5-(methylsulfonyl)phenylamino)-1-methyl-1H-benzimidazole-5-carboxamide | Σ: 0.9% | (M + H)⁺ = 533/535/537 (chlorine and bromine isotopes) | 12.44 min (EX1) |
| 538 | 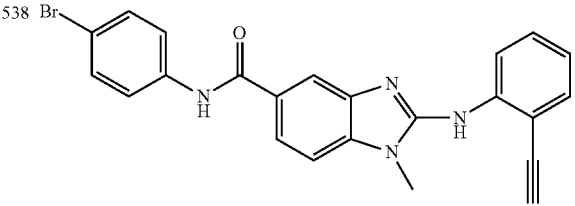<br>N-(4-Bromophenyl)-2-(2-ethynylphenylamino)-1-methyl-1H-benzimidazole-5-carboxamide | Σ: 1.7% | (M + H)⁺ = 445/447 (bromine isotopes) | 11.75 min (EX1) |
| 551 | 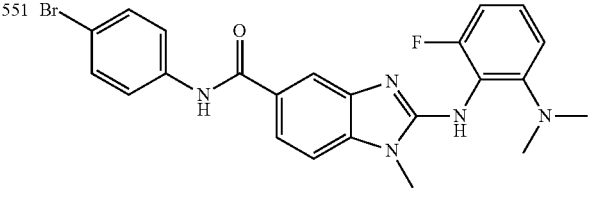<br>N-(4-Bromophenyl)-2-(2-dimethylamino-6-fluorophenylamino)-1-methyl-1H-benzimidazole-5-carboxamide | Σ: 0.7% | (M + H)⁺ = 482/484 (bromine isotopes) | 0.51 (silica gel, ethylacetate) |
| 555 | 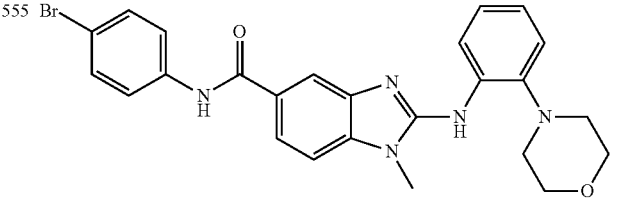<br>N-(4-Bromophenyl)-1-methyl-2-(2-(4-morpholino)phenylamino)-1H-benzimidazole-5-carboxamide | Σ: 1.2% | (M + H)⁺ = 482/484 (bromine isotopes) | 11.55 min (EX1) |

| No. | Structural formula Name | Yield | Mass peak(s) | $R_f$ value or $R_t$ |
|---|---|---|---|---|
| 556 | 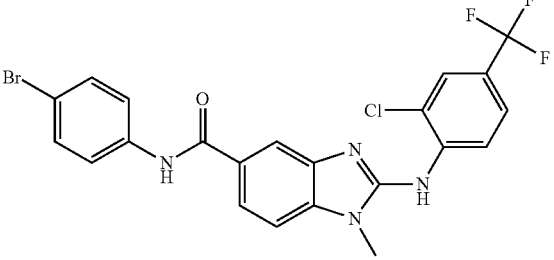 N-(4-Bromophenyl)-2-(2-chloro-4-trifluoromethyl-phenylamino)-1-methyl-1H-benzimidazole-5-carboxamide | Σ: 3.2% | $(M + H)^+$ = 523/525/527 (chlorine and bromine isotopes) | 0.37 (silica gel, petrolether/ ethylacetate = 1:1) |
| 572 | 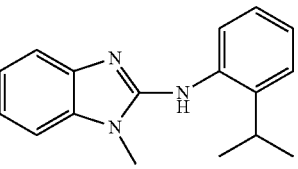 N-(4-Bromophenyl)-2-(2-isopropylphenylamino)-1-methyl-1H-benzimidazole-5-carboxamide | Σ: 1% | $(M + H)^+$ = 463/465 (bromine isotopes) | 0.69 (silica gel, ethylacetate) |
| 557 | 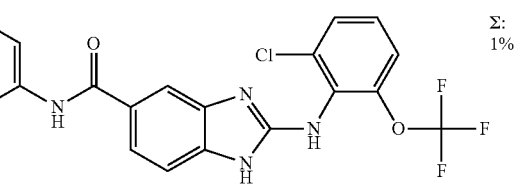 N-(4-Bromophenyl)-2-(2-chloro-6-(trifluoromethoxy)phenylamino)-1H-benzimidazole-5-carboxamide | Σ: 1% | $(M + H)^+$ = 525/527/529 (chlorine and bromine isotopes) | 14.03 min (EX1) |

Example 395

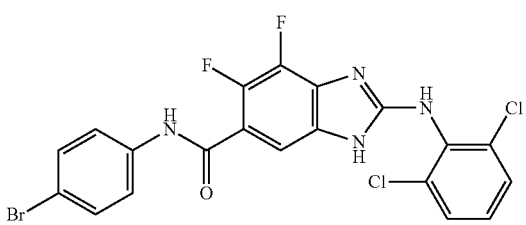 [SMILES: O=C(Nc1ccc(Br)cc1)c1cc2[nH]c(Nc3c(Cl)cccc3Cl)nc2c(F)c1F]

N-(4-Bromophenyl)-2-(2,6-dichlorophenylamino)-4,5-difluoro-1H-benzimidazole-6

(395a) Methyl 4,5-diamino-2,3-difluorobenzoate

Prepared analogously to example 1b by hydrogenation of methyl 4-amino-2,3-difluoro-5-nitrobenzoate using palladium/charcoal 10% in methanol and dichloromethane.

Yield: quant.

mass spectrum: $(M+H)^+=203$ $R_t$ value: 1.25 min (E7)

(395b) Methyl 4-amino-5-(3-(2,6-dichlorophenyl)thioureido)-2,3-difluorobenzoate

Prepared analogously to example 156d from methyl 4,5-diamino-2,3-difluoro-benzoate and 1,3-dichloro-2-isothiocyanato-benzene in DMF.

Yield: quant. (slightly contaminated)

mass spectrum: $(M+H)^+=407/409/411$ (chlorine isotopes)

(395c) Methyl 2-(2,6-dichlorophenylamino)-4,5-difluoro-1H-benzimidazole-6-carboxylate Prepared analogously to example 127e from methyl 4-amino-5-(3-(2,6-dichlorophenyl)-thioureido)-2,3-difluoro-benzoate and DIC in DMF Yield: 69% mass spectrum: $(M+H)^+=372/74/76$ (chlorine isotopes)

$R_t$ value: 1.33 min (F7)

(395d) 2-(2,6-Dichlorophenylamino)-4,5-difluoro-1H-benzimidazole-6-carboxylic acid Prepared analogously to example 3b from methyl 2-(2,6-dichlorophenylamino)-4,5-difluoro-1H-benzimidazole-6-carboxylate and NaOH in methanol.

Yield: 91% mass spectrum: $(M+H)^+=358/60/62$ (chlorine isotopes)

$R_t$ value: 1.2 min (F7)

(395e) N-(4-Bromophenyl)-2-(2,6-dichlorophenylamino)-4,5-difluoro-1H-benzimidazole-6-carboxamide 2-(2,6-Dichlorophenylamino)-4,5-difluoro-1H-benzimidazole-6-carboxylic acid (150 mg 0.42 mmol), TEA (0.15 mL, 1.05 mmol), 4-bromoaniline (70 mg, 0.42 mmol) and 50% solution of PPA (0.3 mL 0.5 mmol) in ethyl acetate in 10 mL acetonitrile was stirred for a weekend at ambient temperature. Then the solvent was removed i.vac. The residue was purified by HPLC.

Yield: 20 mg (9.3%)

mass spectrum: $(M+H)^+$=511/513/515 (chlorine and bromine isotopes)

$R_t$ value: 1.25 min (F7)

Example 405

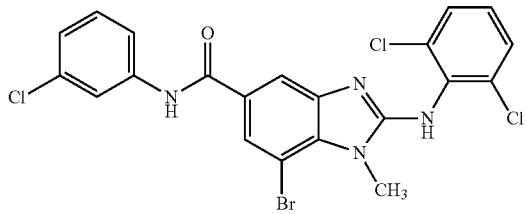 [SMILES: Cn1c(Nc2c(Cl)cccc2Cl)nc2cc(C(=O)Nc3cccc(Cl)c3)cc(Br)c21]

7-Bromo-N-(3-chlorophenyl)-2-(2,6-dichlorophenylamino)-1-methyl-1H-benzimidazole-5-carboxamide

(405a) Methyl 3-bromo-5-nitro-4-(2,2,2-trifluoroacetamido)-benzoate

To methyl 4-amino-3-bromo-5-nitrobenzoate (7.5 g, 27.3 mmol) and pyridine (5.74 mL, 71 mmol) in 200 mL dichloromethane was added trifluoracetic anhydride (5 mL, 35.5 mmol) under ice bath cooling. The mixture was stirred over night at ambient temperature. The solvent was removed in vac. The residue was mixed with water and ethylacetate. The organic layer was washed with water and brine, dried over $Na_2SO_4$ and the solvent was removed i.vac.

Yield: 9.69 g (96%)

$R_f$ value: 0.40 (silica gel; petrolether/ethylacetate=10:4)

(405b) Methyl 3-bromo-4-(methylamino)-5-nitrobenzoate

To methyl 3-bromo-5-nitro-4-(2,2,2-trifluoroacetamido)-benzoate (9.69 g, 26.1 mmol) in 250 mL acetonitrile was added $Cs_2CO_3$ (10.2 g, 31.3 mmol) and methyliodide (3.3 mL, 52.2 mmol). The mixture was heated to 45° C. for 2 h. The solvent was removed in vac. Water and methanol were added and stirred for 20 minutes. The solid was filtered and washed with methanol.

Yield: 6.05 g (80%)

$R_f$ value: 0.48 (silica gel; petrol ether/ethyl acetate=10:4)

(405c) Methyl 3-amino-5-bromo-4-(methylamino)benzoate

Prepared analogously to example 91a from methyl 3-bromo-4-(methylamino)-5-nitrobenzoate using iron powder in acetic acid and ethanol.

Yield: 78%

$R_f$ value: 0.4 (silica gel; petrol ether/ethyl acetate=10:4)

(405d) Methyl 7-bromo-2-(2,6-dichlorophenylamino)-1-methyl-1H-benzimidazole-5-carboxylate Prepared analogously to example 106a from methyl 3-amino-5-bromo-4-(methylamino)-benzoate and DCC in DMF.

Yield: quant. (crude)

(405e) 2-(2,6-Dichlorophenylamino)3H-imidazo[4,5-b]pyridine-6-carboxylic acid Prepared analogously to example 3b from methyl 7-bromo-2-(2,6-dichlorophenylamino)-1-methyl-1H-benzimidazole-5-carboxylate with NaOH in ethanol and water.

Yield: 68%

$R_f$ value: 0.6 (silica gel; petrol ether/ethyl acetate=9:1)

(405f) 7-Bromo-N-(3-chlorophenyl)-2-(2,6-dichlorophenylamino)-1-methyl-1H-benzimidazole-5-carboxamide Prepared analogously to example 3c from 2-(2,6-dichlorophenylamino)-3H-imidazo[4,5-b]pyridine-6-carboxylic acid, 3-chloroaniline TBTU and TEA in DMF and THF.

Yield: 24% mass spectrum: $(M+H)^+$=525/527/529 (chlorine and bromine isotopes)

$R_t$ value: 6.52 min

In analogy with the above described example, the following compounds were prepared:

| No. | Structural formula Name | Yield | Mass peak(s) | $R_f$ value or $R_t$ |
|---|---|---|---|---|
| 492 | 7-Bromo-N-(4-chloropyridin-2-yl)-2-(2,6-dichlorophenylamino)-1-methyl-1H-benzimidazole-5-carboxamide | Σ: 77% | $(M + H)^+$ = 524/526/528 (bromine and chlorine isotopes) | 15.28 min (EX2) |

| Structural formula No. Name | Yield | Mass peak(s) | $R_f$ value or $R_t$ |
|---|---|---|---|
| 500 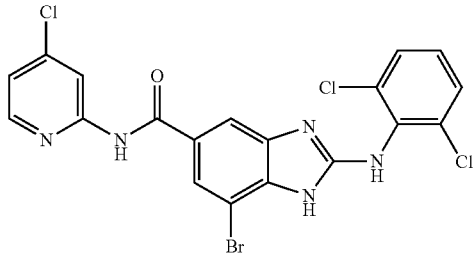 [SMILES: O=C(Nc1cc(Cl)ccn1)c1cc(Br)c2[nH]c(Nc3c(Cl)cccc3Cl)nc2c1]<br>7-Bromo-N-(4-chloropyridin-2-yl)-2-(2,6-dichlorophenylamino)-1H-benzimidazole-5-carboxamide | Σ: 8.3% | $(M+H)^+$ = 510/512/514 (bromine and chlorine isotopes) | 0.18 (silica gel dichloromethane/methanol 97.5:2.5) |
| 514 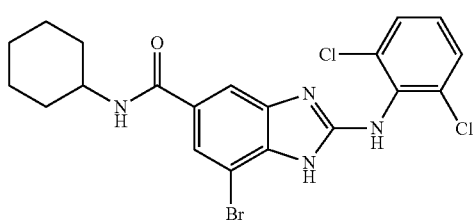 [SMILES: O=C(NC1CCCCC1)c1cc(Br)c2[nH]c(Nc3c(Cl)cccc3Cl)nc2c1]<br>7-Bromo-N-cyclohexyl-2-(2,6-dichlorophenylamino)-1H-benzimidazole-5-carboxamide | Σ: 1% | $(M+H)^+$ = 483/485/487 (bromine and chlorine isotopes) | 5.53 min (EX2) |
| 570 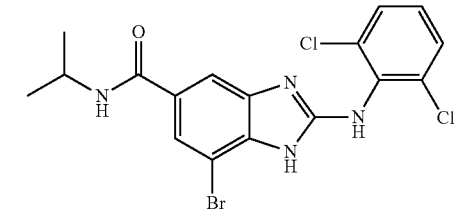 [SMILES: CC(C)NC(=O)c1cc(Br)c2[nH]c(Nc3c(Cl)cccc3Cl)nc2c1]<br>7-Bromo-N-isopropyl-2-(2,6-dichlorophenylamino)-1H-benzimidazole-5-carboxamide | Σ: 2% | $(M+H)^+$ = 443/445/447 (bromine and chlorine isotopes) | 4.28 min (EX2) |

Example 421

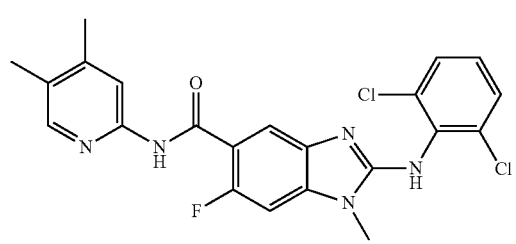 [SMILES: Cc1cnc(NC(=O)c2cc3nc(Nc4c(Cl)cccc4Cl)n(C)c3cc2F)cc1C]

2-(2,6-Dichlorophenylamino)-N-(4,5-dimethylpyridin-2-yl)-6-fluoro-1-methyl-1H-benzimidazole-5-carboxamide (421a) 2,4-Difluoro-5-nitro-benzoic acid ethyl ester Prepared analogously to example 156a from 2,4-difluoro-5-nitro-benzoyl chloride (5.0 g, 22.6 mmol), ethanol and TEA in THF.

Yield: quant.

(421b) 2-Fluoro-4-methylamino-5-nitro-benzoic acid ethyl ester

Prepared analogously to example 156b from 2,4-difluoro-5-nitro-benzoic acid ethyl ester and 2 M methylamine (solution in THF) in THF.

Yield: 69%

(421c) 5-Amino-2-fluoro-4-methylamino-benzoic acid ethyl ester

Prepared analogously to example 14b by hydrogenation of 2-fluoro-4-methylamino-5-nitro-benzoic acid ethyl ester using Raney nickel in THF.

Yield: quant.

mass spectrum: $(M+H)^+$=213

$R_t$ value: 2.19 min (C2)

(421d) Ethyl 5-(3-(2,6-dichlorophenyl)thioureido)-2-fluoro-4-(methylamino)-benzoate Prepared analogously to example 156d from 5-amino-2-fluoro-4-methylamino-benzoic acid ethyl ester and 1,3-dichloro-2-isothiocyanatobenzene in THF.

Yield: 89% mass spectrum: $(M+H)^+$=416/418/420 (chlorine isotopes)

$R_t$ value: 4.28 min (B2)

(421e) Ethyl 2-(2,6-dichlorophenylamino)-6-fluoro-1-methyl-1H-benzimidazole-5-carboxylate Prepared analogously to example 127e from ethyl 5-(3-(2,6-dichlorophenyl)thioureido)-2-fluoro-4-(methylamino)benzoate and DIC in acetonitrile.
Yield: 75%
mass spectrum: $(M+H)^+=382/384/386$ (chlorine isotopes)
$R_t$ value: 3.68 min (B2)

(421f) 2-(2,6-Dichlorophenylamino)-N-(4,5-dimethylpyridin-2-yl)-6-fluoro-1-methyl-1H-benzimidazole-5-carboxamide Prepared analogously to example 131f from ethyl 2-(2,6-dichlorophenylamino)-6-fluoro-1-methyl-1H-benzimidazole-5-carboxylate, 2 M trimethyl aluminium solution in hexane and 4,5-dimethylpyridin-2-amine in THF.
Yield: 13%
mass spectrum: $(M+H)^+=458/460/462$ (chlorine isotopes)
$R_t$ value: 2.15 min (C2)

In analogy with the above described example, the following compounds were prepared:

Example 464

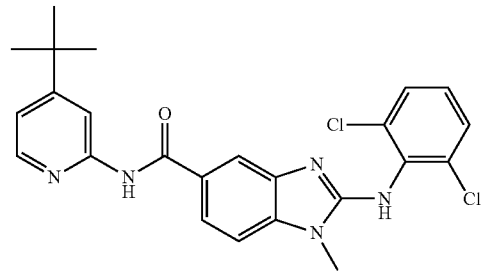 [SMILES: Cn1c(Nc2c(Cl)cccc2Cl)nc2cc(C(=O)Nc3cc(C(C)(C)C)ccn3)ccc21]

N-(4-tert.-Butylpyridin-2-yl)-2-(2,6-dichlorophenylamino)-1-methyl-1H-benzimidazole-5-carboxamide

(464a) Ethyl 3-amino-4-(3-(2,6-dichlorophenyl)-1-methylthioureido)-benzoate

Prepared analogously to example 156d from ethyl 3-amino-4-(methylamino)-benzoate and 1,3-dichloro-2-isothiocyanatobenzene in acetonitrile.
Yield: 85%
mass spectrum: $(M+H)^+=398/400/402$ (chlorine isotopes)
$R_t$ value: 2.88 min (C2)

| No. | Structural formula Name | Yield | Mass peak(s) | $R_f$ value or $R_t$ |
|---|---|---|---|---|
| 533 | 2-(2,6-Dichlorophenylamino)-6-fluoro-1-methyl-N-(4-(piperidin-1-yl)-pyridin-2-yl)-1H-benzimidazole-5-carboxamide | Σ: 27% | $(M + H)^+$ = 513/515/517 (chlorine isotopes) | 1.55 min (E9) |
| 554 | 2-(2,6-Dichlorophenylamino)-6-fluoro-1-methyl-N-(4-(pyrrolidin-1-yl)-pyridin-2-yl)-1H-benzimidazole-5-carboxamide | Σ: 24% | $(M + H)^+$ = 499/501/503 (chlorine isotopes) | 1.48 min (E9) |

(464b) Ethyl 2-(2,6-dichlorophenylamino)-6-fluoro-1-methyl-1H-benzimidazole-5-carboxylate Prepared analogously to example 127e from ethyl 3-amino-4-(3-(2,6-dichlorophenyl)-1-methylthioureido)-benzoate and DIC in acetonitrile
Yield: 86%
mass spectrum: (M+H)$^+$=364/66/68 (chlorine isotopes)
R$_t$ value: 3.15 min (B2)

(464c) N-(4-tert.-Butylpyridin-2-yl)-2-(2,6-dichlorophenylamino)-1-methyl-1H-benzimidazole-5-carboxamide Prepared analogously to example 131f from ethyl 2-(2,6-dichlorophenylamino)-6-fluoro-1-methyl-1H-benzimidazole-5-carboxylate, 2 M trimethyl aluminium solution in hexane and 4-tert.-butylpyridin-2-amine in THF.
Yield: 51%
mass spectrum: (M+H)$^+$=468/70/72 (chlorine isotopes)
R$_t$ value: 1.65 min (E7)
In analogy with the above described example, the following compounds were prepared:

| Structural formula | Yield | Mass peak(s) | R$_f$-value or R$_t$ |
| No. Name | | | |
|---|---|---|---|
| 559 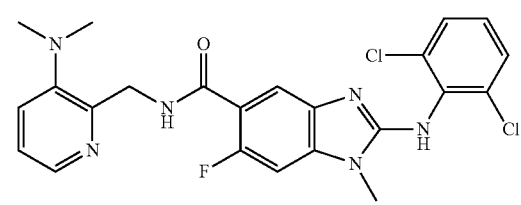<br>2-(2,6-Dichlorophenylamino)-N-(4-dimethylamino-pyridin-2-yl)-1-methyl-1H-benzimidazole-5-carboxamide | Σ: 24% | (M + H)$^+$ = 455/457/459 (chlorine isotopes) | 1.6 min (E7) |

Example 474

2-(2,6-Dichlorophenylamino)-N-((3-dimethylamino-pyridin-2-yl)-methyl)-6-fluoro-1-methyl-1H-benzimidazole-5-carboxamide

(474a) 2,4-Difluoro-5-nitro-benzoic acid ethyl ester

Prepared analogously to example 156a from 2,4-difluoro-5-nitro-benzoyl chloride, ethanol and TEA in THF.
Yield: quant.

(474b) 2-Fluoro-4-methylamino-5-nitro-benzoic acid ethyl ester

Prepared analogously to example 156b from 2,4-difluoro-5-nitro-benzoic acid ethyl ester and 2 M methylamine (solution in THF) in THF
Yield: 69%

(474c) 5-Amino-2-fluoro-4-methylamino-benzoic acid ethyl ester

Prepared analogously to example 14b by hydrogenation of 2-fluoro-4-methylamino-5-nitro-benzoic acid ethyl ester using Raney nickel in THF.
Yield: quant.
mass spectrum: (M+H)$^+$=213
R$_t$ value: 2.19 min (C2)

(474d) Ethyl 5-(3-(2,6-dichlorophenyl)thioureido)-2-fluoro-4-(methylamino)-benzoate Prepared analogously to example 156d from 5-amino-2-fluoro-4-methylamino-benzoic acid ethyl ester and 1,3-dichloro-2-isothiocyanatobenzene in THF.
Yield: 89%
mass spectrum: (M+H)$^+$=416/18/20 (chlorine isotopes)
R$_t$ value: 4.28 min (B2)

(474e) Ethyl 2-(2,6-dichlorophenylamino)-6-fluoro-1-methyl-1H-benzimidazole-5-carboxylate Prepared analogously to example 127e from ethyl 5-(3-(2,6-dichlorophenyl)-thioureido)-2-fluoro-4-(methylamino)-benzoate and DIC in acetonitrile.
Yield: 75%
mass spectrum: (M+H)$^+$=382/384/386 (chlorine isotopes)
R$_t$ value: 3.68 min (B2)

(474f) 2-(2,6-Dichlorophenylamino)-N-((3-dimethylamino-pyridin-2-yl)-methyl)-6-fluoro-1-methyl-1H-benzimidazole-5-carboxamide A mixture of the product obtained in 474e (100 mg, 0.28 mmol), 2-(aminomethyl)-N,N-dimethylpyridin-3-amine dihydrochloride (crude) (101 mg, 0.34 mmol), NMM (114 µL, 1.04 mmol) and 1-chloro-N,N,2-trimethylprop-1-en-1-amine (180 µL, 1.33 mmol) in 10 mL THF was stirred at ambient temperature for 3 h. MeOH was added and the solvent was removed i. vac. The residue was purified by HPLC.
Yield: 61 mg (44%)
mass spectrum: (M+H)$^+$=487/489/491 (chlorine isotopes)
R$_t$ value: 3.68 min (F7)

Example 540

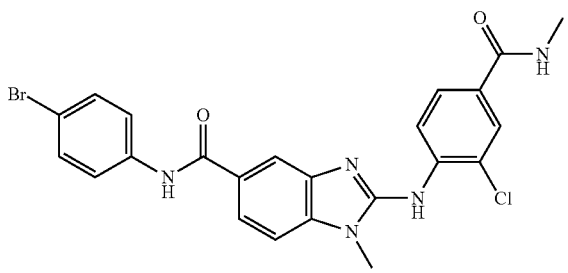 [SMILES: CNC(=O)c1ccc(Nc2nc3cc(C(=O)Nc4ccc(Br)cc4)ccc3n2C)c(Cl)c1]

N-(4-Bromophenyl)-2-(2-chloro-4-(methylcarbamoyl)-phenylamino)-1-methyl-1H-benzimidazole-5-carboxamide (540a) Methyl 4-(5-(4-bromophenylcarbamoyl)-1-methyl-1H-benzimidazol-2-yl-amino)-3-chlorobenzoate Prepared analogously to example 106a from 3-amino-N-(4-bromophenyl)-4-(methylamino)-benzamide and methyl 3-chloro-4-isothiocyanatobenzoate in DMF with EDC.
Yield: 88%

(540b) 4-(5-(4-Bromophenylcarbamoyl)-1-methyl-1H-benzimidazol-2-yl-amino)-3-chlorobenzoic acid Prepared analogously to example 3b from Methyl 4-(5-(4-bromophenyl-carbamoyl)-1-methyl-1H-benzimidazol-2-yl-amino)-3-chlorobenzoate and 2 N NaOH (aq) in dioxan.
Yield: 96%
mp: 206-208° C.
mass spectrum: $(M+H)^+=499/501/503$ (chlorine isotopes)

(540c) N-(4-Bromophenyl)-2-(2-chloro-4-(methylcarbamoyl)-phenylamino)-1-methyl-1H-benzimidazole-5-carboxamide Prepared analogously to example 3c from 4-(5-(4-bromophenylcarbamoyl)-1-methyl-1H-benzimidazol-2-ylamino)-3-chlorobenzoic acid, methylamine (solution in THF), TBTU and TEA in THF.
Yield: 34%
mass spectrum: $(M+H)^+=512/514/516$ (bromine and chlorine isotopes)

In analogy with the above described example, the following compounds were prepared:

| No. | Structural formula Name | Yield | Mass peak(s) | $R_f$ value or $R_t$ |
|---|---|---|---|---|
| 537 | N-(4-Bromophenyl)-2-(5-carbamoyl-2-chlorophenylamino)-1-methyl-1H-benzimidazole-5-carboxamide | Σ: 12% | $(M-H)^- = 498/500/502$ (chlorine and bromine isotopes) | 10.92 min (EX1) |
| 543 | N-(4-Bromophenyl)-2-(4-carbamoyl-2-chlorophenylamino)-1-methyl-1H-benzimidazole-5-carboxamide | Σ: 14% | $(M-H)^- = 498/500/502$ (chlorine and bromine isotopes) | 11.32 min (EX1) |
| 562 | N-(4-Bromophenyl)-2-(2-chloro-4-(dimethylcarbamoyl)-phenylamino)-1-methyl-1H-benzimidazole-5-carboxamide | Σ: 14% | $(M-H)^- = 526/528/530$ (chlorine and bromine isotopes) | 11.55 min (EX1) |

| No. | Structural formula Name | Yield | Mass peak(s) | $R_f$ value or $R_t$ |
|---|---|---|---|---|
| 573 | 3-(5-(4-Bromophenylcarbamoyl)-1-methyl-1H-benzimidazol-2-yl-amino)-4-chlorobenzoic acid | Σ: 84% | $(M-H)^- =$ 499/501/503 (chlorine and bromine isotopes) | 11.42 min (EX1) |
| 574 | N-(4-Bromophenyl)-2-(2-chloro-5-(methylcarbamoyl)-phenylamino)-1-methyl-1H-benzimidazole-5-carboxamide | Σ: 41% | $(M-H)^- =$ 512/514/516 (chlorine and bromine isotopes) | 11.24 min (EX1) |

Example 544

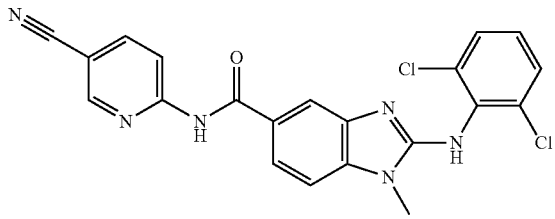 [SMILES: Cn1c(Nc2c(Cl)cccc2Cl)nc2cc(C(=O)Nc3ccc(C#N)cn3)ccc21]

N-(5-Cyanopyridin-2-yl)-2-(2,6-dichlorophenylamino)-1-methyl-1H-benzimidazole-5-carboxamide (544a) 4-(Methylamino)-3-nitrobenzoic acid Prepared analogously to example 156b from 4-fluoro-3-nitrobenzoic acid and 2 M methylamine (solution in THF) in THF.

Yield: 99%

(544b) Methyl 3-nitro-4-(methylamino)-benzoate

The product obtained in example 544a (9.4 g, 47.9 mmol) in 230 mL MeOH was flushed with HCl and stirred at 90° C. for 4 h. The mixture was cooled to ambient temperature and NaHCO₃ was added to pH=7-8. Water was added and the formed precipitate was filtered and dried.

Yield: 98%

(544c) Methyl 3-amino-4-(methylamino)-benzoate

To the product obtained in example 544b (9.9 g, 47.1 mmol) in 100 mL MeOH and 10 mL DMF were added 50 mL NH₄Cl (sat., aq) and 13.2 g (236 mmol) iron. The mixture was heated at 80° C. for 1.5 h, then cooled to ambient temperature, filtered through celite and evaporated to ¾ of starting volume. Then 1 N NaOH was added and the formed precipitate was filtered and dried.

Yield: 93%

(544d) N-(5-Cyanopyridin-2-yl)-2-(2,6-dichlorophenylamino)-1-methyl-1H-benzimidazole-5-carboxamide To the product obtained in example 544c (7.9 g, 43.8 mmol) in 50 mL DMF was added 1,3-dichloro-2-isothiocyanatobenzene (8.95 g, 43.8 mmol). The mixture was stirred at 40° C. for 90 min. Then EDCI (8.4 g, 43.8 mmol) was added and the mixture was stirred at 100° C. for 90 min. The mixture was cooled to ambient temperature, 30 mL water was added and the solvent was removed i.vac. The residue was dissolved in 100 mL ethanol, 70 mL 2 N NaOH were added and the mixture was stirred at 120° C. for 12 h. The mixture was evaporated to ¾ of starting volume, filtered and washed with water. To the separated solid, ethanol was added and the mixture was stirred for 70 min at 100° C., then cooled to ambient temperature, filtered and the solid washed with ethanol and ethylacetate. The crude material was reacted directly without further purification analogously to example 113b with 1-chloro-N,N-2-trimethyl-1-propenylamin in acetonitrile, followed by 6-aminonicotinonitrile and TEA.

Yield: 30 mg (8%)

mp: 234-236° C.

mass spectrum: $(M+H)^+$=437/439/441 (chlorine isotopes)

$R_f$ value: 0.67 (silica gel; 100% ethyl acetate)

In analogy with the above described example, the following compounds were prepared:

| No. | Structural formula Name | Yield | Mass peak(s) | $R_f$ value or $R_t$ |
|---|---|---|---|---|
| 490 | 2-(2,6-Dichlorophenylamino)-N-(5,6-dimethylpyridin-2-yl)-1-methyl-1H-benzimidazole-5-carboxamide | Σ: 2% | $(M + H)^+ =$ 440/442/444 (chlorine isotopes) | 10.1 min (EX1) |
| 494 | N-(5-Chloropyridin-2-yl)-2-(2,6-dichlorophenylamino)-1-methyl-1H-benzimidazole-5-carboxamide | Σ: 10% | $(M + H)^+ =$ 446/448/450 (chlorine isotopes) | 0.38 (silica gel, dichlormethan/ methanol = 10:1) |
| 524 | N-(4-Cyanopyridin-2-yl)-2-(2,6-dichlorophenylamino)-1-methyl-1H-benzimidazole-5-carboxamide | Σ: 7% | $(M + H)^+ =$ 446/448/450 (chlorine isotopes) | 0.42 (silica gel, dichlormethan/ methanol = 10:1) |
| 545 | 2-(2,6-Dichlorophenylamino)-N-(3-ethyl-6-methylpyridin-2-yl)-1-methyl-1H-benzimidazole-5-carboxamide | Σ: 7.5% | $(M + H)^+ =$ 454/456/458 (chlorine isotopes) | 9.96 min (EX1) |

Example 575

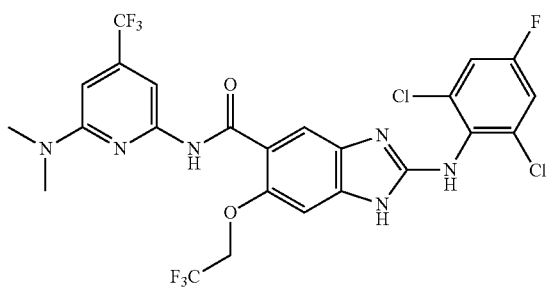 [SMILES: CN(C)c1cc(C(F)(F)F)cc(NC(=O)c2cc3nc(Nc4c(Cl)cc(F)cc4Cl)[nH]c3cc2OCC(F)(F)F)n1]

2-(2,6-Dichloro-4-fluoro-phenylamino)-N-(6-dimethylamino-4-trifluoromethyl-pyridin-2-yl)-6-(2,2,2-trifluorethoxy)-1H-benzimidazole-5-carboxamide (575a) Ethyl 4-Amino-2-fluoro-5-nitro-benzoate Prepared analogously to example 156b from 2,4-difluoro-5-nitrobenzoic acid-ethyl ester and conc. ammonia (aq) in THF.

Yield: 93%

(575b) Ethyl 4-amino-5-nitro-2-(2,2,2-trifluoroethoxy)-benzoate

The product obtained in example 575a (1.8 g, 7.9 mmol) in 20 mL THF was added to a mixture of 2,2,2-trifluoro-ethanol (0.63 mL, 8.8 mmol) with potassium tert.-butylate in 20 mL THF at 5° C. The mixture was stirred for 5 h at 5° C. The mixture is poured into water, the aqueous phase is extracted with ethyl acetate and the combined organic layers concentrated i.vac. after drying over MgSO₄.

Yield: 97%

227

(575c) 4-Amino-5-nitro-2-(2,2,2-trifluoro-ethoxy)-benzoic acid

Prepared analogously to example 3b from the product obtained from 575b with NaOH in ethanol.
Yield: 93%

(575d) 4-Amino-N-(6-dimethylamino-4-trifluoromethyl-pyridin-2-yl)-5-nitro-2-(2,2,2-trifluoroethoxy)-benzamide Prepared analogously to example 74c from the product obtained from 575c and 2-amino-6-dimethylamino-4-trifluoromethyl-pyridine with (1-chloro-2-methyl-propenyl)-dimethyl-amine and TEA in THF.
Yield: 58%, slightly contaminated
mass spectrum: $(M+H)^+=468$; $R_t$ value: 1.57 min (F9).

(575e) 4,5-Diamino-N-(6-dimethylamino-4-trifluoromethyl-pyridin-2-yl)-5-nitro-2-(2,2,2-trifluoroethoxy)-benzamide Prepared analogously to example 1b from the product obtained from 575d via hydrogenation with palladium on charcoal in an ethanol/THF—mixture (1:1).
Yield: quant.

(575f) 2-(2,6-Dichloro-4-fluoro-phenylamino)-N-(6-dimethylamino-4-trifluoromethyl-pyridin-2-yl) 6-(2,2,2-trifluorethoxy)-1H-benzimidazole-5-carboxamide Prepared analogously to example 1c from the product obtained from 575e and 2,6-dichloro-4-fluoro-1-isothiocyanato-benzene with DIC in acetonitrile.
Yield: 34%
mass spectrum: $(M+H)^+=625/627/629$ (chlorine isotopes)
$R_t$ value: 1.49 min (F8)
In analogy with the above described example, the following compounds were prepared:

228

Example 582

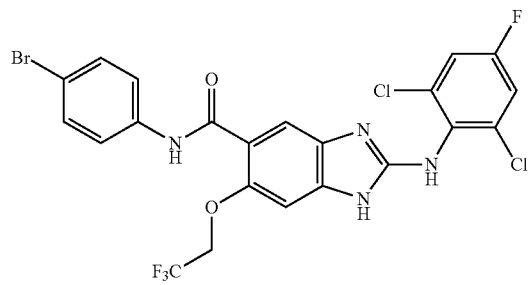 [SMILES: O=C(Nc1ccc(Br)cc1)c1cc2nc(Nc3c(Cl)cc(F)cc3Cl)[nH]c2cc1OCC(F)(F)F]

2-(2,6-Dichloro-4-fluoro-phenylamino)-N-(4-bromophenyl)-6-(2,2,2-trifluorethoxy)-1H-benzimidazole-5-carboxamide

(582a) Ethyl 4-acetamino-2-fluoro-benzoate

Acetanhydride (16.6 ml, 175 mmol) was added to a mixture of ethyl 4-amino-2-fluoro-benzoate (21.4 g, 117 mmol) and 170 mL acetic acid. The mixture was stirred at 60° C. for 2 h, poured into water at 0° C. and by addition of 10M NaOH (aq) adjusted to slightly acidic pH. The precipitate was filtered off, washed with water and dried.
Yield: 24.1 g (92%)
mass spectrum: $(M+H)^+=226$
$R_f$ value: 0.51 (silica gel; eluent: dichloromethane/methanol=9:1)

(582b) Ethyl 4-acetamino-2-fluoro-5-nitro-benzoate

To the product obtained in example 582a (22.8 g, 101 mmol) in 150 mL conc. sulphuric acid was added conc. nitric acid (25 mL, 65%, 563 mmol) at 0° C. The mixture was stirred for 15 min at 0° C. and 2 h at ambient temperature. The mixture is poured into water, neutralized with 10M NaOH (aq) and $K_2CO_3$, the aqueous phase is extracted with ethyl acetate and the combined organic layers concentrated i.vac. after drying over $MgSO_4$. The residue is mixed with dichloromethane, filtered over silica gel and purified by chromatography (silica gel; eluens gradient: dichloromethane/ethanol=99:1->90:10).
Yield: 11.8 g (43%)
mass spectrum: $(M+H)^+=271$
$R_f$ value: 0.64 (silica gel; eluent: dichloromethane/methanol=50:1)

| No. | Structural formula Name | Yield | Mass peak(s) | $R_f$ value or $R_t$ |
|---|---|---|---|---|
| 576 | 2-(2,6-Dichloro-4-fluoro-phenylamino)-N-(4-methyl-6-trifluormethyl-pyridin-2-yl)-6-(2,2,2-trifluorethoxy)-1H-benzimidazole-5-carboxamide | Σ: 6.9% | $(M+H)^+=$ 596/598/600 (chlorine isotopes) | 1.43 min (F8) |

(582c) Ethyl 4-acetamino-5-nitro-2-(2,2,2-trifluoro-ethoxy)-benzoate

Prepared analogously to example 575b from the product obtained from 582b and 2,2,2-trifluoroethanol with KHMDS in THF.
Yield: 99%, slightly contaminated

(582d) 4-Amino-5-nitro-2-(2,2,2-trifluoro-ethoxy)-benzoic acid

Prepared analogously to example 3b from the product obtained from 582c with NaOH (aq) in methanol.
Yield: 76%

(582e) 4,5-Diamino-2-(2,2,2-trifluoroethoxy)-benzoic acid

Prepared analogously to example 1b from the product obtained from 582d by hydrogenation with palladium on charcoal in methanol.
Yield: 87%, slightly contaminated

(582f) 2-(2,6-Dichloro-4-fluoro-phenylamino)-6-(2,2,2-trifluorethoxy)-1H-benzimidazole-5-carboxylic acid Prepared analogously to example 135f from the product obtained from 582e and 2,6-dichloro-4-fluoro-1-isothiocyanato-benzene with N,O-bis-(trimethylsilyl)-trifluoro-acetamide and DIC in acetonitrile.
Yield: 20%

(582 g) 2-(2,6-Dichloro-4-fluoro-phenylamino)-N-(4-bromo-phenyl)-6-(2,2,2-trifluorethoxy)-1H-benzimidazole-5-carboxamide Prepared analogously to example 3c from the product obtained from 582f and 4-bromo-aniline with HATU and TEA in THF and DMF.
Yield: 30%; mass spectrum: $(M+H)^+ = 591/593/595/597$ (bromine and chlorine isotopes); $R_t$ value: 2.85 min (C1).

In analogy with the above described example, the following compounds were prepared:

| No. | Structural formula / Name | Yield | Mass peak(s) | $R_f$ value or $R_t$ |
|---|---|---|---|---|
| 592 | 2-(3,6-Dichloro-2-fluoro-phenylamino)-N-(4-trans-trifluoromethyl-cyclohex-1-yl)-6-(2,2,2-trifluorethoxy)-1H-benzimidazole-5-carboxamide | Σ: 5.4% | $(M + H)^+ =$ 587/589/591 (chlorine isotopes) | |
| 593 | 2-(3,6-Dichloro-2-fluoro-phenylamino)-N-(4-bromophenyl)-6-(2,2,2-trifluorethoxy)-1H-benzimidazole-5-carboxamide | Σ: 4.5% | $(M + H)^+ =$ 591/593/595/597 (bromine and chlorine isotopes) | 2.82 min (C5) |
| 594 | 2-(2-Chloro-3,6-difluoro-phenylamino)-N-(4-trans-trifluoromethyl-cyclohex-1-yl)-6-(2,2,2-trifluorethoxy)-1H-benzimidazole-5-carboxamide | Σ: 10.4% | $(M + H)^+ =$ 571/573/575 (chlorine isotopes) | 3.92 min (B5) |

-continued

| No. | Structural formula Name | Yield | Mass peak(s) | $R_f$-value or $R_t$ |
|---|---|---|---|---|
| 595 | (structure shown) 2-(2-Chloro-3,6-difluoro-phenylamino)-N-(4-bromophenyl)-6-(2,2,2-trifluorethoxy)-1H-benzimidazole-5-carboxamide | Σ: 8.4% | $(M+H)^+$ = 575/577/579/581 (bromine and chlorine isotopes) | 4.18 min (B5) |

Example 583

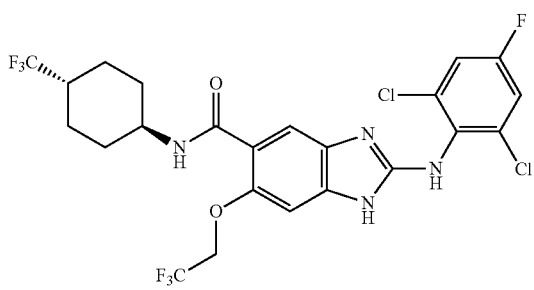 [SMILES: O=C(N[C@H]1CC[C@H](C(F)(F)F)CC1)c1cc2nc(Nc3c(Cl)cc(F)cc3Cl)[nH]c2cc1OCC(F)(F)F]

2-(2,6-Dichloro-4-fluoro-phenylamino)-N-(trans-4-trifluoromethyl-cyclohex-1-yl)-6-(2,2,2-trifluoroethoxy)-1H-benzimidazole-5-carboxamide (583a) trans-4-Trifluoromethyl-cyclohexyl-carboxylic acid chloride A mixture of trans-4-trifluoromethyl-cyclohexyl-carboxylic acid (10.7 g, 54.3 mmol) and thionylchloride (10 mL, 138 mmol) in 100 mL dichloromethane with 200 µL DMF was refluxed for 2 h. The mixture was concentrated i.vac. and triturated with dichloromethane. The residue was reacted without further purification.
Yield: 11.7 g (quant.)

(583b) trans-4-Trifluoromethyl-cyclohexyl-carboxylic amide

Conc. ammonia (aq, 350 mL), was added to the product obtained in example 583a (11.7 g, 54.5 mmol) in 100 mL THF under turbination. The mixture was stirred for 20 mL and the organic solvent evaporated i.vac. The precipitate was filtered off, washed with water and dried at 40° C.
Yield: 9.5 g (90%)

(583c) trans-4-Trifluoromethyl-cyclohexyl-amine-hydrochloride

Bromine (2.7 mL, 52.5 mmol) was added to 200 mL 1N NaOH (aq) and stirred for 10 min at ambient temperature. The product obtained from (583b) was added and the mixture stirred for 45 min at ambient temperature and for 3 h at reflux. The mixture was acidified with conc. HCl (aq) and filtered, then made basic with NaOH (aq) and extracted with diethyl-ether. The aqueous layer was evaporated to dryness. The residue was reacted without further purification.
Yield: 8.35 g (84%)

(583d) 2,6-Dichloro-4-fluoro-1-isothiocyanato-benzene

A mixture of 2,6-dichloro-4-fluoro-aniline (9.0 g, 50 mmol) and 1,1'-thiocarbonyl-di-2(1H)-pyridone (12.8 g, 55 mmol) in 100 mL dichloromethane was stirred for 16 h at ambient temperature. The mixture was evaporated, the residue triturated with petrol ether, filtered, concentrated and purified by chromatography (silica gel; eluens: petrol ether/ethyl acetate=98:2).
Yield: 8.85 g (80%)
mass spectrum: $(M+H)^+$=222/224/226 (chlorine isotopes)

(583e) Ethyl 4-benzylamino-2-fluoro-5-nitro-benzoate

Benzylamine (7.6 mL, 69 mmol) in 30 mL THF was added to ethyl 2,4-difluoro-5-nitro-benzoate (16.0 g, 69 mmol) in 270 mL THF with TEA (19.7 mL, 140 mmol) under stirring at 0° C. The mixture was stirred for 3.5 h at ambient temperature. The mixture was concentrated i.vac., the residue stirred with water, filtered off, washed with water and dried.
Yield: 21.0 g (95%)
mass spectrum: $(M+H)^+$=319
$R_f$-value: 0.65 (silica gel; eluens: petrol ether/ethyl acetate: 7:3)

(583f) Ethyl 4-benzylamino-5-nitro-2-(2,2,2-trifluoroethoxy)-benzoate

Prepared analogously to example 575b from the product obtained from 583e and 2,2,2-trifluoro-ethanol with potassium-tert.-butylate in THF.
Yield: 93%

(583 g) Ethyl 4,5-diamino-2-(2,2,2-trifluoroethoxy)-benzoate

The product obtained from (582f) (6.7 g, 16.8 mmol) in 65 mL ethanol was hydrogenated using palladium(II)hydroxide at 50° C. at 50 psi for 5 h in a Parr apparatus. After filtration the mixture was evaporated to dryness and reacted without further purification.
Yield: 4.81 g (quant.), slightly contaminated
$R_t$ value: 1.38 min (E7)

(583h) Ethyl 4-amino-5-(3-(2,6-dichloro-4-fluoro-phenyl)-thioureido)-2-(2,2,2-trifluoroethoxy)-benzoate The product obtained from (583d) (3.75 g, 16.9 mmol) was added to the product obtained in (583g) (4.70 g, 16.9 mmol) in 80 mL THF and the mixture was stirred at ambient temperature for 16 h. The mixture was evaporated to dryness and reacted without further purification.

Yield: 8.86 g (quant.), slightly contaminated $R_t$ value: 2.08 min (E7)

(583i) 2-(2,6-Dichloro-4-fluoro-phenylamino)-6-(2,2,2-trifluoroethoxy)-1H-benzimidazole-5-carboxylic acid ethyl ester DIC (3.0 mL, 18.9 mmol) was added to the product obtained from (583h) (8.50 g, 17.0 mmol) in 100 mL acetonitrile and stirred at 75° C. for 2.5 h. The mixture was evaporated to dryness and triturated with ethyl acetate, filtered and concentrated i.vac. The residue was purified by chromatography (silica gel, eluens gradient: petrol ether/ethyl acetate=95:5->70:30).

Yield: 5.46 g (69%)

mass spectrum: (M+H)$^+$=466/468/470 (chlorine isotopes)

$R_t$ value: 1.79 min (E7)

(583k) 2-(2,6-Dichloro-4-fluoro-phenylamino)-6-(2,2,2-trifluoroethoxy)-1H-benzimidazole-5-carboxylic acid 70 mL 2M NaOH (aq) were added to the product obtained from (583i) (5.46 g, 11.7 mmol) in 100 mL THF and the mixture stirred at 70° C. for 3d. The organic solvent was evaporated and the residue extracted with diethylether. The aqueous phase was acidified by addition of 4M HCl (aq), the mixture stirred for 16 h and the solid filtered off and dried.

Yield: 3.44 g (67%)

mass spectrum: (M+H)$^+$=438/440/442 (chlorine isotopes)

$R_t$ value: 1.50 min (E7)

(583l) 2-(2,6-Dichloro-4-fluoro-phenylamino)-6-(2,2,2-trifluoroethoxy)-N-(trans-4-trifluoromethyl-cyclohex-1-yl)-1H-benzimidazole-5-carboxamide A mixture of the product obtained in (583k) (219 mg, 0.50 mmol) with TEA (0.35 mL, 2.50 mmol) and TBTU (177 mg, 0.55 mmol) in 7 mL THF and 1 mL DMF was stirred at ambient temperature for 15 min. The product obtained from (583c) (102 mg, 0.50 mmol) was added and the mixture stirred at ambient temperature for 16 h. The organic solvent was evaporated and the residue stirred in $K_2CO_3$ (aq), filtered, dried and purified by chromatography (silica gel; eluens gradient: petrol ether/ethyl acetate=70:30->30:70).

Yield: 180 mg (61%)

mass spectrum: (M+H)$^+$=587/589/591 (chlorine isotopes)

$R_t$ value: 2.54 min (C12)

Example 584

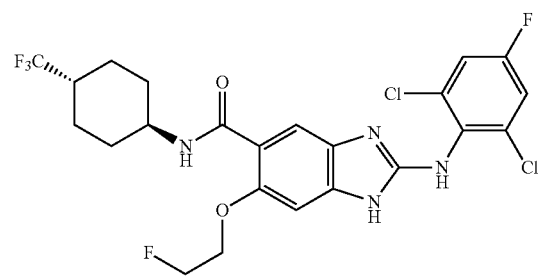 [SMILES: O=C(N[C@H]1CC[C@H](C(F)(F)F)CC1)c1cc2nc(Nc3c(Cl)cc(F)cc3Cl)[nH]c2cc1OCCF]

2-(2,6-Dichloro-4-fluoro-phenylamino)-N-(trans-4-trifluoro-cyclohex-1-yl)-6-(2-fluoroethoxy)-1H-benzimidazole-5-carboxamide

(584a) Ethyl 4-amino-2-(2-fluoroethoxy)-5-nitro-benzoate

Prepared analogously to example 575b from ethyl 4-amino-2-fluoro-5-nitro-benzoate and 2-fluoroethanol with KHMDS in THF.

Yield: 88%

$R_f$ value: 0.50 (silica gel; eluent: dichloromethane/ethanol=19:1)

(584b) 4-Amino-2-(2-fluoroethoxy)-5-nitro-benzoic acid

Prepared analogously to example 3b from the product obtained from 584a with NaOH (aq) in methanol.

Yield: 80%

$R_f$ value: 0.45 (silica gel; eluent: dichloromethane/ethanol=9:1)

(584c) 4,5-Diamino-2-(2-fluoroethoxy)-benzoic acid

Prepared analogously to example 1b from the product obtained from 584b by hydrogenation using palladium on charcoal in methanol and dichloromethane.

Yield: 99%

$R_f$ value: 0.30 (silica gel; eluent: dichloromethane/ethanol=9:1)

(584d) 2-(2,6-Dichloro-4-fluoro-phenylamino)-6-(2-fluoroethoxy)-1H-benzimidazole-5-carboxylic acid Prepared analogously to example 135f from the product obtained from 584c and 2,6-dichloro-4-fluoro-1-isothiocyanato-benzene with N,O-bis-(trimethylsilyl)-trifluoro-acetamide and DIC in acetonitrile.

Yield: 38% mass spectrum: (M+H)$^+$=402/404/406 (chlorine isotopes)

(584e) 2-(2,6-Dichloro-4-fluoro-phenylamino)-N-(trans-4-trifluoromethyl-cyclohex-1-yl)-6-(2-fluoroethoxy)-1H-benzimidazole-5-carboxamide Prepared analogously to example 3c from the product obtained from 584d and trans-4-trifluoromethyl-cyclohexylamine with TBTU and TEA in THF and DMF.

Yield: 45% mass spectrum: (M+H)$^+$=551/553/555 (chlorine isotopes)

$R_t$ value: 2.60 min (C1)

In analogy with the above described example, the following compounds were prepared:

| No. | Structural formula Name | Yield | Mass peak(s) | $R_f$ value or $R_t$ |
|---|---|---|---|---|
| 585 | 2-(2,6-Dichloro-4-fluoro-phenylamino)-N-(4-bromo-phenyl)-6-(2-fluoroethoxy)-1H-benzimidazole-5-carboxamide | FΣ: 13.0% | $(M + H)^+$ = 555/557/559/561 (bromine and chlorine isotopes) | 2.76 min (C1) |
| 586 | 2-(2,6-Dichloro-4-fluoro-phenylamino)-N-(4-bromo-phenyl)-6-(2,2-difluoroethoxy)-1H-benzimidazole-5-carboxamide | FΣ: 10.6% | $(M + H)^+$ = 573/575/577/579 (bromine and chlorine isotopes) | 2.58 min (C4) |
| 587 | 2-(2,6-Dichloro-4-fluoro-phenylamino)-N-(trans-4-trifluoromethyl-cyclohex-1-yl)-6-(2,2-difluoroethoxy)-1H-benzimidazole-5-carboxamide | FΣ: 12.3% | $(M + H)^+$ = 569/571/573 (chlorine isotopes) | 2.29 min (C2) |

Example 588

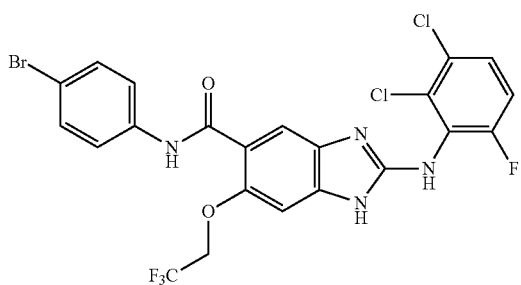 [SMILES: O=C(Nc1ccc(Br)cc1)c1cc2nc(Nc3c(F)ccc(Cl)c3Cl)[nH]c2cc1OCC(F)(F)F]

N-(4-Bromo-phenyl)-2-(2,3-dichloro-6-fluoro-phenylamino)-6-(2,2,2-trifluoroethoxy)-1H-benzimidazole-5-carboxamide (588a) Ethyl 4-amino-5-(3-(2,3-dichloro-6-fluoro-phenyl)-thioureido)-2-(2,2,2-trifluoroethoxy)-benzoate Prepared analogously to example 583h from ethyl-4,5-diamino-2-(2,2,2-trifluoro-ethoxy)-benzoate (synthesis described at example 575) and 2,3-dichloro-6-fluoro-1-isothiocyanato-benzene in acetonitrile.

Yield: 99%

(588b) 2-(2,3-Dichloro-6-fluoro-phenylamino)-6-(2,2,2-trifluoroethoxy)-1H-benzimidazole-5-carboxylic acid ethyl ester Prepared analogously to example 583i from the product obtained from (588a) with DIC in acetonitrile.

Yield: 54%

(588c) N-(4-Bromo-phenyl)-2-(2,3-dichloro-6-fluoro-phenylamino)-6-(2,2,2-trifluoroethoxy)-1H-benzimidazole-5-carboxamide Prepared analogously to example 131f from the product obtained from (588a) and 4-bromoaniline with trimethyl-aluminium in heptan and acetonitrile.
Yield: 59%
mass spectrum: (M+H)$^+$=591/593/595/597 (bromine and chlorine isotopes)
R$_t$ value: 2.82 min (C5)

Example 589

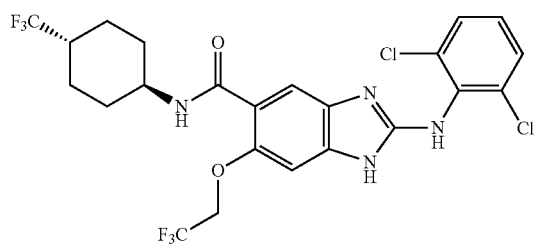 [SMILES: O=C(N[C@H]1CC[C@H](C(F)(F)F)CC1)c1cc2nc(Nc3c(Cl)cccc3Cl)[nH]c2cc1OCC(F)(F)F]

2-(2,6-Dichloro-phenylamino)-6-(2,2,2-trifluoroethoxy)-N-(trans-4-trifluormethyl-cyclohex-1-yl)-1H-benzimidazole-5-carboxamide

(589a) Ethyl 4-amino-5-(3-(2,6-dichloro-phenyl)-thioureido)-2-(2,2,2-trifluoroethoxy)-benzoate Prepared analogously to example 583h from ethyl-4,5-diamino-2-(2,2,2-trifluoro-ethoxy)-benzoate (synthesis described at example 575) and 2,6-dichloro-1-isothiocyanato-benzene in acetonitrile.
Yield: 98%

(589b) 2-(2,6-Dichloro-phenylamino)-6-(2,2,2-trifluoroethoxy)-1H-benzimidazole-5-carboxylic acid ethyl ester Prepared analogously to example 583i from the product obtained from (589a) with DIC in acetonitrile.
Yield: 68%

(589c) 2-(2,6-Dichloro-phenylamino)-6-(2,2,2-trifluoroethoxy)-1H-benzimidazole-5-carboxylic acid Prepared analogously to example 3b from the product obtained from (589b) with NaOH (aq) in methanol.
Yield: 73%
mass spectrum: (M+H)$^+$=418/420/422 (chlorine isotopes)

(589d) 2-(2,6-Dichloro-phenylamino)-6-(2,2,2-trifluoroethoxy)-N-(trans-4-trifluoromethyl-cyclohex-1-yl)-1H-benzimidazole-5-carboxylic acid Prepared analogously to example 3c from the product obtained from (589c) and trans-4-trifluoromethyl-cyclohexylamine with TBTU and TEA in THF and DMF.
Yield: 38%
mass spectrum: (M+H)$^+$=569/571/573 (chlorine isotopes)
R$_t$ value: 2.45 min (C5)

In analogy to the above described example, the following compounds were synthesized:

| No. | Structural formula Name | Yield | Mass peak(s) | R$_f$ value or R$_t$ |
|---|---|---|---|---|
| 590 | 2-(2,6-Dichloro-phenylamino)-N-(4-bromo-phenyl)-6-(2,2,2-trifluoroethoxy)-1H-benzimidazole-5-carboxamide | Σ: 24% | (M + H)$^+$ = 573/575/577/579 (bromine and chlorine isotopes) | 2.56 min (C5) |
| 591 | 2-(2,3-Dichloro-6-fluoro-phenylamino)-6-(2,2,2-trifluoro-ethoxy)-N-(4-trans-trifluoromethyl-cyclohex-1-yl)1H-benzimidazole-5-carboxamide | Σ: 24% | (M + H)$^+$ = 587/589/591 (chlorine isotopes) | 2.61 min (C5) |

Example 599

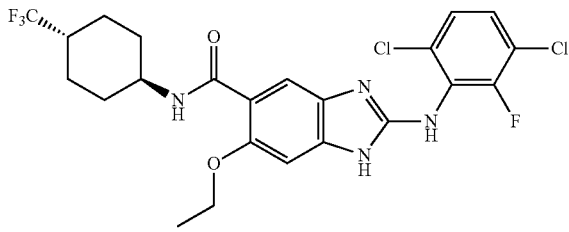 [SMILES: CCOc1cc2[nH]c(Nc3c(Cl)ccc(Cl)c3F)nc2cc1C(=O)N[C@H]1CC[C@H](C(F)(F)F)CC1]

2-(3,6-Dichloro-2-fluoro-phenylamino)-6-ethoxy-N-(trans-4-trifluoromethyl-cyclohex-1-yl)-1H-benzimidazole-5-carboxamide

(599a) Ethyl 4-amino-2-fluoro-5-nitro-benzoate

Conc. ammonia (5.2 mL, 32%, 86.5 mmol) was added to ethyl 2,4-difluoro-5-nitro-benzoate (5.00 g, 21.6 mmol) in 25 mL THF at 0° C. The mixture was stirred at ambient temperature for 16 h. Then the mixture was concentrated i.vac., the residue mixed with water, filtered off and the solid washed with water and dried.

Yield: 4.58 g (93%)
mass spectrum: $(M+H)^+=227$
$R_f$ value: 0.57 (silica gel; cyclohexane/ethyl acetate=3:2)

(599b) Ethyl 4-amino-2-ethoxy-5-nitro-benzoate

KHMDS (1.92 g, 9.64 mmol) was added to a mixture of ethyl 4-amino-2-fluoro-5-nitro-benzoate (2.00 g, 8.77 mmol) and ethanol (0.56 mL, 9.64 mmol) in 70 mL THF at 0° C. The mixture was stirred at 60° C. for 16 h. Then KHMDS (1.92 g, 9.64 mmol) and ethanol (1.2 mL, 20.7 mmol) were added at ambient temperature and the mixture was stirred at 60° C. for 2 h. 100 mL dichloromethane were added and the mixture extracted with sat. $NH_4Cl$ (aq). The organic layer was evaporated, the residue mixed with ethyl acetate, washed with sat. NaCl (aq), dried over $Na_2SO_4$, filtered and evaporated. The residue was purified twice by chromatography (silica gel; eluens: petrol ether/ethyl acetate=1:1 and 2:1).

Yield: 0.95 g (43%)
mass spectrum: $(M+H)^+=255$
$R_t$ value: 1.32 min (F7)

(599c) Ethyl 4,5-diamino-2-ethoxy-benzoate

Prepared analogously to example 1b from the product obtained from (599b) by hydrogenation with palladium on charcoal in ethanol.

Yield: 95%; mass spectrum: $(M+H)^+=225$; $R_t$ value: 0.95 min (F7).

(599d) 2-(3,6-Dichloro-2-fluoro-phenylamino)-6-ethoxy-1H-benzimidazole-5-carboxylic acid ethyl ester Prepared analogously to example 1c from the product obtained from (599c) and 3,6-dichloro-2-fluoro-1-isothiocyanato-benzene with DIC in acetonitrile.

Yield: 71%
mass spectrum: $(M+H)^+=412/414/416$ (chlorine isotopes)
$R_t$ value: 1.23 min (F7)

(599e) 2-(3,6-Dichloro-2-fluoro-phenylamino)-6-ethoxy-1H-benzimidazole-5-carboxylic acid Prepared analogously to example 3b from the product obtained from (599d) with NaOH (aq) in ethanol.

Yield: 91%
mass spectrum: $(M+H)^+=384/386/388$ (chlorine isotopes)
$R_t$ value: 1.12 min (F7)

(599f) 2-(3,6-Dichloro-2-fluoro-phenylamino)-6-ethoxy-N-(trans-4-trifluoromethyl-cyclohex-1-yl)-1H-benzimidazole-5-carboxamide Prepared analogously to example 3c from the product obtained from (589e) and trans-4-trifluoromethyl-cyclohexylamine with TBTU and TEA in THF and DMF.

Yield: 40%
mass spectrum: $(M+H)^+=533/535/537$ (chlorine isotopes)
$R_t$ value: 1.35 min (F7)

In analogy to the above described example, the following compounds were synthesized:

| No. | Structural formula Name | Yield | Mass peak(s) | $R_f$ value or $R_t$ |
|---|---|---|---|---|
| 600 | 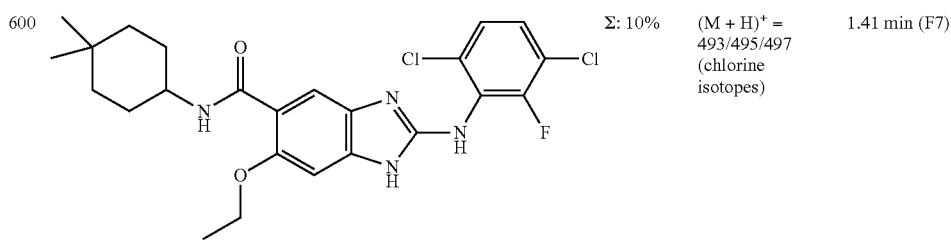<br>2-(3,6-Dichloro-2-fluoro-phenylamino)-N-(4,4-dimethyl-cyclohexyl)-6-ethoxy-1H-benzimidazole-5-carboxamide | Σ: 10% | $(M+H)^+=$ 493/495/497 (chlorine isotopes) | 1.41 min (F7) |

| No. | Structural formula Name | Yield | Mass peak(s) | $R_f$ value or $R_t$ |
|---|---|---|---|---|
| 603 | 2-(3,6-Dichloro-2-fluoro-phenylamino)-N-(3-chloro-phenyl)-6-ethoxy-1H-benzimidazole-5-carboxamide | Σ: 9.3% | (M + H)⁺ = 493/495/497/499 (chlorine isotopes) | 1.39 min (F7) |
| 604 | 2-(3,6-Dichloro-2-fluoro-phenylamino)-N-(4-bromo-phenyl)-6-ethoxy-1H-benzimidazole-5-carboxamide | Σ: 7.6% | (M + H)⁺ = 537/539/541/543 (bromine and chlorine isotopes) | 1.40 min (F7) |
| 605 | 2-(3,6-Dichloro-2-fluoro-phenylamino)-6-ethoxy-N-(4-trans-trifluoromethyl-cyclohex-1-yl)-1-methyl-1H-benzimidazole-5-carboxamide | Σ: 20% | (M + H)⁺ = 547/549/541 (chlorine isotopes) | 1.45 min (F7) |
| 607 | 2-(3,6-Dichloro-2-fluoro-phenylamino)-6-ethoxy-N-(4,4-dimethyl-cyclohex-1-yl)-1-methyl-1H-benzimidazole-5-carboxamide | Σ: 17% | (M + H)⁺ = 507/509/511 (chlorine isotopes) | 1.54 min (F7) |
| 609 | 2-(3,6-Dichloro-2-fluoro-phenylamino)-6-ethoxy-N-(spiro[2.5]oct-6-yl)-1-methyl-1H-benzimidazole-5-carboxamide | Σ: 18% | (M + H)⁺ = 505/507/509 (chlorine isotopes) | 1.54 min (F7) |

-continued

| No. | Structural formula Name | Yield | Mass peak(s) | $R_f$ value or $R_t$ |
|---|---|---|---|---|
| 610 | 2-(3,6-Dichloro-2-fluoro-phenylamino)-N-(4-bromo-phenyl)-6-isopropoxy-1H-benzimidazole-5-carboxamide | Σ: 11.4% | $(M + H)^+$ = 549/551/553/555 (bromine and chlorine isotopes) | 1.43 min (F7) |
| 611 | 2-(3,6-Dichloro-2-fluoro-phenylamino)-6-isopropoxy-N-cyclohexyl-1H-benzimidazole-5-carboxamide | Σ: 16% | $(M + H)^+$ = 479/481/483 (chlorine isotopes) | 1.32 min (F7) |
| 614 | 2-(3,6-Dichloro-2-fluoro-phenylamino)-N-(3-chloro-phenyl)-6-isopropoxy-1H-benzimidazole-5-carboxamide | Σ: 6.6% | $(M + H)^+$ = 507/509/511/513 (chlorine isotopes) | 1.43 min (F7) |
| 615 | 2-(3,6-Dichloro-2-fluoro-phenylamino)-6-isopropoxy-N-(spiro[2.5]oct-6-yl)-1H-benzimidazole-5-carboxamide | Σ: 6.6% | $(M + H)^+$ = 505/507/509 (chlorine isotopes) | 1.39 min (F7) |
| 618 | 2-(3,6-Dichloro-2-fluoro-phenylamino)-6-isopropoxy-N-(4,4-dimethyl-cyclohex-1-yl)-1H-benzimidazole-5-carboxamide | Σ: 2.2% | $(M - H)^-$ = 505/507/509 (chlorine isotopes) | 1.42 min (F7) |

-continued

| No. | Structural formula Name | Yield | Mass peak(s) | $R_f$ value or $R_t$ |
|---|---|---|---|---|
| 620 | 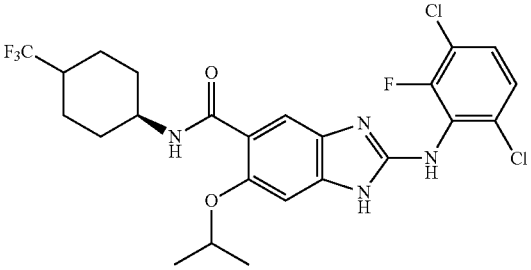<br>2-(3,6-Dichloro-2-fluoro-phenylamino)-6-isopropoxy-N-(4-trans-trifluoromethyl-cyclohex-1-yl)-1H-benzimidazole-5-carboxamide | Σ: 5.2% | $(M + H)^+$ = 547/549/541 (chlorine isotopes) | 1.34 min (F7) |
| 624 | 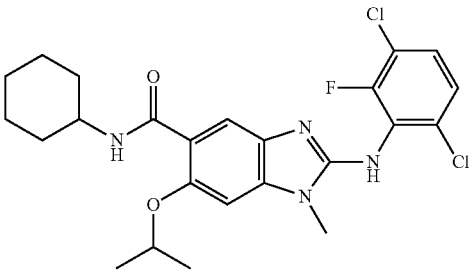 [SMILES: CC(C)Oc1cc2c(cc1C(=O)NC1CCCCC1)nc(Nc1c(Cl)ccc(Cl)c1F)n2C]<br>2-(3,6-Dichloro-2-fluoro-phenylamino)-6-isopropoxy-N-cyclohexyl-1-methyl-1H-benzimidazole-5-carboxamide | Σ: 13% | $(M - H)^-$ = 493/495/497 (chlorine isotopes) | 0.34 (silica gel; dichloromethane/ ethanol = 19:1) |
| 625 | 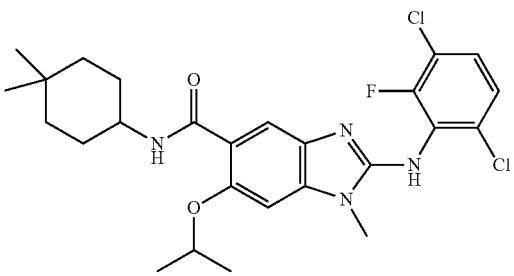 [SMILES: CC(C)Oc1cc2c(cc1C(=O)NC1CCC(C)(C)CC1)nc(Nc1c(Cl)ccc(Cl)c1F)n2C]<br>2-(3,6-Dichloro-2-fluoro-phenylamino)-6-isopropoxy-N-(4,4-dimethyl-cyclohex-1-yl)-1-methyl-1H-benzimidazole-5-carboxamide | Σ: 14% | $(M - H)^-$ = 521/523/525 (chlorine isotopes) | 0.42 (silica gel; dichloromethane/ ethanol = 19:1) |
| 644 | 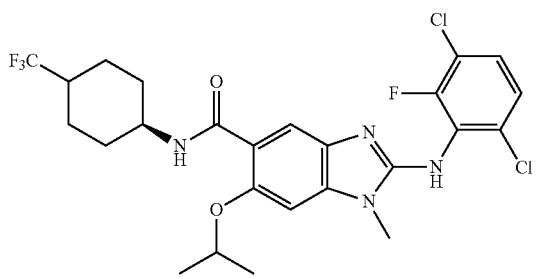<br>2-(3,6-Dichloro-2-fluoro-phenylamino)-6-isopropoxy-N-(4-trans-trifluoromethyl-cyclohex-1-yl)-1-methyl-1H-benzimidazole-5-carboxamide | Σ: 18% | $(M + H)^+$ = 561/563/565 (chlorine isotopes) | 0.42 (silica gel, dichlormethane/ ethanol = 19:1) |

| No. | Structural formula / Name | Yield | Mass peak(s) | $R_f$ value or $R_t$ |
|---|---|---|---|---|
| 646 | 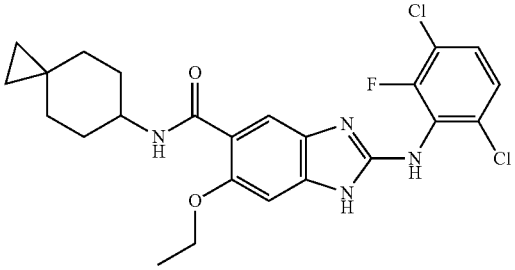 [SMILES: CCOc1cc2[nH]c(Nc3c(Cl)ccc(Cl)c3F)nc2cc1C(=O)NC1CCC2(CC1)CC2]<br>2-(3,6-Dichloro-2-fluoro-phenylamino)-6-ethoxy-N-(spiro[2.5]oct-6-yl)-1H-benzimidazole-5-carboxamide | Σ: 12.3% | (M + H)$^+$ = 491/493/495 (chlorine isotopes) | 0.33 (silica gel, dichlormethane/ ethanol = 19:1) |
| 648 | 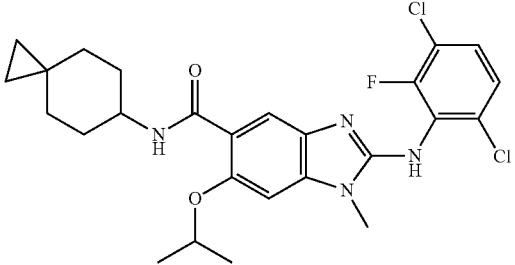 [SMILES: CC(C)Oc1cc2c(cc1C(=O)NC1CCC3(CC1)CC3)nc(Nc1c(Cl)ccc(Cl)c1F)n2C]<br>2-(3,6-Dichloro-2-fluoro-phenylamino)-6-isopropoxy-N-(spiro[2.5]oct-6-yl)-1-methyl-1H-benzimidazole-5-carboxamide | Σ: 15% | (M + H)$^+$ = 519/521/523 (chlorine isotopes) | 0.42 (silica gel, dichlormethane/ ethanol = 19:1) |

Example 602

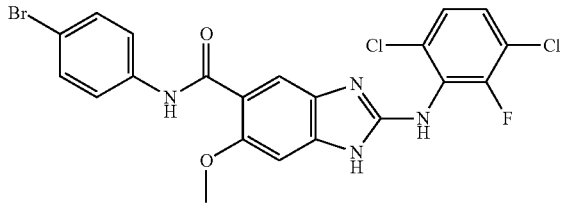 [SMILES: COc1cc2[nH]c(Nc3c(Cl)ccc(Cl)c3F)nc2cc1C(=O)Nc1ccc(Br)cc1]

2-(3,6-Dichloro-2-fluoro-phenylamino)-6-methoxy-N-(4-bromophenyl)-1H-benzimidazole-5-carboxamide (602a) Ethyl 4-amino-2-methoxy-5-nitro-benzoate A mixture of 4-amino-2-methoxy-5-nitro-benzoic acid (22.2 g, 94.2 mmol) and 10 mL conc. sulphuric acid in 250 mL ethanol was refluxed for 2 h. Then the mixture was concentrate i. vac., the residue mixed with water at 0° C. and conc. ammonia. The precipitate was filtered off, washed with water and dried.

Yield: 20.7 g (91%)
mass spectrum: (M+H)$^+$=241
$R_t$ value: 1.76 min (E7)

(602b) Ethyl 4,5-diamino-2-methoxy-benzoate

Prepared analogously to example 1b from the product obtained from (602a) by hydrogenation with Raney-nickel in THF.

Yield: 99%
mass spectrum: (M+H)$^+$=211
$R_t$ value: 0.74 min (E7)

(602c) 2-(3,6-Dichloro-2-fluoro-phenylamino)-6-methoxy-1H-benzimidazole-5-carboxylic acid ethyl ester Prepared analogously to example 1c from the product obtained from (602b) and 3,6-dichloro-2-fluoro-1-isothiocyanato-benzene with DIC in acetonitrile.

Yield: 82%
mass spectrum: (M+H)$^+$=398/400/402 (chlorine isotopes)
$R_t$ value: 1.15 min (F7)

(602d) 2-(3,6-Dichloro-2-fluoro-phenylamino)-6-methoxy-1H-benzimidazole-5-carboxylic acid Prepared analogously to example 3b from the product obtained from (602c) with NaOH (aq) in ethanol. Yield: 98%; mass spectrum: (M+H)$^+$=370/372/374 (chlorine isotopes); $R_t$ value: 1.07 min (F7).

(602e) 2-(3,6-Dichloro-2-fluoro-phenylamino)-6-methoxy-N-(4-bromophenyl)-1H-benzimidazole-5-carboxamide Prepared analogously to example 3c from the product obtained from (589d) and trans-4-trifluoromethyl-cyclohexylamine with HATU and TEA in THF and DMF.

Yield: 48%
mass spectrum: (M+H)$^+$=523/525/527/529 (bromine and chlorine isotopes)
$R_t$ value: 1.36 min (F7)

In analogy to the above described example, the following compounds were synthesized:

| No. | Structural formula / Name | Yield | Mass peak(s) | $R_f$ value or $R_t$ |
|---|---|---|---|---|
| 612 | 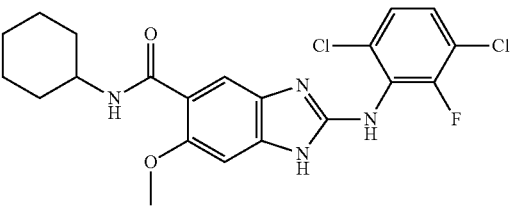 [SMILES: COc1cc2[nH]c(Nc3c(Cl)ccc(Cl)c3F)nc2cc1C(=O)NC1CCCCC1]<br>2-(3,6-Dichloro-2-fluoro-phenylamino)-N-cyclohexyl-6-methoxy-1H-benzimidazole-5-carboxamide | Σ: 34% | (M + H)⁺ = 451/453/455 (chlorine isotopes) | 1.24 min (F7) |
| 613 | 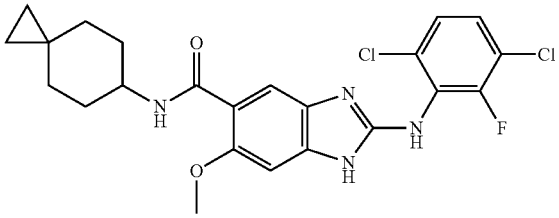 [SMILES: COc1cc2[nH]c(Nc3c(Cl)ccc(Cl)c3F)nc2cc1C(=O)NC1CCC2(CC1)CC2]<br>2-(3,6-Dichloro-2-fluoro-phenylamino)-N-(spiro[2.5]oct-6-yl)-6-methoxy-1H-benzimidazole-5-carboxamide | Σ: 64% | (M + H)⁺ = 477/479/481 (chlorine isotopes) | 1.30 min (F7) |
| 616 | 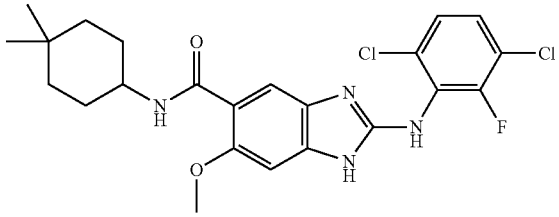 [SMILES: COc1cc2[nH]c(Nc3c(Cl)ccc(Cl)c3F)nc2cc1C(=O)NC1CCC(C)(C)CC1]<br>2-(3,6-Dichloro-2-fluoro-phenylamino)-N-(4,4-dimethyl-cyclohex-1-yl)-6-methoxy-1H-benzimidazole-5-carboxamide | Σ: 43% | (M + H)⁺ = 479/481/483 (chlorine isotopes) | 1.32 min (F7) |
| 617 | 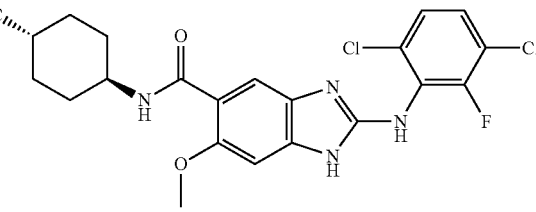<br>2-(3,6-Dichloro-2-fluoro-phenylamino)-6-methoxy-N-(4-trans-trifluoromethyl-cyclohex-1-yl)-1H-benzimidazole-5-carboxamide | Σ: 41% | (M + H)⁺ = 519/521/523 (chlorine isotopes) | 1.28 min (F7) |
| 619 | 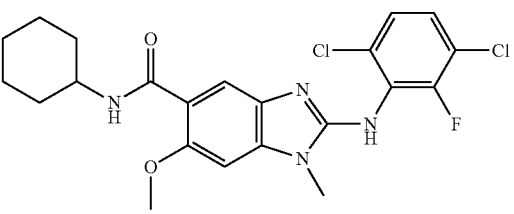 [SMILES: COc1cc2c(cc1C(=O)NC1CCCCC1)nc(Nc1c(Cl)ccc(Cl)c1F)n2C]<br>2-(3,6-Dichloro-2-fluoro-phenylamino)-6-methoxy-N-cyclohexyl-1-methyl-1H-benzimidazole-5-carboxamide | Σ: 18% | (M + H)⁺ = 465/467/469 (chlorine isotopes) | 0.37 (silica gel; dichloromethane/ ethanol _ 19:1) |

| No. | Structural formula Name | Yield | Mass peak(s) | R$_f$ value or R$_t$ |
|---|---|---|---|---|
| 621 | 2-(3,6-Dichloro-2-fluoro-phenylamino)-6-methoxy-N-(4,4-dimethyl-cyclohex-1-yl)-1-methyl-1H-benzimidazole-5-carboxamide | Σ: 24% | (M + H)$^+$ = 493/495/497 (chlorine isotopes) | 0.36 (silica gel; dichloromethane/ethanol _ 19:1) |
| 622 | 2-(6-Chloro-2-fluoro-3-methyl-phenylamino)-6-methoxy-N-(4-trans-trifluoromethyl-cyclohex-1-yl)-1H-benzimidazole-5-carboxamide | Σ: 34% | (M + H)$^+$ = 499/501 (chlorine isotopes) | 1.79 min (E7) |
| 626 | 2-(6-Chloro-2-fluoro-3-methyl-phenylamino)-6-methoxy-N-(4,4-dimethyl-cyclohex-1-yl-1H-benzimidazole-5-carboxamide | Σ: 19% | (M + H)$^+$ = 459/461 (chlorine isotopes) | 1.87 min (E7) |
| 628 | 2-(6-Chloro-2-fluoro-3-methyl-phenylamino)-6-methoxy-N-cyclohexyl-1H-benzimidazole-5-carboxamide | Σ: 22% | (M + H)$^+$ = 431/433 (chlorine isotopes) | 1.72 min (E7) |
| 643 | 2-(3,6-Dichloro-2-fluoro-phenylamino)-6-methoxy-N-(trans-4-trifluoromethyl-cyclohex-1-yl)-1-methyl-1H-benzimidazole-5-carboxamide | Σ: 26% | (M + H)$^+$ = 533/535/537 (chlorine isotopes) | 0.44 (silica gel; dichloromethane/ethanol _ 19:1) |

| No. | Structural formula Name | Yield | Mass peak(s) | R_f value or R_t |
|---|---|---|---|---|
| 645 | 2-(3,6-Dichloro-2-fluoro-phenylamino)-6-methoxy-N-(spiro[3.5]oct-6-yl)-1-methyl-1H-benzimidazole-5-carboxamide | Σ: 27% | (M + H)⁺ = 491/493/495 (chlorine isotopes) | 0.33 (silica gel; dichloromethane/ ethanol _ 19:1) |
| 647 | 2-(6-Chloro-2-fluoro-3-methyl-phenylamino)-6-methoxy-N-(trans-4-trifluoromethyl-cyclohex-1-yl)-1-methyl-1H-benzimidazole-5-carboxamide | Σ: 26% | (M + H)⁺ = 513/515 (chlorine isotopes) | 1.84 min (E7) |
| 650 | 2-(6-Chloro-2-fluoro-3-methyl-phenylamino)-6-methoxy-N-(4,4-dimethyl-cyclohex-1-yl)-1-methyl-1H-benzimidazole-5-carboxamide | Σ: 36% | (M + H)⁺ = 473/475 (chlorine isotopes) | 1.88 min (E7) |
| 651 | 2-(6-Chloro-2-fluoro-3-methyl-phenylamino)-6-methoxy-N-cyclohexyl-1-methyl-1H-benzimidazole-5-carboxamide | Σ: 23% | (M + H)⁺ = 445/447 (chlorine isotopes) | 1.71 min (E7) |
| 652 | 2-(2,3,5,6-tetrafluoro-phenylamino)-6-methoxy-N-(4,4-dimethy-cyclohex-1-yl)-1-methyl-1H-benzimidazole-5-carboxamide | Σ: 58% | (M + H)⁺ = 479 | 3.42 min (C5) |

Example 632

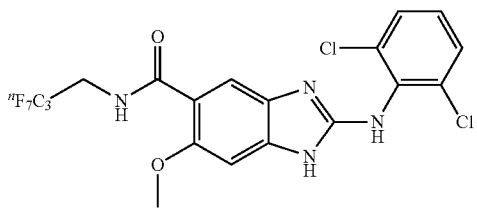

N-(2,2,3,3,4,4,4-heptafluoro-butyl)-2-(2,6-dichlorophenylamino)-6-methoxy-1H-benzimidazole-5-carboxamide (632a) 2-(2,6-Dichlorophenylamino)-6-methoxy-1H-benzimidazole-5-carboxylic acid methyl ester Trimethylsilyl-diazomethane (2M solution in hexane, 4.54 mL, 9.1 mmol) was added to 2-(2,6-dichlorophenylamino)-6-methoxy-1H-benzimidazole-5-carboxylic acid in 25 mL methanol with 50 ml dichloromethane at 0° C. The mixture was stirred at 0° C. for 5 min and then at ambient temperature for 16.5 h. 2 mL Acetic acid were added, the mixture evaporated i.vac., the residue in 15 mL methanol was poured in NaHCO$_3$ (aq) and the mixture stirred. The precipitate was filtered off, washed with water and coevaporated with toluene.

Yield: 1.60 g (91%), slightly contaminated
mass spectrum: (M+H)$^+$=366/368/370 (chlorine isotopes)
R$_t$ value: 1.03 min (F8)

(632b) N-(2,2,3,3,4,4,4-heptafluoro-butyl)-2-(2,6-dichlorophenylamino)-6-methoxy-1H-benzimidazole-5-carboxamide Prepared analogously to example 464c from the product obtained from (632a) and 2,2,3,3,4,4,4-heptafluoro-butylamine with trimethylaluminium in toluol and dioxan Yield: 24%
mass spectrum: (M+H)$^+$=533/535/537 (chlorine isotopes)
R$_t$ value: 2.26 min (C5)

In analogy with the above described example, the following compounds were prepared:

| No. | Structural formula Name | Yield | Mass peak(s) | R$_f$ value or R$_t$ |
|---|---|---|---|---|
| 633 | 2-(2,6-Dichlorophenylamino)-N-(5-trifluoromethyl-pyridin-2-yl)-6-methoxy-1H-benzimidazole-5-carboxamide | Σ: 9.1% | (M + H)$^+$ = 496/498/500 (chlorine isotopes) | 2.34 min (C5) |
| 634 | 2-(2,6-Dichlorophenylamino)-N-(4-chloro-5-methyl-pyridin-2-yl)-6-methoxy-1-methyl-1H-benzimidazole-5-carboxamide | Σ: 14% | (M + H)$^+$ = 490/492/494/496 (chlorine isotopes) | 1.30 min (F8) |

Biological Data

Title compounds of the examples were tested in the biological test described above and were found to exhibit 50% inhibition of mPGES-1 at a concentration of 10 μM or below. For example, the following representative compounds of the examples exhibited the following percentage inhibitions at 10 μM (unless otherwise specified):

| example | % inhib. | example | % inhib. | example | % inhib. | example | % inhib. |
|---|---|---|---|---|---|---|---|
| 1 | 100 | 64 | 97 | 139 | 98 | 194 | 98 |
| 3 | 95 | 66 | 100 | 140 | 80 | 195 | 92 |
| 4 | 100 | 67 | 100 (1 μM) | 141 | 93 | 197 | 100 |

-continued

| example | % inhib. | example | % inhib. | example | % inhib. | example | % inhib. |
|---|---|---|---|---|---|---|---|
| 5 | 100 | 68 | 100 (1 μM) | 142 | 100 | 198 | 100 |
| 6 | 99 | 69 | 100 (1 μM) | 143 | 100 | 199 | 100 |
| 7 | 100 | 70 | 100 (1 μM) | 144 | 97 | 200 | 98 |
| 9 | 93 | 71 | 95 (1 μM) | 145 | 100 | 201 | 100 |
| 10 | 98 | 74 | 97 | 146 | 97 | 202 | 100 |
| 12 | 99 | 75 | 95 | 147 | 94 | 203 | 100 |
| 13 | 100 | 76 | 97 | 148 | 100 | 205 | 97 |
| 19 | 91 | 77 | 96 | 149 | 100 | 206 | 100 |
| 20 | 97 | 78 | 90 | 150 | 100 | 207 | 97 |
| 22 | 100 | 79 | 100 | 152 | 95 | 208 | 100 |
| 23 | 70 | 80 | 92 | 153 | 98 | 209 | 100 |
| 24 | 68 | 81 | 84 | 155 | 100 | 210 | 100 |
| 25 | 100 | 84 | 100 | 156 | 100 | 211 | 100 |
| 26 | 98 | 89 | 97 | 157 | 100 | 212 | 100 |
| 27 | 97 | 100 | 94 | 158 | 100 | 213 | 65 |
| 28 | 88 | 106 | 82 | 159 | 98 | 214 | 100 |
| 29 | 100 | 107 | 99 | 160 | 98 | 215 | 96 |
| 30 | 100 (1 μM) | 108 | 100 | 161 | 98 | 216 | 64 |
| 31 | 100 | 109 | 100 | 162 | 100 | 217 | 54 |
| 32 | 100 | 110 | 96 | 163 | 100 | 218 | 100 |
| 33 | 100 | 111 | 100 | 164 | 100 | 219 | 100 |
| 34 | 69 | 112 | 97 | 165 | 98 | 220 | 96 |
| 35 | 91 | 113 | 91 | 166 | 100 | 221 | 87 |
| 36 | 51 | 114 | 80 | 167 | 93 | 222 | 74 |
| 37 | 100 | 116 | 92 | 168 | 100 | 223 | 87 |
| 38 | 100 | 117 | 100 | 169 | 94 | 224 | 100 |
| 39 | 96 | 118 | 80 | 170 | 100 | 225 | 80 |
| 40 | 95 | 120 | 96 | 171 | 94 | 226 | 64 |
| 41 | 98 | 121 | 95 | 172 | 97 | 227 | 77 |
| 42 | 100 | 122 | 99 | 173 | 97 | 228 | 86 |
| 43 | 89 | 123 | 95 | 175 | 100 | 229 | 91 |
| 44 | 62 | 124 | 98 | 179 | 97 | 230 | 99 |
| 45 | 72 | 125 | 100 | 180 | 98 | 231 | 86 |
| 46 | 100 | 126 | 92 | 181 | 100 | 232 | 91 |
| 47 | 98 | 127 | 100 | 182 | 99 | 233 | 67 |
| 48 | 100 | 128 | 100 | 183 | 100 | 234 | 77 |
| 51 | 89 | 129 | 92 | 184 | 98 | 235 | 79 |
| 52 | 100 | 130 | 93 | 185 | 98 | 236 | 83 |
| 53 | 100 | 131 | 96 | 186 | 91 | 237 | 87 |
| 54 | 96 | 132 | 97 | 187 | 98 | 238 | 100 |
| 55 | 93 | 133 | 100 | 188 | 96 | 239 | 96 |
| 56 | 100 | 134 | 100 | 189 | 94 | 240 | 80 |
| 57 | 96 | 135 | 100 | 190 | 75 | 241 | 100 |
| 58 | 90 | 136 | 98 | 191 | 99 | 242 | 70 |
| 61 | 91 | 137 | 100 | 192 | 100 | 243 | 93 |
| 62 | 100 | 138 | 100 | 193 | 99 | 244 | 96 |
| 245 | 97 | 302 | 86 | 378 | 100 | 470 | 100 |
| 246 | 100 | 303 | 90 | 380 | 100 | 474 | 100 |
| 247 | 92 | 304 | 98 | 381 | 100 | 475 | 100 |
| 248 | 73 | 305 | 100 | 382 | 100 | 476 | 100 |
| 249 | 96 | 308 | 96 | 383 | 100 | 483 | 95 |
| 250 | 73 | 309 | 98 | 384 | 100 | 484 | 95 |
| 251 | 71 | 312 | 100 | 385 | 99 | 488 | 98 |
| 252 | 68 | 313 | 99 | 387 | 100 | 489 | 98 |
| 253 | 100 | 314 | 97 | | | | |
| 254 | 100 | 316 | 100 | 390 | 100 | 491 | 99 |
| 255 | 100 | 317 | 98 | 391 | 100 | 492 | 98 |
| 256 | 100 | 318 | 100 | 392 | 100 | 494 | 99 |
| 257 | 100 | 319 | 100 | 395 | 100 | 496 | 100 |
| 258 | 83 | 320 | 100 | 397 | 99 | 498 | 100 |
| 259 | 89 | 321 | 93 | 398 | 96 | 499 | 100 |
| 260 | 84 | 322 | 100 | 399 | 99 | 500 | 100 |
| 261 | 92 | 326 | 96 | 402 | 100 | 501 | 98 |
| 262 | 61 | 327 | 100 | 404 | 100 | 502 | 96 |
| 263 | 93 | 328 | 95 | 405 | 100 | 507 | 98 |
| 264 | 90 | 329 | 89 | 407 | 100 | 510 | 99 |
| 265 | 97 | 333 | 94 | 408 | 100 | 512 | 99 |
| 266 | 100 | 334 | 100 | | | | |
| 267 | 94 | 335 | 95 | 412 | 100 | 514 | 95 |
| 268 | 94 | 336 | 85 | 415 | 100 | 516 | 97 |
| 269 | 85 | 341 | 92 | 416 | 100 | 519 | 95 |
| 270 | 96 | 347 | 100 | 418 | 100 | 524 | 98 |
| 271 | 98 | 349 | 100 | 419 | 100 | 525 | 98 |
| 272 | 90 | 350 | 99 | 420 | 100 | 526 | 93 |
| 273 | 100 | 351 | 100 | 421 | 99 | 529 | 93 |
| 274 | 100 | 352 | 71 | 422 | 100 | 533 | 91 |
| 275 | 96 | 353 | 75 | 423 | 100 | 534 | 80 |

-continued

| example | % inhib. | example | % inhib. | example | % inhib. | example | % inhib. |
|---|---|---|---|---|---|---|---|
| 276 | 100 | 354 | 100 | 426 | 98 | 536 | 89 |
| 277 | 99 | 355 | 100 | 428 | 100 | 537 | 99 |
| 278 | 92 | 356 | 100 | 430 | 100 | 538 | 85 |
| 279 | 97 | 357 | 100 | 432 | 100 | 539 | 94 |
| 280 | 100 | 358 | 100 | 433 | 99 | 540 | 44 |
| 281 | 100 | 359 | 100 | 436 | 99 | 542 | 97 |
| 282 | 100 (1 μM) | 362 | 100 | 437 | 97 | 543 | 91 |
| 283 | 100 (1 μM) | 363 | 100 | 441 | 97 | 544 | 91 |
| 284 | 100 | 367 | 100 | 442 | 99 | 545 | 89 |
| 285 | 100 | 368 | 100 | 443 | 100 | 546 | 85 |
| 286 | 100 | 369 | 100 | 447 | 99 | 548 | 93 |
| 287 | 92 | 370 | 100 | 450 | 99 | 551 | 94 |
| 288 | 100 | 371 | 100 | 452 | 93 | 552 | 77 |
| 291 | 71 | 372 | 98 | 456 | 100 | 554 | 84 |
| 292 | 100 | 373 | 100 | 457 | 100 | 555 | 70 |
| 293 | 87 | 374 | 100 | 458 | 99 | 556 | 74 |
| 297 | 97 | 375 | 100 | 464 | 99 | 557 | 69 |
| 298 | 100 | 376 | 100 | 465 | 100 | 558 | 77 |
| 559 | 85 | 612 | 99 | 577 | 100 | 626 | 92 (1 μM) |
| 561 | 77 | 613 | 91 | 578 | 100 | 627 | 94 (1 μM) |
| 562 | 97 | 614 | 100 | 579 | 100 | 628 | 98 (1 μM) |
| 563 | 75 | 615 | 96 | 580 | 100 | 629 | 99 (1 μM) |
| 564 | 70 | 616 | 100 | 581 | 100 | 630 | 100 |
| 568 | 60 | 617 | 100 | 582 | 100 | 631 | 100 |
| 569 | 81 | 618 | 91 | 583 | 95 | 632 | 99 |
| 570 | 84 | 619 | 94 | 584 | 96 | 633 | 99 |
| 571 | 86 | 620 | 100 | 585 | 100 | 634 | 97 |
| 572 | 45 | 621 | 99 | 586 | 100 | 639 | 99 |
| 573 | 60 | 622 | 96 (1 μM) | 587 | 97 | 640 | 100 |
| 574 | 56 | 623 | 93 (1 μM) | 588 | 100 | 641 | 97 (1 μM) |
| 575 | 82 | 624 | 100 (1 μM) | 589 | 100 | 642 | 100 (1 μM) |
| 576 | 96 | 625 | 99 (1 μM) | 590 | 96 | 643 | 100 (1 μM) |
| 591 | 99 | 616 | 100 | 645 | 100 (1 μM) | | |
| 592 | 97 | 617 | 100 | 646 | 99 (1 μM) | | |
| 593 | 97 | 618 | 91 | 647 | 97 (1 μM) | | |
| 594 | 94 | 619 | 94 | 648 | 100 (1 μM) | | |
| 595 | 100 | 620 | 100 | 649 | 96 (1 μM) | | |
| 596 | 95 | 621 | 99 | 650 | 100 (1 μM) | | |
| 597 | 100 | 622 | 96 (1 μM) | 651 | 100 (1 μM) | | |
| 598 | 100 | 623 | 93 (1 μM) | 652 | 94 (1 μM) | | |
| 599 | 92 | 624 | 100 (1 μM) | 653 | 92 (1 μM) | | |
| 600 | 94 | 625 | 99 (1 μM) | 654 | 99 (1 μM) | | |
| 601 | 92 | 626 | 92 (1 μM) | | | | |
| 602 | 100 | 627 | 94 (1 μM) | | | | |
| 603 | 90 | 628 | 98 (1 μM) | | | | |
| 604 | 100 | 629 | 99 (1 μM) | | | | |
| 605 | 93 | 630 | 100 | | | | |
| 606 | 94 | 631 | 100 | | | | |
| 607 | 97 | 632 | 99 | | | | |
| 608 | 92 | 633 | 99 | | | | |
| 609 | 99 | 634 | 97 | | | | |
| 610 | 87 | 639 | 99 | | | | |
| 611 | 90 | 640 | 100 | | | | |
| 612 | 99 | 641 | 97 (1 μM) | | | | |
| 613 | 91 | 642 | 100 (1 μM) | | | | |
| 614 | 100 | 643 | 100 (1 μM) | | | | |
| 615 | 96 | 644 | 96 (1 μM) | | | | |

The invention claimed is:

1. A compound of formula Ib,

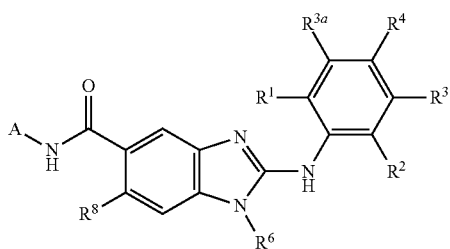

Ib in which $R^1$ and $R^2$ independently represent chloro, bromo, fluoro, $C_{1-3}$ alkyl (which latter alkyl group is optionally substituted by one or more fluoro-atoms);

$R^3$, $R^{3a}$ and $R^4$:

independently represent hydrogen, chloro, bromo, fluoro, $C_{1-3}$-alkyl (which latter alkyl group is optionally substituted by one or more fluoro atoms);

$R^6$ represents hydrogen or $C_{1-4}$ alkyl optionally substituted by one or more fluoro atoms;

$R^8$ represent hydrogen, fluoro, chloro, —O—$C_{1-4}$ alkyl (optionally substituted by one or more fluoro atoms);

A represents phenyl, $C_{3-10}$ cycloalkyl, $C_{1-12}$ linear or branched alkyl, all of which are optionally substituted by one or more substituents selected from $R^9$;

$R^9$ represents, on each occasion when used herein:
  halo, $-OR^{y10}$; $C_{1-7}$ alkyl, cycloalkyl, (which latter two groups are optionally substituted by one or more substituents selected from fluoro, $-OR^{y10}$;

$R^{y10}$ represents hydrogen or $C_{1-4}$ alkyl optionally substituted by one or more halo atoms or $-OC_{1-2}$ alkyl groups;

or a pharmaceutically acceptable salt thereof.

2. A compound according to claim 1, which is selected from the following compounds or a pharmaceutically acceptable salt thereof:

| Compound Number | Compound Name |
|---|---|
| 1 | 2-(2,6-Dichloro-phenylamino)-1H-benzimidazole-5-carboxylic acid phenyl-amide; |
| 3 | 2-(2,6-Dichloro-phenylamino)-1H-benzimidazole-5-carboxylic acid o-tolylamide; |
| 4 | 2-(2,6-Dichloro-phenylamino)-1H-benzimidazole-5-carboxylic acid m-tolylamide; |
| 5 | 2-(2,6-Dichloro-phenylamino)-1H-benzimidazole-5-carboxylic acid p-tolylamide; |
| 6 | 2-(2-Trifluoromethyl-phenylamino)-1H-benzimidazole-5-carboxylic acid-phenyl-amide; |
| 7 | 2-(2,5-Dichloro-phenylamino)-1H-benzimidazole-5-carboxylic acid-phenylamide; |
| 9 | 2-(2-Chloro-phenylamino)-1H-benzimidazole-5-carboxylic acid-phenylamide; |
| 10 | 2-(o-Tolyl-amino)-1H-benzimidazole-5-carboxylic acid-phenylamide; |
| 11 | 2-(2-Methoxy-phenylamino)-1H-benzimidazole-5-carboxylic acid-phenylamide; |
| 12 | 2-(2-Chloro-6-methyl-phenylamino)-1H-benzimidazole-5-carboxylic acid-phenylamide; |
| 13 | 2-(2,6-Dimethyl-phenylamino)-1H-benzimidazole-5-carboxylic acid-phenylamide; |
| 19 | 2-(2-Chloro-6-fluoro-phenylamino)-1H-benzimidazole-5-carboxylic acid-phenylamide; |
| 20 | 2-(2,6-Dichloro-phenylamino)-1-methyl-1H-benzimidazole-5-carboxylic acid phenylamide; |
| 22 | 2-(2,6-Dichloro-phenylamino)-1H-benzimidazole-5-carboxylic acid (3-cyano-phenyl)-amide; |
| 51 | 2-(2,6-Dichloro-phenylamino)-7-methyl-1H-benzimidazole-5-carboxylic acid (4-bromo-phenyl)-amide; |
| 52 | 2-(2,6-Dichloro-phenylamino)-7-methyl-1H-benzimidazole-5-carboxylic acid (4-chloro-3-fluoro-phenyl)-amide; |
| 53 | 2-(2,6-Dichloro-phenylamino)-6-chloro-1H-benzimidazole-5-carboxylic acid (4-bromo-phenyl)-amide; |
| 54 | 2-(2,6-Dichloro-phenylamino)-6-chloro-1H-benzimidazole-5-carboxylic acid (4-bromo-3-fluoro-phenyl)-amide; |
| 55 | 2-(2,6-Dichloro-phenylamino)-6-chloro-1H-benzimidazole-5-carboxylic acid (4-chloro-3-fluoro-phenyl)-amide; |
| 56 | 2-(2,6-Dichloro-phenylamino)-6-chloro-1H-benzimidazole-5-carboxylic acid (3-chloro-phenyl)-amide; |
| 57 | 2-(2,6-Dichloro-phenylamino)-6-chloro-1H-benzimidazole-5-carboxylic acid (4-iodo-phenyl)-amide; |
| 64 | 2-(2,6-Dichloro-phenylamino)-1H-benzimidazole-5-carboxylic acid (4,4-dimethyl-cyclohexyl)-amide; |
| 66 | 2-(2,6-Dichloro-phenylamino)-1H-benzimidazole-5-carboxylic acid (4-bromo-phenyl)-amide; |
| 67 | 2-(2,6-Dichloro-phenylamino)-1H-benzimidazole-5-carboxylic acid (4-chloro-3-fluoro-phenyl)-amide; |
| 68 | 2-(2,6-Dichloro-phenylamino)-1H-benzimidazole-5-carboxylic acid (4-bromo-3-fluoro-phenyl)-amide; |
| 69 | 2-(2,6-Dichloro-phenylamino)-1H-benzimidazole-5-carboxylic acid (3-bromo-phenyl)-amide; |
| 70 | 2-(2,6-Dichloro-phenylamino)-1H-benzimidazole-5-carboxylic acid (3-bromo-4-fluoro-phenyl)-amide; |
| 71 | 2-(2,6-Dichloro-phenylamino)-1H-benzimidazole-5-carboxylic acid (3-chloro-4-fluoro-phenyl)-amide; |
| 84 | 2-(2,6-Dichloro-phenylamino)-1H-benzimidazole-5-carboxylic acid (4-iodo-phenyl)-amide; |
| 106 | 2-(2-Trifluoromethoxy-phenylamino)-1H-benzimidazole-5-carboxylic acid (4-bromo-phenyl)-amide; |
| 107 | 2-(2,4,6-Trichloro-phenylamino)-1H-benzimidazole-5-carboxylic acid (4-bromo-phenyl)-amide; |
| 108 | 2-(2,3-Dichloro-phenylamino)-1H-benzimidazole-5-carboxylic acid (4-bromo-phenyl)-amide; |

| Compound Number | Compound Name |
|---|---|
| 109 | 2-(2,4-Dichloro-phenylamino)-1H-benzimidazole-5-carboxylic acid (4-bromo-phenyl)-amide; |
| 110 | 2-(2,6-Dichloro-phenylamino)-1H-benzimidazole-5-carboxylic acid (5-chloro-2-methyl-phenyl)-amide |
| 111 | 2-(2,6-Dichloro-phenylamino)-1H-benzimidazole-5-carboxylic acid (3,4-dichloro-phenyl)-amide; |
| 112 | 2-(2,6-Dichloro-phenylamino)-1H-benzimidazole-5-carboxylic acid (3,5-dichloro-phenyl)-amide; |
| 113 | 2-(2,6-Dichloro-phenylamino)-1H-benzimidazole-5-carboxylic acid (2-trifluoromethyl-phenyl)-amide; |
| 114 | 2-(2,6-Diethyl-phenylamino)-1H-benzimidazole-5-carboxylic acid (4-bromophenyl)-amide; |
| 121 | 2-(2,6-Dichloro-phenylamino)-6-fluoro-1H-benzimidazol-5-carboxylic acid (4-bromo-3-fluoro-phenyl)-amide; |
| 122 | 2-(2,6-Dichloro-phenylamino)-6-methyl-1H-benzimidazol-5-carboxylic acid (4-tert.-butyl-phenyl)-amide; |
| 123 | 2-(2,6-Dichloro-phenylamino)-6-methyl-1H-benzimidazol-5-carboxylic acid (4,4-dimethyl-cyclohexyl)-amide; |
| 124 | 2-(2,6-Dichloro-phenylamino)-6-fluoro-1H-benzimidazol-5-carboxylic acid (4-chloro-3-fluoro-phenyl)-amide; |
| 135 | 2-(2,6-Dichloro-phenylamino)-6-methoxy-1-methyl-1H-benzimidazole-5-carboxylic acid cyclohexylamide; |
| 137 | 2-(2,6-Dichloro-phenylamino)-3H-benzimidazole-5-carboxylic acid cyclohexylamide; |
| 140 | 2-(2,6-Dichloro-phenylamino)-1H-benzimidazole-5-carboxylic acid (2,2-dimethyl-propyl)-amide; |
| 141 | 2-(2,6-Dichloro-phenylamino)-3H-benzimidazole-5-carboxylic acid propylamide; |
| 143 | 2-(2,6-Dichloro-phenylamino)-6-fluoro-3H-benzimidazole-5-carboxylic acid (3-chloro-phenyl)-amide; |
| 144 | 2-(2,6-Dichloro-phenylamino)-6-fluoro-3H-benzimidazole-5-carboxylic acid (4-bromo-phenyl)-amide; |
| 145 | 2-(2,6-Dichloro-phenylamino)-6-methyl-1H-benzimidazole-5-carboxylic acid (4-chloro-3-fluorophenyl)-amide; |
| 147 | 2-(2,6-Dichloro-phenylamino)-3H-benzimidazole-5-carboxylic acid (4,4-difluoro-cyclohexyl)-amide; |
| 148 | 2-(2,6-Dichloro-phenylamino)-6-methyl-1H-benzimidazole-5-carboxylic acid (4-tert.-butyl-cyclohexyl)-amide; |
| 149 | 2-(2,6-Dichloro-phenylamino)-6-fluoro-3H-benzimidazole-5-carboxylic acid (4,4-difluoro-cyclohexyl)-amide; |
| 155 | 2-(2,6-Dichloro-phenylamino)-6-fluoro-1H-benzimidazole-5-carboxylic acid (trans-4-trifluoromethyl-cyclohexyl)-amide; |
| 156 | 2-(2,6-Dichloro-phenylamino)-6-fluoro-1-methyl-1H-benzimidazole-5-carboxylic acid (4,4-difluoro-cyclohexyl)-amide; |
| 157 | 2-(2,6-Dichloro-phenylamino)-6-fluoro-1-methyl-1H-benzimidazole-5-carboxylic acid (4,4-dimethyl-cyclohexyl)-amide; |
| 158 | 2-(2,6-Dichloro-phenylamino)-6-fluoro-1-methyl-1H-benzimidazole-5-carboxylic acid (trans-4-trifluoromethyl-cyclohexyl)-amide; |
| 159 | 2-(2,6-Dichloro-phenylamino)-6-fluoro-1-methyl-1H-benzimidazole-5-carboxylic acid cyclohexylamide; |
| 161 | 2-(2,6-Dichloro-phenylamino)-1H-benzimidazole-5-carboxylic acid (trans-4-trifluoromethyl-cyclohexyl)-amide; |
| 164 | 2-(2,6-Dichloro-phenylamino)-6-fluoro-1-methyl-1H-benzimidazole-5-carboxylic acid (1-methyl-cyclohexyl)-amide; |
| 166 | 2-(2,6-Dichloro-phenylamino)-6-fluoro-1-methyl-1H-benzimidazole-5-carboxylic acid octylamide; |
| 167 | 2-(2,6-Dichloro-phenylamino)-6-fluoro-1-methyl-1H-benzimidazole-5-carboxylic acid (4-bromo-phenyl)-amide; |
| 168 | 2-(2,6-Dichloro-phenylamino)-1H-benzimidazole-5-carboxylic acid (cis-4-trifluoromethyl-cyclohexyl)-amide; |
| 169 | 2-(2,6-Dichloro-phenylamino)-6-fluoro-1H-benzimidazole-5-carboxylic acid (cis-4-trifluoromethyl-cyclohexyl)-amide; |
| 170 | 2-(2,6-Dichloro-phenylamino)-6-fluoro-1-methyl-1H-benzimidazole-5-carboxylic acid (cis-4-trifluoromethyl-cyclohexyl)-amide; |
| 171 | 2-(2,6-Difluoro-phenylamino)-1-methyl-1H-benzimidazole-5-carboxylic acid (trans-4-trifluoromethyl-cyclohexyl)-amide; |
| 172 | 2-(2,6-Difluoro-phenylamino)-1-methyl-1H-benzimidazole-5-carboxylic acid (4,4-dimethyl-cyclohexyl)-amide; |
| 173 | 2-(2,6-Difluoro-phenylamino)-1-methyl-1H-benzimidazole-5-carboxylic acid (4-bromo-phenyl)-amide; |
| 175 | 2-(2,6-Dichloro-phenylamino)-6-fluoro-1-methyl-1H-benzimidazole-5-carboxylic acid ((3R)-3-methyl-cyclopentyl)-amide; |

| Compound Number | Compound Name |
| --- | --- |
| 180 | 2-(2,6-Dichloro-phenylamino)-1-(2-methoxy-ethyl)-1H-benzimidazole-5-carboxylic acid (4,4-dimethyl-cyclohexyl)-amide; |
| 181 | 2-(2,6-Dichloro-phenylamino)-1-(2-methoxy-ethyl)-1H-benzimidazole-5-carboxylic acid (3-chloro-phenyl)-amide; |
| 199 | 2-(2,6-Dichloro-phenylamino)-6-methoxy-3H-benzimidazole-5-carboxylic acid cyclohexylamide; |
| 200 | 2-(2,6-Dichloro-phenylamino)-6-methoxy-3H-benzimidazole-5-carboxylic acid 2-trifluoromethyl-benzylamide; |
| 213 | 2-(2,6-Dichloro-phenylamino)-1H-benzimidazole-5-carboxylic acid cyclohexyl-amide; |
| 214 | 2-(2,6-Dichloro-phenylamino)-1H-benzimidazole-5-carboxylic acid cycloheptylamide; |
| 215 | 2-(2,6-Dichloro-phenylamino)-1H-benzimidazole-5-carboxylic acid (4-methyl-cyclohexyl)-amide; |
| 216 | 2-(2,6-Dichloro-phenylamino)-1H-benzimidazole-5-carboxylic acid ((1R,4R)-4-methoxy-cyclohexyl)-amide; |
| 218 | 2-(2,6-Dichloro-phenylamino)-1H-benzimidazole-5-carboxylic acid (3,3,5-trimethyl-cyclohexyl)-amide; |
| 219 | 2-(2,6-Dichloro-phenylamino)-1H-benzimidazole-5-carboxylic acid cyclopentylmethyl-amide; |
| 224 | 2-(2,6-Dichloro-phenylamino)-1H-benzimidazole-5-carboxylic acid (3-methanesulfonyl-phenyl)-amide; |
| 225 | 2-(2,6-Dichloro-phenylamino)-1H-benzimidazole-5-carboxylic acid (4,4-difluoro-cyclohexyl)-amide; |
| 226 | 2-(2,6-Dichloro-phenylamino)-1H-benzimidazole-5-carboxylic acid (3-hydroxy-cyclohexyl)-amide; |
| 228 | 2-(2,6-Dichloro-phenylamino)-1H-benzimidazole-5-carboxylic acid (2-trifluoromethyl-cyclohexyl)-amide; |
| 229 | 2-(2,6-Dichloro-phenylamino)-1H-benzimidazole-5-carboxylic acid (3-trifluoromethyl-cyclohexyl)-amide; |
| 230 | 2-(2,6-Dichloro-phenylamino)-1H-benzimidazole-5-carboxylic acid (4-trifluoromethyl-cyclohexyl)-amide; |
| 231 | 2-(2,6-Dichloro-phenylamino)-1H-benzimidazole-5-carboxylic acid (1-cyano-cyclohexyl)-amide; |
| 237 | 2-(2,6-Dichloro-phenylamino)-1-methyl-1H-benzimidazole-5-carboxylic acid (2-hydroxy-cyclohexyl)-amide; |
| 238 | 2-(2,6-Dichloro-phenylamino)-1-methyl-1H-benzimidazole-5-carboxylic acid cycloheptylamide; |
| 239 | 2-(2,6-Dichloro-phenylamino)-1-methyl-1H-benzimidazole-5-carboxylic acid (4-methyl-cyclohexyl)-amide; |
| 240 | 2-(2,6-Dichloro-phenylamino)-1-methyl-1H-benzimidazole-5-carboxylic acid (trans-4-methoxy-cyclohexyl)-amide; |
| 241 | 2-(2,6-Dichloro-phenylamino)-1-methyl-1H-benzimidazole-5-carboxylic acid (3,3,5-trimethyl-cyclohexyl)-amide; |
| 243 | 2-(2,6-Dichloro-phenylamino)-1-methyl-1H-benzimidazole-5-carboxylic acid cyclopentylmethyl-amide; |
| 249 | 2-(2,6-Dichloro-phenylamino)-1-methyl-1H-benzimidazole-5-carboxylic acid (4,4-difluoro-cyclohexyl)-amide; |
| 253 | 2-(2,6-Dichloro-phenylamino)-1-methyl-1H-benzimidazole-5-carboxylic acid (1-methyl-cyclohexyl)-amide; |
| 254 | 2-(2,6-Dichloro-phenylamino)-1-methyl-1H-benzimidazole-5-carboxylic acid (2-trifluoromethyl-cyclohexyl)-amide; |
| 255 | 2-(2,6-Dichloro-phenylamino)-1-methyl-1H-benzimidazole-5-carboxylic acid (3-trifluoromethyl-cyclohexyl)-amide; |
| 256 | 2-(2,6-Dichloro-phenylamino)-1-methyl-1H-benzimidazole-5-carboxylic acid (4-trifluoromethyl-cyclohexyl)-amide; |
| 279 | 2-(2-Bromo-phenylamino)-1H-benzimidazole-5-carboxylic acid (4-bromo-phenyl)-amide; |
| 280 | N-(3-Chloro-2-methylphenyl)-2-(2,6-dichlorophenylamino)-1H-benzimidazole-5-carboxamide; |
| 281 | 2-(2,6-Dichloro-phenylamino)-1H-benzimidazole-5-carboxylic acid (2,5-dichloro-phenyl)-amide; |
| 282 | 2-(2,6-Dichloro-phenylamino)-1H-benzimidazole-5-carboxylic acid (4-chloro-3-trifluoromethyl-phenyl)-amide; |
| 283 | 2-(2,6-Dichloro-phenylamino)-1H-benzimidazole-5-carboxylic acid (3-trifluoromethyl-phenyl)-amide; |
| 284 | 2-(2,6-Dichloro-phenylamino)-1H-benzimidazole-5-carboxylic acid (2-chloro-phenyl)-amide; |
| 285 | 2-(2,6-Dichloro-phenylamino)-1H-benzimidazole-5-carboxylic acid (3-fluoro-phenyl)-amide; |

| Compound Number | Compound Name |
|---|---|
| 286 | 2-(2,6-Dichloro-phenylamino)-1H-benzimidazole-5-carboxylic acid (3-chloro-4-methyl-phenyl)-amide; |
| 287 | 2-(2,6-Dichloro-phenylamino)-1H-benzimidazole-5-carboxylic acid (3,4,5-trichloro-phenyl)-amide; |
| 288 | 2-(2,6-Dichloro-phenylamino)-1H-benzimidazole-5-carboxylic acid cyclohexylmethyl-amide; |
| 291 | 2-(5-Chloro-2-trifluoromethoxy-phenylamino)-1H-benzimidazole-5-carboxylic acid (4-bromo-phenyl)-amide; |
| 292 | 2-(2,6-Dichloro-phenylamino)-1H-benzimidazole-5-carboxylic acid (2-chloro-5-trifluoromethyl-phenyl)-amide; |
| 297 | 2-(2,6-Dichloro-phenylamino)-1-methyl-1H-benzimidazole-5-carboxylic acid (3-chloro-phenyl)-amide; |
| 298 | 2-(2,6-Dichloro-phenylamino)-1-methyl-1-H-benzimidazole-5-carboxylic acid (4-bromo-phenyl)-amide; |
| 308 | 2-(2,6-Dichloro-phenylamino)-1-methyl-1H-benzimidazole-5-carboxylic acid (4,4-dimethyl-cyclohexyl)-amide; |
| 312 | 2-(2,6-Dichloro-phenylamino)-1H-benzimidazole-5-carboxylic acid (2,3,4-trichloro-phenyl)-amide; |
| 313 | 2-(2,6-Dichloro-phenylamino)-1H-benzimidazole-5-carboxylic acid (2,4,6-trichloro-phenyl)-amide; |
| 316 | 2-(2,6-Dichloro-phenylamino)-1-methyl-1H-benzimidazole-5-carboxylic acid (4-bromo-phenyl)-amide; |
| 317 | 2-(2,6-Dichloro-phenylamino)-1-methyl-1H-benzimidazole-5-carboxylic acid cyclohexylamide; |
| 318 | 2-(2,6-Dimethyl-phenylamino)-1-methyl-1H-benzimidazole-5-carboxylic acid (4-bromo-phenyl)-amide; |
| 320 | 1-Methyl-2-(2-trifluoromethoxy-phenylamino)-1H-benzimidazole-5-carboxylic acid (4-bromo-phenyl)-amide; |
| 322 | 2-(2,6-Dichloro-3-methyl-phenylamino)-1H-benzimidazole-5-carboxylic acid (4-bromo-phenyl)-amide; |
| 326 | 7-Bromo-2-(2,6-dichloro-phenylamino)-1-methyl-1H-benzimidazole-5-carboxylic acid cyclohexylamide; |
| 333 | 2-(3-Chloro-2-trifluoromethyl-phenylamino)-1H-benzimidazole-5-carboxylic acid (4-bromo-phenyl)-amide; |
| 334 | 2-(2-Chloro-6-fluoro-phenylamino)-1H-benzimidazole-5-carboxylic acid (4-bromo-phenyl)-amide; |
| 350 | 7-Bromo-2-(2,6-dichloro-phenylamino)-1H-benzimidazole-5-carboxylic acid 2-trifluoromethyl-benzylamide; |
| 351 | 7-Bromo-2-(2,6-dichloro-phenylamino)-1H-benzimidazole-5-carboxylic acid (3-chloro-phenyl)-amide; |
| 352 | 7-Bromo-2-(2,6-dichloro-phenylamino)-1-methyl-1H-benzimidazole-5-carboxylic acid ethylamide; |
| 353 | 7-Bromo-2-(2,6-dichloro-phenylamino)-1-methyl-1H-benzimidazole-5-carboxylic acid isopropylamide; |
| 354 | N-(4-tert.-Butylcyclohexyl)-2-(2-chloro-6-fluorophenylamino)-6-fluoro-1-methyl-1H-benzimidazole-5-carboxamide; |
| 355 | 2-(2,6-Dichlorophenylamino)-N-(3,3-dimethylcyclohexyl)-6-fluoro-1-methyl-1H-benzimidazole-5-carboxamide; |
| 356 | N-((1r,4r)-4-tert.-Butylcyclohexyl)-2-(2,6-dichlorophenylamino)-6-fluoro-1H-benzimidazole-5-carboxamide; |
| 357 | N-((1r,4r)-4-tert.-Butylcyclohexyl)-2-(2-chloro-6-fluorophenylamino)-6-fluoro-1H-benzimidazole-5-carboxamide; |
| 358 | N-(4-Bromophenyl)-2-(2-fluoro-6-trifluoromethyl-phenylamino)-1-methyl-1H-benzimidazole-5-carboxamide; |
| 359 | N-(4-Bromophenyl)-2-(2,6-dichlorophenylamino)-6-methoxy-1-methyl-1H-benzimidazole-5-carboxamide |
| 362 | N-(4-Ethylcyclohexyl)-2-(2-chloro-6-fluorophenylamino)-6-fluoro-1-methyl-1H-benzimidazole-5-carboxamide; |
| 363 | 2-(2-Chloro-6-fluorophenylamino-N-(4-isopropylcyclohexyl)-6-fluoro-1-methyl-1H-benzimidazole-5-carboxamide; |
| 368 | 2-(2-Chloro-6-fluorophenylamino-N-(4-isopropylcyclohexyl)-6-fluoro-1-methyl-1H-benzimidazole-5-carboxamide; |
| 369 | 2-(2,6-Dichlorophenylamino)-6-methoxy-1-methyl-N-((1r,4r)-4-trifluoromethyl-cyclohexyl)-1H-benzimidazole-5-carboxamide; |
| 371 | N-(4-Bromophenyl)-2-(2,6-dichlorophenylamino)-6-methoxy-1H-benzimidazole-5-carboxamide; |
| 373 | 2-(2,6-Dichlorophenylamino)-6-fluoro-N-hexyl-1-methyl-1H-benzimidazole-5-carboxamide; |
| 374 | N-((1s,4s)-4-tert.-Butylcyclohexyl)-2-(2,6-dichlorophenylamino)-6-fluoro-1H-benzimidazole-5-carboxamide; |
| 375 | 2-(2,6-Dichlorophenylamino)-6-fluoro-N-(1r,4r)-4-isopropylcyclohexyl)-1H-benzimidazole-5-carboxamide; |

| Compound Number | Compound Name |
|---|---|
| 376 | 2-(2,6-Dichlorophenylamino)-6-methoxy-N-((1r,4r)-4-trifluoromethyl-cyclohexyl)-1H-benzimidazole-5-carboxamide; |
| 378 | N-((1s,4s)-4-tert.-Butylcyclohexyl)-2-(2-chloro-6-fluorophenylamino)-6-fluoro-1H-benzimidazole-5-carboxamide; |
| 380 | N-(4-Bromophenyl)-2-(2,5-dichlorophenylamino)-1-methyl-1H-benzimidazole-5-carboxamide; |
| 381 | N-(4-Bromophenyl)-2-(2-chloro-6-fluorophenylamino)-1-methyl-1H-benzimidazole-5-carboxamide; |
| 382 | N-(4-Bromophenyl)-2-(2-chloro-6-methylphenylamino)-1-methyl-1H-benzimidazole-5-carboxamide; |
| 383 | 2-(2,6-Dichlorophenylamino)-6-methoxy-N-((3-trifluoromethyl-pyridin-2-yl)-methyl)-1H-benzimidazole-5-carboxamide; |
| 384 | 2-(2-Chloro-6-fluorophenylamino)-6-fluoro-1-methyl-N-(spiro[2.5]octan-6-yl-1H-benzimidazole-5-carboxamide; |
| 385 | N-(4-Bromophenyl)-2-(4-fluoro-2-trifluoromethyl-phenylamino)-1-methyl-1H-benzimidazole-5-carboxamide; |
| 390 | 2-(2-Chloro-6-fluorophenylamino)-N-(3-cyclopropylpropyl)-6-fluoro-1-methyl-1H-benzimidazole-5-carboxamide; |
| 391 | 2-(2,6-Dichlorophenylamino)-6-fluoro-1-methyl-N-pentyl-1H-benzimidazole-5-carboxamide; |
| 392 | 2-(2-Chloro-6-fluorophenylamino)-N-(3-ethylcyclopentyl)-6-fluoro-1-methyl-1H-benzimidazole-5-carboxamide; |
| 395 | N-(4-Bromophenyl)-2-(2,6-dichlorophenylamino)-4,5-difluoro-1H-benzimidazole-6-carboxamide; |
| 397 | N-(2-Cyclobutylethyl)-2-(2,6-dichlorophenylamino)-6-fluoro-1-methyl-1H-benzimidazole-5-carboxamide; |
| 398 | N-(3-Cyclopropylpropyl)-2-(2,6-dichlorophenylamino)-6-fluoro-1-methyl-1H-benzimidazole-5-carboxamide; |
| 399 | 2-(2-Chloro-6-fluorophenylamino)-6-fluoro-N-(spiro[2.5]octan-6-yl)-1H-benzimidazole-5-carboxamide; |
| 402 | N-(4-Bromophenyl)-2-(2,4-dichloro-6-methylphenylamino)-1-methyl-1H-benzimidazole-5-carboxamide; |
| 404 | 2-(2-Chloro-6-fluorophenylamino)-N-(3,3-dimethylcyclohexyl)-6-fluoro-1-methyl-1H-benzimidazole-5-carboxamide; |
| 405 | 7-Bromo-N-(3-chlorophenyl)-2-(2,6-dichlorophenylamino)-1-methyl-1H-benzimidazole-5-carboxamide; |
| 408 | 2-(2,6-Dichlorophenylamino)-6-fluoro-1-methyl-N-(4-methylpentyl)-1H-benzimidazole-5-carboxamide; |
| 412 | 2-(2,6-Dichlorophenylamino)-N-(3-ethylcyclopentyl)-6-fluoro-1-methyl-1H-benzimidazole-5-carboxamide; |
| 415 | 2-(2,6-Dichlorophenylamino)-6-fluoro-1-methyl-N-(spiro[2.4]heptan-5-yl)-1H-benzimidazole-5-carboxamide; |
| 416 | (R)-2-(2,6-Dichlorophenylamino)-6-fluoro-N-(hexan-2-yl)-1-methyl-1H-benzimidazole-5-carboxamide; |
| 419 | 2-(2,6-Dichlorophenylamino)-6-fluoro-1-methyl-N-(spiro[2.5]octan-6-yl)-1H-benzimidazole-5-carboxamide; |
| 420 | 2-(2,6-Dichloro-4-fluorophenylamino)-N-(4,4-dimethylcyclohexyl)-1-methyl-1H-benzimidazole-5-carboxamide; |
| 423 | N-(4-Bromophenyl)-2-(2-chloro-5-trifluoromethyl-phenylamino)-1-methyl-1H-benzimidazole-5-carboxamide; |
| 428 | 2-(2,6-Dichlorophenylamino)-6-fluoro-N-isopentyl-1-methyl-1H-benzimidazole-5-carboxamide; |
| 430 | 2-(2-Chloro-6-fluorophenylamino)-N-(4,4-dimethylcyclohexyl)-6-fluoro-1-methyl-1H-benzimidazole-5-carboxamide; |
| 432 | 2-(2,6-Dichloro-4-fluorophenylamino)-1-methyl-N-((1R,4R)-4-trifluoromethyl-cyclohexyl)-1H-benzimidazole-5-carboxamide; |
| 433 | N-(4-Bromophenyl)-2-(4-chloro-2-trifluoromethyl-phenylamino)-1-methyl-1H-benzimidazole-5-carboxamide; |
| 436 | 2-(2,6-Dichlorophenylamino)-1-methyl-N-(spiro[2.4]heptan-5-yl)-1H-benzimidazole-5-carboxamide; |
| 437 | 2-(2,6-Dichlorophenylamino)-N-(4-ethylcyclohexyl)-6-fluoro-1-methyl-1H-benzimidazole-5-carboxamide; |
| 441 | 2-(2-Chloro-6-fluorophenylamino)-1-methyl-N-(spiro[2.5]octan-6-yl)-1H-benzimidazole-5-carboxamide; |
| 442 | 2-(2,6-Dichlorophenylamino)-6-fluoro-1-methyl-N-((1R,3R)-3-methylcyclohexyl)-1H-benzimidazole-5-carboxamide; |
| 443 | (S)-2-(2,6-Dichlorophenylamino)-6-fluoro-N-(hexan-2-yl)-1H-benzimidazole-5-carboxamide; |
| 447 | 2-(2,6-Dichlorophenylamino)-N-(3,3-dimethylcyclobutyl)-6-fluoro-1-methyl-1H-benzimidazole-5-carboxamide; |
| 450 | (S)-2-(2,6-Dichlorophenylamino)-6-fluoro-N-(hexan-2-yl)-1-methyl-1H-benzimidazole-5-carboxamide; |

| Compound Number | Compound Name |
|---|---|
| 456 | N-(4-Bromophenyl)-2-(2-chloro-4-fluorophenylamino)-1-methyl-1H-benzimidazole-5-carboxamide; |
| 457 | (R)-2-(2,6-Dichlorophenylamino)-6-fluoro-N-(hexan-2-yl)-1H-benzimidazole-5-carboxamide; |
| 458 | 2-(2-Chloro-6-fluorophenylamino)-6-fluoro-N-hexyl-1-methyl-1H-benzimidazole-5-carboxamide; |
| 475 | 2-(2,6-Dichlorophenylamino)-N-((1r,4r)-4-(difluoromethyl)cyclohexyl)-6-fluoro-1-methyl-1H-benzimidazole-5-carboxamide; |
| 476 | 2-(2-Chloro-6-fluorophenylamino)-N-((1r,4r)-4-(difluoromethyl)cyclohexyl)-6-fluoro-1-methyl-1H-benzimidazole-5-carboxamide; |
| 483 | 2-(2,6-Dichlorophenylamino)-1-methyl-N-(spiro[2.5]octan-6-yl)-1H-benzimidazole-5-carboxamide; |
| 484 | N-(2-Cyclopropylethyl)-2-(2,6-dichlorophenylamino)-6-fluoro-1-methyl-1H-benzimidazole-5-carboxamide; |
| 488 | 2-(2-Chloro-6-fluorophenylamino)-N-(spiro[2.5]octan-6-yl)-1H-benzimidazole-5-carboxamide; |
| 489 | N-(4-Bromophenyl)-2-(2-chloro-4,6-dimethylphenylamino)-1-methyl-1H-benzimidazole-5-carboxamide; |
| 496 | 2-(2,6-Dichlorophenylamino)-N-((1r,4r)-4-(difluoromethyl)cyclohexyl)-6-fluoro-1H-benzimidazole-5-carboxamide; |
| 499 | N-(4-Bromophenyl)-2-(2-chloro-6-(dimethylamino)phenylamino)-1-methyl-1H-benzimidazole-5-carboxamide; |
| 501 | 2-(2-Chloro-6-fluorophenylamino)-6-fluoro-1-methyl-N-((3R)-3-methylcyclopentyl)-1H-benzimidazole-5-carboxamide; |
| 502 | 2-(2-Chloro-6-fluorophenylamino)-N-(2-cyclopropylethyl)-6-fluoro-1-methyl-1H-benzimidazole-5-carboxamide; |
| 512 | N-(4-Bromophenyl)-2-(2-chloro-4-methylphenylamino)-1-methyl-1H-benzimidazole-5-carboxamide; |
| 514 | 7-Bromo-N-cyclohexyl-2-(2,6-dichlorophenylamino)-1H-benzimidazole-5-carboxamide; |
| 516 | N-(Cyclobutylmethyl)-2-(2,6-dichlorophenylamino)-6-fluoro-1-methyl-1H-benzimidazole-5-carboxamide; |
| 519 | N-(4-Bromophenyl)-2-(2,4-dichlorophenylamino)-1-methyl-1H-benzimidazole-5-carboxamide; |
| 526 | N-(4-Bromophenyl)-2-(2-chloro-5-(methylsulfonyl)phenylamino)-1-methyl-1H-benzimidazole-5-carboxamide; |
| 537 | N-(4-Bromophenyl)-2-(5-carbamoyl-2-chlorophenylamino)-1-methyl-1H-benzimidazole-5-carboxamide; |
| 540 | N-(4-Bromophenyl)-2-(2-chloro-4-(methylcarbamoyl)-phenylamino)-1-methyl-1H-benzimidazole-5-carboxamide; |
| 546 | 2-(2-Chloro-6-fluorophenylamino)-N-(cyclopropylmethyl)-6-fluoro-1-methyl-1H-benzimidazole-5-carboxamide; |
| 551 | N-(4-Bromophenyl)-2-(2-dimethylamino-6-fluorophenylamino)-1-methyl-1H-benzimidazole-5-carboxamide; |
| 556 | N-(4-Bromophenyl)-2-(2-chloro-4-trifluoromethyl-phenylamino)-1-methyl-1H-benzimidazole-5-carboxamide; |
| 557 | N-(4-Bromophenyl)-2-(2-chloro-6-(trifluoromethoxy)phenylamino)-1H-benzimidazole-5-carboxamide; |
| 562 | N-(4-Bromophenyl)-2-(2-chloro-4-(dimethylcarbamoyl)-phenylamino)-1-methyl-1H-benzimidazole-5-carboxamide; |
| 570 | 7-Bromo-N-isopropyl-2-(2,6-dichlorophenylamino)-1H-benzimidazole-5-carboxamide; |
| 572 | N-(4-Bromophenyl)-2-(2-isopropylphenylamino)-1-methyl-1H-benzimidazole-5-carboxamide; |
| 573 | 3-(5-(4-Bromophenylcarbamoyl)-1-methyl-1H-benzimidazol-2-yl-amino)-4-chlorobenzoic acid; or |
| 574 | N-(4-Bromophenyl)-2-(2-chloro-5-(methylcarbamoyl)-phenylamino)-1-methyl-1H-benzimidazole-5-carboxamide. |

3. A compound according to claim 1, which is selected from the following compounds or a pharmaceutically acceptable salt thereof:

| Compound Number | Compound Name |
|---|---|
| 578 | 2-(2,6-Dichloro-4-fluoro-phenylamino)-N-(4-bromo-phenyl)-1-methyl-1H-benzimidazole-5-carboxamide |
| 579 | 2-(2,6-Dichloro-4-fluoro-phenylamino)-6-methoxy-N-(trans-4-trifluoromethyl-cyclohex-1-yl)-1H-benzimidazole-5-carboxamide |

| Compound Number | Compound Name |
|---|---|
| 581 | 2-(2,6-Dichloro-4-fluoro-phenylamino)-6-methoxy-N-(4-bromo-phenyl)-1H-benzimidazole-5-carboxamide |
| 582 | 2-(2,6-Dichloro-4-fluoro-phenylamino)-N-(4-bromo-phenyl)-6-(2,2,2-trifluorethoxy)-1H-benzimidazole-5-carboxamide |
| 583 | 2-(2,6-Dichloro-4-fluoro-phenylamino)-N-(trans-4-trifluoromethyl-cyclohex-1-yl)-6-(2,2,2-trifluoroethoxy)-1H-benzimidazole-5-carboxamide |
| 584 | 2-(2,6-Dichloro-4-fluoro-phenylamino)-N-(trans-4-trifluoro-cyclohex-1-yl)-6-(2-fluoroethoxy)-1H-benzimidazole-5-carboxamide |
| 585 | 2-(2,6-Dichloro-4-fluoro-phenylamino)-N-(4-bromo-phenyl)-6-(2-fluoroethoxy)-1H-benzimidazole-5-carboxamide |
| 586 | 2-(2,6-Dichloro-4-fluoro-phenylamino)-N-(4-bromo-phenyl)-6-(2,2-difluoroethoxy)-1H-benzimidazole-5-carboxamide |
| 587 | 2-(2,6-Dichloro-4-fluoro-phenylamino)-N-(trans-4-trifluoromethyl-cyclohex-1-yl)-6-(2,2-difluoroethoxy)-1H-benzimidazole-5-carboxamide |
| 588 | N-(4-Bromo-phenyl)-2-(2,3-dichloro-6-fluoro-phenylamino)-6-(2,2,2-trifluoroethoxy)-1H-benzimidazole-5-carboxamide |
| 589 | 2-(2,6-Dichloro-phenylamino)-6-(2,2,2-trifluoroethoxy)-N-(trans-4-trifluoromethyl-cyclohex-1-yl)-1H-benzimidazole-5-carboxamide |
| 590 | 2-(2,6-Dichloro-phenylamino)-N-(4-bromo-phenyl)-6-(2,2,2-trifluoroethoxy)-1H-benzimidazole-5-carboxamide |
| 591 | 2-(2,3-Dichloro-6-fluoro-phenylamino)-6-(2,2,2-trifluoro-ethoxy)-N-(4-trans-trifluoromethyl-cyclohex-1-yl) 1H-benzimidazole-5-carboxamide |
| 592 | 2-(3,6-Dichloro-2-fluoro-phenylamino)-N-(4-trans-trifluoromethyl-cyclohex-1-yl)-6-(2,2,2-trifluorethoxy)-1H-benzimidazole-5-carboxamide |
| 593 | 2-(3,6-Dichloro-2-fluoro-phenylamino)-N-(4-bromophenyl)-6-(2,2,2-trifluorethoxy)-1H-benzimidazole-5-carboxamide |
| 594 | 2-(2-Chloro-3,6-difluoro-phenylamino)-N-(4-trans-trifluoromethyl-cyclohex-1-yl)-6-(2,2,2-trifluorethoxy)-1H-benzimidazole-5-carboxamide |
| 595 | 2-(2-Chloro-3,6-difluoro-phenylamino)-N-(4-bromophenyl)-6-(2,2,2-trifluorethoxy)-1H-benzimidazole-5-carboxamide |
| 596 | 2-(3,6-Dichloro-2-fluoro-phenylamino)-N-(4,4-dimethyl-cyclohex-1-yl)-6-fluoro-1H-benzimidazole-5-carboxamide |
| 597 | 2-(3,6-Dichloro-2-fluoro-phenylamino)-N-(trans-4-trifluoromethyl-cyclohex-1-yl)-6-fluoro-1H-benzimidazole-5-carboxamide |
| 598 | 2-(3,6-Dichloro-2-fluoro-phenylamino)-N-(3-chlorphenyl)-6-fluoro-1H-benzimidazole-5-carboxamide |
| 599 | 2-(3,6-Dichloro-2-fluoro-phenylamino)-6-ethoxy-N-(trans-4-trifluoromethyl-cyclohex-1-yl)-1H-benzimidazole-5-carboxamide |
| 600 | 2-(3,6-Dichloro-2-fluoro-phenylamino)-N-(4,4-dimethyl-cyclohexyl)-6-ethoxy-1H-benzimidazole-5-carboxamide |
| 601 | 2-(3,6-Dichloro-2-fluoro-phenylamino)-6-fluoro-N-(trans-4-trifluoromethyl-cyclohex-1-yl)-1-methyl-1H-benzimidazole-5-carboxamide |
| 602 | 2-(3,6-Dichloro-2-fluoro-phenylamino)-6-methoxy-N-(4-bromophenyl)-1H-benzimidazole-5-carboxamide |
| 603 | 2-(3,6-Dichloro-2-fluoro-phenylamino)-N-(3-chloro-phenyl)-6-ethoxy-1H-benzimidazole-5-carboxamide |
| 604 | 2-(3,6-Dichloro-2-fluoro-phenylamino)-N-(4-bromo-phenyl)-6-ethoxy-1H-benzimidazole-5-carboxamide |
| 605 | 2-(3,6-Dichloro-2-fluoro-phenylamino)-6-ethoxy-N-(4-trans-trifluoromethyl-cyclohex-1-yl)-1-methyl-1H-benzimidazole-5-carboxamide |
| 606 | 2-(3,6-Dichloro-2-fluoro-phenylamino)-6-fluoro-N-(spiro[2.5]oct-6-yl)-1-methyl-1H-benzimidazole-5-carboxamide |
| 607 | 2-(3,6-Dichloro-2-fluoro-phenylamino)-6-ethoxy-N-(4,4-dimethyl-cyclohex-1-yl)-1-methyl-1H-benzimidazole-5-carboxamide |
| 608 | 2-(3,6-Dichloro-2-fluoro-phenylamino)-N-(spiro[2.5]oct-6-yl)-6-fluoro-1H-benzimidazole-5-carboxamide |
| 609 | 2-(3,6-Dichloro-2-fluoro-phenylamino)-6-ethoxy-N-(spiro[2.5]oct-6-yl)-1-methyl-1H-benzimidazole-5-carboxamide |
| 610 | 2-(3,6-Dichloro-2-fluoro-phenylamino)-N-(4-bromo-phenyl)-6-isopropoxy-1H-benzimidazole-5-carboxamide |
| 611 | 2-(3,6-Dichloro-2-fluoro-phenylamino)-6-isopropoxy-N-cyclohexyl-1H-benzimidazole-5-carboxamide |
| 612 | 2-(3,6-Dichloro-2-fluoro-phenylamino)-N-cyclohexyl-6-methoxy-1H-benzimidazole-5-carboxamide |
| 613 | 2-(3,6-Dichloro-2-fluoro-phenylamino)-N-(spiro[2.5]oct-6-yl)-6-methoxy-1H-benzimidazole-5-carboxamide |
| 614 | 2-(3,6-Dichloro-2-fluoro-phenylamino)-N-(3-chloro-phenyl)-6-isopropoxy-1H-benzimidazole-5-carboxamide |
| 615 | 2-(3,6-Dichloro-2-fluoro-phenylamino)-6-isopropoxy-N-(spiro[2.5]oct-6-yl)-1H-benzimidazole-5-carboxamide |

-continued

| Compound Number | Compound Name |
|---|---|
| 616 | 2-(3,6-Dichloro-2-fluoro-phenylamino)-N-(4,4-dimethyl-cyclohex-1-yl)-6-methoxy-1H-benzimidazole-5-carboxamide |
| 617 | 2-(3,6-Dichloro-2-fluoro-phenylamino)-6-methoxy-N-(4-trans-trifluoromethyl-cyclohex-1-yl)-1H-benzimidazole-5-carboxamide |
| 618 | 2-(3,6-Dichloro-2-fluoro-phenylamino)-6-isopropoxy-N-(4,4-dimethyl-cyclohex-1-yl)-1H-benzimidazole-5-carboxamide |
| 619 | 2-(3,6-Dichloro-2-fluoro-phenylamino)-6-methoxy-N-cyclohexyl-1-methyl-1H-benzimidazole-5-carboxamide |
| 620 | 2-(3,6-Dichloro-2-fluoro-phenylamino)-6-isopropoxy-N-(4-trans-trifluoromethyl-cyclohex-1-yl)-1H-benzimidazole-5-carboxamide |
| 621 | 2-(3,6-Dichloro-2-fluoro-phenylamino)-6-methoxy-N-(4,4-dimethyl-cyclohex-1-yl)-1-methyl-1H-benzimidazole-5-carboxamide |
| 622 | 2-(6-Chloro-2-fluoro-3-methyl-phenylamino)-6-methoxy-N-(4-trans-trifluoromethyl-cyclohex-1-yl)-1H-benzimidazole-5-carboxamide |
| 623 | 2-(6-Chloro-2-fluoro-3-methyl-phenylamino)-6-fluoro-N-cyclohexyl-1-methyl-1H-benzimidazole-5-carboxamide |
| 624 | 2-(3,6-Dichloro-2-fluoro-phenylamino)-6-isopropoxy-N-cyclohexyl-1-methyl-1H-benzimidazole-5-carboxamide |
| 625 | 2-(3,6-Dichloro-2-fluoro-phenylamino)-6-isopropoxy-N-(4,4-dimethyl-cyclohex-1-yl)-1-methyl-1 H-benzimidazole-5-carboxamide |
| 626 | 2-(6-Chloro-2-fluoro-3-methyl-phenylamino)-6-methoxy-N-(4,4-dimethyl-cyclohex-1-yl-1H-benzimidazole-5-carboxamide |
| 627 | 2-(6-Chloro-2-fluoro-3-methyl-phenylamino)-6-fluoro-N-(4,4-dimethyl-cyclohex-1-yl)-1-methyl-1H-benzimidazole-5-carboxamide |
| 628 | 2-(6-Chloro-2-fluoro-3-methyl-phenylamino)-6-methoxy-N-cyclohexyl-1H-benzimidazole-5-carboxamide |
| 629 | 2-(6-Chloro-2-fluoro-3-methyl-phenylamino)-6-fluoro-N-(trans-4-trifluoromethyl-cyclohex-1-yl)-1-methyl-1H-benzimidazole-5-carboxamide |
| 632 | N-(2,2,3,3,4,4-heptafluoro-butyl)-2-(2,6-dichlorophenylamino)-6-methoxy-1H-benzimidazole-5-carboxamide |
| 639 | 2-(2,6-Dichloro-3-cyanomethyl-phenylamino)-N-(4-bromphenyl)-6-methoxy-1H-benzimidazol-5-carboxamide |
| 640 | 2-(2,5-Di-(trifluoromethyl)-phenylamino)-N-(4-bromphenyl)-6-methoxy-1-methyl-1H-benzimidazol-5-carboxamide |
| 641 | 2-(5-Methyl-2-trifluoromethyl-phenylamino)-N-(4-bromphenyl)-6-methoxy-1-methyl-1H-benzimidazol-5-carboxamide |
| 642 | 2-(5-Fluoro-2-trifluoromethyl-phenylamino)-N-(4-bromphenyl)-6-methoxy-1-methyl-1H-benzimidazol-5-carboxamide |
| 643 | 2-(3,6-Dichloro-2-fluoro-phenylamino)-6-methoxy-N-(trans-4-trifluoromethyl-cyclohex-1-yl)-1-methyl-1H-benzimidazole-5-carboxamide |
| 644 | 2-(3,6-Dichloro-2-fluoro-phenylamino)-6-isopropoxy-N-(4-trans-trifluoromethyl-cyclohex-1-yl)-1-methyl-1H-benzimidazole-5-carboxamide |
| 645 | 2-(3,6-Dichloro-2-fluoro-phenylamino)-6-methoxy-N-(spiro[2.5]oct-6-yl)-1-methyl-1H-benzimidazole-5-carboxamide |
| 646 | 2-(3,6-Dichloro-2-fluoro-phenylamino)-6-ethoxy-N-(spiro[2.5]oct-6-yl)-1H-benzimidazole-5-carboxamide |
| 647 | 2-(6-Chloro-2-fluoro-3-methyl-phenylamino)-6-methoxy-N-(trans-4-trifluoromethyl-cyclohex-1-yl)-1-methyl-1H-benzimidazole-5-carboxamide |
| 648 | 2-(3,6-Dichloro-2-fluoro-phenylamino)-6-isopropoxy-N-(spiro[2.5]oct-6-yl)-1-methyl-1H-benzimidazole-5-carboxamide |
| 649 | 2-(6-Chloro-2-fluoro-3-methyl-phenylamino)-N-cyclohexyl-6-fluoro-1H-benzimidazole-5-carboxamide |
| 650 | 2-(6-Chloro-2-fluoro-3-methyl-phenylamino)-6-methoxy-N-(4,4-dimethyl-cyclohex-1-yl)-1-methyl-1H-benzimidazole-5-carboxamide |
| 651 | 2-(6-Chloro-2-fluoro-3-methyl-phenylamino)-6-methoxy-N-cyclohexyl-1-methyl-1H-benzimidazole-5-carboxamide |
| 652 | 2-(2,3,5,6-tetrafluoro-phenylamino)-6-methoxy-N-(4,4-dimethyl-cyclohex-1-yl)-1-methyl-1H-benzimidazole-5-carboxamide |
| 653 | 2-(6-Chloro-2-fluoro-3-methyl-phenylamino)-N-(trans-4-trifluoromethyl-cyclohex-1-yl)-6-fluoro-1H-benzimidazole-5-carboxamide: or |
| 654 | 2-(5-Fluoro-2-trifluoromethyl-phenylamino)-N-(4-bromphenyl)-6-methoxy-1-methyl-1H-benzimidazol-5-carboxamide. |

4. A pharmaceutical formulation comprising a compound according to claim 1, or a pharmaceutically acceptable salt thereof, and a pharmaceutically acceptable adjuvant, diluent or carrier.

* * * * *